United States Patent
Maresca, Jr. et al.

(10) Patent No.: US 7,331,248 B2
(45) Date of Patent: *Feb. 19, 2008

(54) METHOD AND APPARATUS FOR DETECTING AND LOCATING EXPLOSIVES, BIOLOGICAL, AND CHEMICAL SUBSTANCES IN DUCTS AND STRUCTURES USING TRACERS

(75) Inventors: Joseph W. Maresca, Jr., Sunnyvale, CA (US); Wesley L. Bratton, Richland, WA (US)

(73) Assignee: Vista Engineering Technologies, Inc., Kennewick, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/960,653

(22) Filed: Oct. 6, 2004

(65) Prior Publication Data

US 2006/0248941 A1 Nov. 9, 2006

Related U.S. Application Data

(60) Provisional application No. 60/509,312, filed on Oct. 6, 2003, provisional application No. 60/509,316, filed on Oct. 6, 2003.

(51) Int. Cl.
*G01M 19/00* (2006.01)
*G01N 37/00* (2006.01)

(52) U.S. Cl. .................. 73/865.8; 73/61.62; 422/62; 436/52; 436/56

(58) Field of Classification Search .............. 73/28.01, 73/28.04, 28.05, 28.06, 863.22, 863.23, 40.07, 73/40.7, 865.8, 865.9, 61.62, 60.11; 436/52, 436/56; 422/62

See application file for complete search history.

(56) References Cited

U.S. PATENT DOCUMENTS

| | | | | |
|---|---|---|---|---|
| 3,342,990 A | * | 9/1967 | Barrington et al. | 250/288 |
| 3,425,264 A | * | 2/1969 | Hans | 73/40.5 R |
| 3,729,983 A | * | 5/1973 | Coppens | 73/40.7 |
| 3,762,212 A | * | 10/1973 | Morley et al. | 73/40.7 |
| 4,754,638 A | * | 7/1988 | Brayman et al. | 73/40.7 |
| 5,416,323 A | * | 5/1995 | Hoots et al. | 250/302 |
| 5,535,253 A | * | 7/1996 | Loisy et al. | 376/250 |
| 5,681,983 A | * | 10/1997 | Seigeot | 73/40.7 |
| 5,767,390 A | * | 6/1998 | Chapman, IV | 73/40.7 |

(Continued)

*Primary Examiner*—Michael Cygan
(74) *Attorney, Agent, or Firm*—David H. Jaffer; Pillsbury Winthrop Shaw Pittman LLP

(57) ABSTRACT

A method and an apparatus for detecting, locating, and quantifying explosive materials and devices, and naturally occurring and man-made dangerous or hazardous biological and chemical materials and devices in ducts or piping systems, or other fluid flow systems in buildings such as residential, office, industrial, and power plants, transportation systems such as ships, airplanes, subways, and trains, and various types of infrastructure such as dams, tunnels, or bridges, and in the rooms, compartments, enclosures, containers, or difficult to access areas in these buildings, transportation systems, and structures. The preferred embodiment of this detection and location method uses a conservative tracer and one or more interactive tracers that are injected into the duct or area to be searched at one location and then monitored at the same or another location in the duct or area. Alternative embodiments, which are quicker and just as accurate for detection and location, require only the use of interactive tracers. Detection, location, and quantification are accomplished by analysis of the characteristic features of measured curves of tracer concentration. Various types of interactive tracers may be used, including partitioning and reactive tracer gaseous tracers.

5 Claims, 99 Drawing Sheets

U.S. PATENT DOCUMENTS

| | | | |
|---|---|---|---|
| 5,817,927 A * | 10/1998 | Chen et al. | 73/40.7 |
| 5,939,619 A * | 8/1999 | Achter et al. | 73/40.7 |
| 5,939,679 A | 8/1999 | Olsson | |
| 6,321,595 B1 * | 11/2001 | Pope et al. | 73/152.39 |
| 6,329,165 B1 * | 12/2001 | Chattoraj et al. | 435/29 |
| 6,359,645 B1 | 3/2002 | Sivacoe | |
| 6,464,633 B1 | 10/2002 | Hosoda et al. | |
| 6,730,227 B2 * | 5/2004 | Zeiher et al. | 210/650 |
| 6,793,699 B2 * | 9/2004 | Coleman et al. | 48/194 |

* cited by examiner

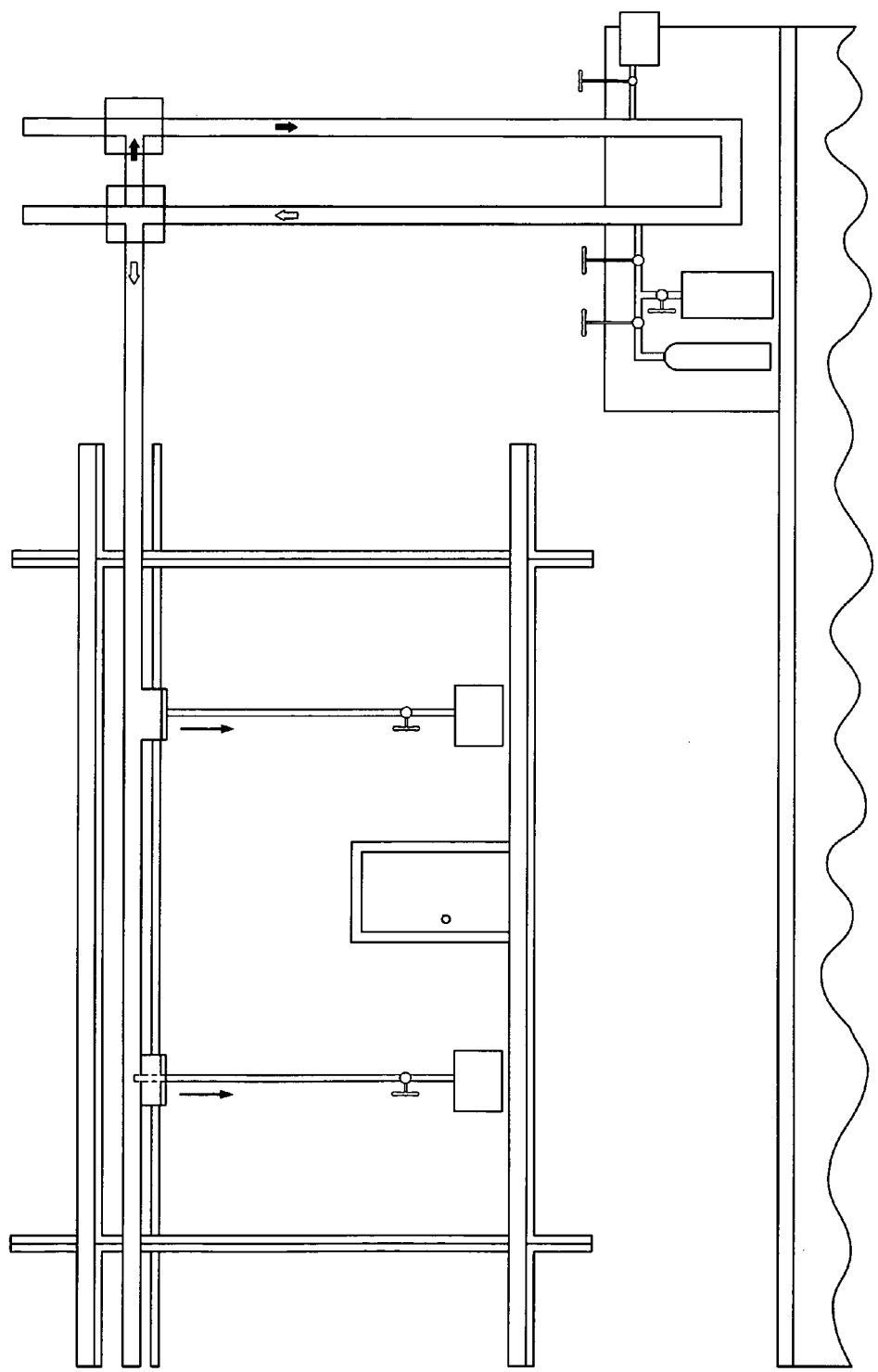
FIG.5ℓ

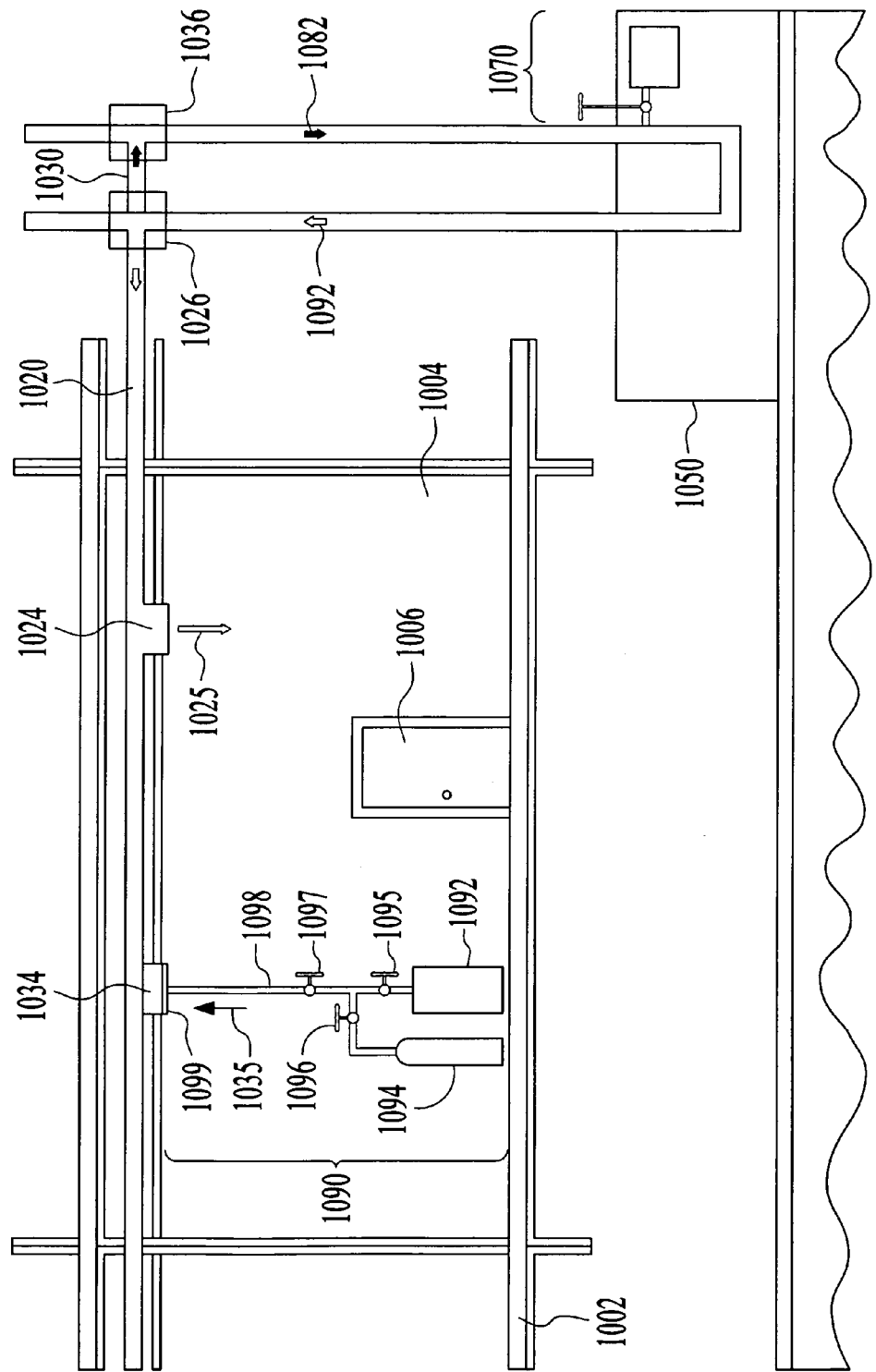

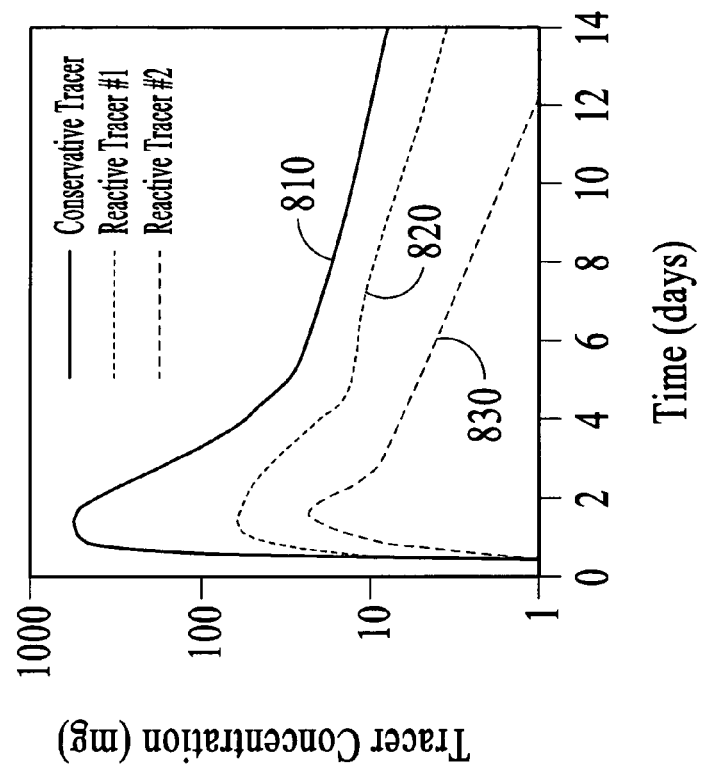
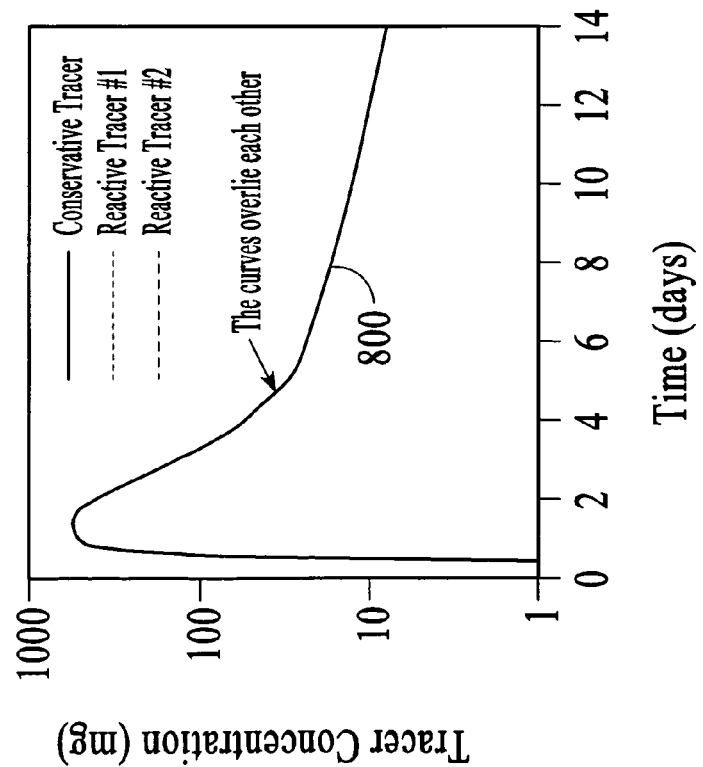
FIG. 32
a) Reactive tracer concentration curves when there is no contamination present.
b) Reactive tracer concentration curves when contamination is encountered in the test zone

METHOD AND APPARATUS FOR DETECTING AND LOCATING EXPLOSIVES, BIOLOGICAL, AND CHEMICAL SUBSTANCES IN DUCTS AND STRUCTURES USING TRACERS

CROSS-REFERENCE TO RELATED APPLICATIONS

This application claims the benefit of U.S. Provisional Application No. 60/509,312 filed Oct. 6, 2003, and U.S. Provisional Application No. 60/509,316 filed Oct. 6, 2003, the disclosures of which are incorporated by reference.

BACKGROUND OF THE INVENTION 1.0 Field of the Invention

A method and an apparatus for detecting and locating explosive, biological, chemical, and radioactive devices in ducts, piping, or other fluid flow systems in or on the exterior of various structures such as buildings, transportation systems (airplanes, ships, trains, buses, etc.), and various types of infrastructure (containers, packages, luggage, fluid flow systems, ducts, pipes, conduits, dams, bridges, tunnels, etc.) is described. The method and apparatus can also be used to detect and locate these dangerous or hazardous materials in the rooms, compartments, enclosures, containers, or difficult to access areas in these buildings, transportation systems, and infrastructure, either through the ductwork or by access into that portion of the structure (e.g., room) to be searched. The method can also be used to quantify the magnitude of the threat. This method and apparatus can also be used to detect, locate, and/or quantify the levels of naturally occurring biological and chemical hazards, such as mold and bacteria, which may develop in the ductwork, walls, or other parts of these structures. This detection, location, and quantification method uses a conservative and one or more interactive tracers that are injected into the duct at one location and then monitored at the same or another location in the duct. This method can also be used in a non-fluid flow system, such as a room, by injecting the tracers into the room or a specific area in a structure and then withdrawing the tracers through the injection point or another point in the room, the duct system, or another room in the structure. The ductwork can also be used as a communication network to detect the presence of a biological, chemical or explosive threat in a room or area or all rooms or areas within a building or structure without physically accessing that room or area. This invention is related to the invention disclosed in U.S. patent application Ser. No. 10/960,407, filed Oct. 6, 2004, titled Method and Apparatus for Locating Leak Holes in a Pipeline Using Tracers.

In the preferred embodiment, the tracers are introduced into the room or the area to be interrogated through the inlet vent of the inlet duct and then are returned to the return duct through the return vent. Provided the tracer injection and tracer measurement systems are appropriately located (e.g., the building's HVAC unit), all rooms and all of the ductwork can be interrogated. For most threat applications, both detection and location are required. For some applications, like the detection of dangerous or hazardous materials such as explosives, biological and chemical agents in the ductwork or in a room, quantification may not be essential once the threat is detected and located, because these threats must be removed regardless of their magnitude. For other applications, like the detection of mold and bacteria in the ductwork, quantification is important, because the quantity of mold or bacteria detected in the ductwork may not be sufficient to warrant the removal until it reaches a critical level. Detection, location, and quantification are accomplished by analysis of the characteristic features of the measured curves of tracer concentration obtained with a gas chromatograph (GC) or a sensor system that senses or measures the magnitude of the specific substances of interest. Various types of interactive tracers may be used, including partitioning and reactive gaseous tracers.

This method and apparatus has many different types of applications in many different types of structures. The specific application will depend on the threat and whether a targeted measurement is being made or a monitoring system is being used. The method will also depend on what type of information (detection, location, or quantification) is required. The method will also depend on whether the threat is believed to be in the ductwork, in the rooms or areas accessible through the ductwork, or in rooms or areas regardless of access through flow channels such as the ductwork.

A slug of the tracers, which may include both conservative and interactive tracers, can be introduced into the ductwork or areas to be searched or monitored, transported through the ductwork or areas to be searched or monitored with an inert gas, and then measured at another location in the ductwork or structure. Instead of a slug of tracers, the entire ductwork or areas to be searched or monitored could be filled first with the interactive tracers and then measured at the same or another location in the ductwork or areas by use of an inert gas to transport the tracers to the measurement point or by withdrawing the tracers under a vacuum. The ductwork or other piping (e.g., electrical conduit) that may access one or more rooms in the building or one or more areas within the various building, transportation, or structures can be used to introduce the tracers into the rooms or areas to be searched or monitored and then measured by producing a flow stream that pulls the tracers back out of the rooms or areas or is sensed at a point that specifically accesses each room or area.

Various types of interactive tracers may be used, including partitioning and reactive tracer gases. The tracers are selected specifically to detect and/or locate, and/or measure the concentration of the specific hazardous materials or devices of interest. Different tracers are usually required to detect explosives, biohazards, or dangerous chemicals or gases. There may be more than one tracer and/or type (e.g., reactive or partitioning) of tracer to use for each type of threat target. The tracer that might be used to detect the explosive TNT may not necessarily be the one used to detect the explosive C4. If detection is the primary objective, then a tracer that interacts with the threat substance the quickest would be the best choice. Both reactive and partitioning tracers will suffice. If the threat target material also needs to be located, then a partitioning tracer would be the preferred choice, because the structure being interrogated can be rapidly flushed once the tracer has had time to partition into the hazardous material and the arrival time of the tracer partitioning back into the flow stream can be measured. This measurement will take more time and needs better fluid flow controls than the detection measurement. Quantification can be accomplished with both reactive and partitioning tracers.

1.2 Brief Discussion of Prior Art

At the present time, the methods used to detect dangerous or hazardous substances such as explosives, biological, or chemical agents require a personal, mechanical, or robotic search of the ductwork, the piping system, or each room or area where the explosives may be hidden. An individual or a team of individuals must visually access and search each area where dangerous or hazardous substances are suspected. In a building, this may require a room-by-room search. It may require a person crawling through the ductwork, or by placing a robotic crawler with a camera or chemical sensing device attached in the ductwork. Dogs, which are very adept at detecting the presence of explosives, for example, are often used. Dogs are very effective and can increase the speed and safety of a search operation. Various explosive sensing and measurement devices may also be used to detect the presence of explosives from the chemical or physical properties of the explosives. These sensing devices must also be brought to each area to be searched and are generally carried by the individuals of the search team. However, they can be attached to a robotic system for safety (e.g., in a room search) or when the search area cannot be accessed by an individual or a dog (e.g., small ducts, sewer pipe).

The current approach to detection is very labor intensive and very slow; thus, it is very expensive. Since it can be slow and tedious, the presence of dangerous or hazardous substances can also be missed by the individuals as they tire or get careless. More importantly, this approach also requires the a priori knowledge that dangerous or hazardous substances might be present in the building, transportation system, or infrastructure so that a search can be initiated.

A remote sensing system is needed that can check an entire building, transportation system, or structure without an individual or animal physically accessing the area to be search. This remote sensing system can be used when dangerous or hazardous substances are suspected, or more importantly, it can be used as a remote monitoring system to routinely check a building, transportation system or structure in which a biological, chemical or explosive threat is not suspected, but may be a potential terrorist target. The presence of such a monitoring system also serves as a threat deterrent.

In addition to terrorist targets, there is a need to detect, locate and quantify naturally occurring hazardous biological and chemical materials that may be present in the ductwork of the buildings, transportation systems, and infrastructure without having to physically access and search the ductwork. Mold tends to be a significant problem.

Inspection of ductwork, piping, and small areas is difficult to do with people and animals. Many of the piping and duct systems or large sections of piping and ducts are inaccessible and external inspection techniques that require access to the outside wall of the pipe cannot be used. Many of the pipes or ducts are buried underground, or are located beneath the floor of a building or beneath paved areas. Because direct access to the external wall of the pipe or duct is not frequently possible, methods that involve internal inspection of the inside of these systems need to be used.

A common measurement approach for determining whether or not a pipe of duct contains hazardous materials is to use a camera to inspect the inside of the pipe. For short sections of pipe, a small camera is inserted into the pipe on a cable. For example, in U.S. Pat. No. 6,359,645, Sivacoe describes a method of inspecting a pipe, by pushing a video camera through the pipe on a cable. In U.S. Pat. No. 5,939,679, Olsson describes an electromechanical system for inspecting the inside of pipes over distances of several hundred feet for defects and obstructions using a push-cable that mechanically and electrically connects a video camera head to a push reel and video circuit.

A camera and other pipe inspection sensors can be mounted on a robotic vehicle, which is inserted into the pipe and allowed to move down the pipe. For example, in U.S. Pat. No. 6,464,633, Hovis, et al., describes a crawler for inspection of the integrity of 3- to 4-in. diameter piping, where the crawler can carry sensors or a camera to perform the inspection. This approach is acceptable for larger diameter piping, but for small piping, the robotic vehicle may be too large to be used or not be able to move past bends and constrictions in the pipe. The robotic vehicle can be instrumented with a camera, chemical sensors, and sample collectors. Where access to the pipe is possible, the pipe is sometimes cut and analyzed for contamination in the laboratory.

In general, most methods of finding hazardous materials require the insertion of a physical device into the pipe such as a cable or crawler. In addition to cameras and video system, there are a variety of sensors that can detect biological and chemical hazardous materials.

The method of the present invention uses tracers to detect, and/or locate, and/or quantify the threat materials in a pipe or duct, where at least one of the tracers does not interact with the contaminant of interest in the pipe, and one or more tracers that do. Depending on how the measurement is to be done and the requirements on the accuracy and reliability of the measurement, a tracer that does not interact with the target may not be required.

The method described here is very similar to the one described in the patent application submitted by the inventors for characterizing contamination in pipes, ducts, and other fluid flow systems [1], where characterization includes detection, location, and quantification of the contaminant. However, the application objective is very different and the present invention can also use the ducts, pipes, and fluid flow systems as a communication network to apply the method. In addition, the present invention can be used to detect the presence of the hazardous material in a non-fluid flow system such as a room or a container.

Tracers have been used for characterizing subsurface contamination between monitoring wells such as Dense Non-Aqueous Phase Liquids (DNAPLs), Non-Aqueous Phase Liquids (NAPLs), and Light Non-Aqueous Phase Liquids (LNAPL's) such as unleaded gasoline and diesel. Such methods have been used in both the saturated zone using the natural groundwater flow at the tracer carrier fluid or in the vadose zone using an established air flow field as the tracer carrier. In U.S. Pat. No. 6,321,595, Pope, et. al., teaches a method of characterization of organic contaminants in subsurface formations such as nonaqueous phase liquids by injecting partitioning and non-partitioning tracers at one well point and measuring the arrival times of these tracers at another well point. This subsurface tracer approach has also been used to detect releases of a hazardous liquids from underground and above ground storage tanks. This subsurface application has not been used to detect explosives, biohazards, or poisonous chemicals placed in the soil and intended to kill humans. While none of these approaches have been used to identify the presence of these threat materials or any contamination inside a pipe or a duct or a room or a structure, these methods have identified a variety of partitioning tracers that might be used in the method of the present invention.

Advantages. There are a number of important advantages of the method of the present invention over the physical, mechanical, or robotic inspection and measurement systems currently used for detecting, and/or locating, and/or quantifying explosives or biological or chemical substances. The first advantage of the proposed invention is that the same procedure will work on ducts, pipes, conduit, or any fluid flow system of any size and nearly any length. The same method will also work for rooms, compartments, containers, or difficult to access areas associated with buildings, transportation systems, and infrastructure. Tracers are just as easily injected into a small diameter duct, an entire duct system, or a room or a tunnel with and without ductwork.

The second advantage of the proposed invention is that the injected tracers can easily interrogate the entire duct or area within in a building, transportation system, or structure without having to physically place a monitoring device in each duct or area to be interrogated. Gas tracers also inspect the entire surface of the duct or area, including any crevices or nooks that may be difficult to inspect using video approaches. This will result in a more complete and thorough detection capability.

The third advantage of the proposed invention is that it can be used to interrogate an entire building, transportation system, or structure with only a single measurement point.

The fourth advantage of the proposed invention is that there are no moving parts or equipment that has to enter the duct or area to be interrogated. For ducts or areas that may contain explosive vapors or contaminants that could ignite, the interactive tracer technique offers an approach that remains safe. In addition, since no mechanical equipment enters the duct or area to be interrogated, this eliminates the possibility of equipment malfunction or getting "stuck."

The fifth advantage of the proposed invention is that it can be operated more cost effectively and more safely than other techniques without sacrificing performance. Humans and animals are not placed in harms way for detection or location of the substance of interest.

The sixth advantage is that the proposed invention can also quantify the magnitude of the substances to be detected and located.

The seventh advantage of the proposed invention is that it can be used as a one-time measurement like that provided in a test service or it can be permanently installed in the structure for routine monitoring of the structure.

The eighth advantage is that the same system can monitor or test the health of the building for naturally occurring mold and/or bacteria contamination and can also monitor or test the building for dangerous or hazardous substances placed purposefully to damage the people or the building.

SUMMARY OF THE INVENTION

It is the object of this invention to provide a method and an apparatus for detecting dangerous substances such as explosives, chemicals, and both man-made and naturally occurring hazardous biological substances and devices that may be located in a duct, pipe, conduit, or other type of fluid flow system without having to physically, robotically, or mechanical enter the system.

It is another object of this invention to provide a method and an apparatus for detecting dangerous substances such as explosives, chemicals, and biological substances and devices that may be located in a room, enclosure, compartment, container, or difficult to access area within a building, transportation system, or structure without having to physically enter area being interrogated.

It is another object of this invention to provide a method and an apparatus for detecting the presence of specific substances in the interrogated area.

It is another object of this invention to provide a method and an apparatus for interrogating an entire or large part of a building, transportation system, or structure for hazardous substances using the ductwork as a means of communication to these potential locations where such substances may be found.

Another object of this invention is to provide a method and an apparatus for determining the concentration of specific substances that were detected.

Yet another object of this invention is to provide a method and an apparatus for determining the location of the specific substances that were detected.

Another object of this invention is to provide a method and an apparatus for determining whether or not the building, transportation system, or structure is free of specific hazardous substances.

Yet another object of this invention is to provide a method and an apparatus for determining whether or not the dangerous or hazardous substance detected in a building, transportation system, or structure is at a level where removal is required.

Still another object of this invention is to provide a method and an apparatus for determining whether or not the building, transportation system, or structure can be safely entered once hazardous substances have been removed.

It is the object of this invention to provide a method and an apparatus for detecting, quantifying, and locating naturally occurring mold and/or bacteria that may be hazardous to human health that may develop in the ductwork, walls, and other areas of a building, transportation system, or structure.

The method and apparatus of the preferred embodiment of the present invention requires the injection of a "slug" of two or more tracers into a fluid flow system (e.g., duct) or area to be interrogated (e.g., room), where at least one of the tracers interacts with the dangerous or hazardous substance of interest and at least one of the tracers does not. The tracers are injected into the duct or room at one location, and then the tracers are extracted at another location in the duct or room. At least one of the tracers does not interact with the dangerous or hazardous substance or the other tracers, and this non-interactive tracer is used as a reference to determine the changes that occur to the tracers that do interact with the substance. Another fluid, which does not interact with any of the tracers or the dangerous or hazardous substance, is used to advect or transport the tracers from the injection point to the extraction point in the system. The concentrations of the extracted tracers are then measured as a function of time or for a specific period of time. The magnitude of the measured concentration or the temporal history of the measured concentration of the interactive tracers relative to the non-interactive or reference tracers are used to detect, locate, and quantify the dangerous or hazardous substance of interest. The fluid flow system may, for example, be a duct, a pipe, electrical conduit, or a tunnel.

Alternatively, another approach is to introduce enough partitioning tracer at the beginning of the duct test to cover the entire duct, then stop the flow, and allow the tracer to interact with dangerous or hazardous substance. After a period of time, an advection flow field is established, and GC samples are collected and analyzed. This approach can be used to detect, quantify and locate the dangerous or hazardous substance.

The method and apparatus of the present invention, however, is not limited to a fluid flow system. It can be used, for example, to detect a hazardous threat in a room, a building, an airplane, a ship, or a train. The fluid flow channel in these enclosures (e.g., ducts, electrical conduit, or pipe) may, for example, only serve as a means of accessing the entire system. The fluid flow system may not be needed to access the area to be interrogated. The tracers may be injected directly into the room or enclosure to be monitored from outside the room, and the measurement system, also located outside the room, may sample the air in the room being pulled out of the room with a pump. This might be a mode of operation for finding weapons, explosives, or the enemy hiding in a room or a building.

The method and apparatus of the present invention will be described in terms of gaseous tracers. However, the same method is applicable for fluid flow system containing a liquid.

Both partitioning and reactive gaseous tracers can be used in the method of the present invention. The concentration of a reactive tracer will decrease after the tracer interacts with a contaminant; also, the chemical composition or physical properties of the reactive tracer may change. Detection is accomplished by using this loss of concentration. The concentration of a partitioning tracer will only temporarily decrease after the tracer interacts with a contaminant. The partitioning tracer initially interacts with the dangerous or hazardous substance, and then re-enters the fluid flow system at a later point in time in accordance with its partitioning properties. Detection is accomplished by using this initial concentration loss, or the difference in the time of arrival of the tracers, or the resulting changes in the temporal distribution of the measured concentration at the extraction point. Each type of tracer has its advantages, and one or both types may be used together. The selection of the type of tracer depends on the nature of the dangerous or hazardous substance to be characterized.

The method and apparatus of the preferred embodiment of the present invention is applied using gaseous partitioning tracers. FIG. 1 is a simplified illustration of the preferred embodiment of the present invention 10 for application between two points in a duct (or pipe, etc.). The method and apparatus of the present invention requires the injection of a "slug" of two or more tracers 20 into a fluid flow system 30 with different partitioning coefficients ($K_i$). One of the tracers is a conservative tracer 76, i.e., it will not dissolve, adhere, or interact with the hazardous substance 50 of interest. The other tracer or tracers 72, 74 are selected so they will dissolve, adhere or interact with the hazardous substance of interest. The tracers are transported or advected from the injection point 52 (at one location in the pipe) to one or more extraction points 54 (at other locations in the pipe) by a gas flow field established in the pipe prior to the injection of the tracers 22. The gas flow field used to transport the tracers is typically nitrogen or air, because they do not generally interact with the tracers or the hazardous substances in the fluid flow system. The velocity of the advection flow field is selected so that the tracers have enough time to fully dissolve, adhere or interact with the hazardous substance before the leading edge of the tracer reaches the extraction point. At that point, no more tracer is introduced into the line. With the valve 62 open, the time history of the concentration 70 of the partitioning 72, 74 and conservative 76 tracers at the extraction point in the pipe, can be measured, and the presence and amount of the contaminant within the pipe or duct can be determined. Detection and quantification can be accomplished using the difference in the mean arrival time of the partitioning and conservative tracers, or the difference in the levels of concentration between the conservative and partitioning tracers.

The location of the contaminant can be determined by introducing a perturbation to the advection flow field or flushing the conservative and partitioning tracers in the line, and then measuring the mean time of arrival of the partitioning tracers that are still being eluted from the contamination in the system. Alternatively, another approach is to introduce enough partitioning tracer at the beginning of the duct test to cover the entire duct, then stop the flow, and allow the tracer to interact with dangerous or hazardous substance. After a period of time, an advection flow field is established, and GC samples are collected and analyzed. This characterization method is referred to as PCUT (Pipeline Characterization Using Tracers).

The method and apparatus for detecting and locating hazardous substances or devices in a duct (or room) are identical to those described in references [1-3] for detecting and locating contamination in pipes, ducts, and other types of fluid flow systems using the PCUT technology. The main difference is that the target chemicals to be detected are not contamination from the liquid or gas contents of the pipe or duct, but rather the chemicals found in the dangerous or hazardous biological, chemical or explosives substances or devices. The conservative and interactive tracers, as well as the advection gas, need to be selected for one or more of the chemicals found in these hazardous substances. Several interactive tracers may be used that specifically target different chemical components of the hazardous substances to minimize the possibility of false alarms. Another small difference is that the application of the PCUT method described in this disclosure is mainly intended for use in the HVAC ducts found in buildings, transportation systems (e.g., ships, airplanes, trains), and other structures (e.g., dams, bridges, and tunnels). The ductwork may be a hiding place and a delivery system for the hazardous substance. This would be particularly true for biological and chemical agents. On the other hand, the ductwork may serve only as a means to transport the tracers to the rooms or enclosures where explosives may be hidden. The inlet vent will allow the tracers to enter the room, and the return vent will draw the tracers back into the ductwork for analysis at the measurement point.

While the measurement system of the method and apparatus are described in terms of a GC, there are many optical and chemical based sensors design to detect specific chemicals that can be used in its place. In general, quantification of the hazardous substance is not as relevant as detection and location. In this regard, detection is initially more important than location. So reactive tracers may be used to monitor or detect the hazardous substance and partitioning tracers may be used to locate these substances. If the measurement goal is only detection, than a transport flow stream of known velocity is not necessary. Also, the transport velocity can be as fast as possible consistent with the time required for the tracer to have had sufficient time to interact with the hazardous substance to be detectable. A known transport velocity is needed for location.

The same method and apparatus can also be used to remotely monitor the biological and chemical health of a building to detect and locate the presence levels of hazardous materials such as mold and bacteria in the ductwork of a building, transportation system, or other type of structure. In this application, quantification is an important part of the measurement to determine if the mold or bacteria is at a high enough level to require removal.

BRIEF DESCRIPTION OF THE DRAWINGS

FIGS. 5i-5n are simplified illustrations of a alternative embodiments of the present invention shown in FIGS. 5a-5h, except a tracer measurement system has been added to the central HVAC unit.

FIG. 6a is a simplified illustration of an alternative embodiment of the present invention with a tracer injection system located in a room in a building and attached to a return vent to inject tracers directly into the return ductwork of a building through a return vent and a tracer measurement system located in a centrally located HVAC unit to sample the tracer gases coming from all rooms and ductwork in the building.

FIGS. 7d-6f are simplified illustrations of alternative embodiments of the present invention shown in FIGS. 7a-7c, except a tracer injection system has been added to the central HVAC unit.

FIG. 32a illustrates tracer elution time histories for reactive tracers without contamination.

FIG. 32b illustrates tracer concentration time histories for reactive tracers with contamination.

DESCRIPTION OF THE PREFERRED EMBODIMENT

Figure 1:
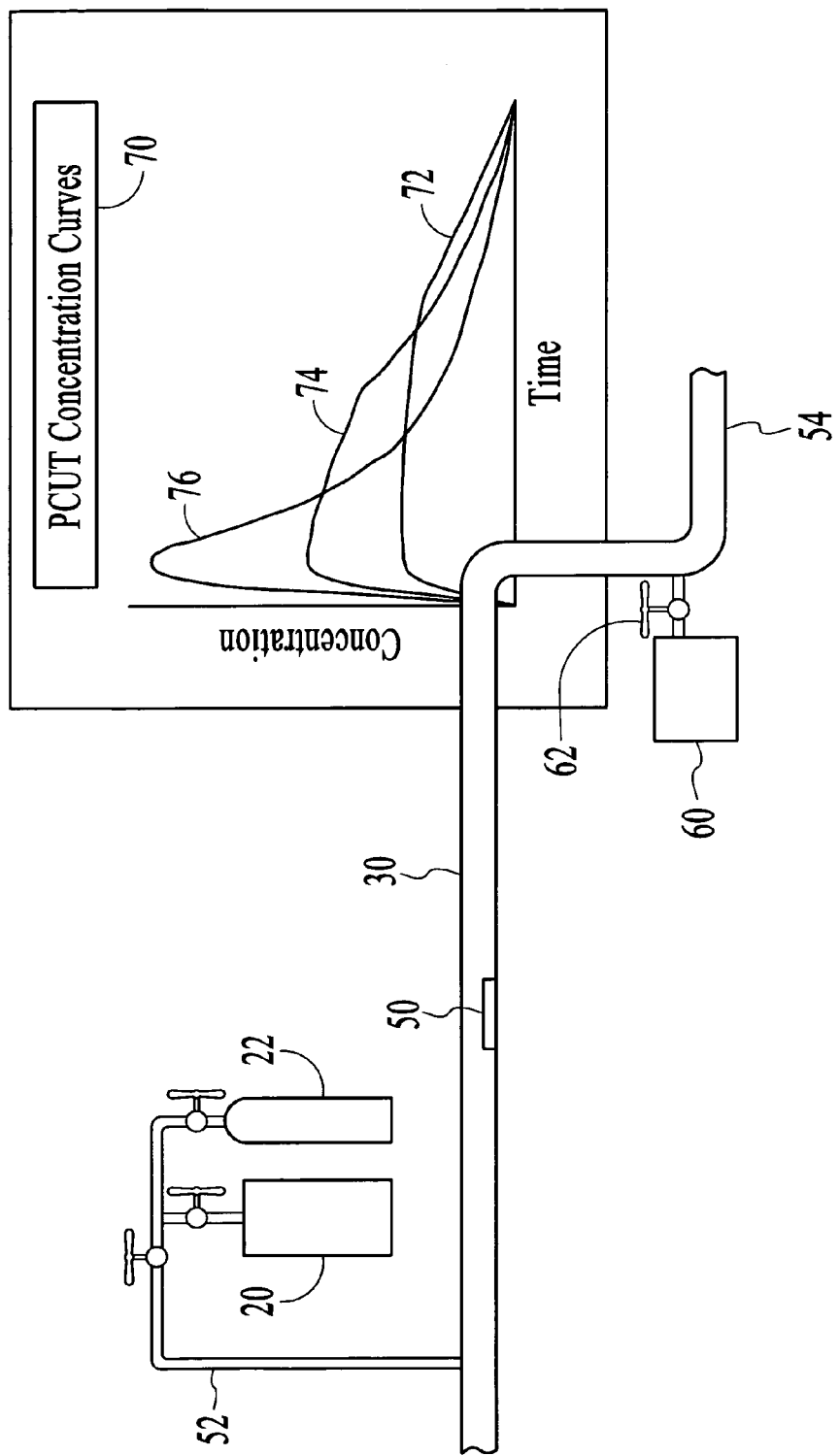
FIG. 1 is a simplified illustration of the preferred embodiment of the present invention using gaseous partitioning tracers to detect and locate dangerous or hazardous biological, chemical or explosive materials and devices. The time history of the elution curves of tracer concentration for both the conservative and the partitioning tracers are shown.

An important application of the present invention is for detection of dangerous and hazardous substances in ducts, pipes, tunnels, and other fluid flow systems in buildings, transportation systems, and infrastructure. This application of the method would be one of the most common and is very difficult and expensive to address with conventional physical inspection techniques because of access problems. This application may include the hiding of explosives, bio-hazardous materials, and chemical substances in the ductwork, piping, tunnels, or other such areas. For the purposes of description, the method and apparatus of the invention will be described in terms of HVAC ducts found in buildings. However, it should be clear from the building illustrations how the invention would be applied for pipes, tunnels, and other fluid flow systems, and how the invention would be used in various types of buildings (e.g., residential, office, high rises, nuclear and convention power plans, industrial processing facilities, power plants, industrial facilities, government buildings, etc.), various transportation systems such as ships (a floating building), submarines, airplanes, trains, and subways, and various types of infrastructure such as dams, tunnels, and bridges, which typically contain the same elements as buildings for operation and maintenance, i.e., rooms, enclosures and the like in communication with ducts or other means of supplying air (for ventilation, heating or cooling).

There are two basic detection approaches that may be used. The first is to inject a slug of tracers into a duct and then transport these tracers through the duct with an inert gas. If the flow rate, and therefore flow velocity, is known, then the location of the dangerous or hazardous substance can also be determined. The second approach is to inject sufficient tracer at the beginning of a measurement to inundate the entire duct system and then allow the tracer to interact with the hazardous substance to be detected before transporting the tracers to a measurement point. Again, if the flow velocity is known, the location of the dangerous or hazardous substance can be determined too. The amount of tracer being released has to be sufficient to cover the entire duct or duct system at low enough concentrations to be safe for humans and high enough concentrations to be detectable.

There are two basic types of measurement applications. The first is a special test of the duct, the duct system, or any rooms in communication with the ductwork for the threat substances. In this application, portable equipment supplied by a testing service is typically used to perform the test. The second is a periodic or continuous monitoring of the duct, the duct system, or any rooms in communication with the ductwork for the threat substances. In this application, the equipment is usually permanently installed in the duct or duct system that will be monitored. Because the duct system supplies air to each room through one or more vents in each room and each room returns the air to the duct system through one or more returns, the rooms in communication with the duct system can or will be tested for hazardous substances at the same time the ducts are tested. The ducts can be tested without testing the rooms by closing the inlet vents to the room before conducting a tracer test. One or more rooms can be tested by keeping the inlet and return vents open for those rooms to be tested. FIGS. 5-11 presents alternative embodiments of the method and apparatus of the present invention that allow specific parts of the ductwork or specific rooms in the building to be specifically monitored or tested for dangerous or hazardous substances.

Tracer injection and tracer measurement system located at the central HVAC unit. The most straightforward application of the invention is to locate the tracer injection and tracer measurement units at the central HVAC unit in the building, transportation system, or infrastructure. This application methodology is straightforward for detection, but can produce location ambiguities in large buildings or complicated duct systems because similar arrival times from different parts of the duct system may be possible. However, the location estimates in such systems can be isolated to several well-defined locations, and special measurements (or tracer injections) at the duct vents in one or more rooms (or the rooms themselves) can resolve the location ambiguities.

Tracer injection located at the central HVAC unit and tracer measurement located at a duct inlet vent. In this application, the duct system and the rooms in communication with the ductwork can be monitored by injection of the tracer into the ductwork at one central location (e.g., at the HVAC unit) and then to make the tracer measurements at one or more duct vents on a room-by-room or floor-by-floor basis. This application of the technology can be used to resolve location ambiguities in systems that might occur if only a centralized tracer injection and tracer measurement unit is used. It can also be used to test only a section of the duct system.

Tracer injection located at an inlet or return duct vent and tracer measurement located at the central HVAC unit. In this application, the tracer is injected into the ductwork on a room-by-room or floor-by-floor basis and then monitored at one central location (e.g., at the HVAC unit). This application will provide better location estimates because the path of the tracers injected into the ductwork will be more limited and better defined than the path of the tracers injected into the entire system at the HVAC unit. This approach can also be used to test only a part of the duct system.

Tracer injection located at an inlet or return duct vent and tracer measurement located at an inlet or return duct vent. In this application, the tracer is injected into the ductwork in one room and measured in another room.

Detection of dangerous and hazardous substances in rooms, compartments, enclosures, or other areas in buildings, transportation systems, and Infrastructure. In this application the rooms, compartments, enclosures, or other areas in buildings, transportation systems, and infrastructure can be tested for the presence of dangerous and hazardous substances. A common application is to determine whether or not explosives, weapons, or persons carrying weapons are hidden in a room without entering the room and physically searching the room. In this application, tracers may be injected into the room through the ductwork or directly into the room. The tracer measurements can be at the entry to the room or through the ductwork. The methodology used depends on the nature of the threat.

At the present time, a room-by-room search is made when looking for people and munitions. This process can be made safer and accomplished quicker using tracers. The same method used to determine whether or not dangerous substances are located in the ductwork that are consistent with a secure room can be used to detect the presence of a threat in the room. This requires that the inlet and outlet vents to each room are open to the duct system. In addition, the tracer can be injected directly into the room and then measured at an outlet vent in another room, at the central HVAC unit, or at the entry of the room. The tracer can be injected into the duct system from the central HVAC unit or another return vent in the duct system and then measured at the entry to the room. A pump may be used at the measurement to increase the speed of the measurement. Finally, both the tracer injection point and the tracer measurement point can be accomplished at the entry to the room.

The various applications of the technology summarized above are illustrated in FIGS. 2-11 and are described in more detail in Section 4.1. A description and demonstration of the method and apparatus for a simple fluid flow system is summarized in Section 4.2 and illustrated in FIGS. 12-25.

4.1 Application Illustrations of the Method and Apparatus of the Present Invention FIGS. 2-11 describe the application of the method and apparatus of the present invention in terms of a dangerous or hazardous threat to a room, a floor, or an entire building, whereby the ductwork in the building can be used to transport the tracers that will detect the threat in the ductwork or within one or more rooms in the building. While a large number of tracer injection and measurement systems are included in these figures, the figures are not meant to be inclusive. They are intended to illustrate the fact that the actual application of the tracer injection and measurement system may need to be different from one application to another to address the threat. However, the invention applies to all of the various tracer injection and tracer measurement configurations. The method and apparatus of the present invention are also not limited to building applications, but can be applied to numerous types of buildings, transportation systems, and infrastructure. In the spirit of this invention, there is no fundamental difference between detecting, locating, or quantifying a dangerous or hazardous threat in a building, or a ship, a train, an airplane, a sports arena, a nuclear or conventional power plant, industrial processing facilities, a tunnel, a bridge, or a dam, etc. In all cases, there is some type of duct or piping network used for ventilation, heating or cooling. The method and apparatus also work for a single room, compartment or enclosure without ductwork or without using the ductwork system.

FIGS. 2-4 describe the overall method and apparatus as applied to an entire building structure with ductwork. FIG. 2 presents the preferred and several simple alternative embodiments of the present invention that indicate how the system might be implemented. The preferred embodiment locates the tracer injection unit 1060 and the tracer measurement unit 1070 in the building's 1000 HVAC unit 1050. FIG. 2 also illustrates several alternative embodiments of the present invention in which an additional tracer injection unit 1090 (FIG. 2*e*) (or more than one) and/or an additional tracer measurement unit 1080 (FIG. 2*d*) (or more than one), which can be located in one or more rooms 1004, 1005 (FIG. 4*a*) in the building 1000, can be used in conjunction with the centrally located tracer injection unit 1060 and tracer measurement unit 1070 located in the building's 1000 HVAC unit 1050.

FIGS. 5-8 describes in more detail the various alternative embodiments suggested in FIG. 2. FIGS. 9-11 describe the present invention for use in a single room that can include the use of a central tracer injection or tracer measurement system. These systems may have application in rooms that may be too dangerous to enter or that may not be easily accessed.

FIGS. 12-25 are figures that were used to describe and demonstrate the method and apparatus of the present invention for detection, quantification, and location of hazardous chemicals that contaminate the pipe or ductwork in a structure. Diesel fuel was used in the demonstration of the method, but any substance that interacted with a tracer could also have been used [1].

Description of FIGS. 2-11. FIG. 2 presents seven simplified illustrations of the preferred embodiment of the present invention 1016 to detect, and/or locate, and/or quantify dangerous or hazardous biological, chemical or explosive materials and devices in either the ductwork 1010 including the issue ductwork 1014 and the return ductwork 1012, or a room 1004 in a building 1000 using a tracer injection 1060 and tracer measurement 1070 system 1016 located at the central HVAC unit 1050. The apparatus used for detection and location can be located in the central HVAC unit 1050 used to ventilate, heat, and cool the building 1000. Additional measurement points can be used to supplement the system to improve the speed, reliability and accuracy of the method; in particular, when the ductwork or building is complex more than one tracer measurement or tracer injection system may be needed to resolve location ambiguities.

Figure 2A:
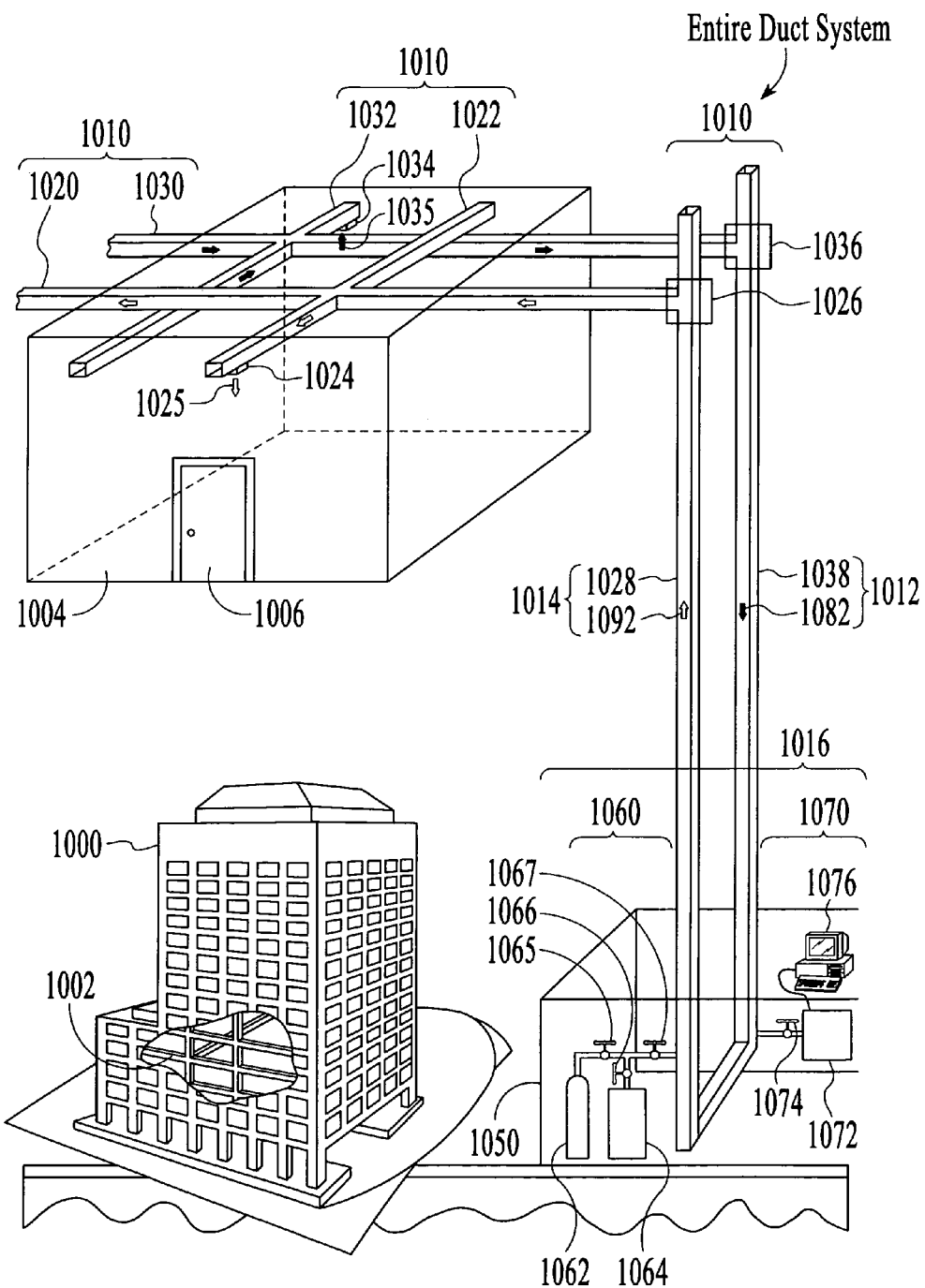
FIG. 2a is a simplified illustration of the preferred embodiment of the present invention to detect and locate dangerous or hazardous biological, chemical or explosive materials and devices in either the ductwork or rooms in a building using a centrally located tracer injection and measurement system.
Figure 4A:
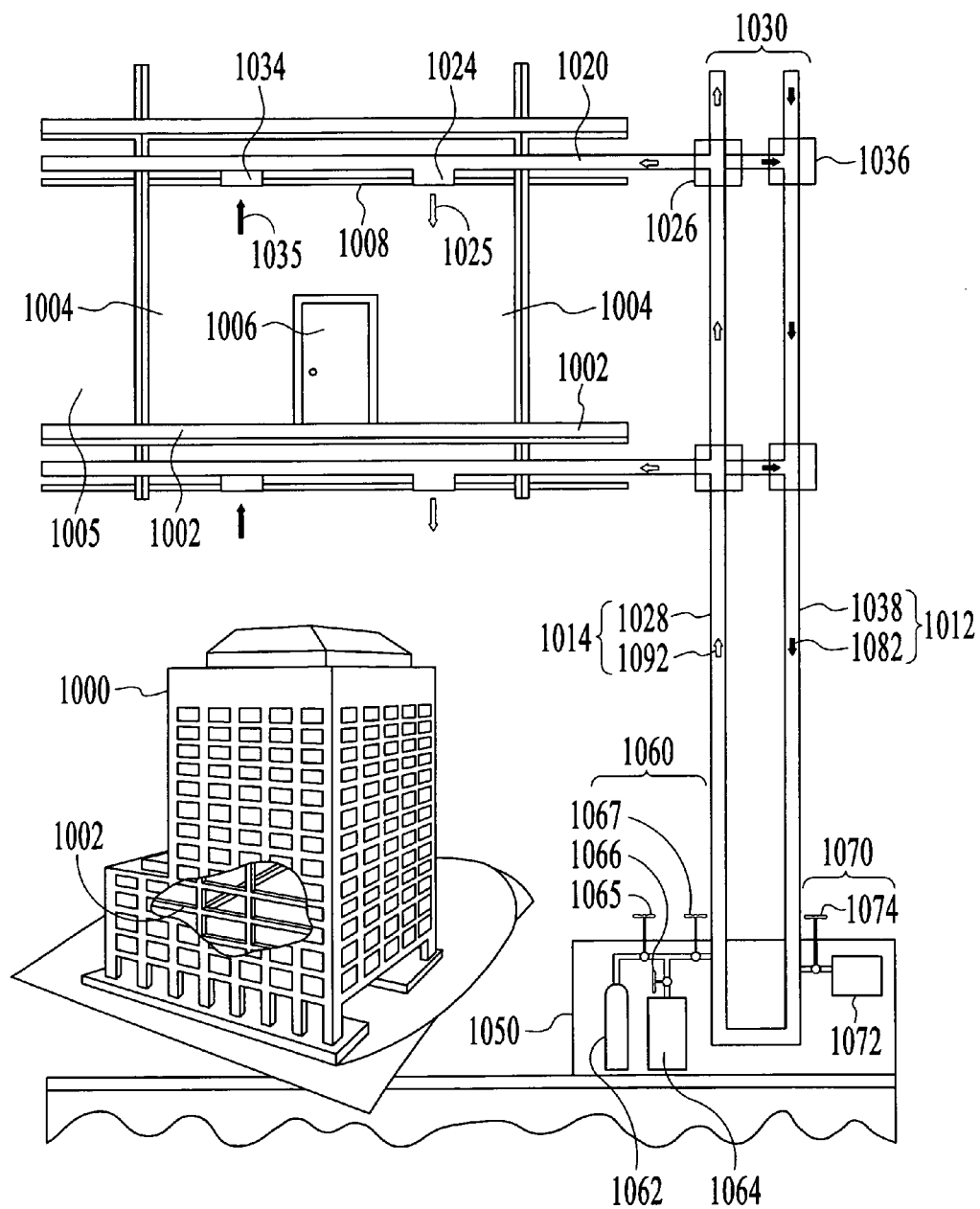
FIG. 4a is a simplified illustration of the preferred embodiment of the present invention to detect and locate dangerous or hazardous biological, chemical or explosive materials and devices in either the ductwork or a room in a building using a tracer injection and measurement system centrally located in the HVAC unit heating or cooling the room or building.

The PCUT system is comprised of a tracer injection and advection system 1060 and a tracer measurement system 1070. The tracer injection system 1060 is located in or in the immediate vicinity of the structure's HVAC unit 1050 and connects into the ventilation delivery ductwork 1028 (FIG. 4a) and the header 1026 on each floor 1002 of the building 1000. The return duct 1038 and header 1036 are illustrated in FIG. 4a. The flow 1092 in the issue duct 1023 and the flow 1038 in the return duct 1038 are also shown. Three valves 1065, 1066, and 1066 can be used to control the injection of tracers from container 1064 and the advection gas from gas bottle 1062. In a permanently monitoring system, especially where the advection gas is air or the structure or ductwork to be tested is large, a compressor would replace the gas bottle 1062 shown in FIG. 2a. The valve 1067 can be used to isolate the ductwork from the tracer injection unit 1060. Valve 1065 is used to introduce or stop the flow of the advection gas used to transport the tracers through the duct 1030 (FIG. 4a) or to flush the ductwork 1030. Valve 1066 is used to introduce or stop the flow of tracer gas into the ductwork 1030. The tracer measurement unit 1070 is comprised of a means of detecting and/or measuring the concentration of the tracer gases returned to the central HVAC unit 1050 through the ductwork 1014. The tracer measurement means 1070, as shown in FIG. 2a, is comprised of a gas chromatograph 1072 and a processing unit 1076, which may consist of a computer. This measurement system can be used to periodically sample the tracer gases or can be used in real-time as a continuous monitoring system. With a GC 1072, the concentration of each tracer can be measured as a function of time. With these concentration curves, the detection, location, and quantification measurements can be made. The tracer measurement unit 1070, can be greatly simplified by replacing the GC 1072 and the computer 1076 with a simple sensor detection system that is sensitive and detects the presence of the tracers used in the measurement. Fiber-optic and chemical reactive sensor chips are available that target specific chemical compounds. While all three measurements, detection, location, and quantification could be accomplished with a measurement system that is simpler than a GC, such measurement system is best used for detection and location.

Figure 2B:
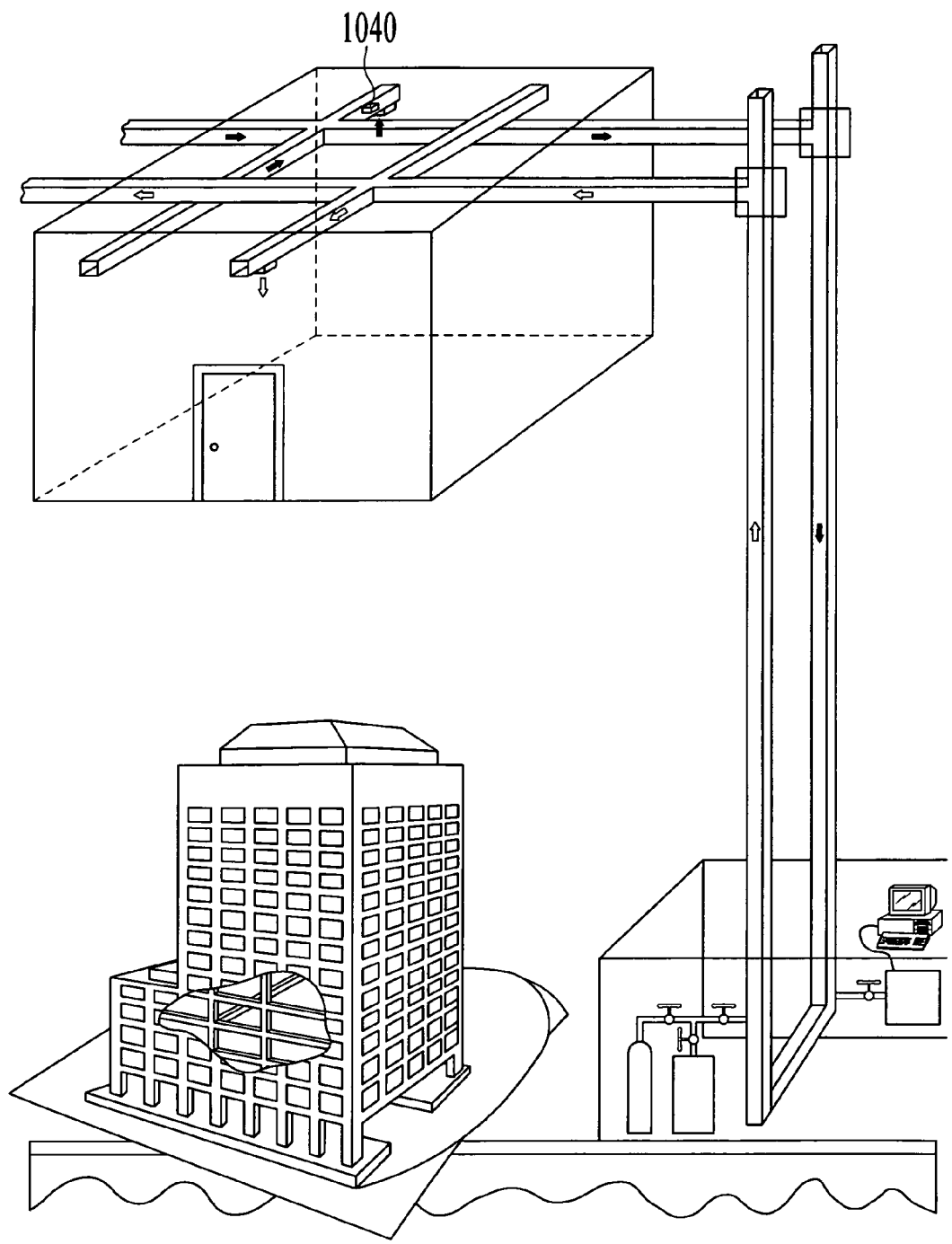
FIG. 2b is a simplified illustration of the preferred embodiment of the present invention shown in FIG. 2a to detect and locate dangerous or hazardous biological, chemical or explosive materials and devices in the ductwork of a room or building.
Figure 2C:
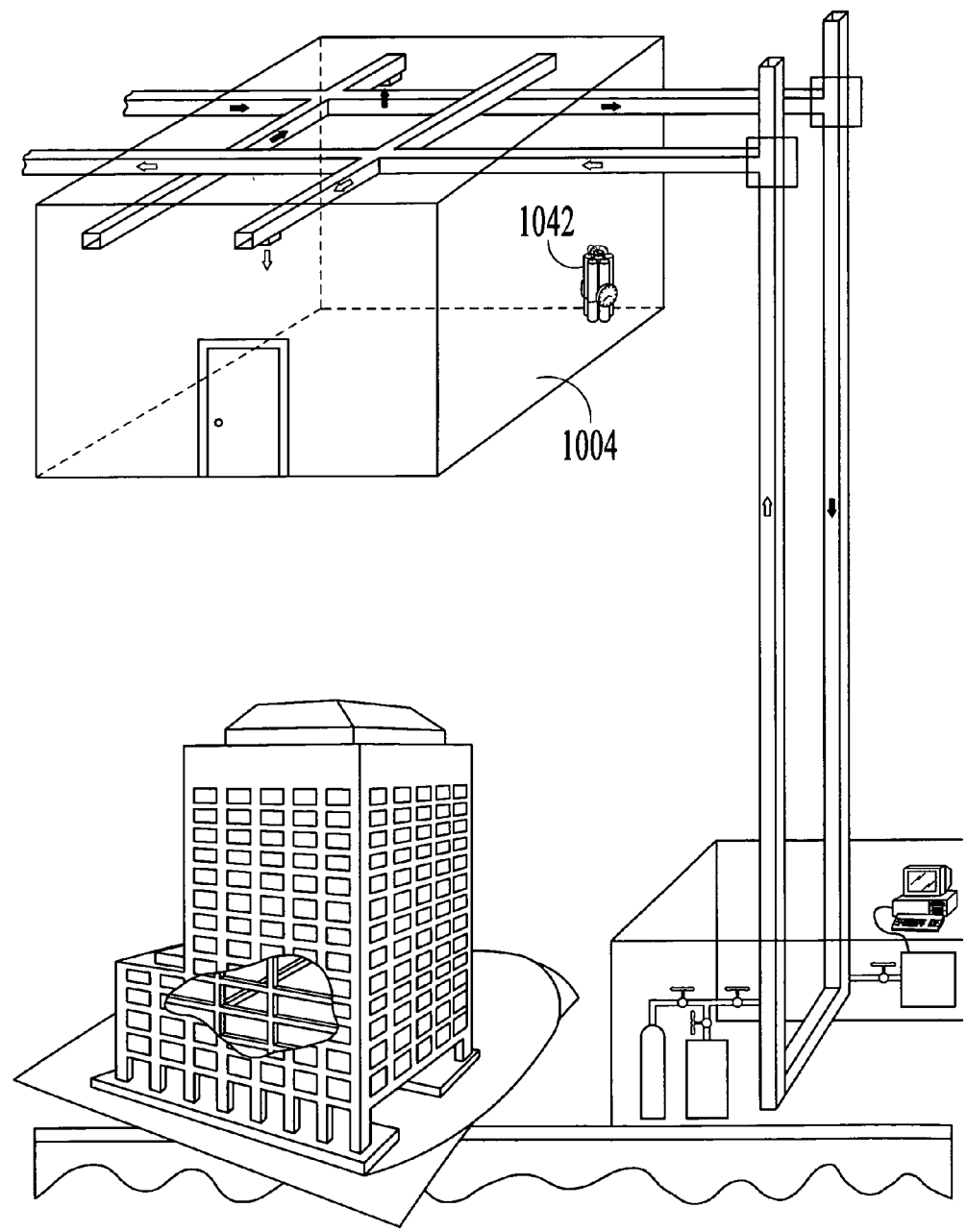
FIG. 2c is a simplified illustration of an alternative embodiment of the present invention shown in FIG. 2a to detect and locate dangerous or hazardous biological, chemical or explosive materials and devices in a room or building using the ductwork to transport the tracers.
Figure 2D:
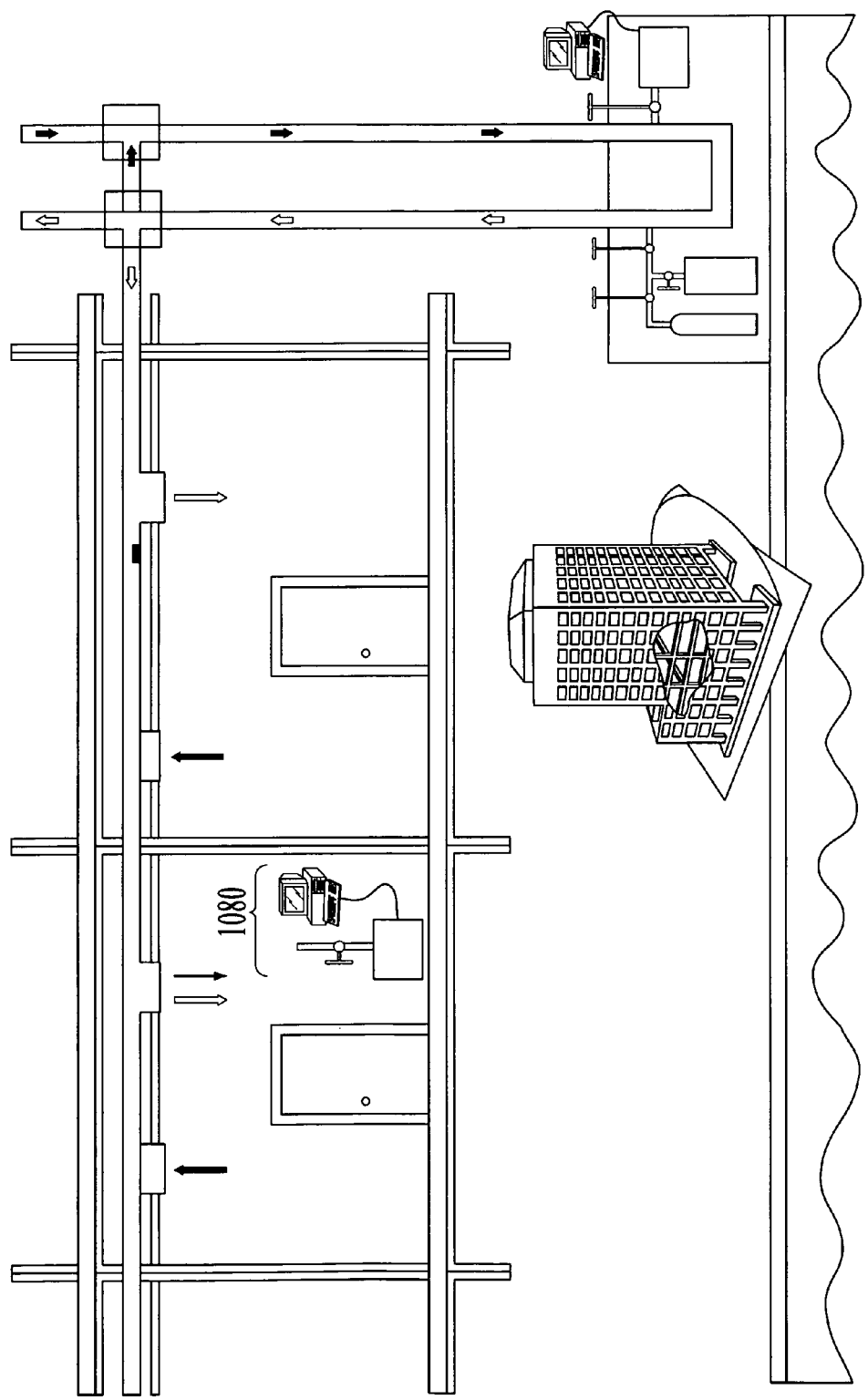
FIG. 2d is a simplified illustration of an alternative embodiment of the present invention shown in FIG. 2b to detect and locate dangerous or hazardous biological, chemical or explosive materials and devices in the ductwork of a room or building using an additional tracer measurement system located in a room in the building.
Figure 2E:
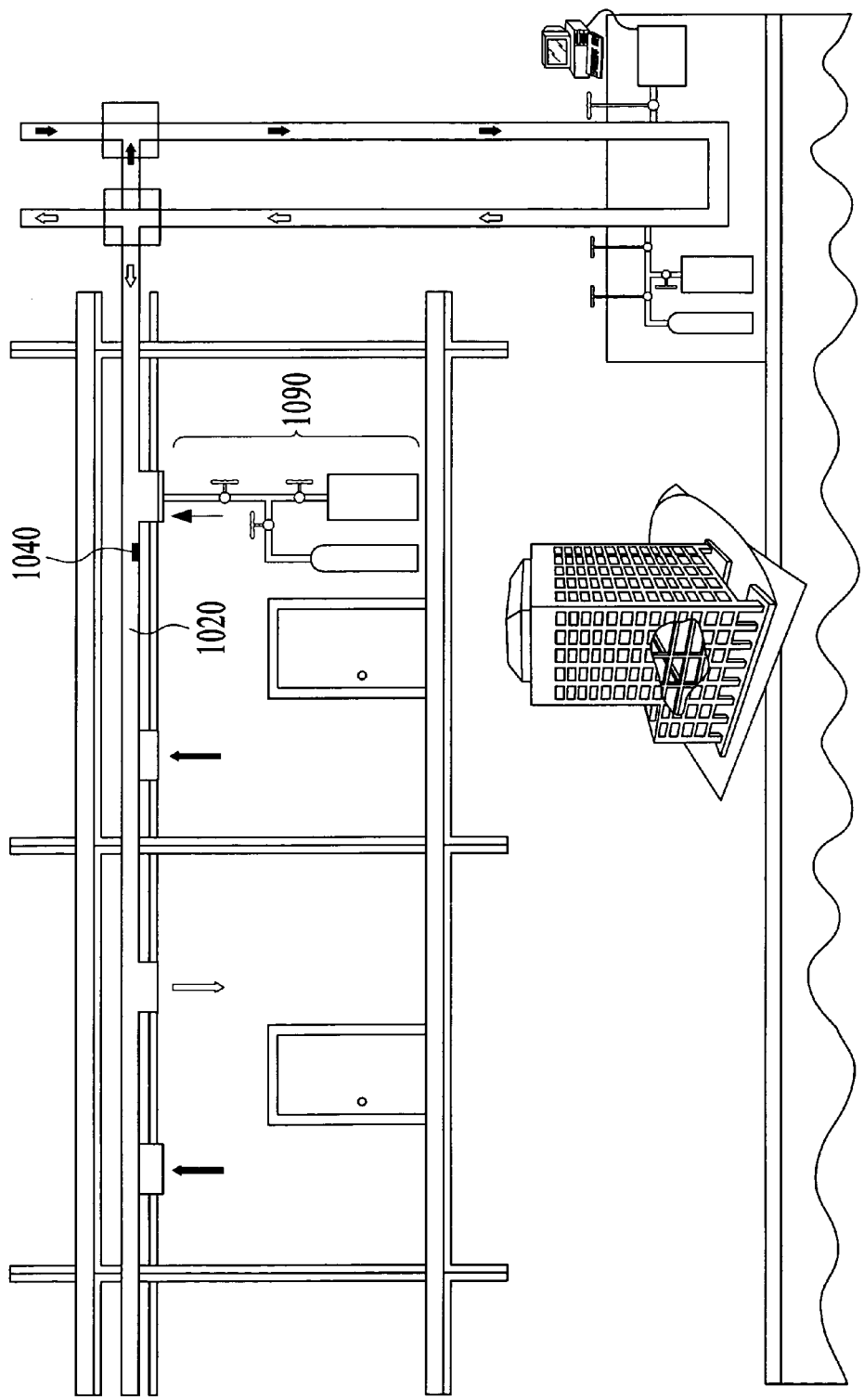
FIG. 2e is a simplified illustration of an alternative embodiment of the present invention shown in FIG. 2b to detect and locate dangerous or hazardous biological, chemical or explosive materials and devices in the ductwork of a room or building using an additional tracer injection system located in a room in the building.
Figure 2F:
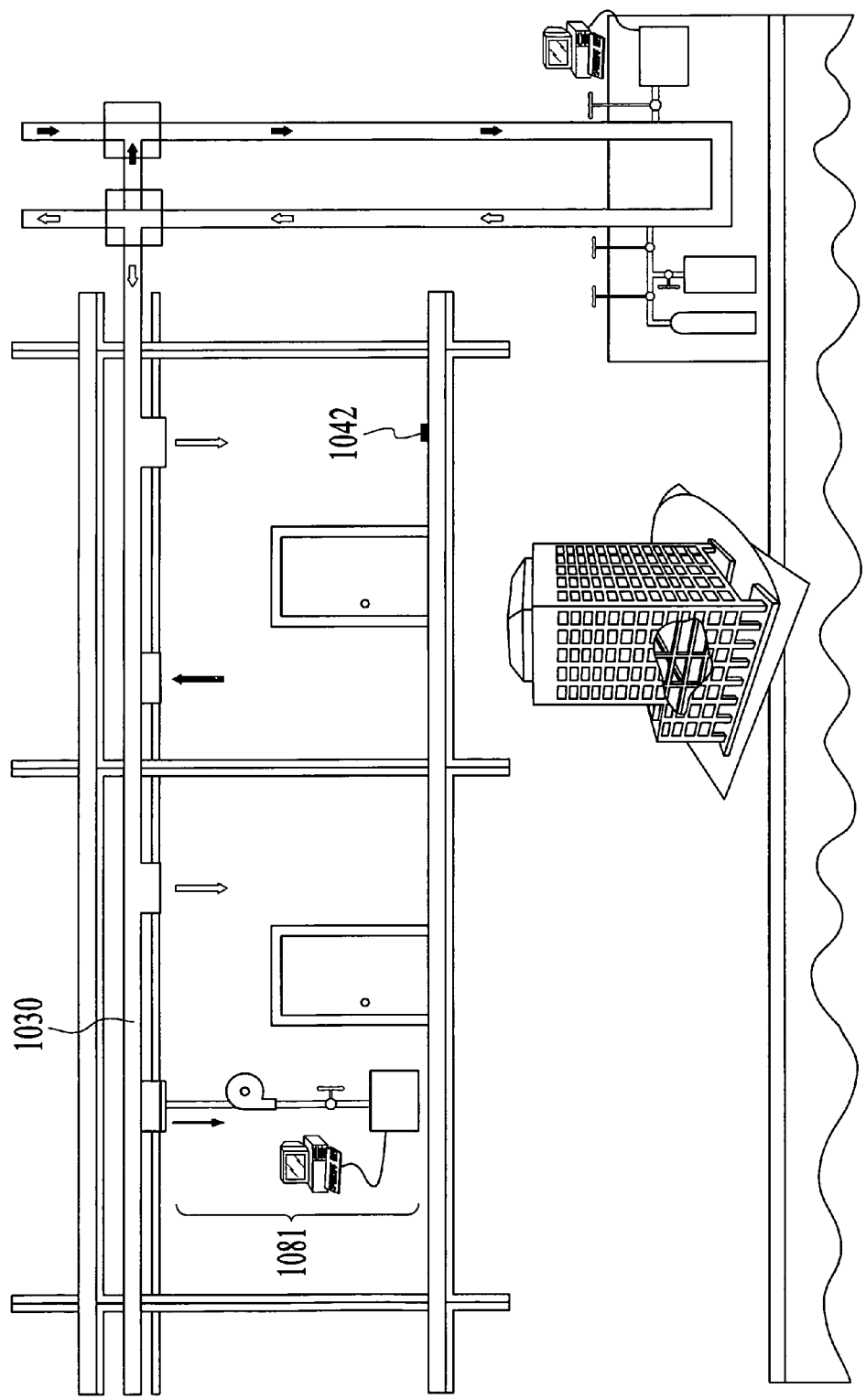
FIG. 2f is a simplified illustration of an alternative embodiment of the present invention shown in FIG. 2c to detect and locate dangerous or hazardous biological, chemical or explosive materials and devices in a room or building using an additional tracer measurement system located in a room in the building.
Figure 2G:
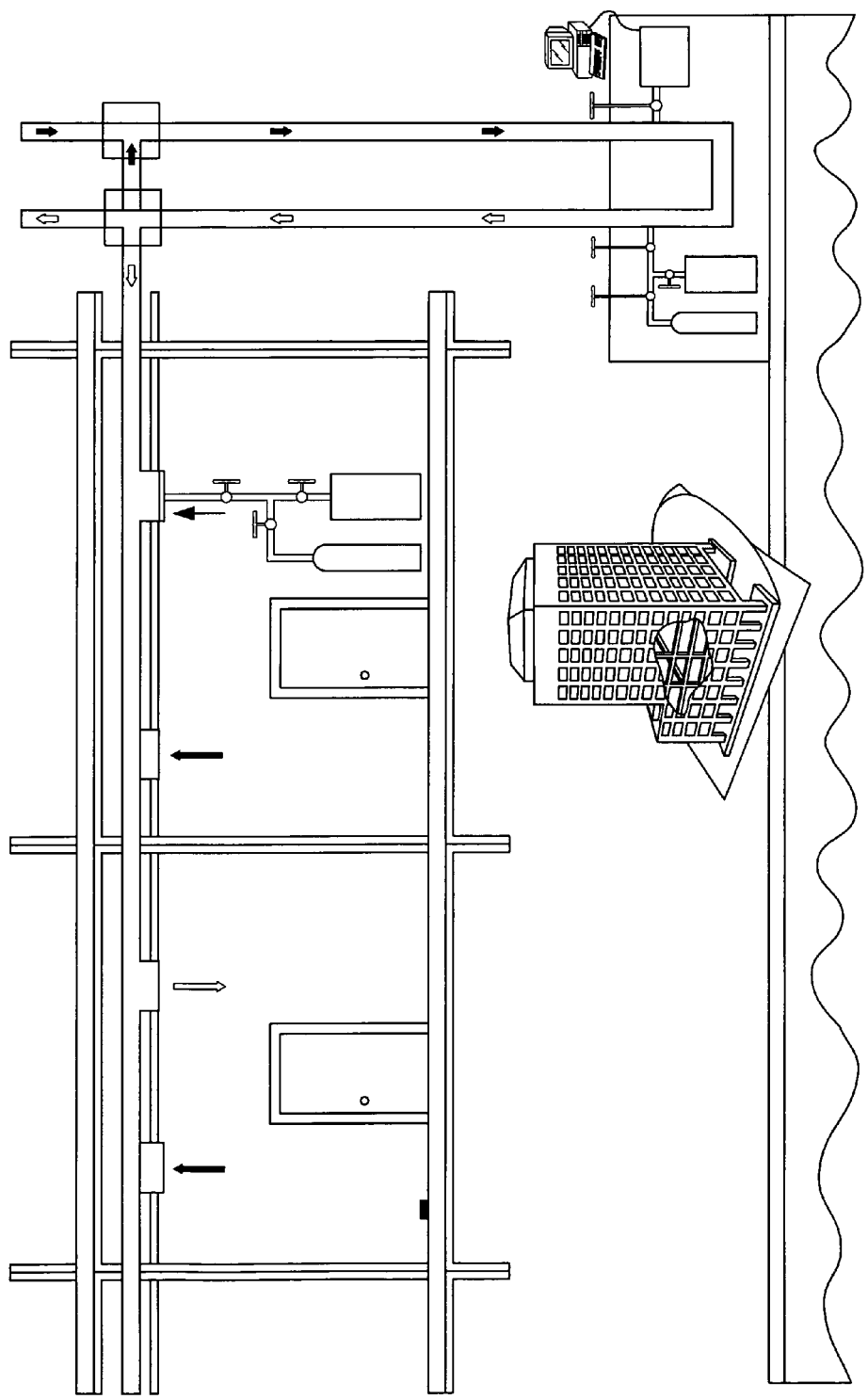
FIG. 2g is a simplified illustration of an alternative embodiment of the present invention shown in FIG. 2c to detect and locate dangerous or hazardous biological, chemical or explosive materials and devices in a room or building using an additional tracer injection system located in a room in the building.

The dangerous or hazardous substance is shown in a room duct downstream 1040 of the room inlet vent in FIG. 2b and in the room 1042 in FIG. 2c. FIGS. 2d and 2e show a room measurement system 1080 and a tracer injection system 1090 that can be used to augment the central PCUT measurement system 1016. The tracer measurement systems 1080, 1081 illustrated in FIG. 2d and FIG. 2f can be used to detect the presence of dangerous or hazardous substance 1040, 1042 in the ductwork 1020, 1030 or dangerous or hazardous substances 1042 in a room 1004 (FIG. 2c). Similarly, the tracer injection systems shown in FIG. 2e and FIG. 2g can be used to add different tracers to the building for measurement at the central tracer measurement system 1070.

As configured in FIG. 2a, the tracers can be introduced from the tracer injection unit 1060 at the HVAC unit, 1050, into the inlet duct 1028. The advection gas from 1062 is used to transport 1092 the tracers up through the duct system to a floor 1002 in the building 1000 through an inlet header 1026 and to each room 1004 where a hazardous threat may be hidden in the room 1004 or ductwork 1020, 1022. The tracers in the ductwork over the room 1020, 1022, 1030, 1032 or in the room 1004 return to the tracer measurement unit 1070 through the room return ducts 1032, 1030, through a return header 1036 and down to the tracer measurement unit 1070 through ductwork 1038. Thus, the tracer measurements made at the tracer measurement unit 1070 will examine the presence of dangerous or hazardous substances in either the room or the ductwork. The entire building can be examined in this way.

If only the ductwork is to be tested, then the room vents 1024, 1034 can be closed before the measurement is made, or the test can be set up to mainly test the ductwork. This might be accomplished by introducing the tracer into the ductwork and then briefly stopping the airflow until the tracer has had sufficient time to interact with any dangerous or hazardous substances in the ductwork before re-introducing the airflow. Also, this can be accomplished by introducing additional tracers into the ductwork within one or more rooms 1004 on a floor 1002 or one or more additional floors 1002 in the building 1000 and/or making special tracer measurements at these locations.

Such additional measurements may be required once the detection is made in a complex building or structure to resolve location ambiguities. More than one location may be possible in a complex network, because the time-of-arrival of the tracer gas may be the same for different locations within the ductwork. This is better understood when viewing a plan view of the ductwork in a floor of a building as shown in FIG. 3. As an example, it would not be possible to determine the location of a detected threat substance from a duct that tees left and right from the main duct. This is illustrated in FIG. 3b between the location of the hazardous substance 1040 at A and two other possible locations at B and C in the inlet ductwork. A location ambiguity is also possible from a location in the return ductwork but it would be located in the next set of laterals to the left of the return ductwork shown in FIG. 3b. An ambiguity could also occur between a detection between two floors. The location of the hazardous material 1040 at location A could also be mistaken for a location in the inlet duct or inlet laterals near the main inlet header of on the floor immediately above the one shown in FIG. 3*b*. The additional tracer measurement in a room 1004 with the tracer measurement unit 1080 shown in FIG. 5, for example, would be one method of resolving these ambiguities.

Figure 3A:
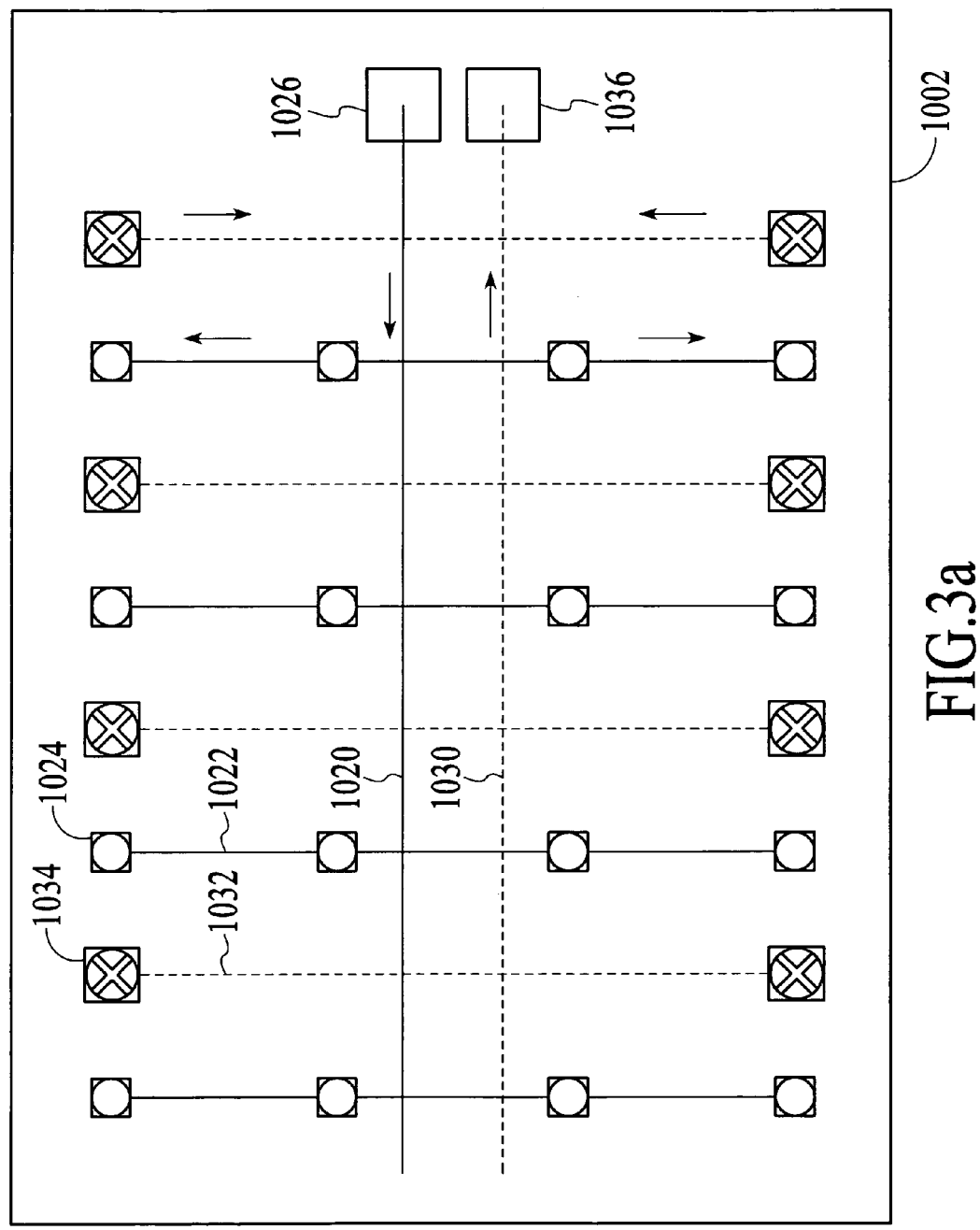
FIG. 3a illustrates the ductwork located in the ceiling of a building floor.
Figure 3B:
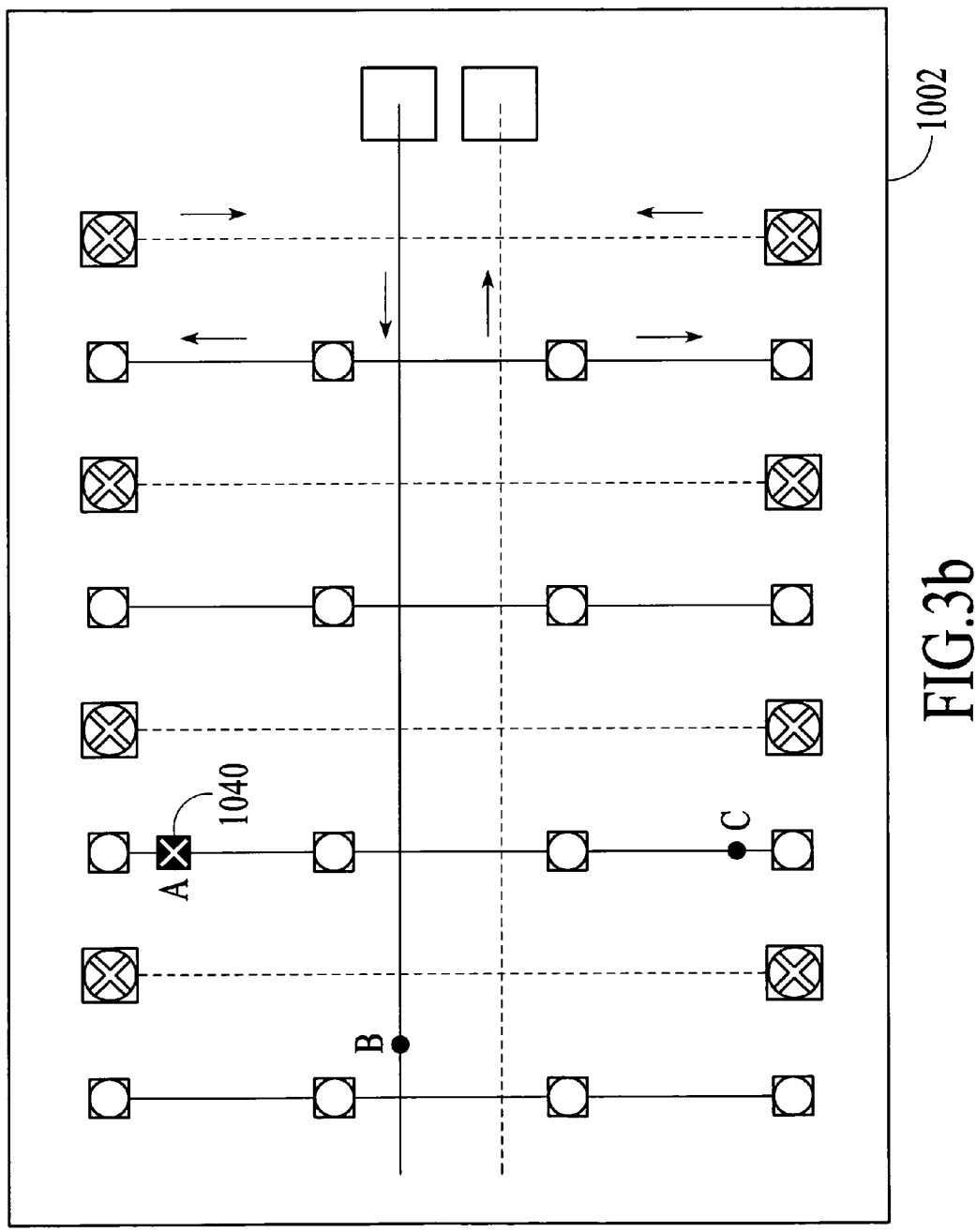
FIG. 3b illustrates the ductwork located in the ceiling of a building floor with dangerous or hazardous biological, chemical or explosive materials and devices in the ductwork.

FIG. 3*a* the ductwork located in the ceiling of a building floor with both the inlet 1020, 1022 and return 1030, 1032 ductwork connected to their respective headers 1026, 1036. The inlet vents 1024 bringing air into the room and the return vents 1034 removing air from the room are also shown. FIG. 3*b* illustrates the ductwork located in the ceiling of a building floor with dangerous or hazardous biological, chemical or explosive materials and devices in the ductwork 1040.

Figure 4B:
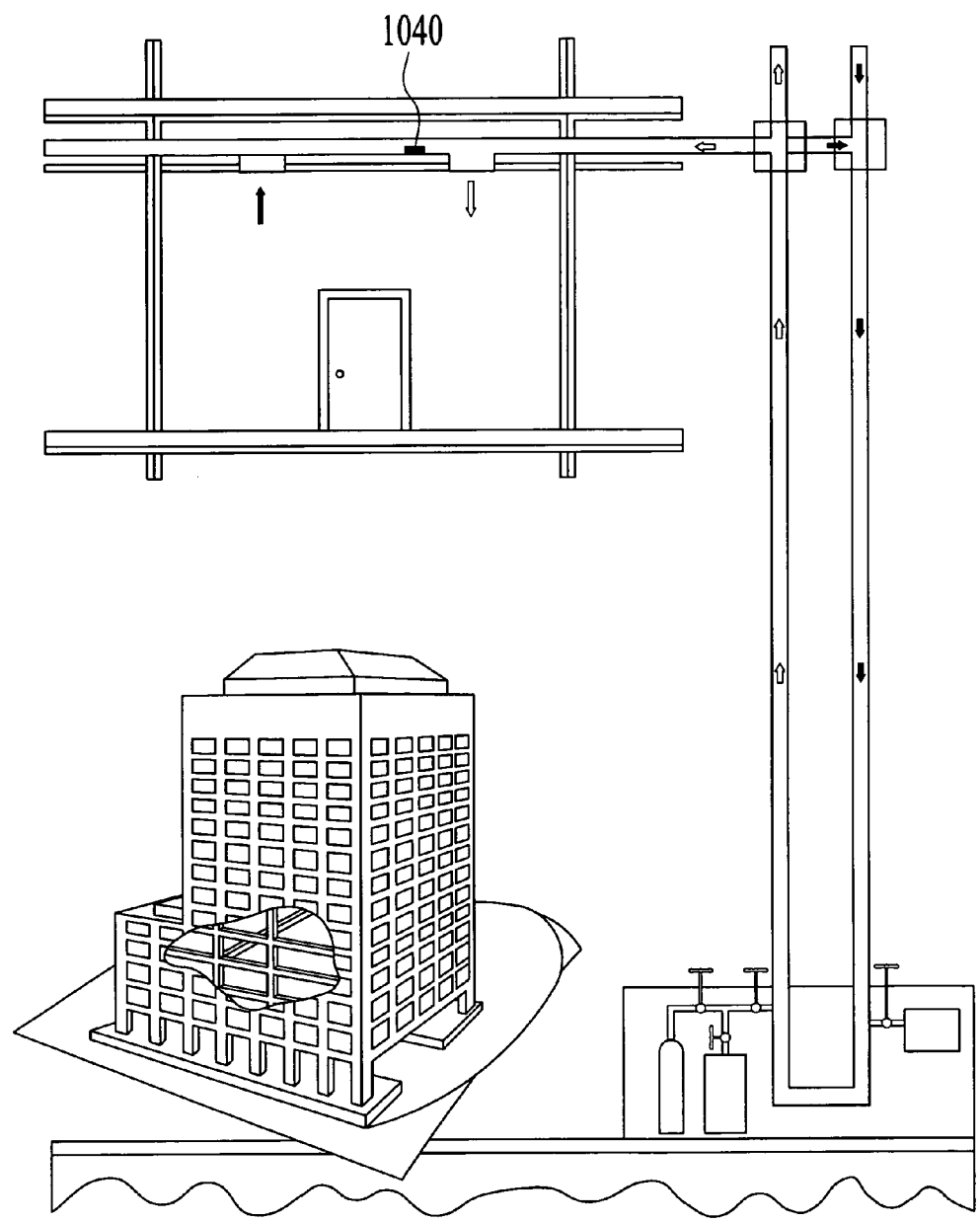
FIG. 4b shows a simplified view of FIG. 4a with an explosive in the ductwork.
Figure 4C:
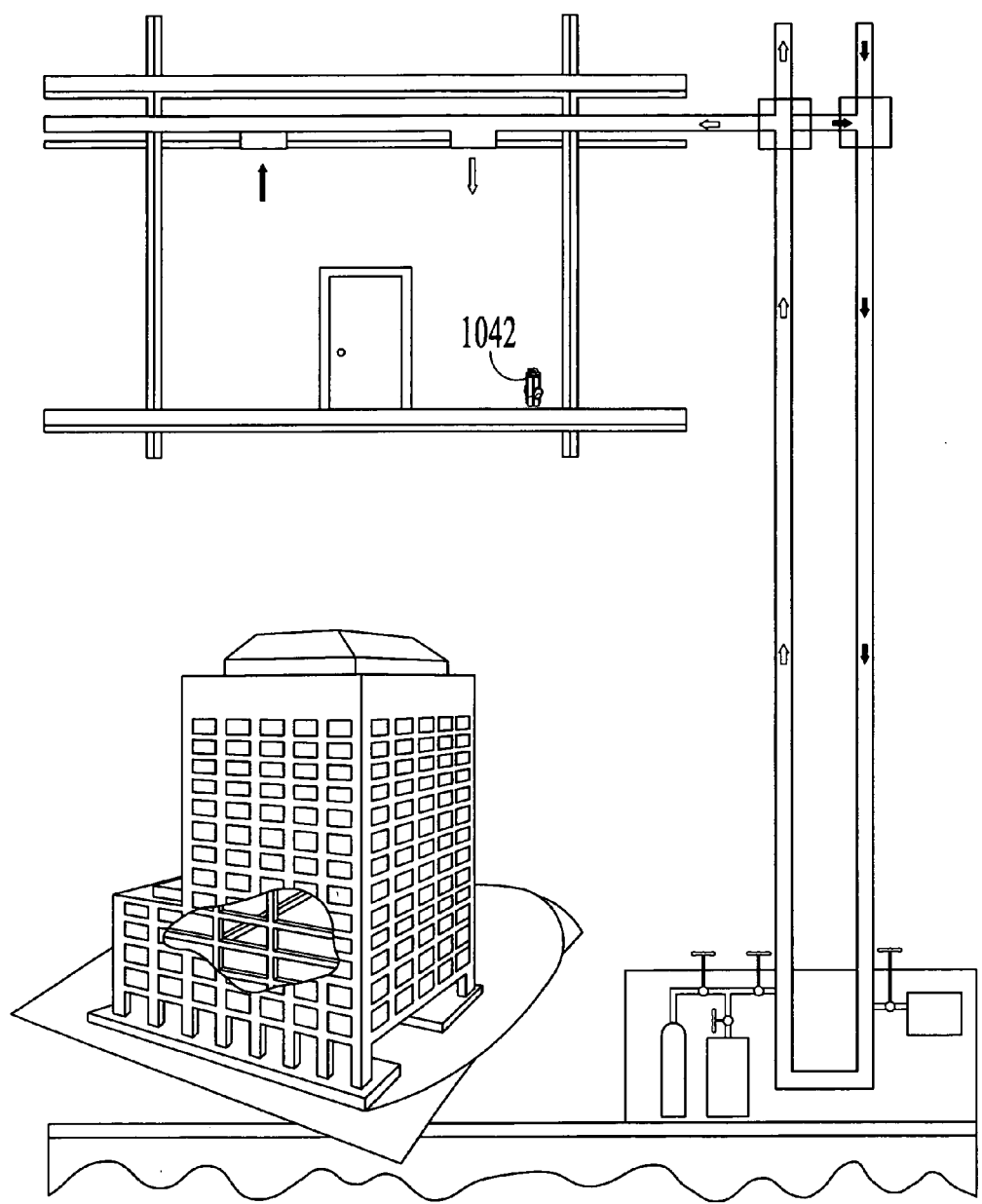
FIG. 4c shows a simplified view of FIG. 4a with an explosive in a room of the building.
Figure 4D:
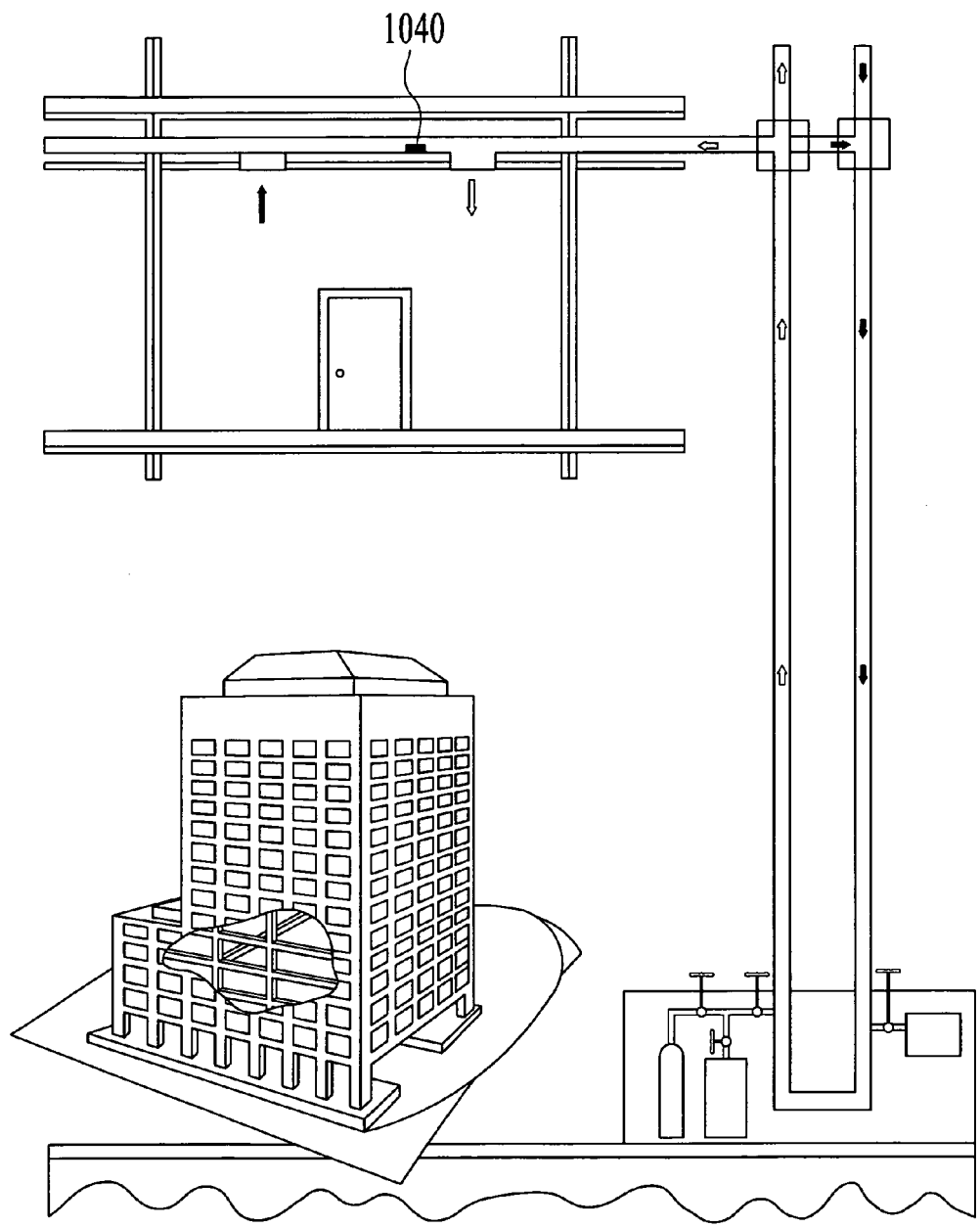
FIG. 4f shows a profile view of FIG. 4d.
Figure 4E:
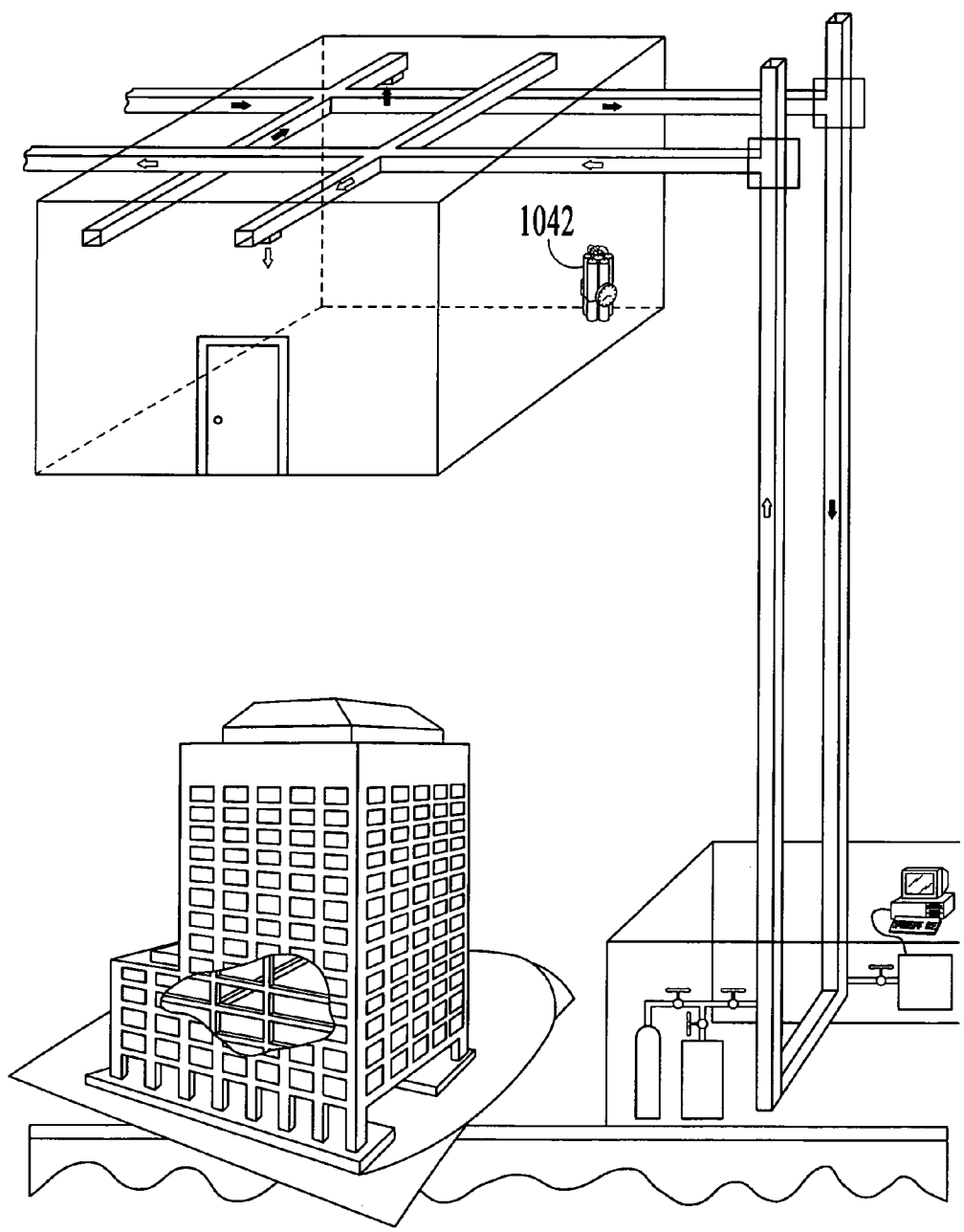
Figure 4F:
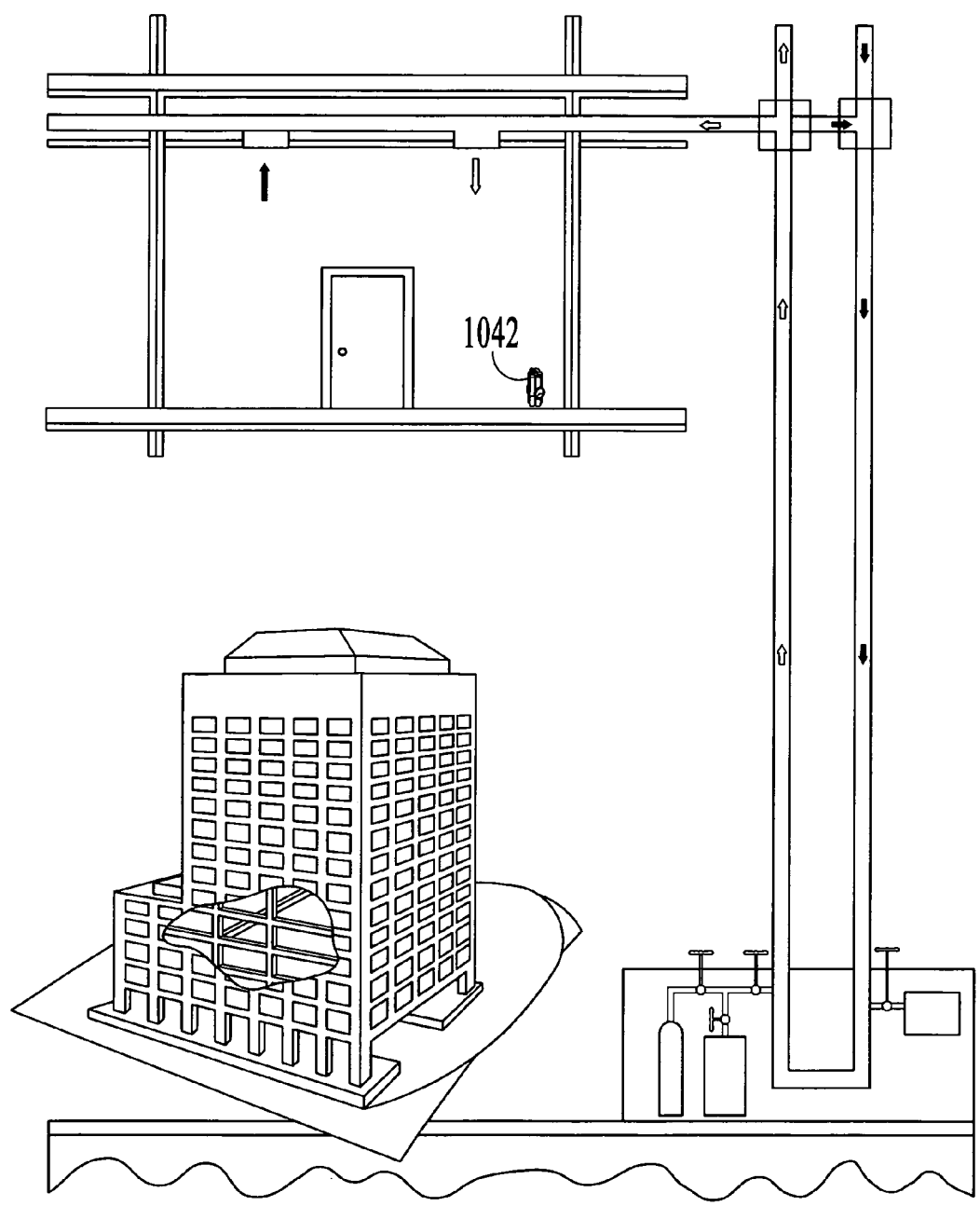
Figure 5A:
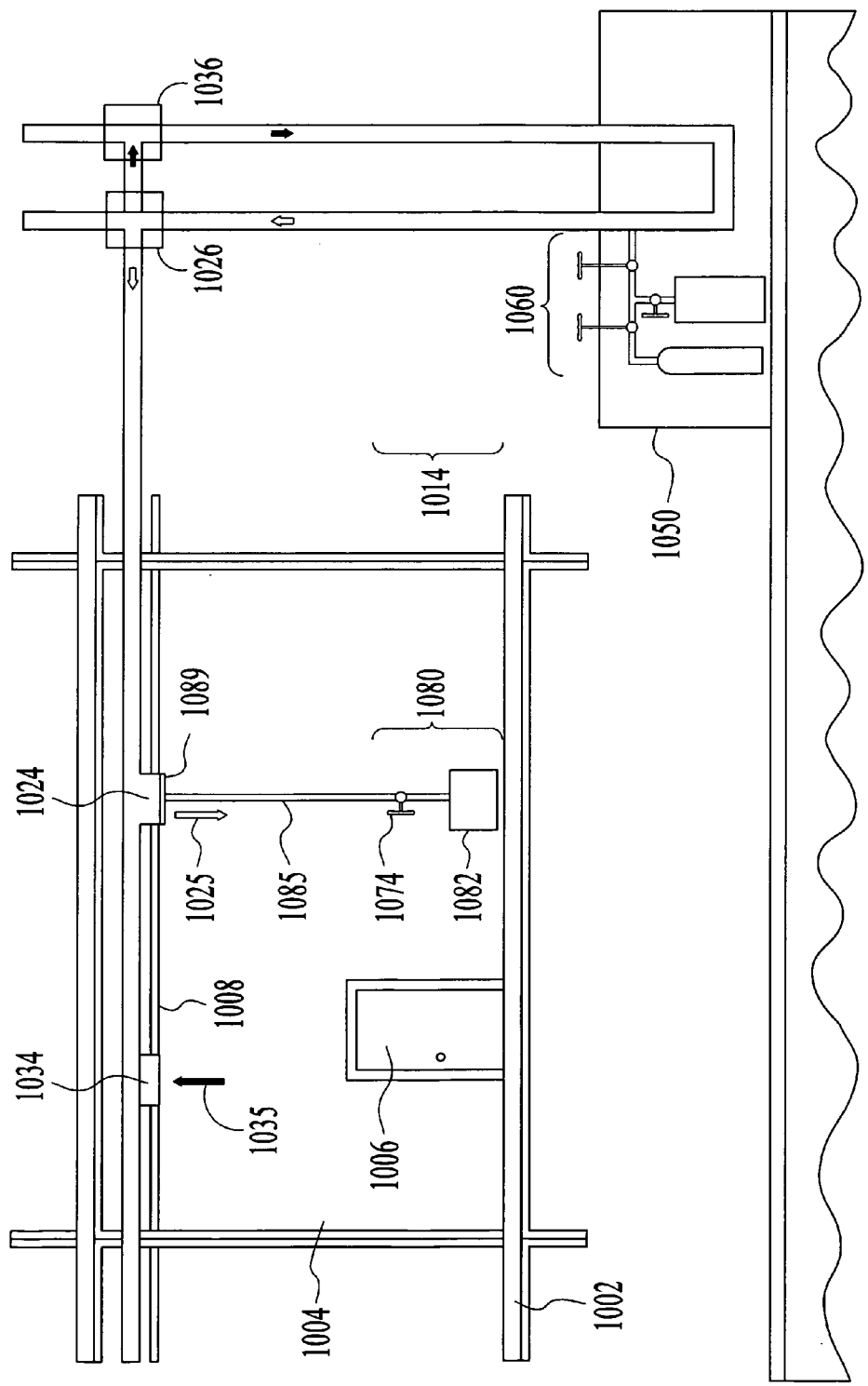
FIG. 5a is a simplified illustration of an alternative embodiment of the present invention with a tracer injection system located in a centrally located HVAC unit to inject tracers throughout the building and a tracer measurement system located in a room in a building and attached to a specific inlet invent to sample the tracer gases coming out of that inlet vent.
Figure 5B:
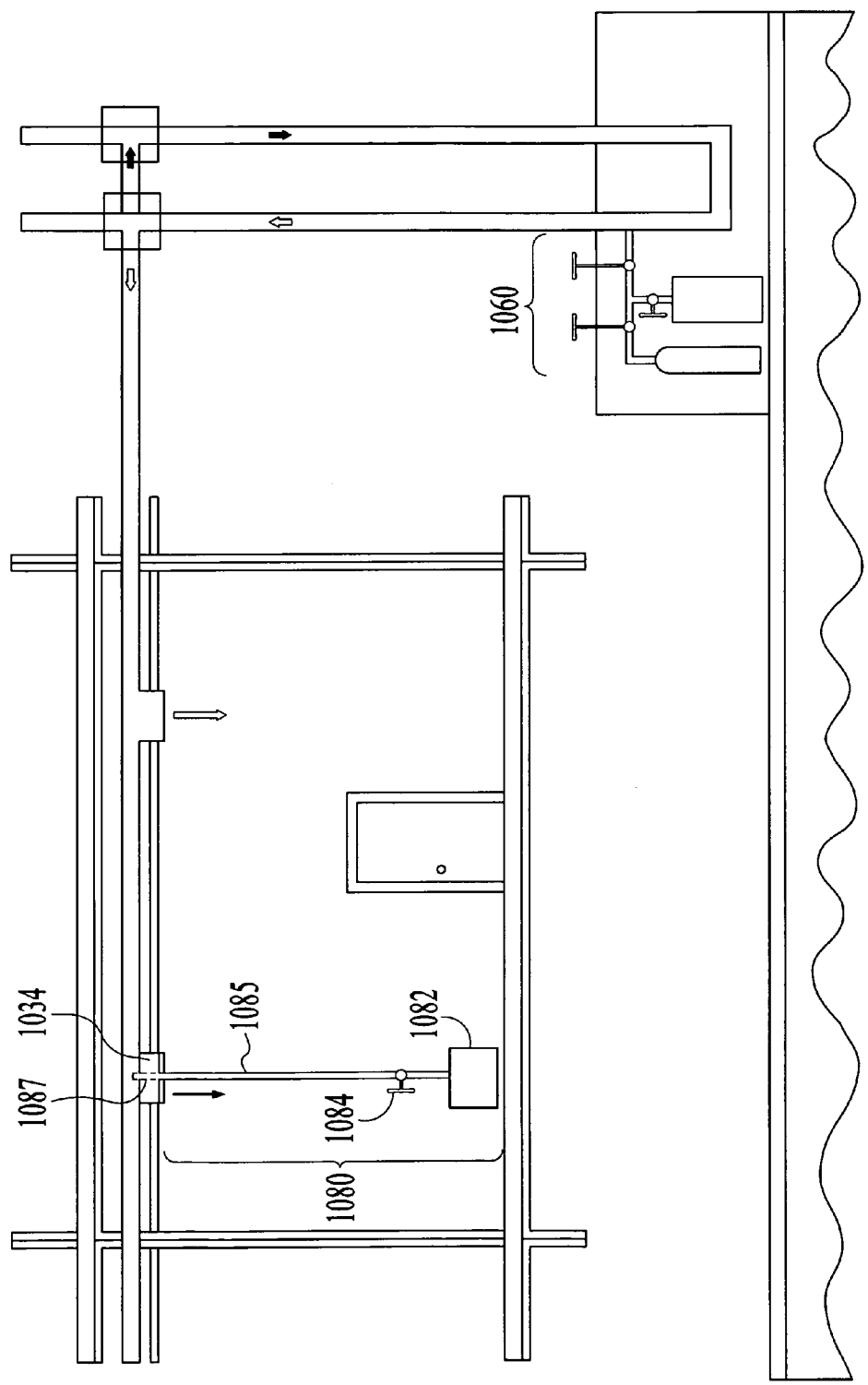
FIG. 5b is a simplified illustration of an alternative embodiment of the present invention with a tracer injection system located in a centrally located HVAC unit to inject tracers throughout the building and a tracer measurement system located in a room in a building with a conduit sampling means insert into the return ductwork through a return vent in the room to sample the tracer gases in the return ductwork.
Figure 5C:
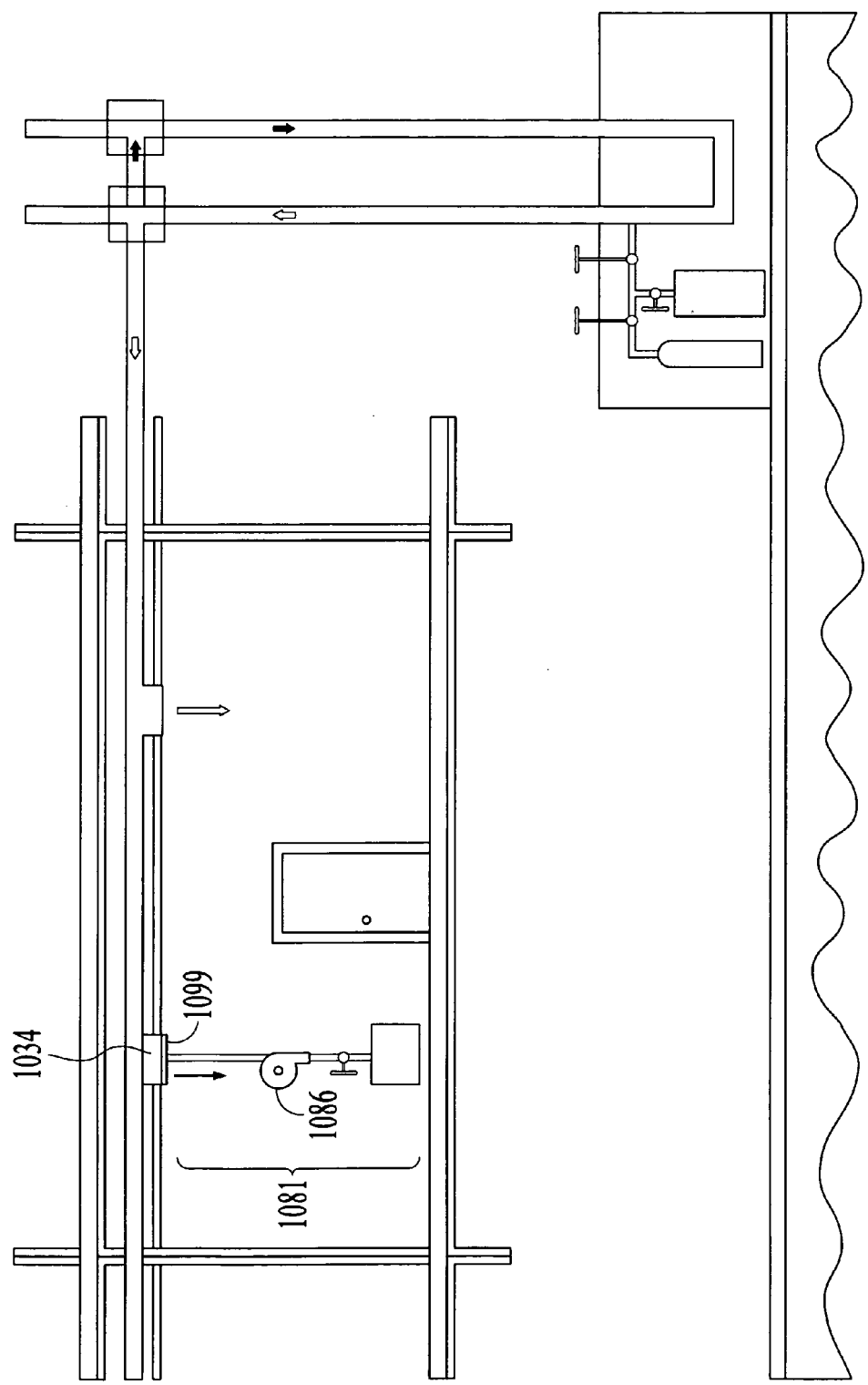
FIG. 5c is a simplified illustration of an alternative embodiment of the present invention with a tracer injection system located in a centrally located HVAC unit to inject tracers throughout the building and a tracer measurement system located in a room in a building and attached to an return vent to sample the tracer gases in the return ductwork from that return duct vent in the room using a small pump to pull the gases into the measurement system.
Figure 5D:
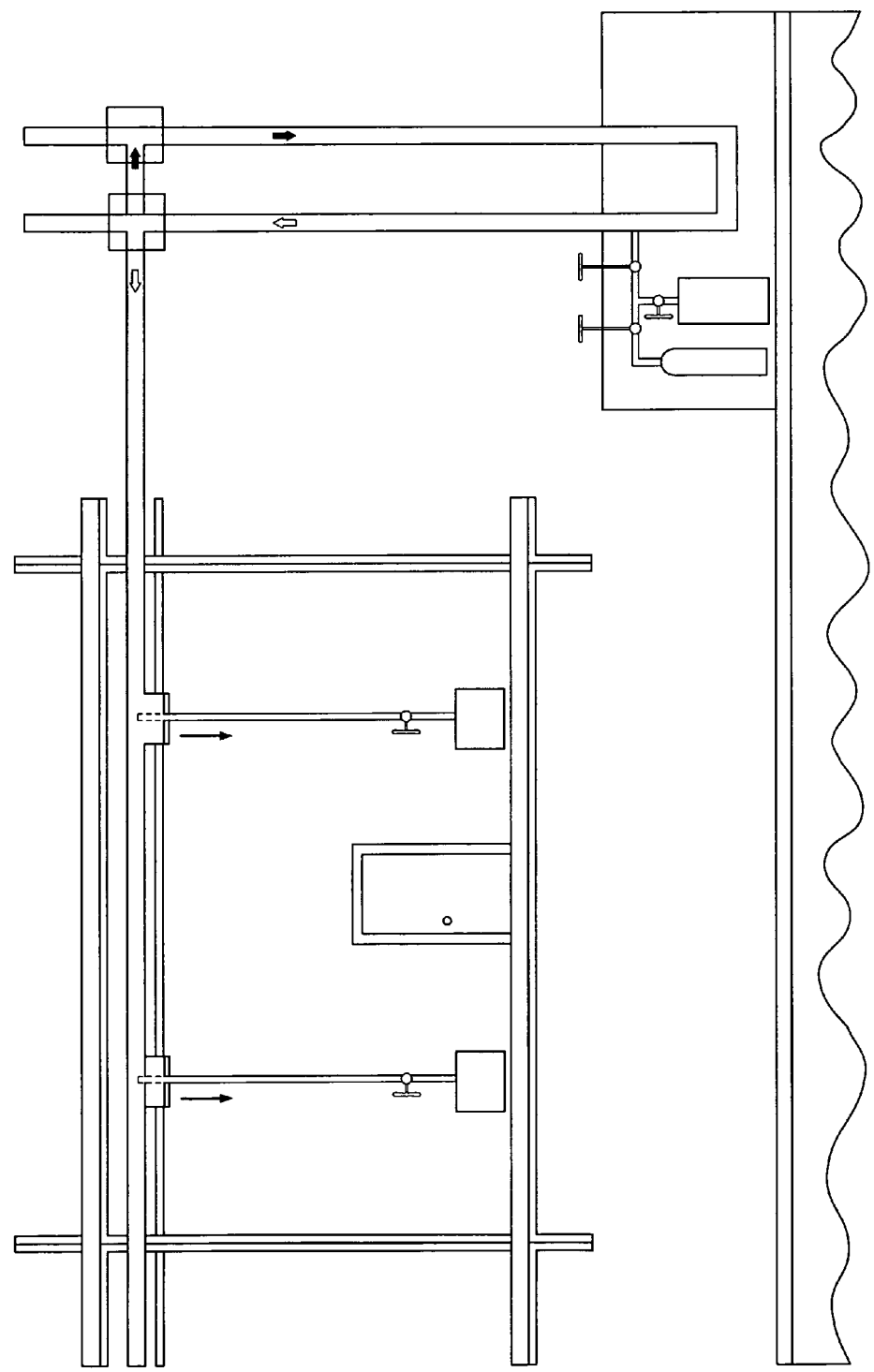
FIG. 5d is a simplified illustration of an alternative embodiment of the present invention that combines the tracer measurement systems illustrated in FIGS. 5a and 5b in a single room.
Figure 5E:
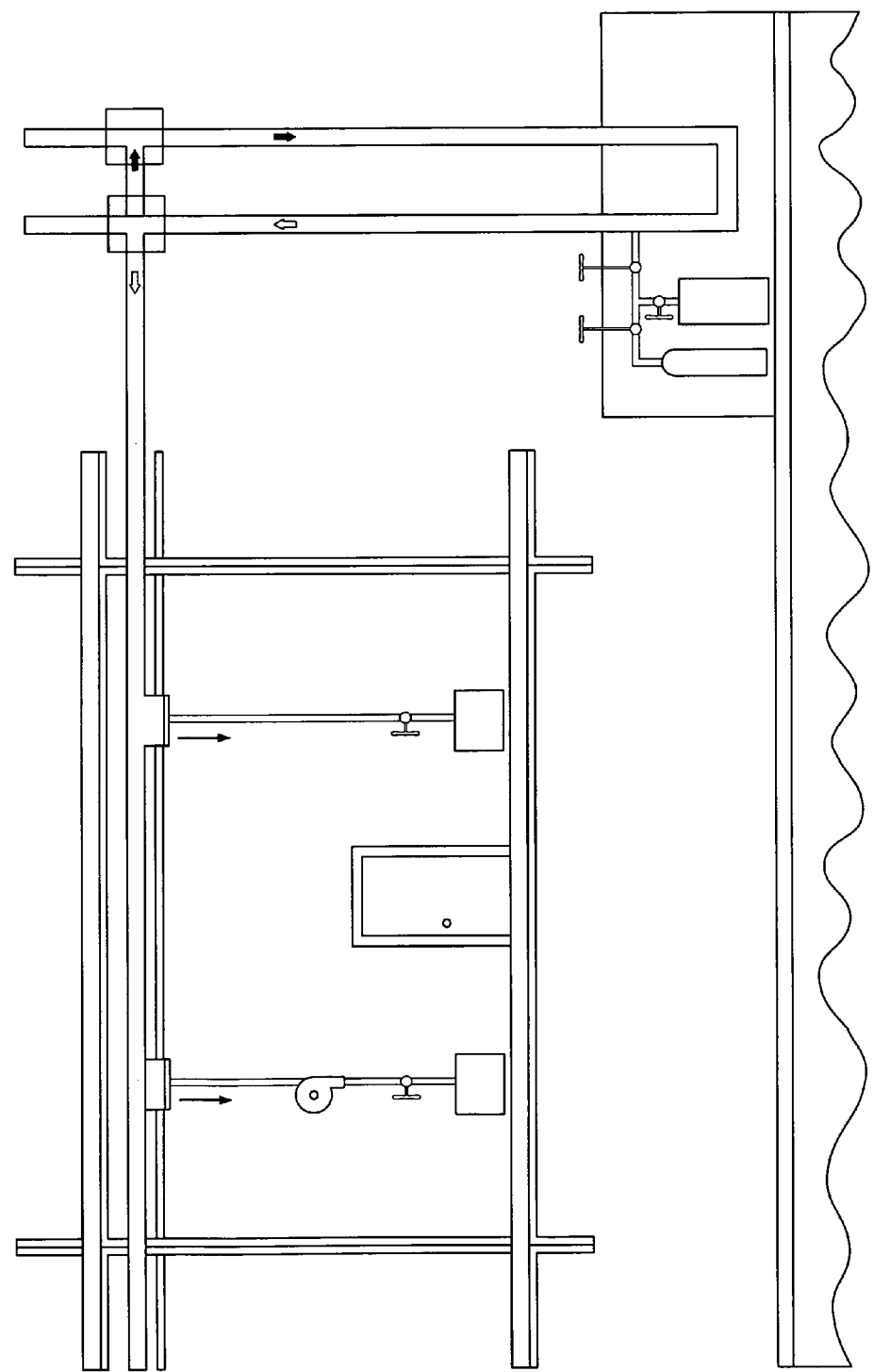
FIG. 5e is a simplified illustration of an alternative embodiment of the present invention that combines the tracer measurement systems illustrated in FIGS. 5a and 5c in a single room.
Figure 5F:
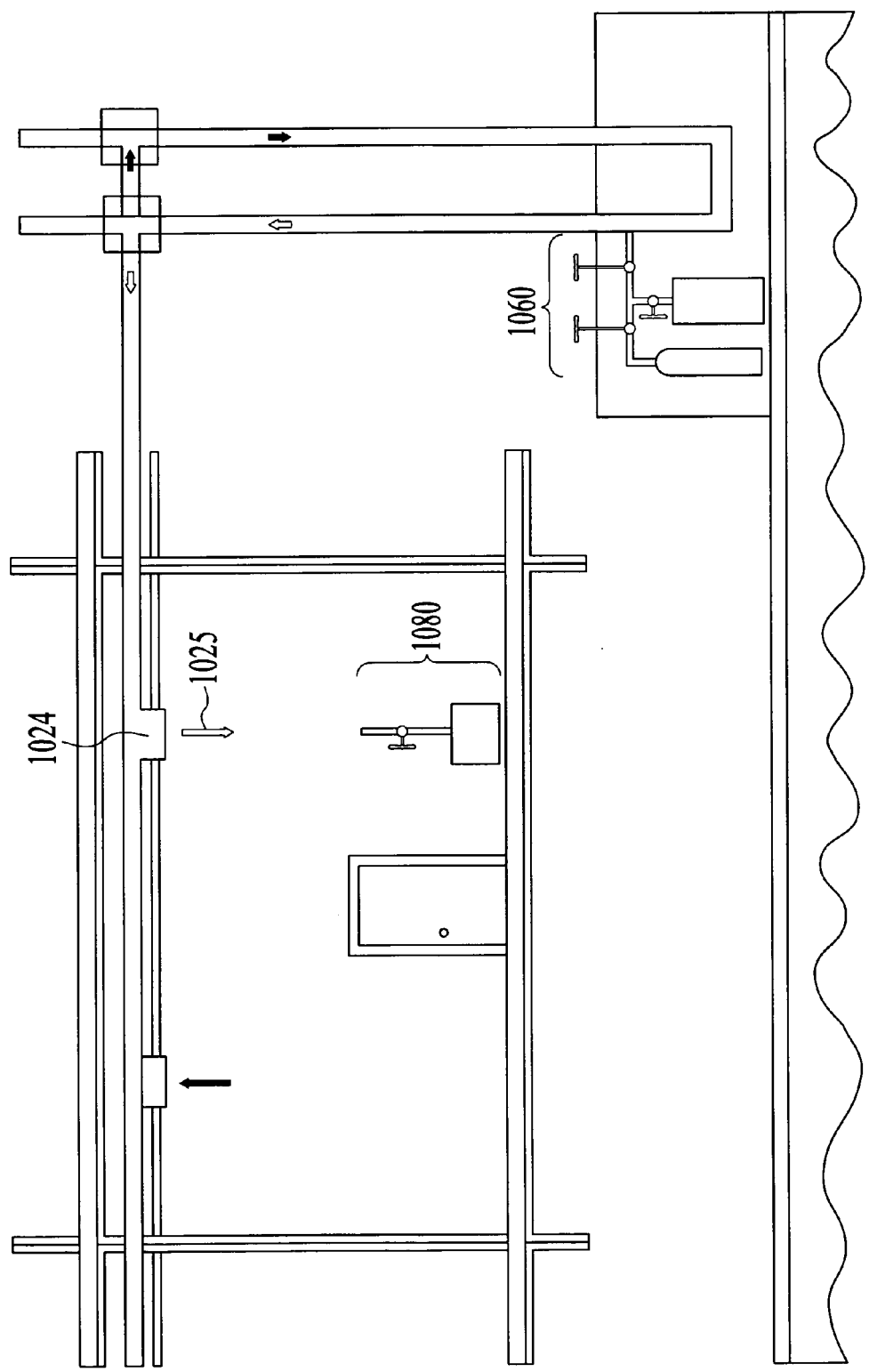
FIG. 5f is a simplified illustration of an alternative embodiment of the present invention with a tracer injection system located in a centrally located HVAC unit to inject tracers throughout the building and a tracer measurement system located in a room in a building to sample the tracer gases coming out of that inlet vent and the gases in the room.
Figure 5G:
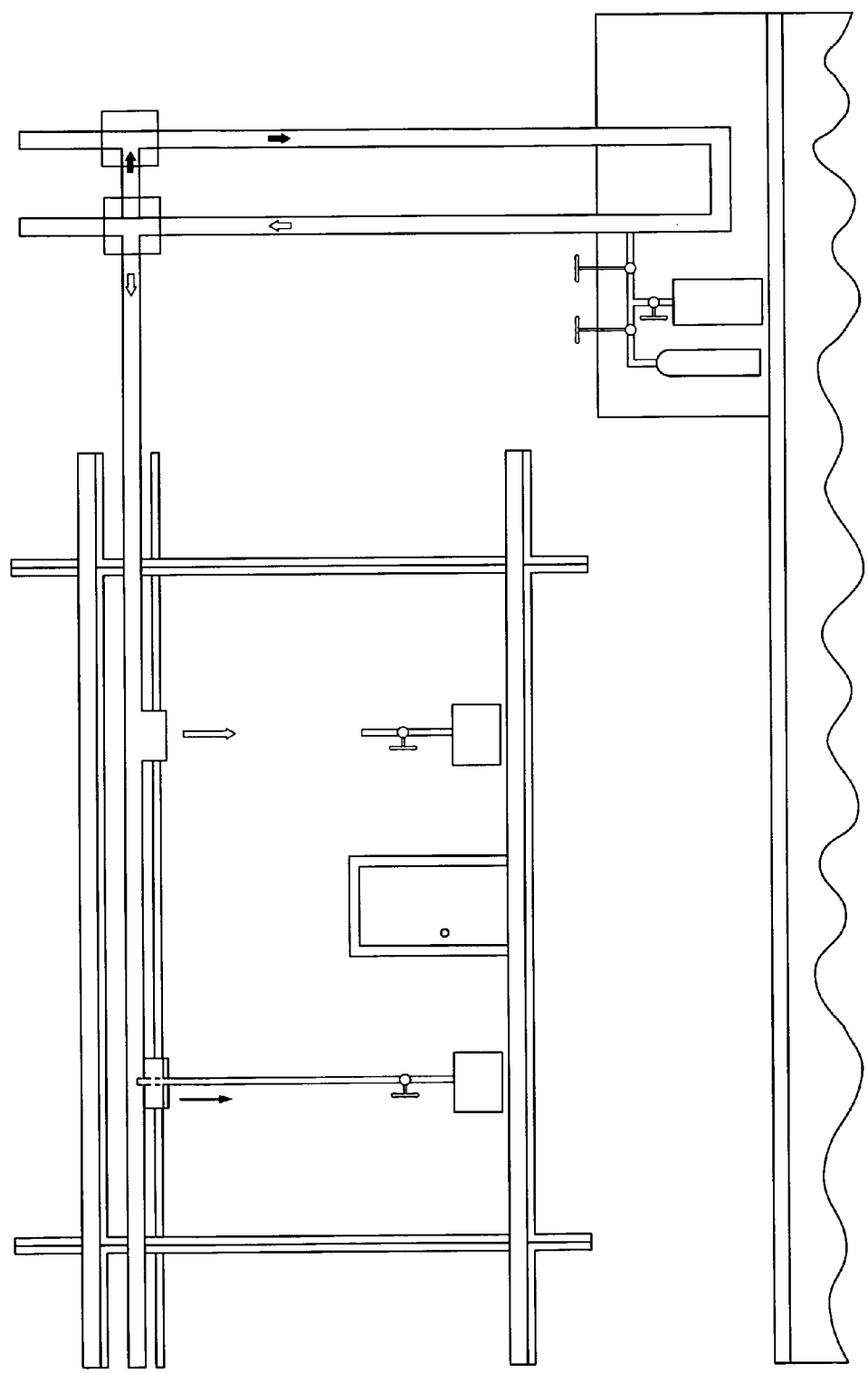
FIG. 5g is a simplified illustration of an alternative embodiment of the present invention combining the room-based tracer measurement units shown in FIGS. 5b and 5f.
Figure 5H:
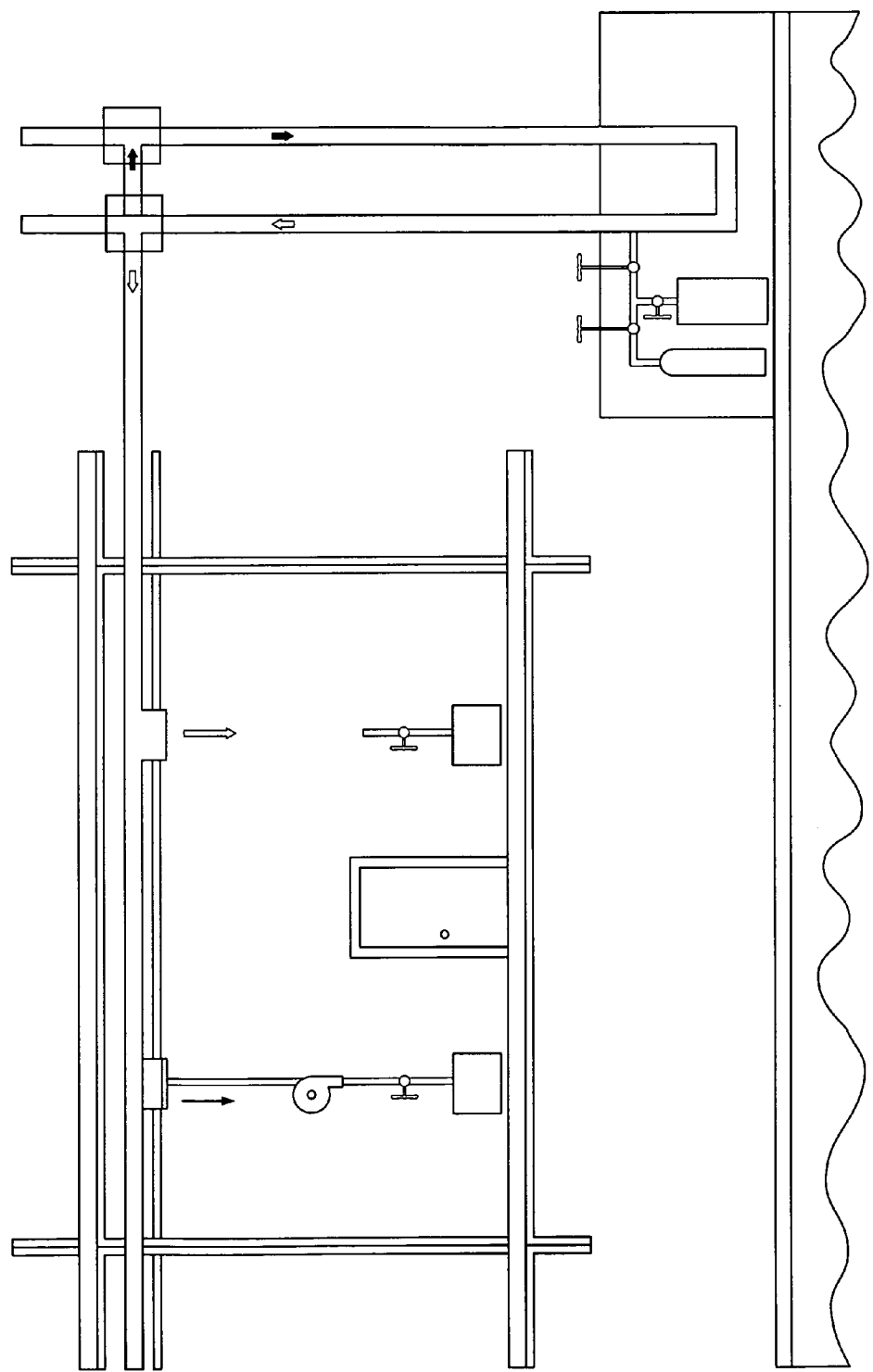
FIG. 5h is a simplified illustration of an alternative embodiment of the present invention combining the room-based tracer measurement units shown in FIGS. 5c and 5f.
Figure 5I:
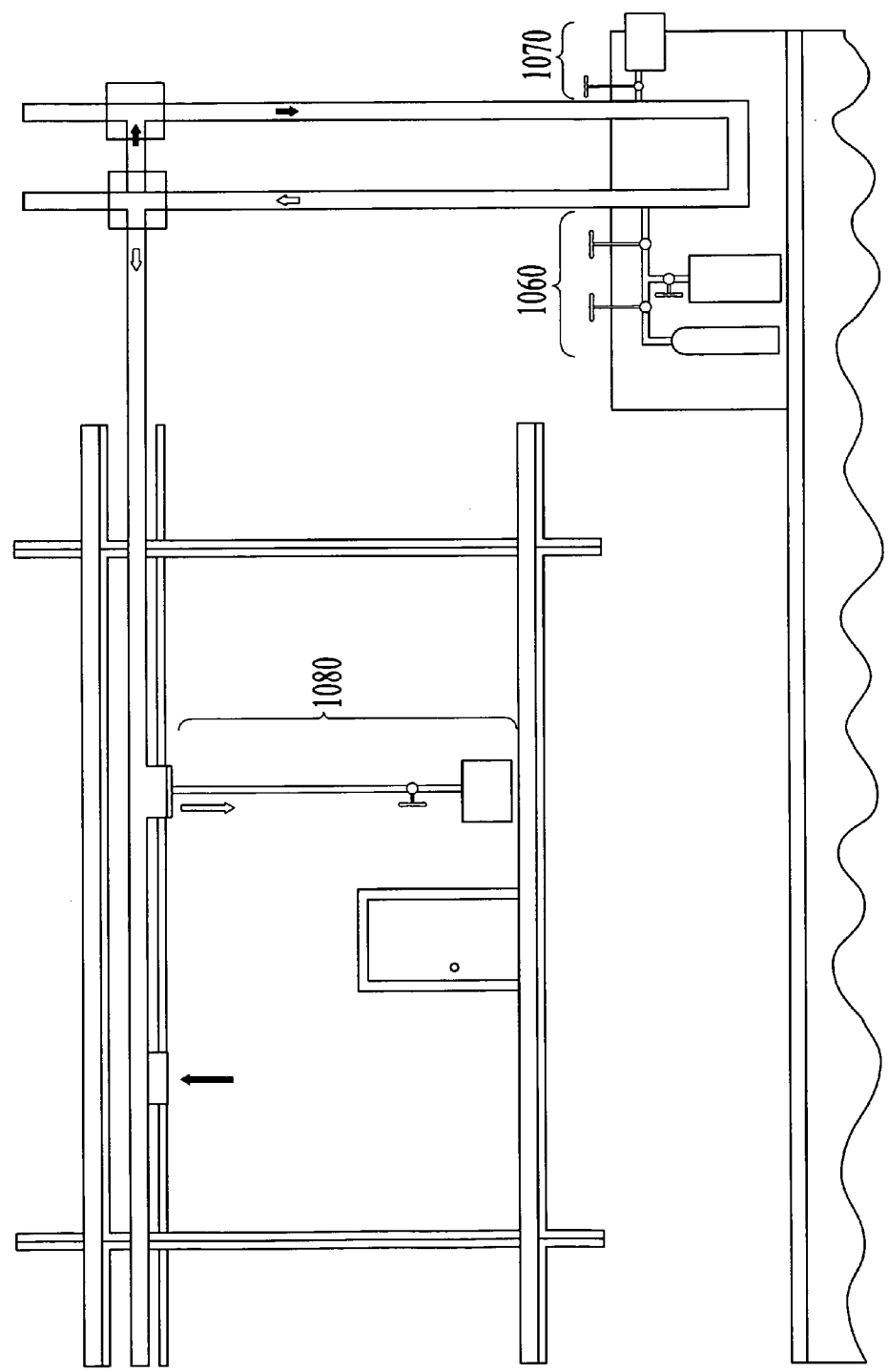
Figure 5J:
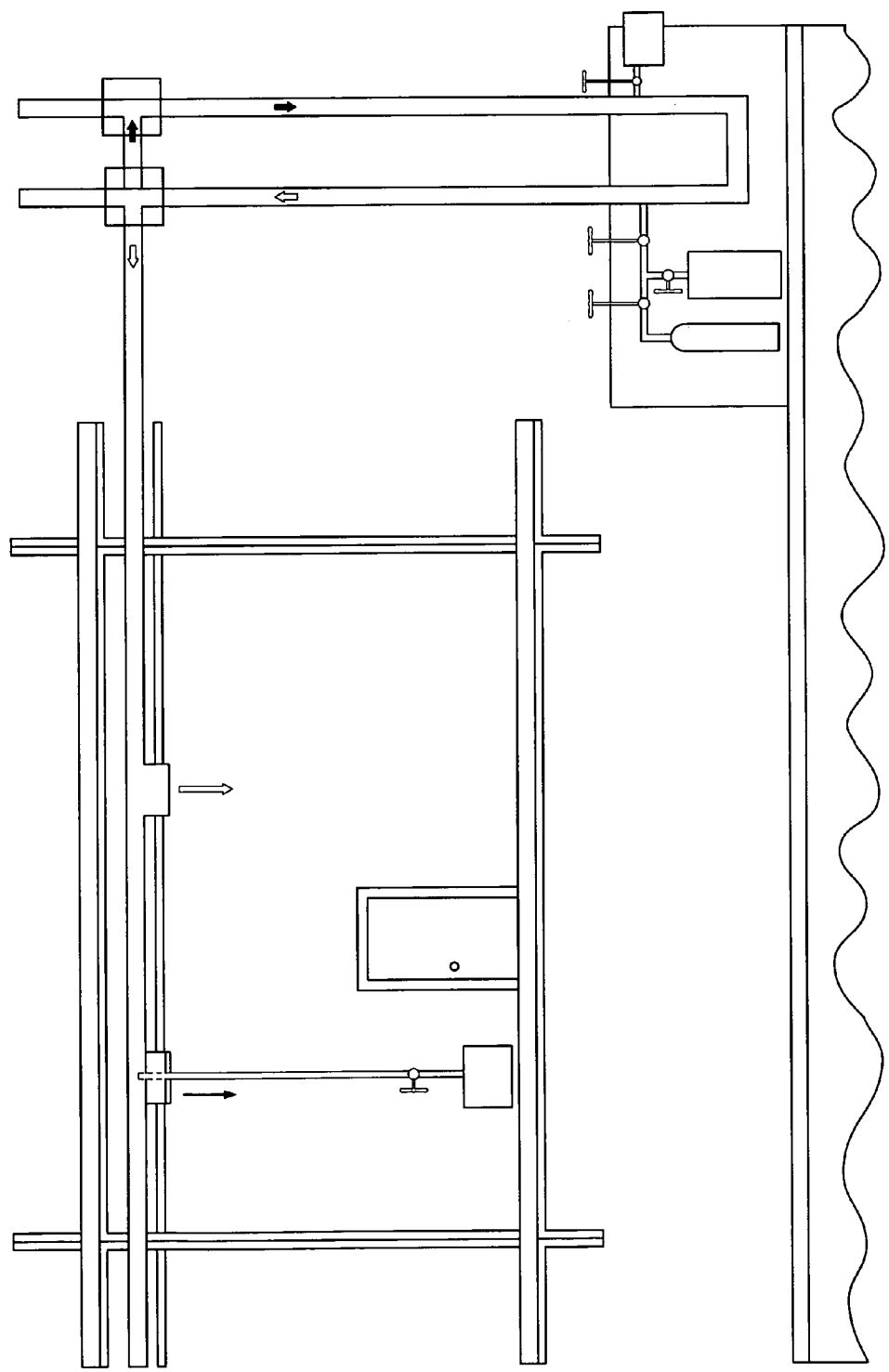
Figure 5K:
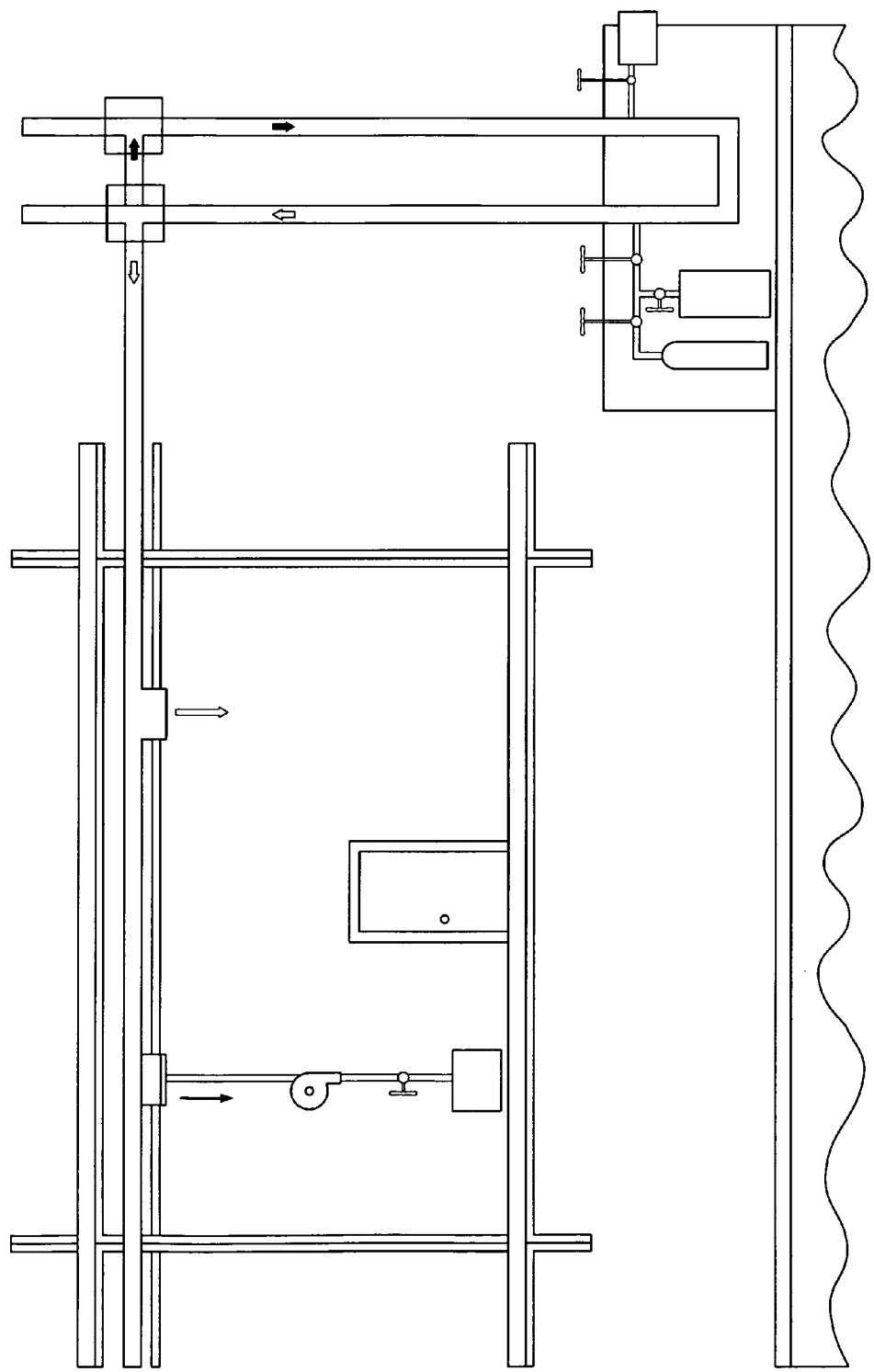
Figure 5M:
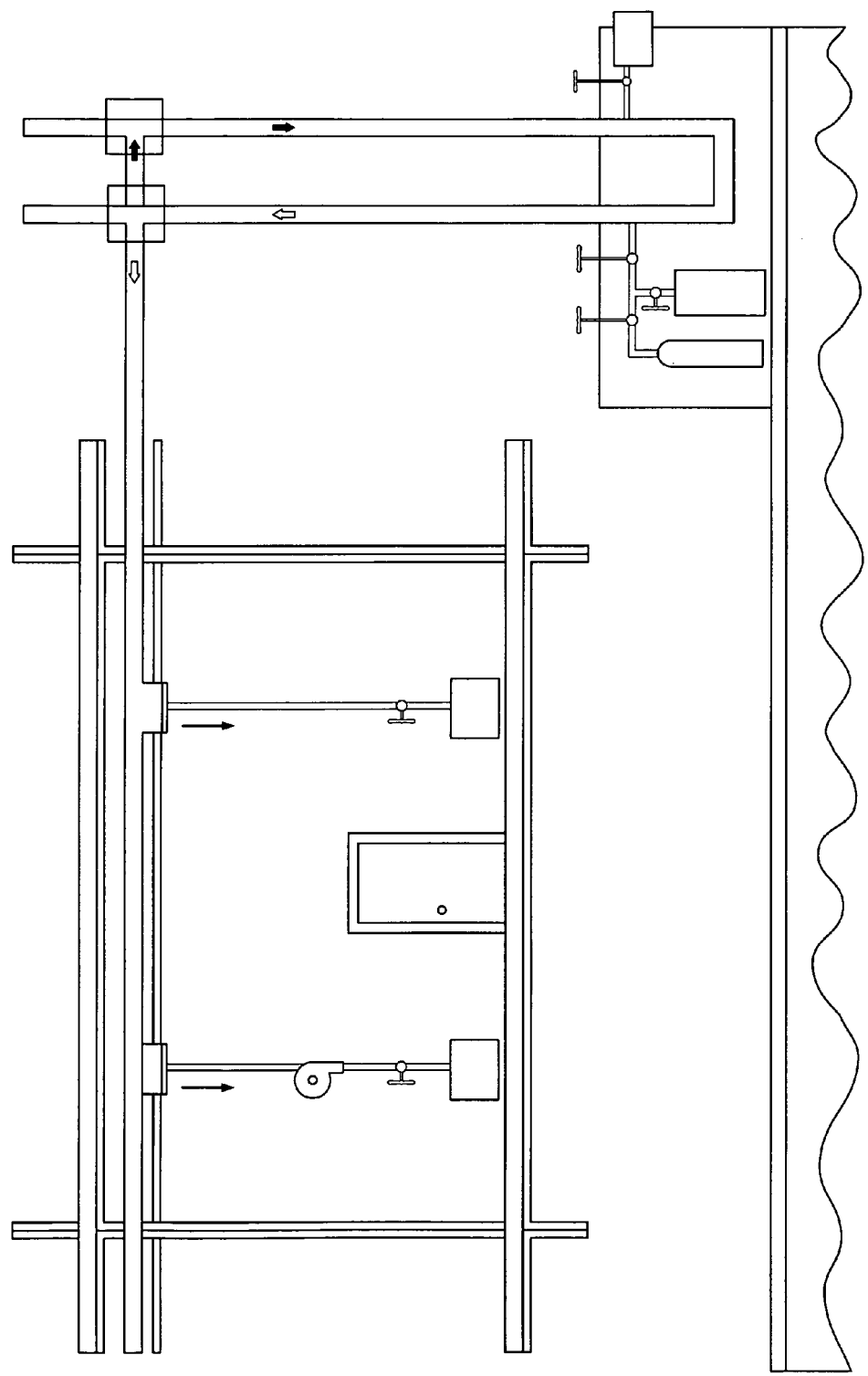
Figure 5N:
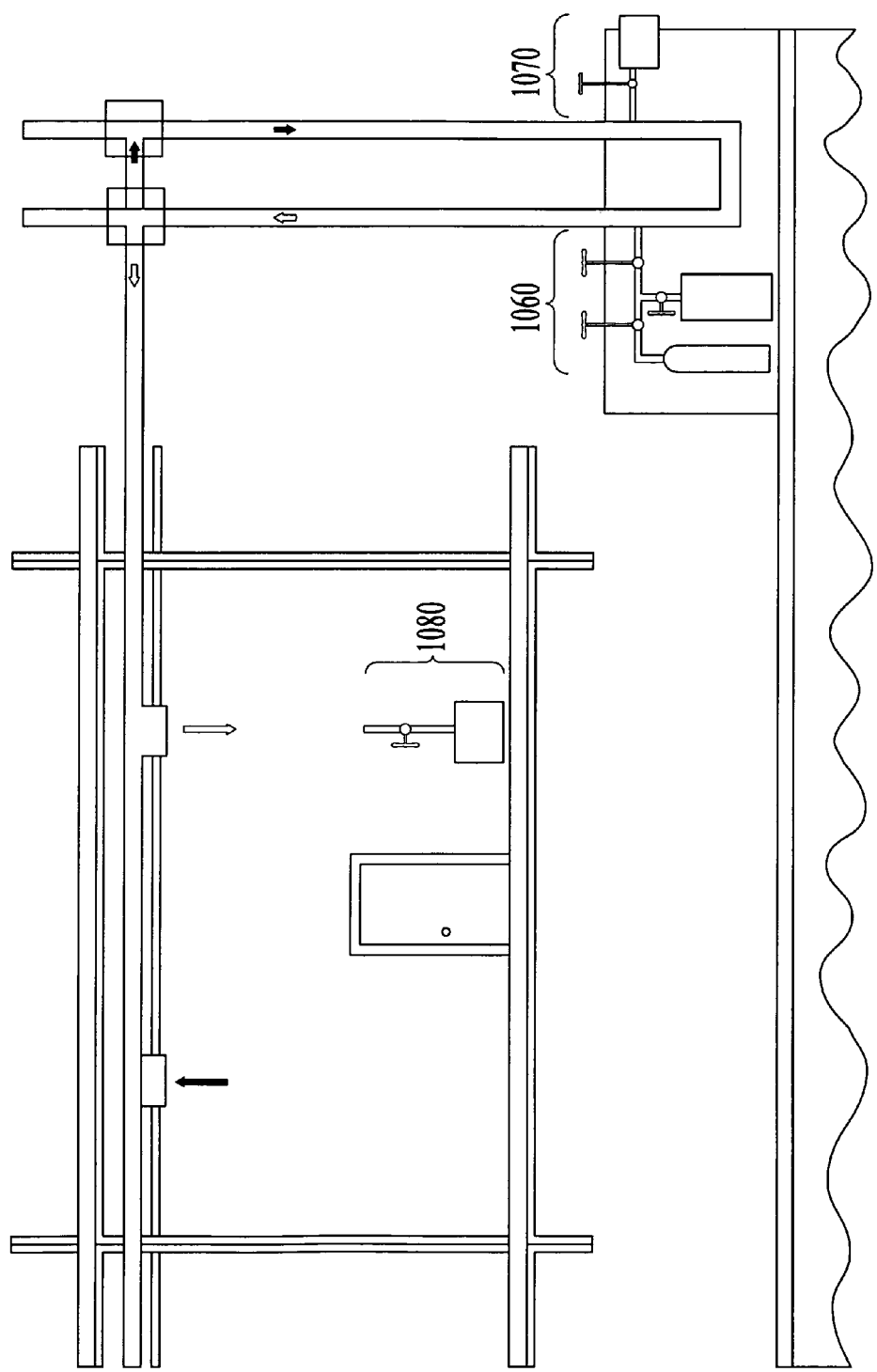

FIGS. 4*a* and 4*b* show two views of the building ductwork 1014 on a floor 1002 in building 1000 illustrated in FIGS. 2 and 3 with the tracer injection and measurement system centrally located in the HVAC unit 1050 in the basement of the building 1000. In this illustration, the inlet 1020, (1022 not shown) ductwork above the false ceiling 1008, which emanates from the inlet header 1026 and brings air 1025 into the room 1004 at inlet vent 1024, and the return ductwork 1030, (1032 not shown) ductwork, which emanates from the return header 1036 and returns air 1035 from room 1004 at return vent 1034, is shown. FIGS. 4*b* through 4*c* show several views of possible locations for the dangerous or hazardous substances 1040, 1042 in the ductwork and in the room, respectively.

FIGS. 5-8 illustrate alternative locations and configuration for the tracer injection and measurement units that either complement or add to the central location in the central HVAC units illustrated in FIGS. 2-4. FIG. 5*a* is a simplified illustration of an alternative embodiment of the present invention shown in FIG. 4*a* with a tracer injection system 1060 located in a centrally located HVAC unit 1050 to inject tracers throughout the building and a tracer measurement system 1080 located in a room 1004 in a building and attached to an inlet vent to sample the tracer gases coming out of a specific inlet vent 1024 of the building duct system 1014. The tracer measurement unit 1080 in FIG. 5*a* is identical to the one 1070 shown in the HVAC unit in FIG. 2*a* except that a tube 1085 connects the unit 1080 to the inlet vent 1024 with a cover plate 1089 to channel all of the air coming out of the vent 1024 to the tracer measurement unit 1080. FIG. 5*b* illustrates the placement of a tracer measurement system 1080 located at the return vent with a conduit sampling means 1087 inserted into the return ductwork through a return vent in the room to sample the tracer gases in the return ductwork vent in the second room. FIG. 5*c* illustrates a tracer measurement system 1081, with a pump 1086 to pull the tracer gases in the return duct into the measurement system 1081, which is attached to the return duct 1034 with a cover plate 1099. (While not shown in any of the illustrations, a pump could also be used to draw air into the inlet-vent-based measurement systems, but this would not usually be necessary unless the air flow needed to be increased to reduce the time of the measurement or to obtain a larger sample in a given time period.) FIGS. 5*d* and 5*e* illustrate the use of two tracer measurement systems 1080 in a room. FIG. 5*f* illustrates the room-based tracer measurement unit 1080 that does not include a means of channeling the air from the inlet vent 1024 to the unit 1080. In this application, the tracer measurement unit 1080 is simply placed in the room 1004 and samples the tracer gases in the room and coming out of the inlet vent. FIGS. 5*g* and 5*h* add the tracer measurement units illustrated in FIGS. 5*b* and 5*c* to FIG. 5*f*. FIGS. 5*i*-5*n* are simplified illustrations of a alternative embodiments of the present invention shown in FIGS. 5*a*-5*h*, except a tracer measurement system has been added to the central HVAC unit.

Figure 6B:
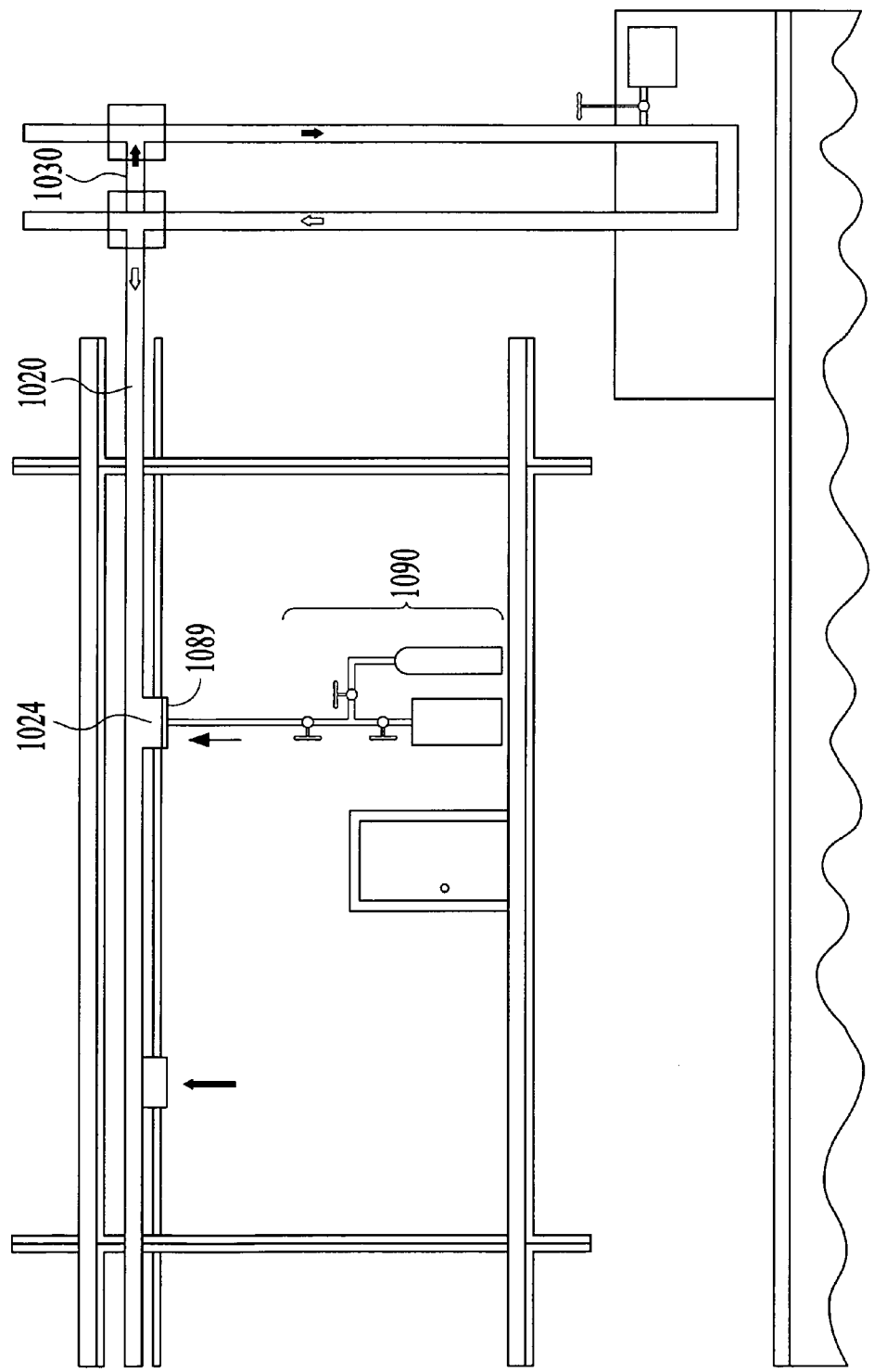
FIG. 6b is a simplified illustration of an alternative embodiment of the present invention with a tracer injection system located in a room in a building and attached to an inlet vent to inject tracers directly into the inlet ductwork of a building through a inlet vent and a tracer measurement system located in a centrally located HVAC unit to sample the tracer gases coming from all rooms and ductwork in the building.
Figure 6C:
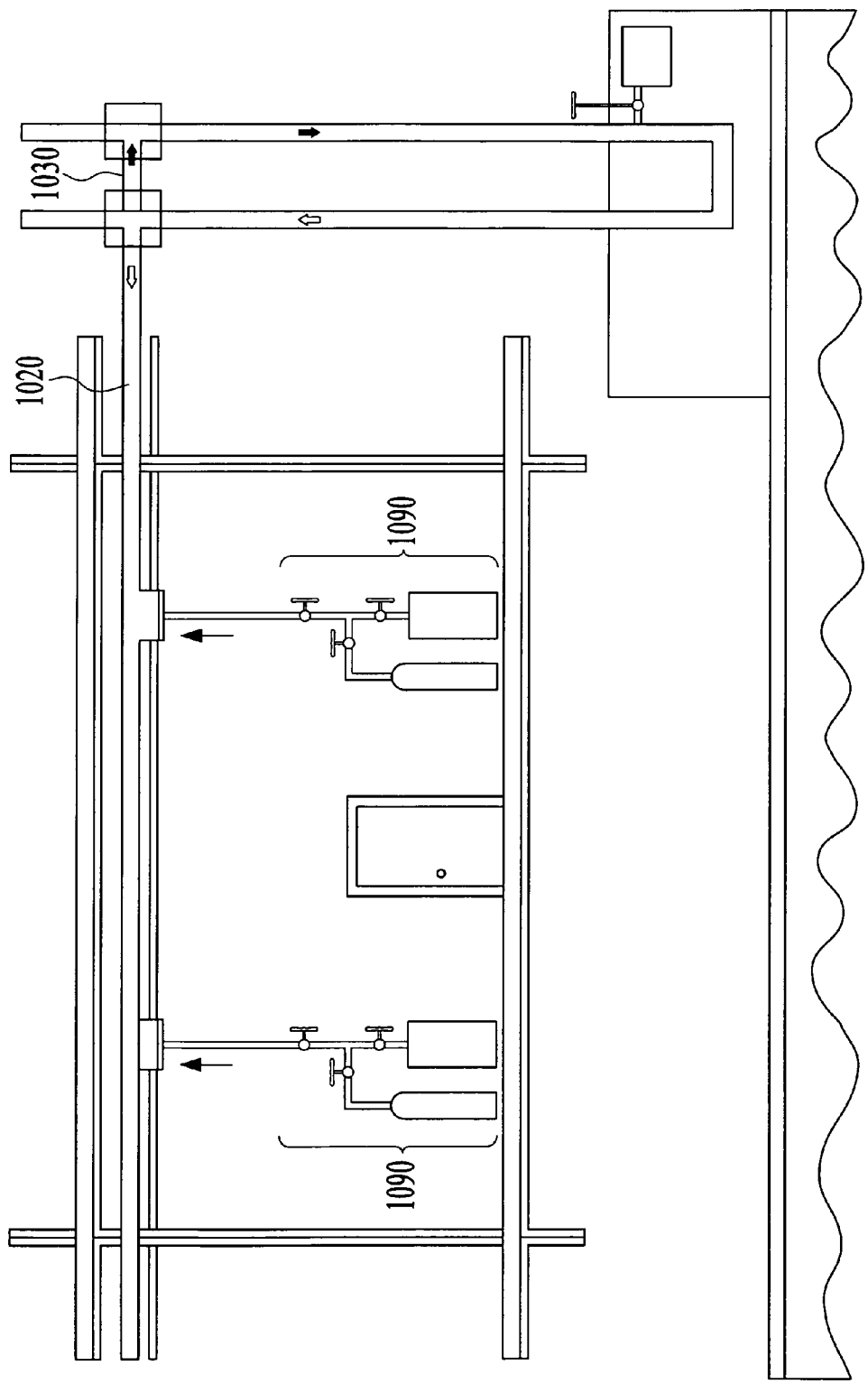
FIG. 6c is a simplified illustration of an alternative embodiment of the present invention that combines the tracer injection systems illustrated in FIGS. 6a and 6b in a single room.
Figure 6D:
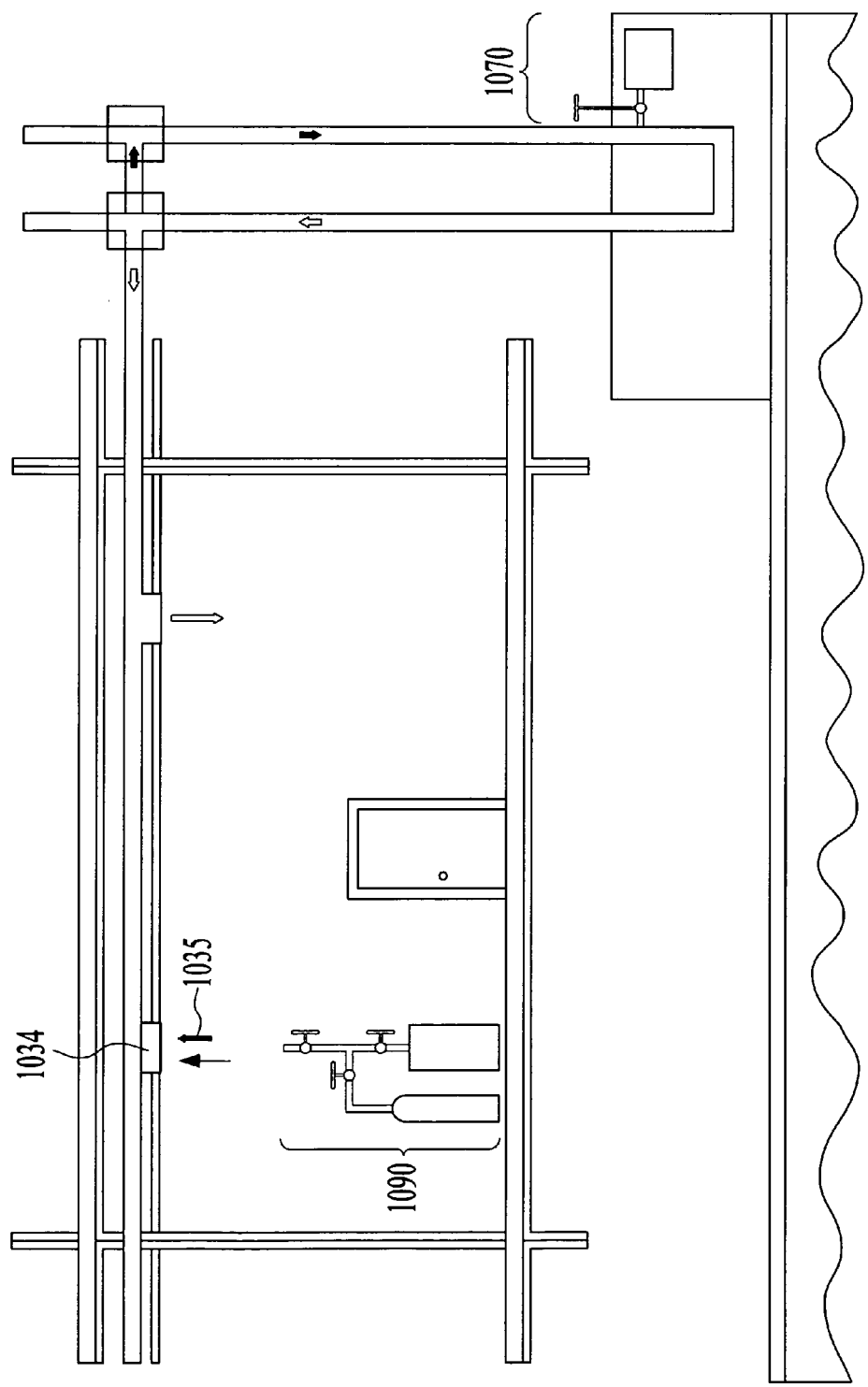
FIG. 6d is a simplified illustration of an alternative embodiment of the present invention shown in FIG. 6a whereby the tracer injection system is not attached to the return vent.
Figure 6E:
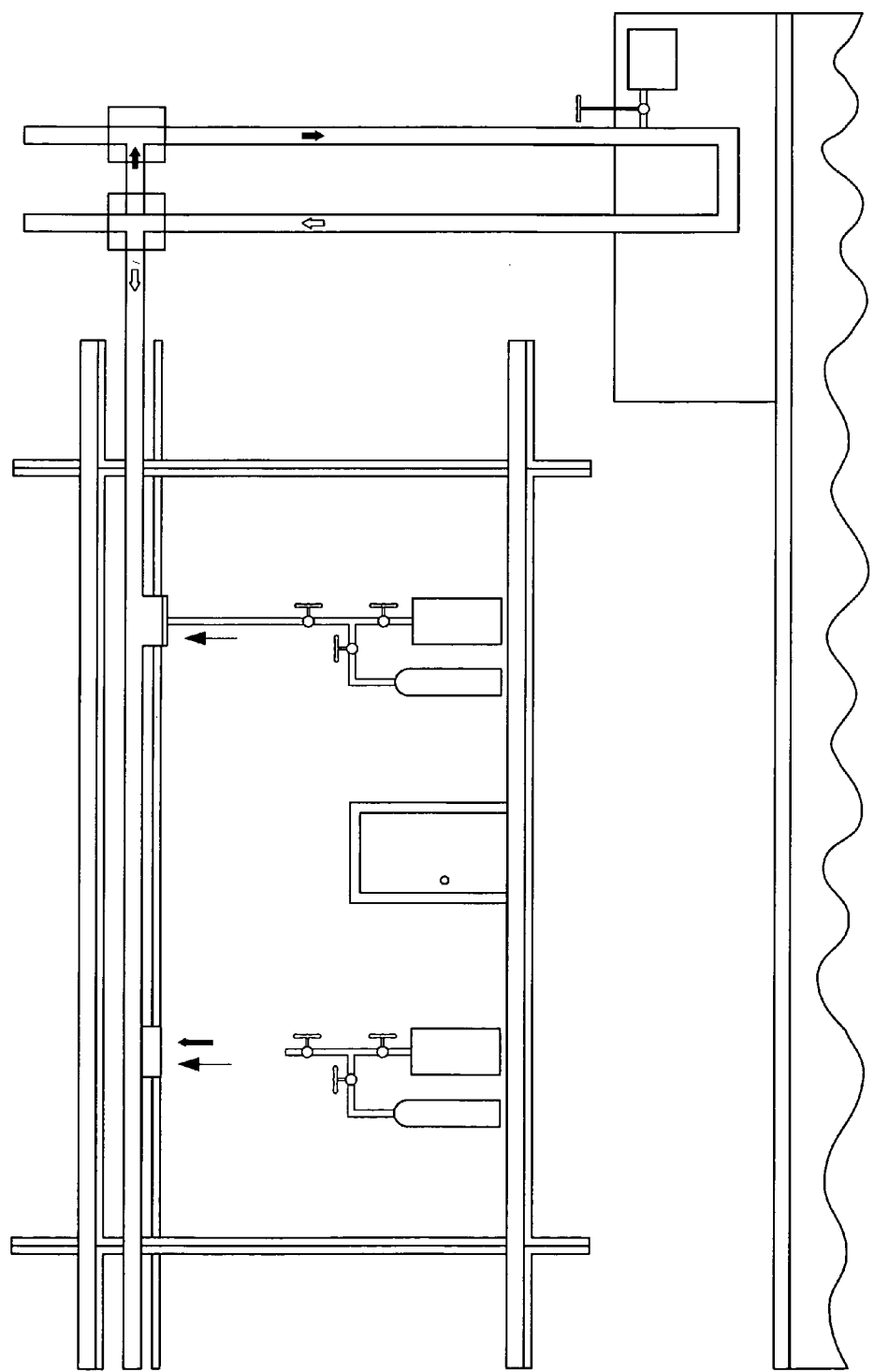
FIG. 6e is a simplified illustration of an alternative embodiment of the present invention shown in FIG. 6c whereby one of the tracer injection systems is not attached to the return vent.
Figure 6F:
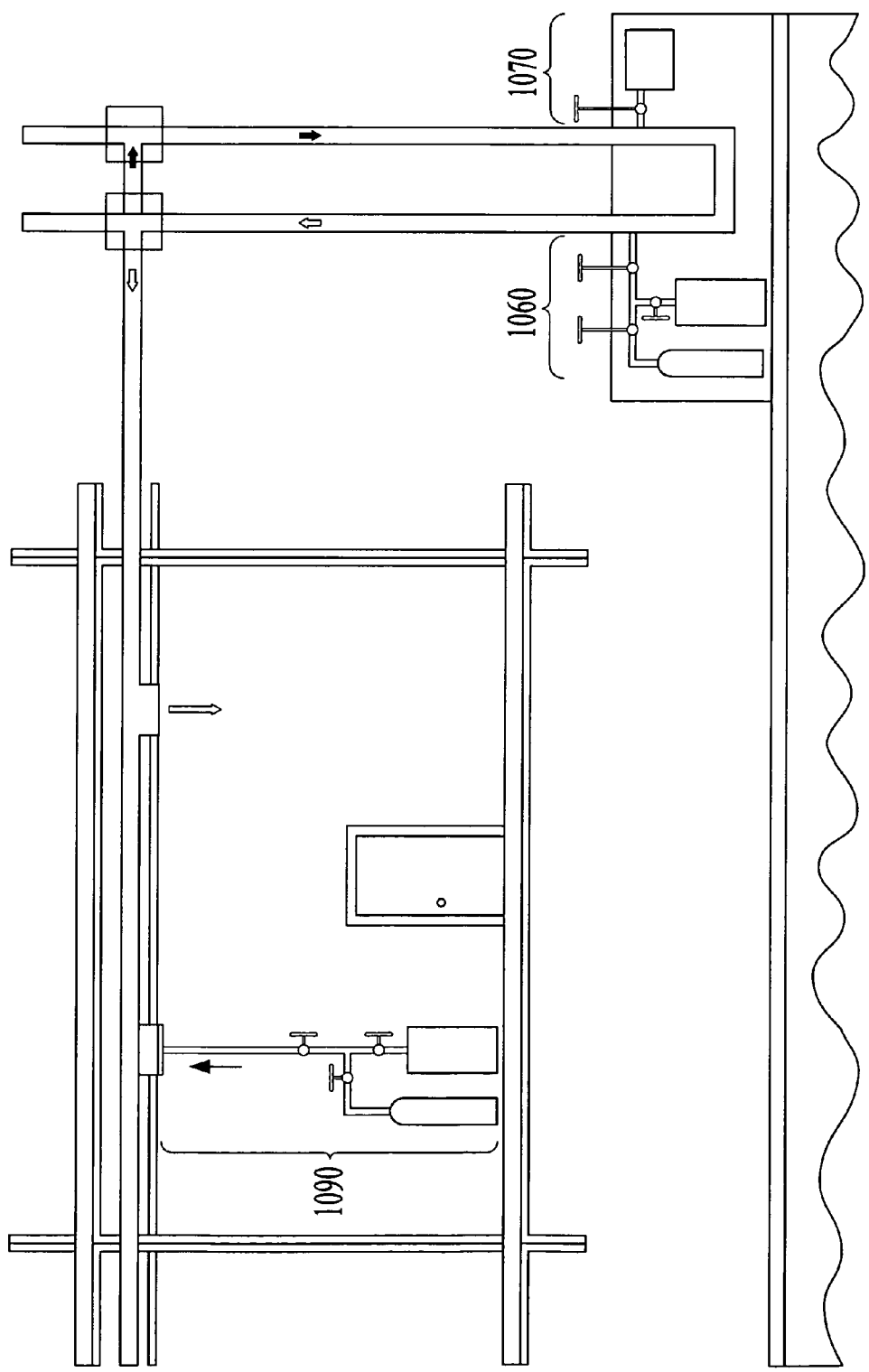
FIGS. 6f-6j are simplified illustrations of alternative embodiments of the present invention shown in FIGS. 6a-6e, except a tracer injection system has been added to the central HVAC unit.
Figure 6G:
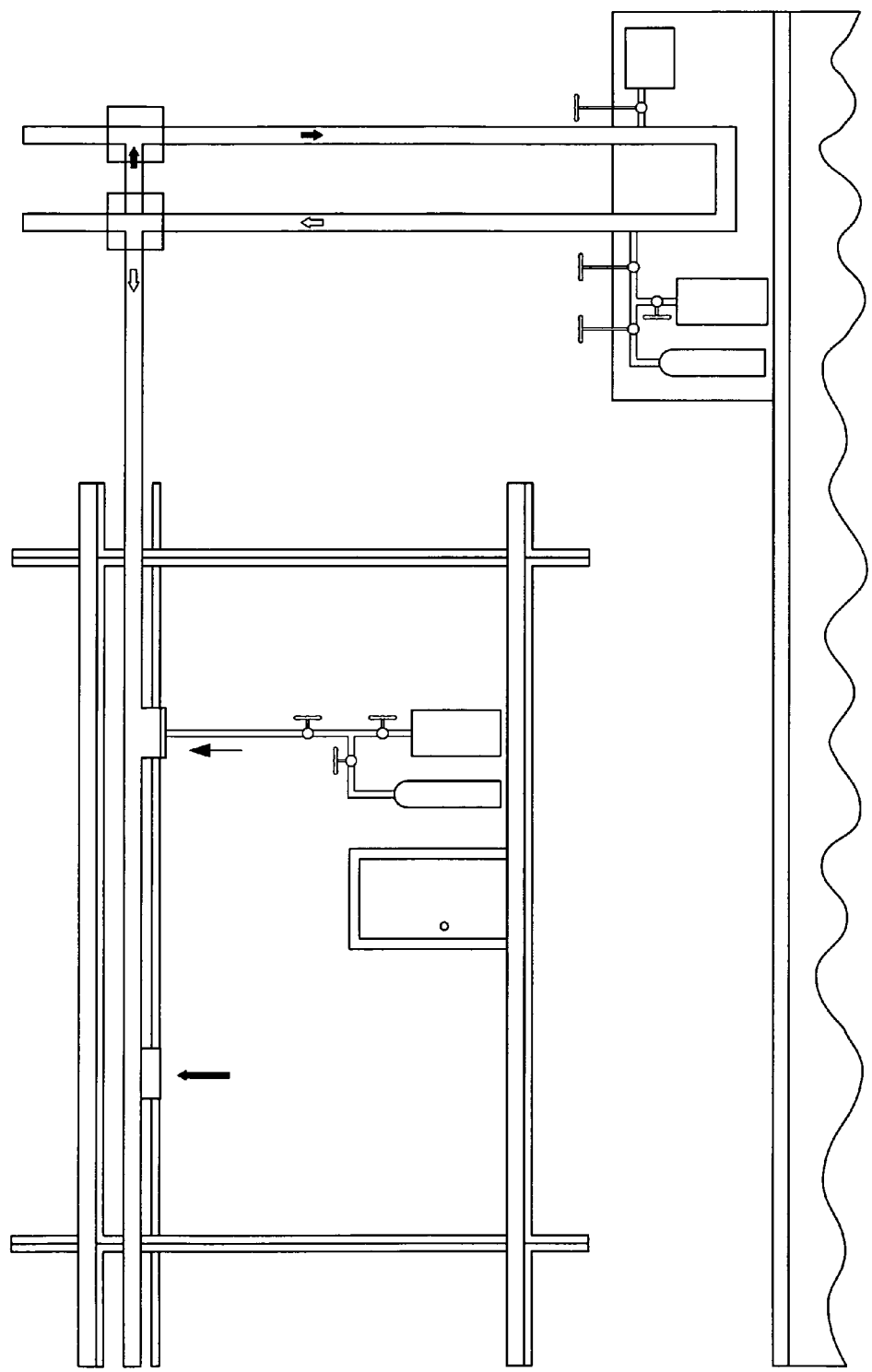
Figure 6H:
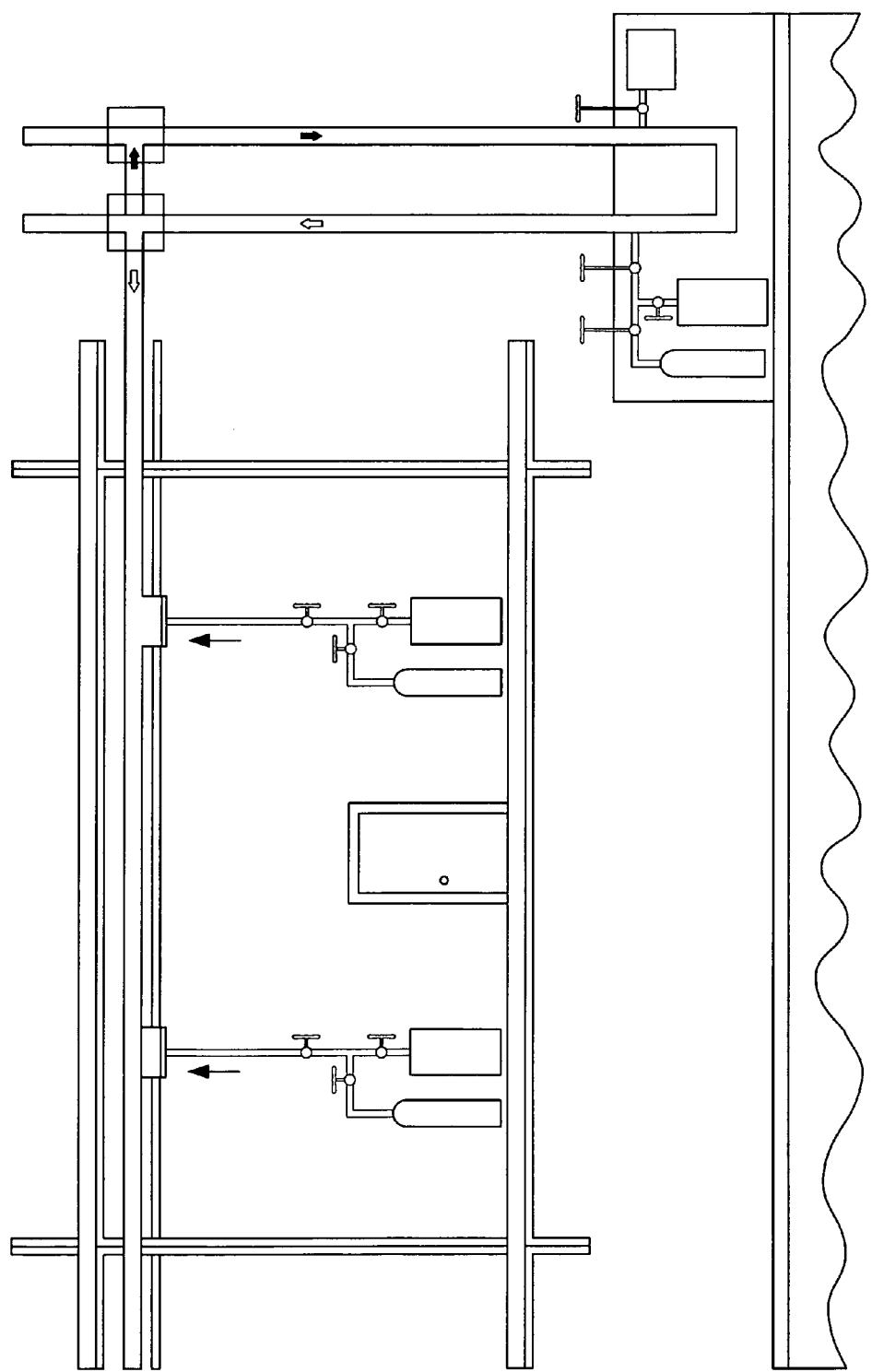
Figure 6I:
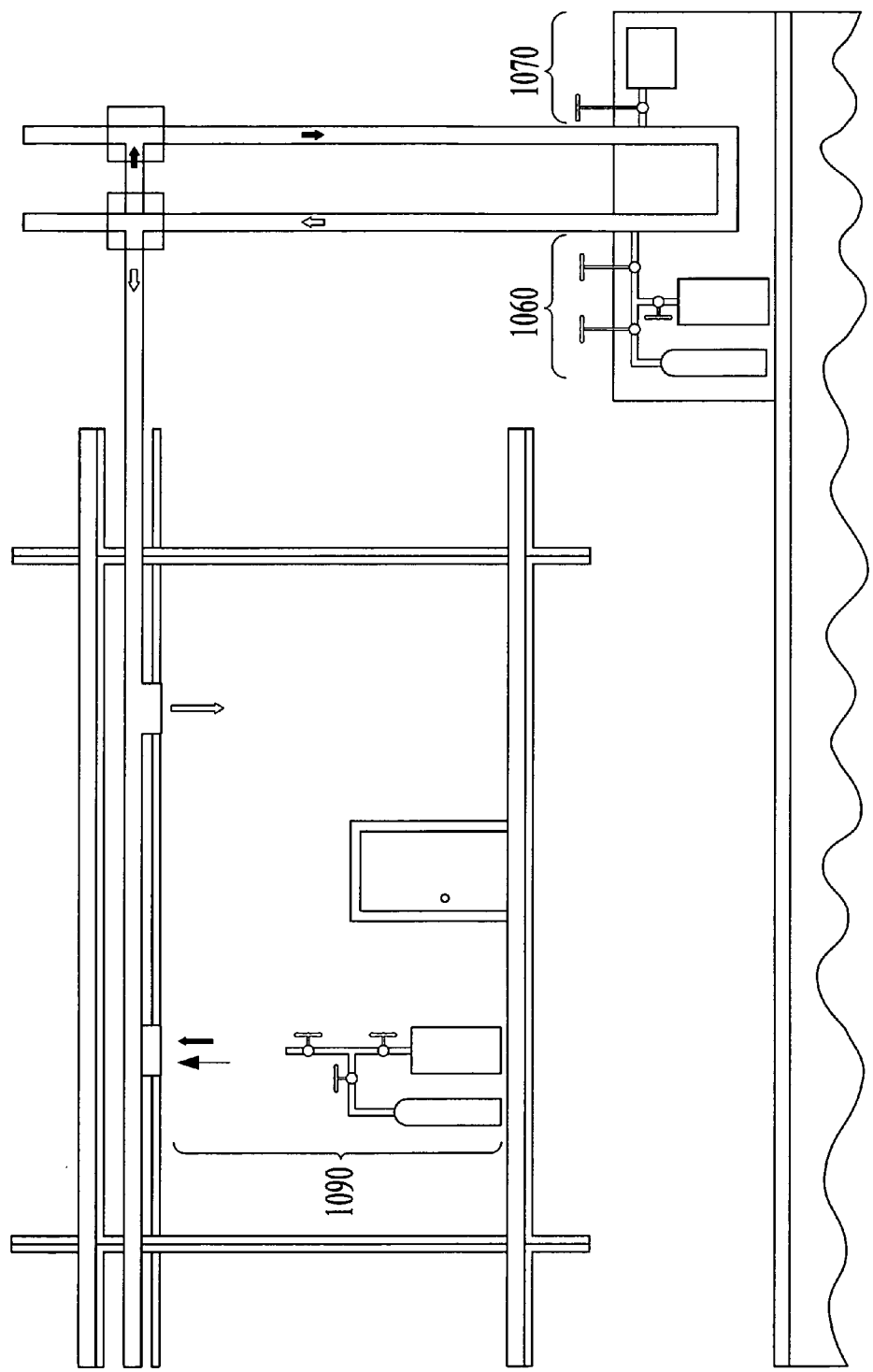
Figure 6J:
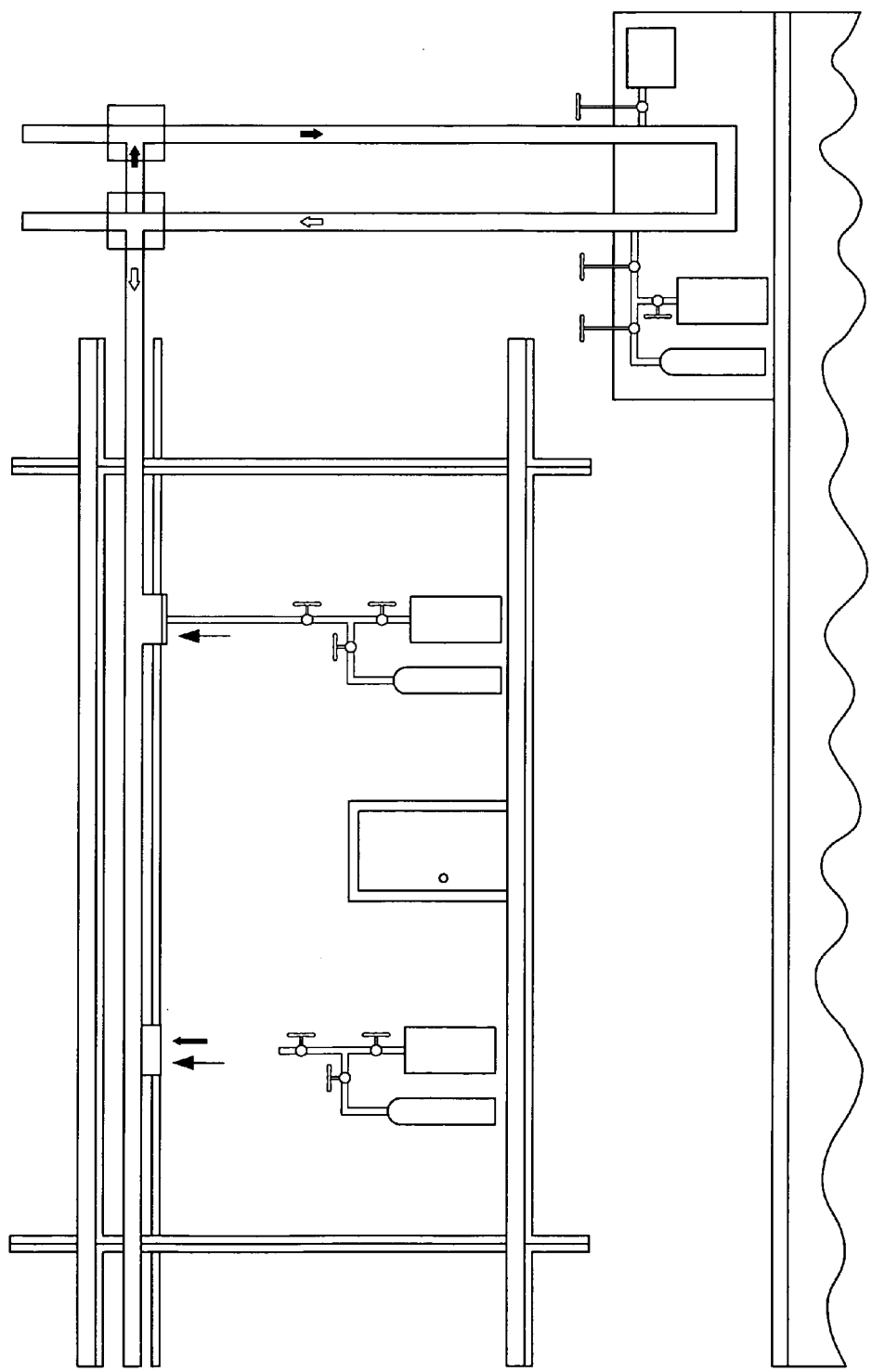
Figure 7A:
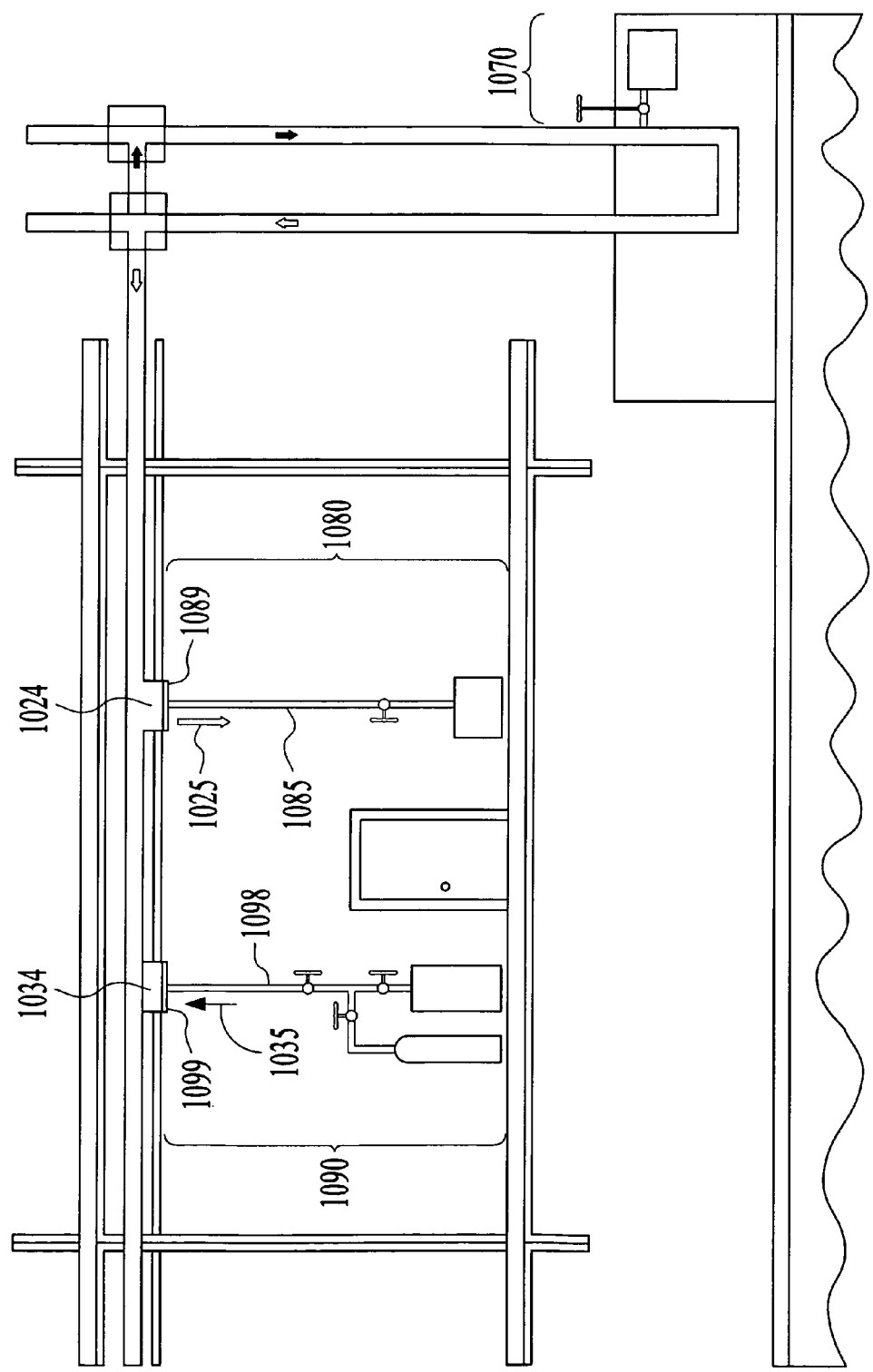
FIG. 7a is a simplified illustration of an alternative embodiment of the present invention with a tracer injection system located in a room in a building and attached to a return vent to inject tracers into the return ductwork of the building and two tracer measurement systems, one located at the central HVAC unit to samples gas from all rooms and ducts in the building and one located in the same room as the tracer injection system and attached to an inlet vent to sample the tracer gases coming out of the inlet vent.
Figure 7B:
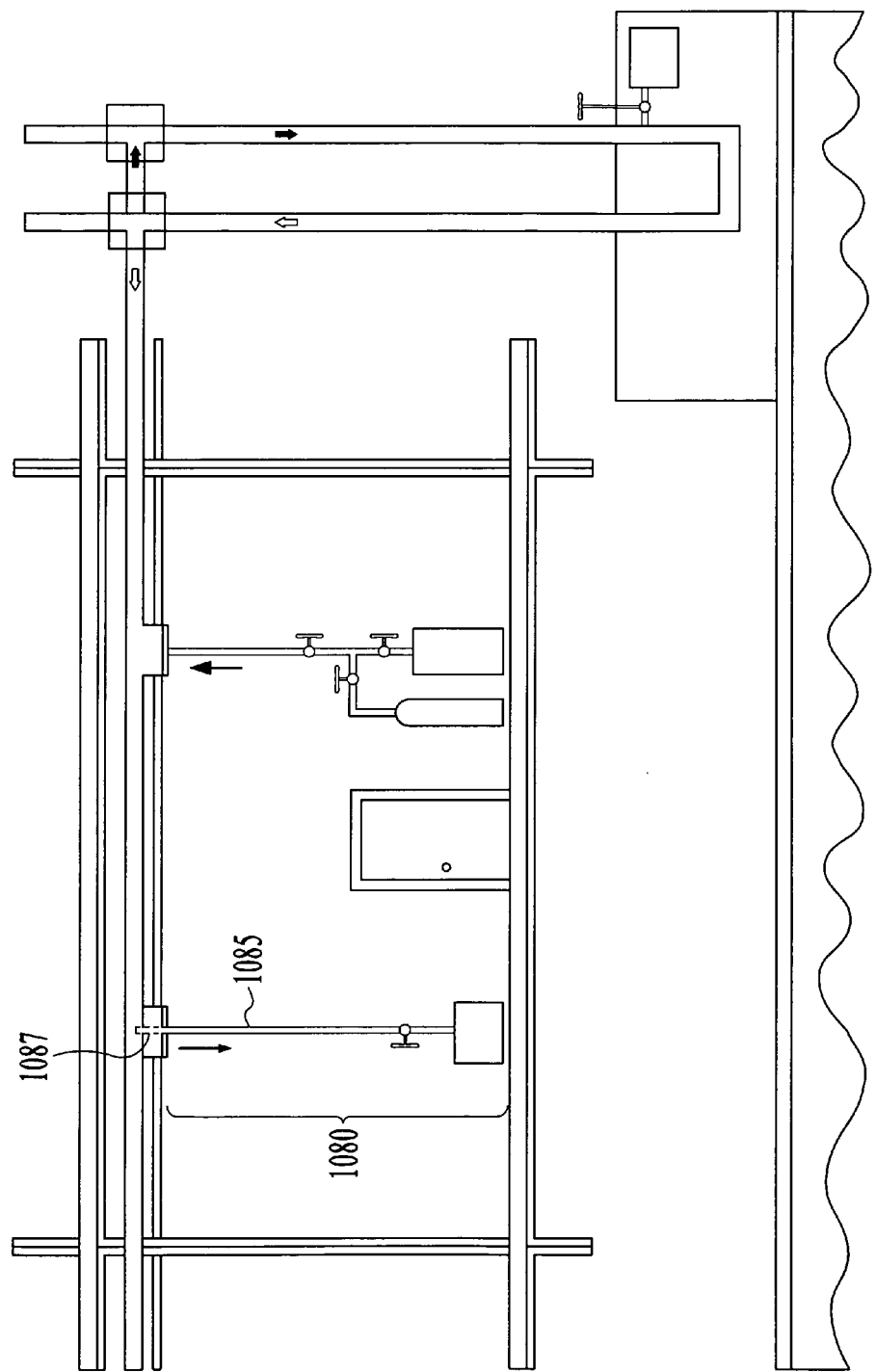
FIG. 7b is a simplified illustration of an alternative embodiment of the present invention with a tracer injection system located in a room in a building and attached to a inlet vent to inject tracers into the inlet ductwork of the building and two tracer measurement systems, one located at the central HVAC unit to samples gas from all rooms and ducts in the building and one located in the same room as the tracer injection system and attached to a return vent with a conduit sampling means insert into the return ductwork through a return vent in the room to sample the tracer gases in the return ductwork.
Figure 7C:
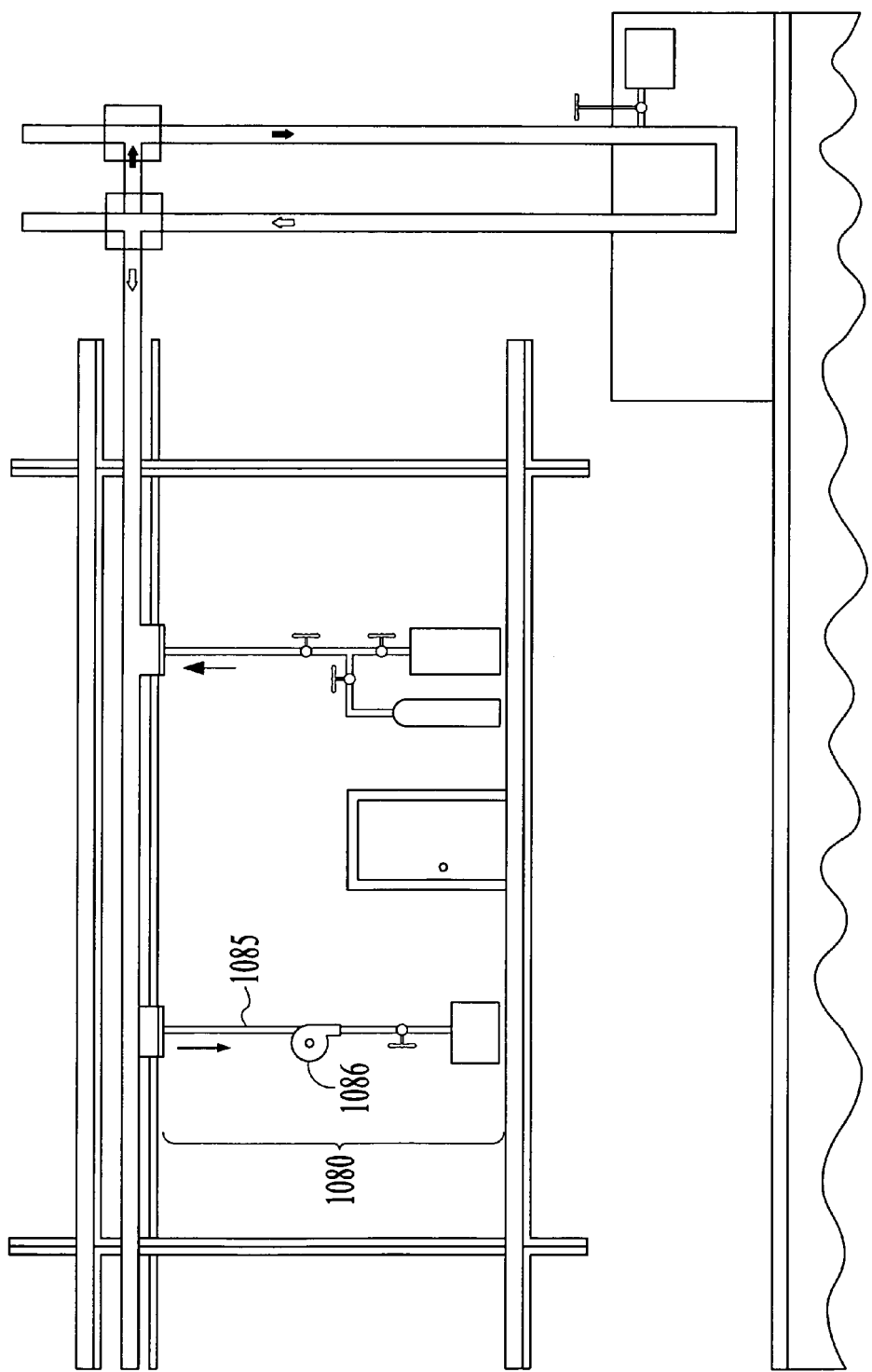
FIG. 7c is a simplified illustration of an alternative embodiment of the present invention with a tracer injection system located in a room in a building and attached to a inlet vent to inject tracers into the inlet ductwork of the building and two tracer measurement systems, one located at the central HVAC unit to samples gas from all rooms and ducts in the building and one located in the same room as the tracer injection system and attached to a return vent to sample the tracer gases in the return ductwork from that return duct vent in the room using a small pump to pull the gases into the measurement system.
Figure 7D:
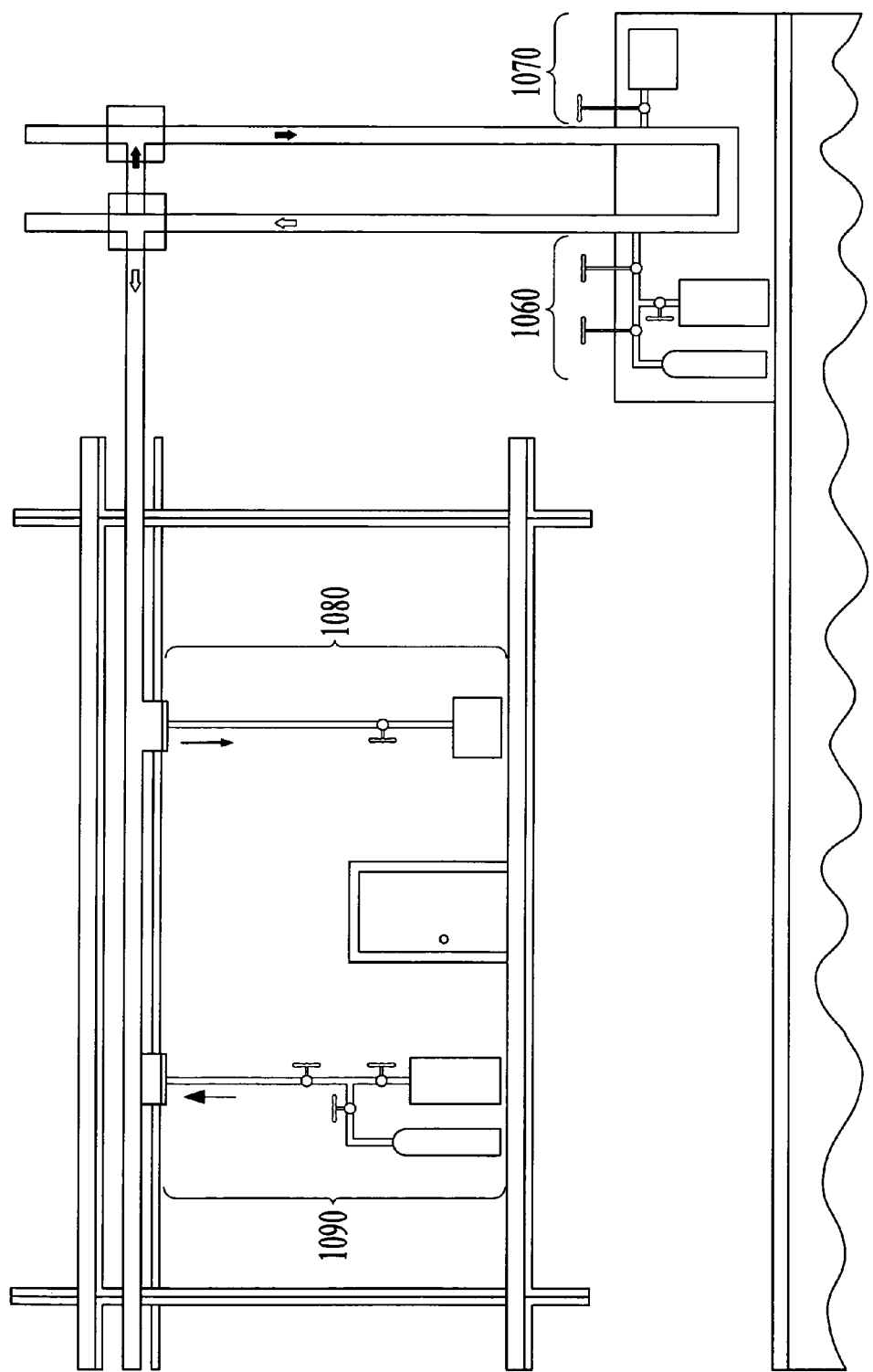
Figure 7E:
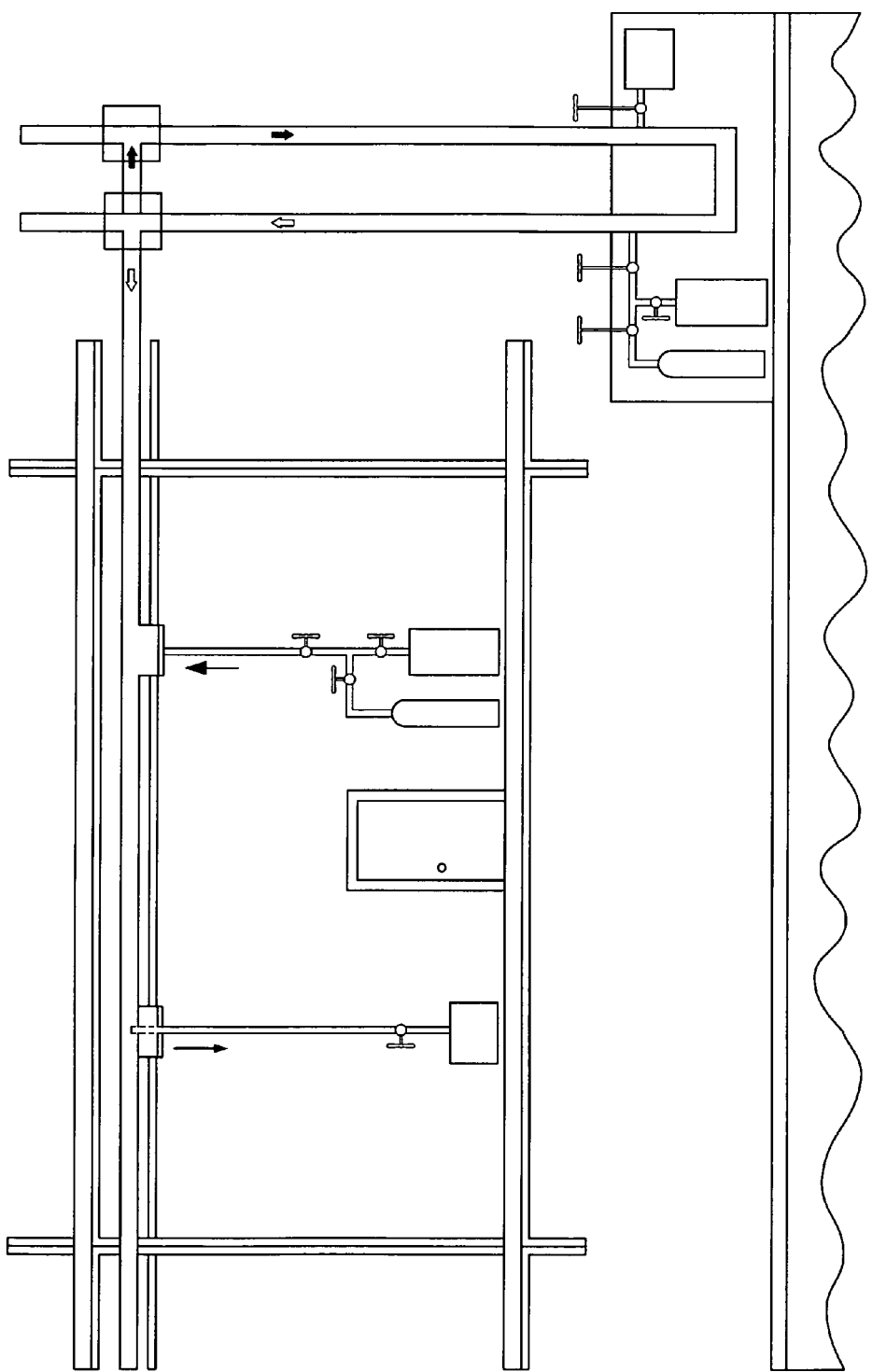
Figure 7F:
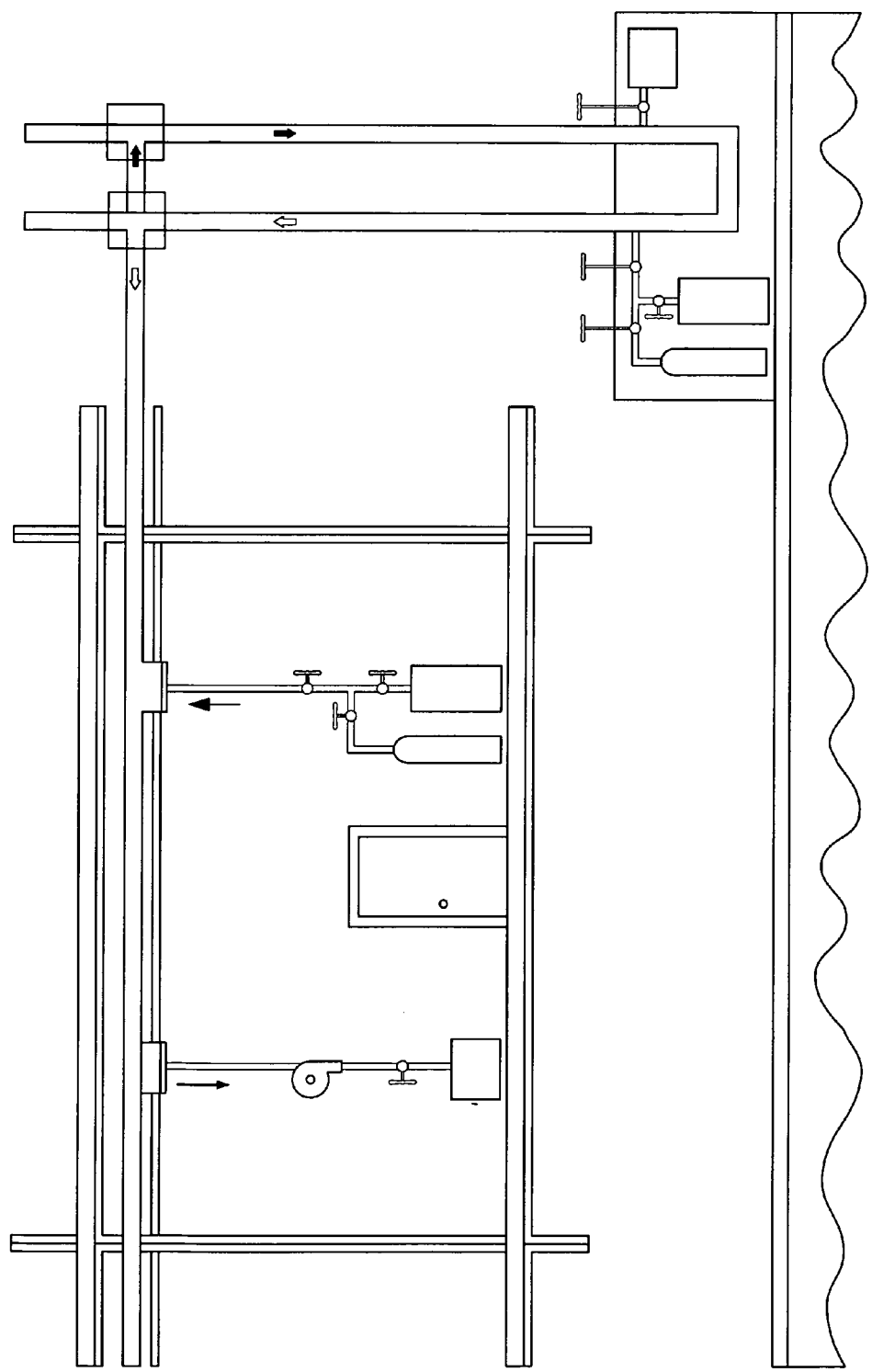
Figure 7G:
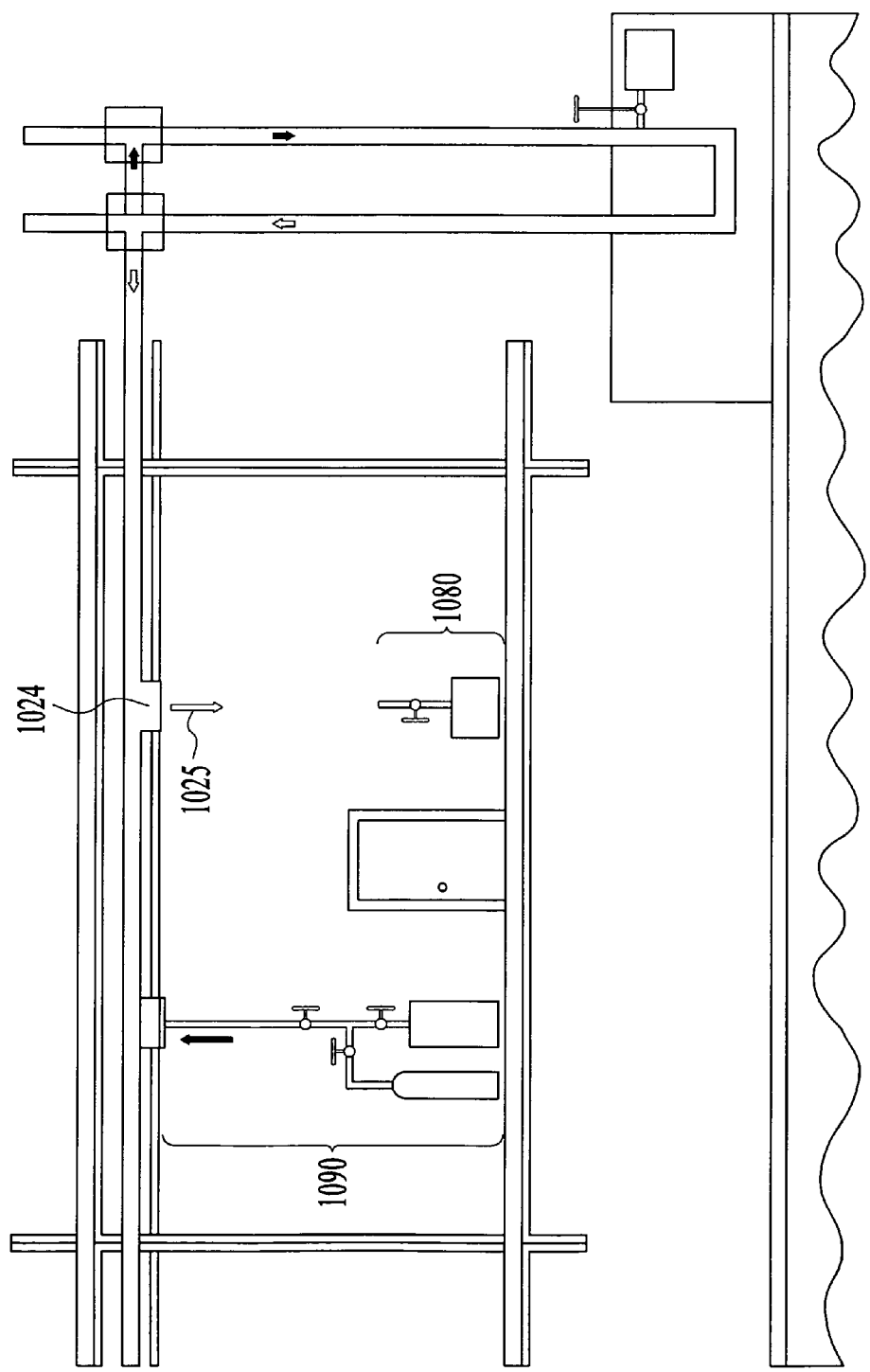
FIGS. 7g are simplified illustrations of alternative embodiments of the present invention shown in FIGS. 7a, except tracer measurement system is not attached to the inlet vent and will sample tracers gases in the room and coming from the inlet vent.
Figure 7H:
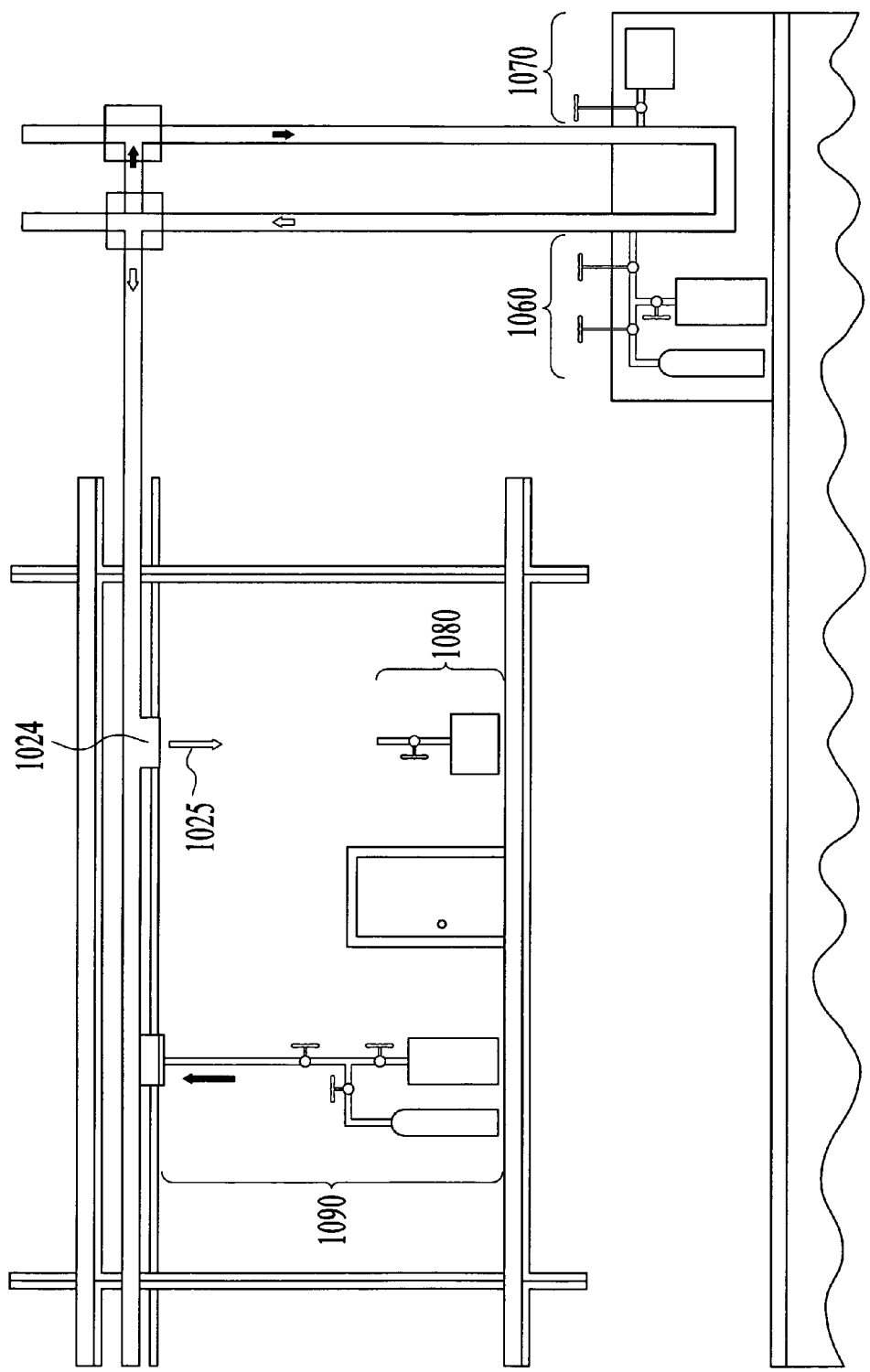
FIGS. 7h are simplified illustrations of alternative embodiments of the present invention shown in FIGS. 7g, except a tracer injection system has been added to the central HVAC unit.

FIG. 6*a* is a simplified illustration of an alternative embodiment of the present invention with a tracer injection system 1090 located in a room 1004 in a building 1000 and attached to a return vent 1034 to inject tracers directly into the return ductwork 1030 of a building through a return vent 1034 and a tracer measurement system 1070 located in a centrally located HVAC unit 1050 to sample the tracer gases coming from all rooms and ductwork 1010 in the building. The tracer injection unit 1090 in FIG. 6*a* is identical to the one 1060 shown in the HVAC unit 1050 in FIG. 2*a* except that a tube 1098 connects the unit 1090 to the return vent 1034 with a cover plate 1099 to channel all of the air coming out of tracer injection unit 1090 into the return ductwork 1030. In FIG. 6*b,* the tracer injection unit 1090 shown in FIG. 6*a* was moved to the inlet vent 1024 to introduce tracer gases into the inlet duct 1020 and the other rooms in the building 1000. The cover plate 1089 is placed over the vent 1024 to insure that all of the tracer goes into the duct 1020. FIG. 6*c* illustrates the use of two injection systems 1090, 1091 in a room to supply tracer to the return ductwork 1030, the inlet ductwork 1020, and the rooms in the building 1000. FIG. 6*d* illustrates a room-based tracer injection unit 1090 that does not include a means of channeling the tracer gases coming out of the tracer injection unit 1090 directly into the return duct 1030. In this application, the tracer injection unit 1090 is simply placed in the room 1004, and the injected gases enter the return duct 1030 with the air 1035 (FIG. 4*a*) that has been circulated throughout the room 1004. This is a fairly inefficient method of injecting tracers into the ductwork, but can be used if the room needs to be interrogated for hazardous substances or if access to a return vent 1034 is not possible, convenient, or safe. FIG. 6*e* adds a second tracer injection unit 1090 to the room 1004 to supply tracer gases to the inlet ductwork 1020. In this case, the tracer injection unit 1090 is attached directly to the inlet vent 1024 so that the tracer gases can be injected into the ductwork. If it were not, the air flow 1025 (FIG. 4*a*) into the room 1004 would prevent the tracer gases from entering the inlet ductwork 1020. FIGS. 6*f*-6*j* are simplified illustrations of alternative embodiments of the present invention shown in FIGS. 6*a*-6*e,* except a tracer injection system 1060 has been added to the central HVAC unit 1050.

FIG. 7 illustrates a tracer injection and measurement system located in a room. It combines the tracer injection unit 1090 illustrated in FIG. 6*a* and the tracer measurement unit 1080 illustrated in FIG. 5*a*. A tracer measurement unit 1070 is included in the central HVAC unit 1050 to sample the tracer gases that were introduced at the return vent 1034 in the room 1004. FIGS. 7*a*-7*h* illustrate the various locations for and combinations of tracer injection and tracer measurement that might be possible.

Figure 8A:
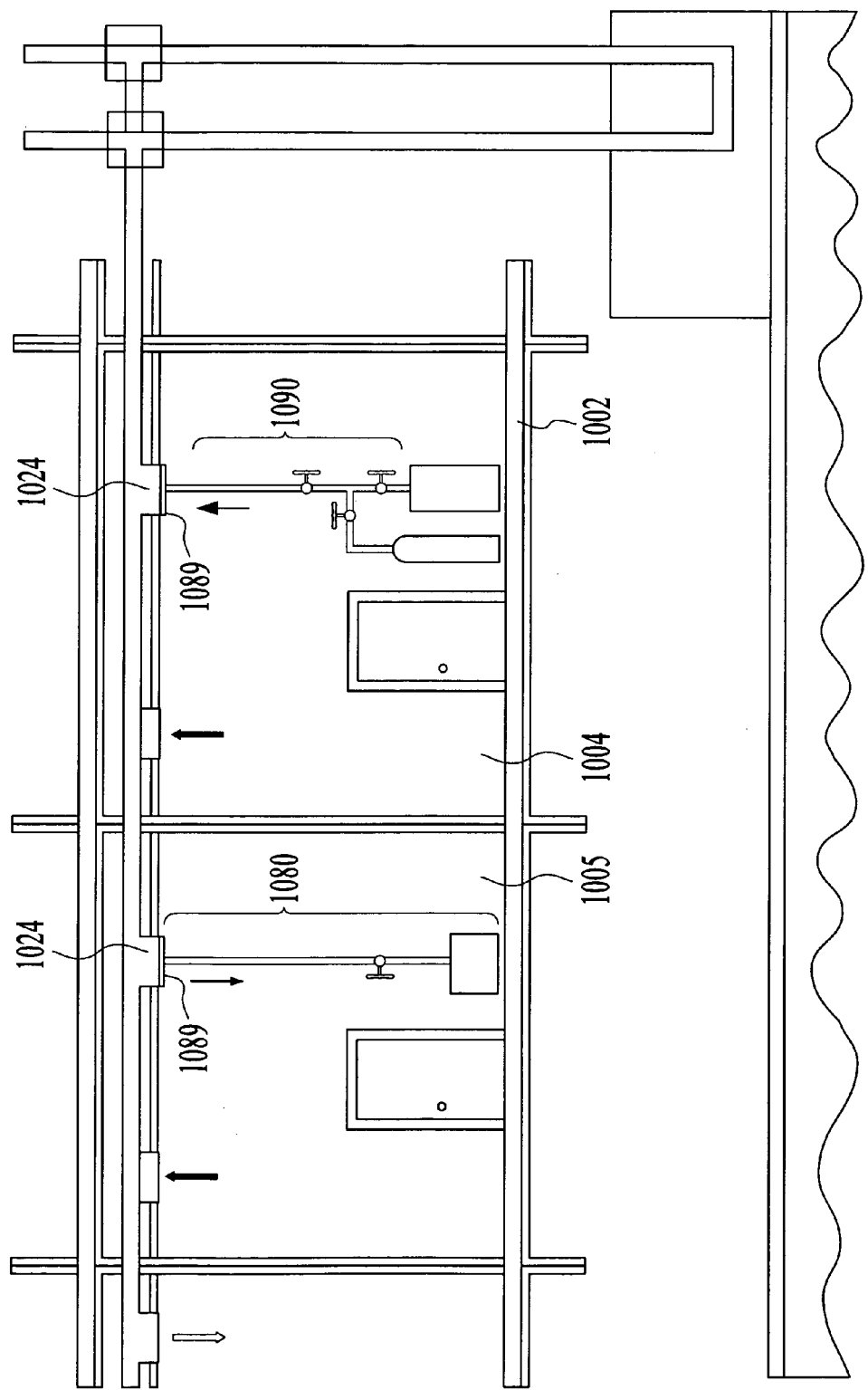
FIG. 8a is a simplified illustration of an alternative embodiment of the present invention with a tracer injection system located in a room in a building and attached to an inlet vent in a room to inject tracers into the inlet ductwork of the building and a tracer measurement system located in another room and attached to an inlet vent to sample the tracer gases coming out of an inlet vent in the second room.
Figure 8B:
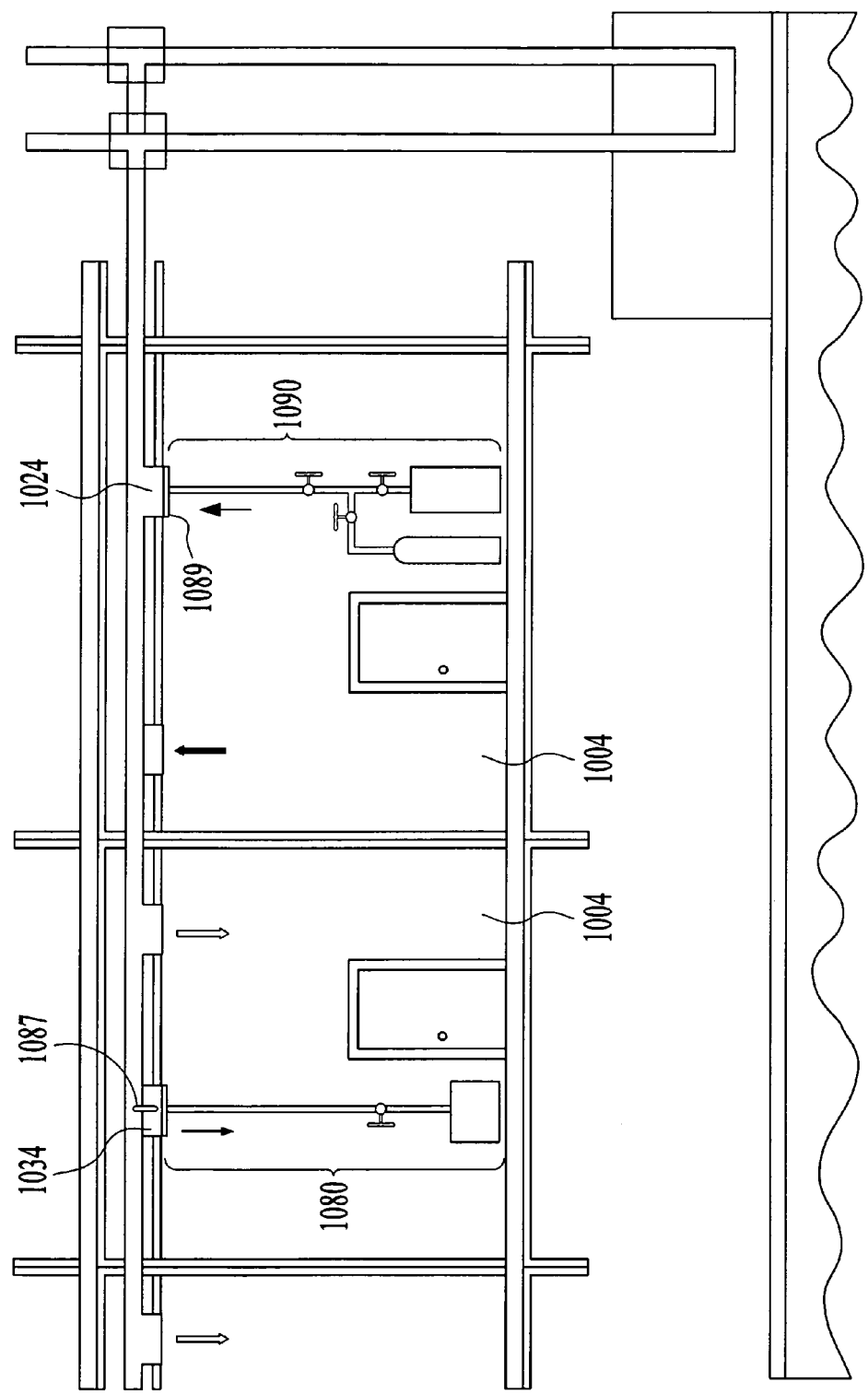
FIG. 8b is a simplified illustration of an alternative embodiment of the present invention with a tracer injection system located in a room in a building and attached to an inlet vent in a room to inject tracers into the inlet ductwork of the building and a tracer measurement system located in another room and attached to a return vent with a conduit sampling means insert into the return ductwork through a return vent in the room to sample the tracer gases in the return ductwork vent in the second room.
Figure 8C:
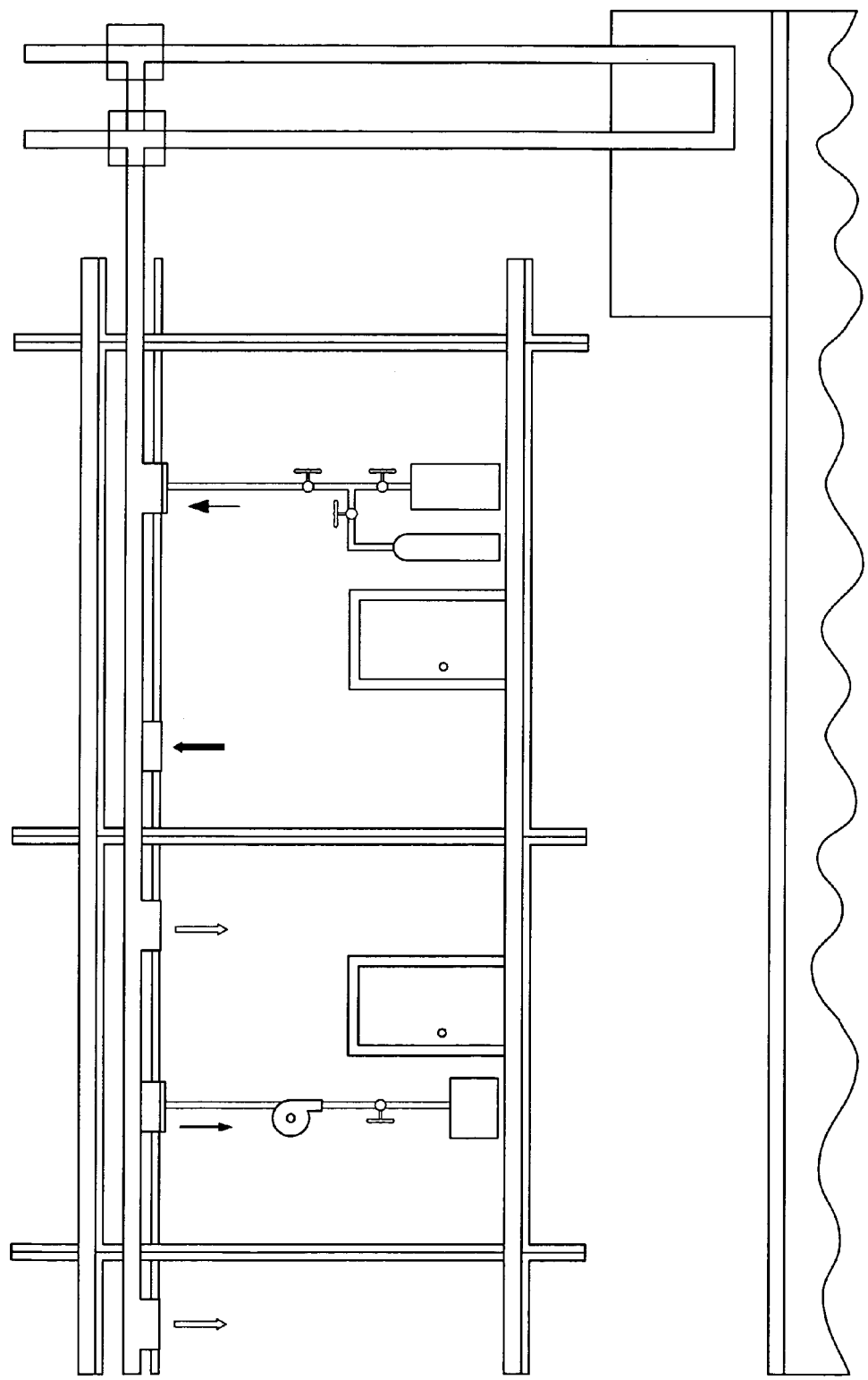
FIG. 8c is a simplified illustration of an alternative embodiment of the present invention with a tracer injection system located in a room in a building and attached to an inlet vent in a room to inject tracers into the inlet ductwork of the building and a tracer measurement system located in another room and attached to a return vent to sample the tracer gases in the return ductwork from that return duct vent in the room using a small pump to pull the gases into the measurement system in the second room.
Figure 8D:
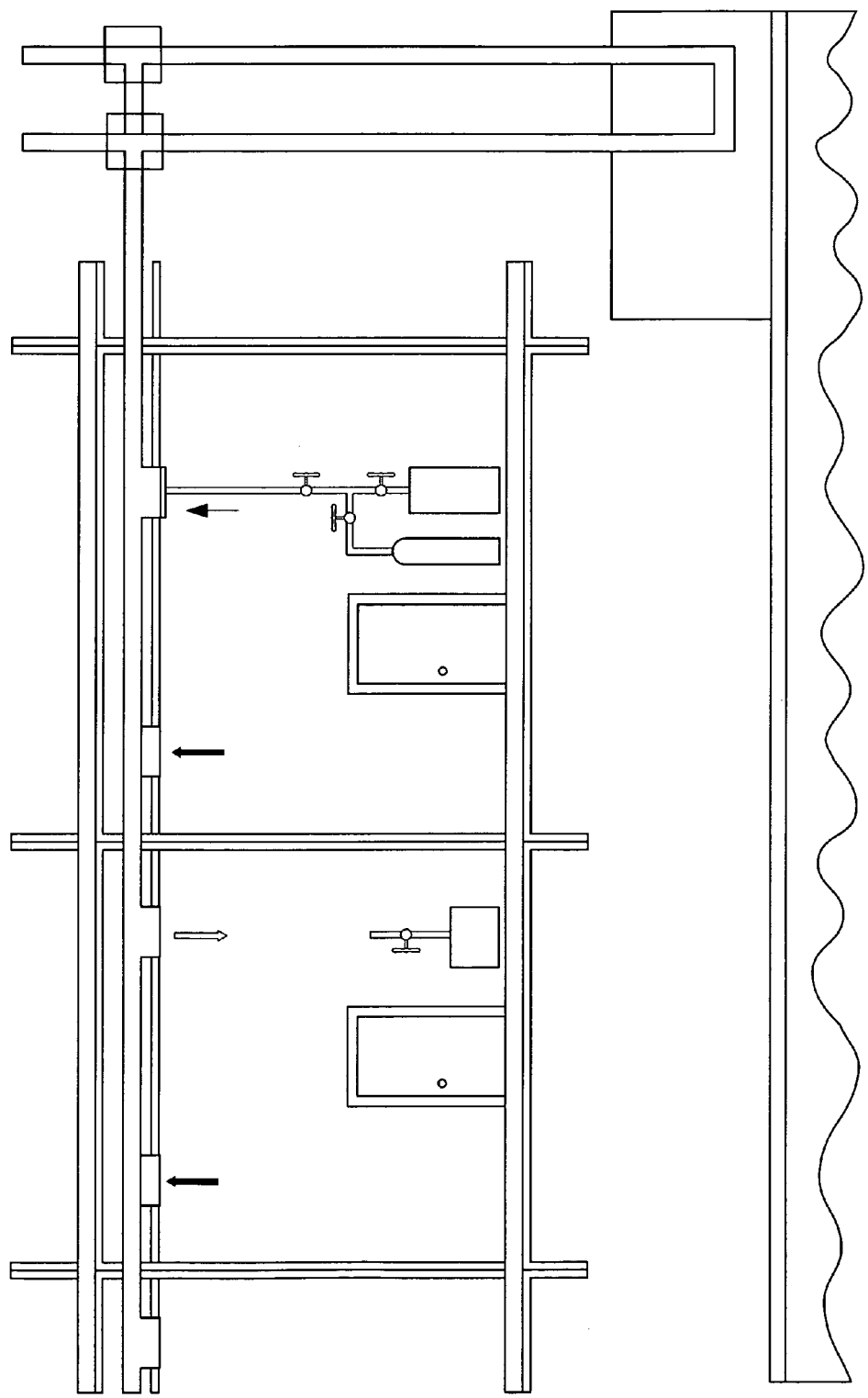
FIG. 8d is a simplified illustration of an alternative embodiment of the present invention shown in FIG. 8a whereby the tracer measurement system in the room is not attached to the inlet vent.
Figure 8E:
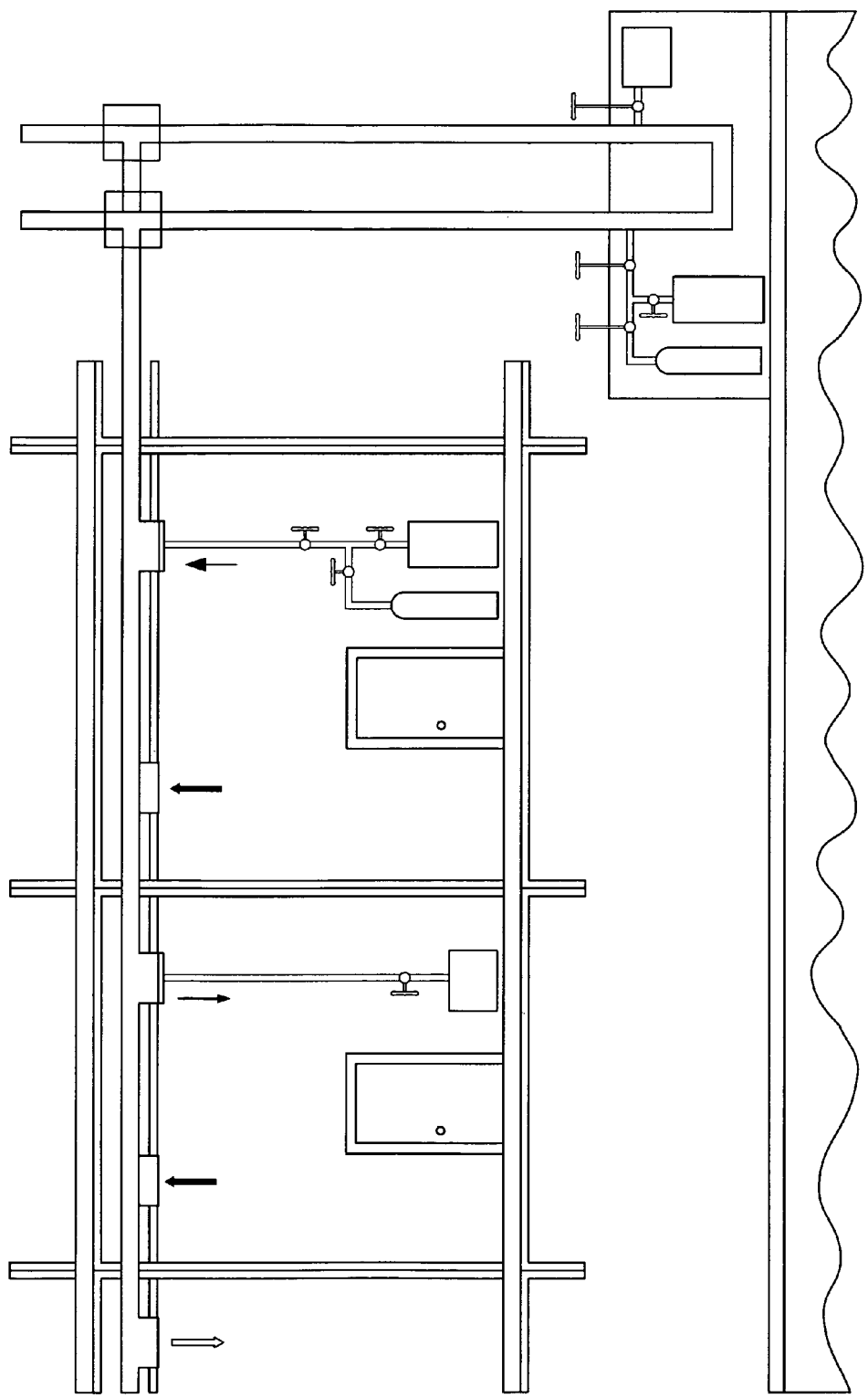
FIGS. 8e-8h are simplified illustrations of alternative embodiments of the present invention shown in FIGS. 8a-8d, except a tracer injection system and a tracer measurement system has been added to the central HVAC unit.
Figure 8F:
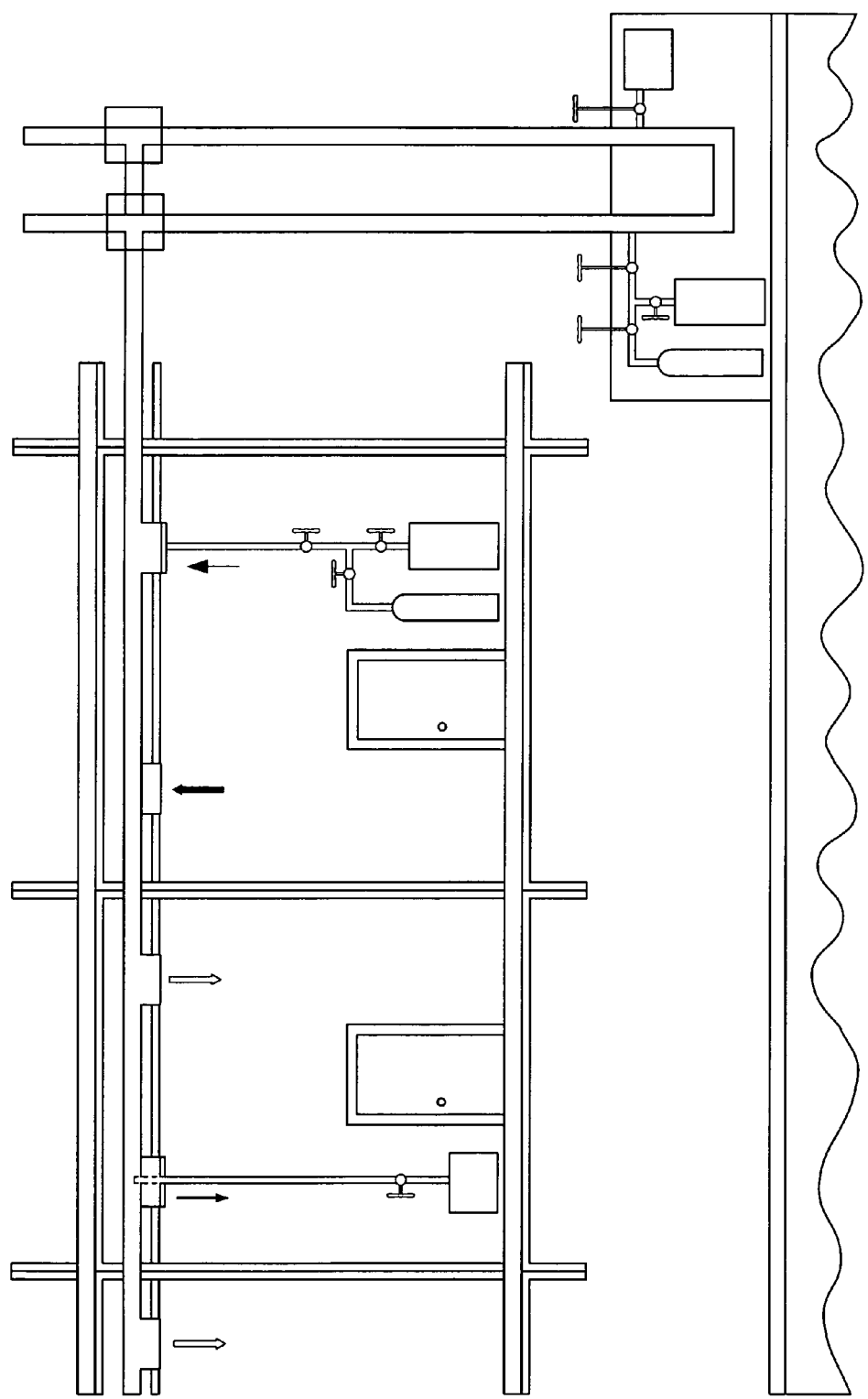
Figure 8G:
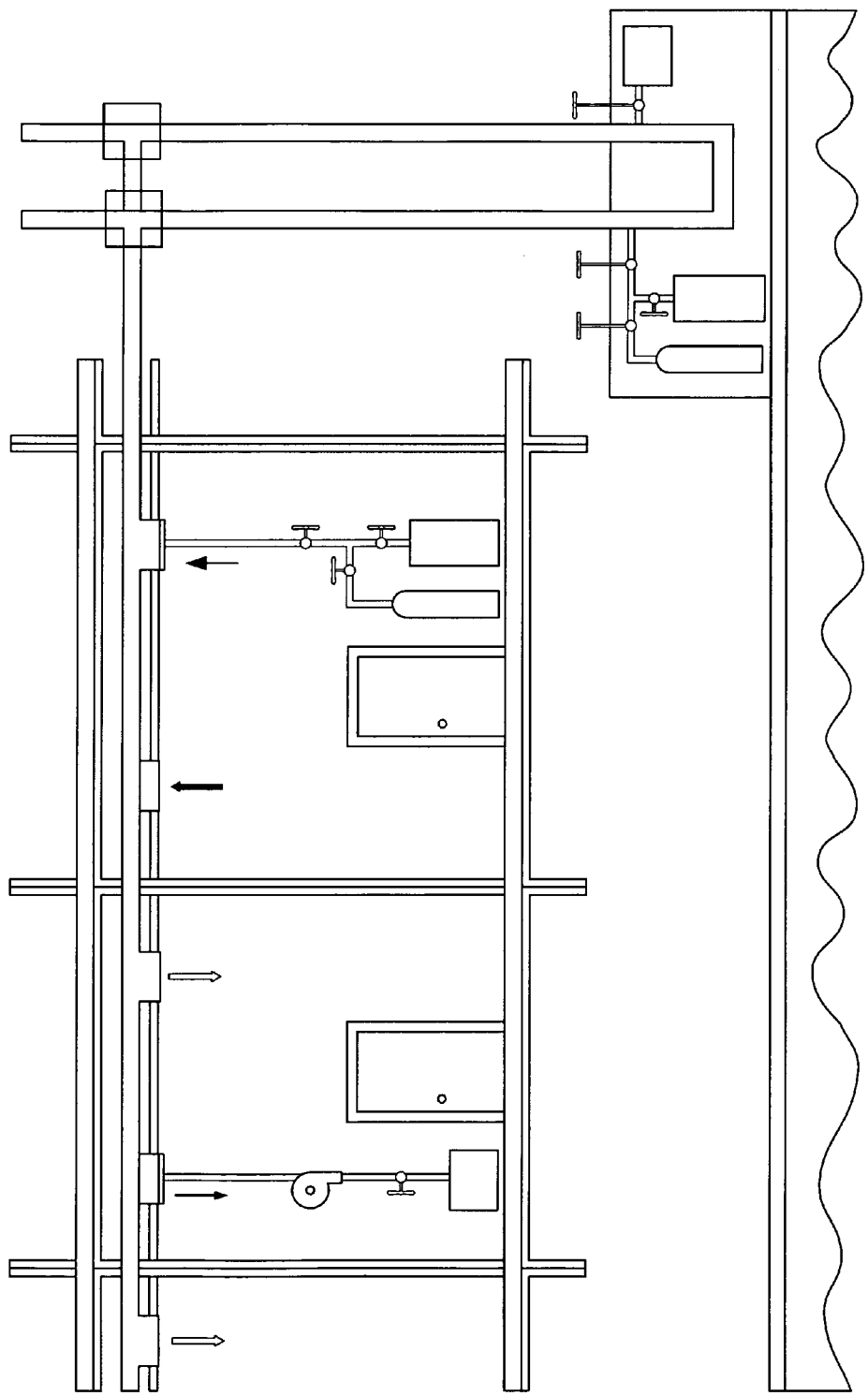
Figure 8H:
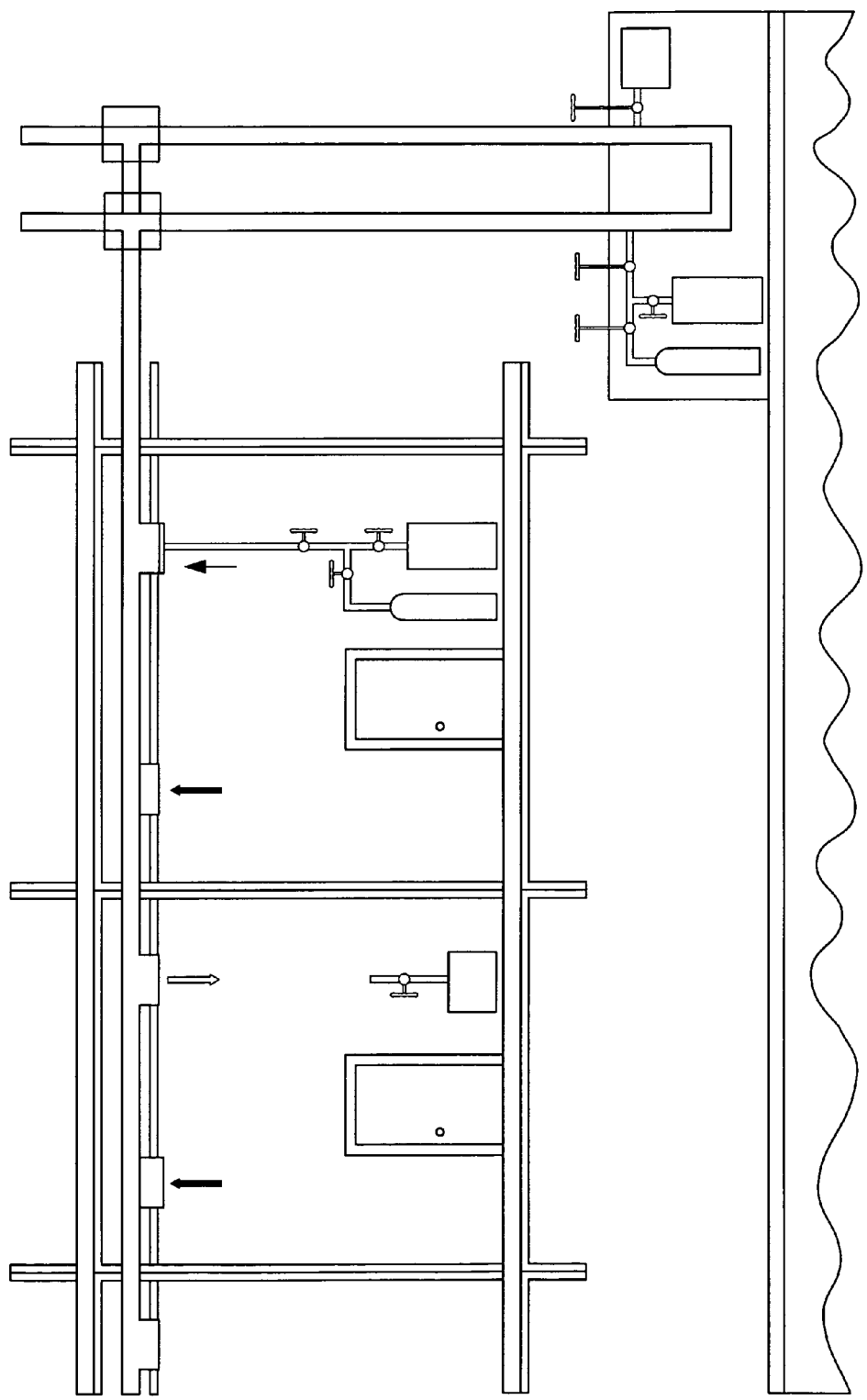
Figure 8I:
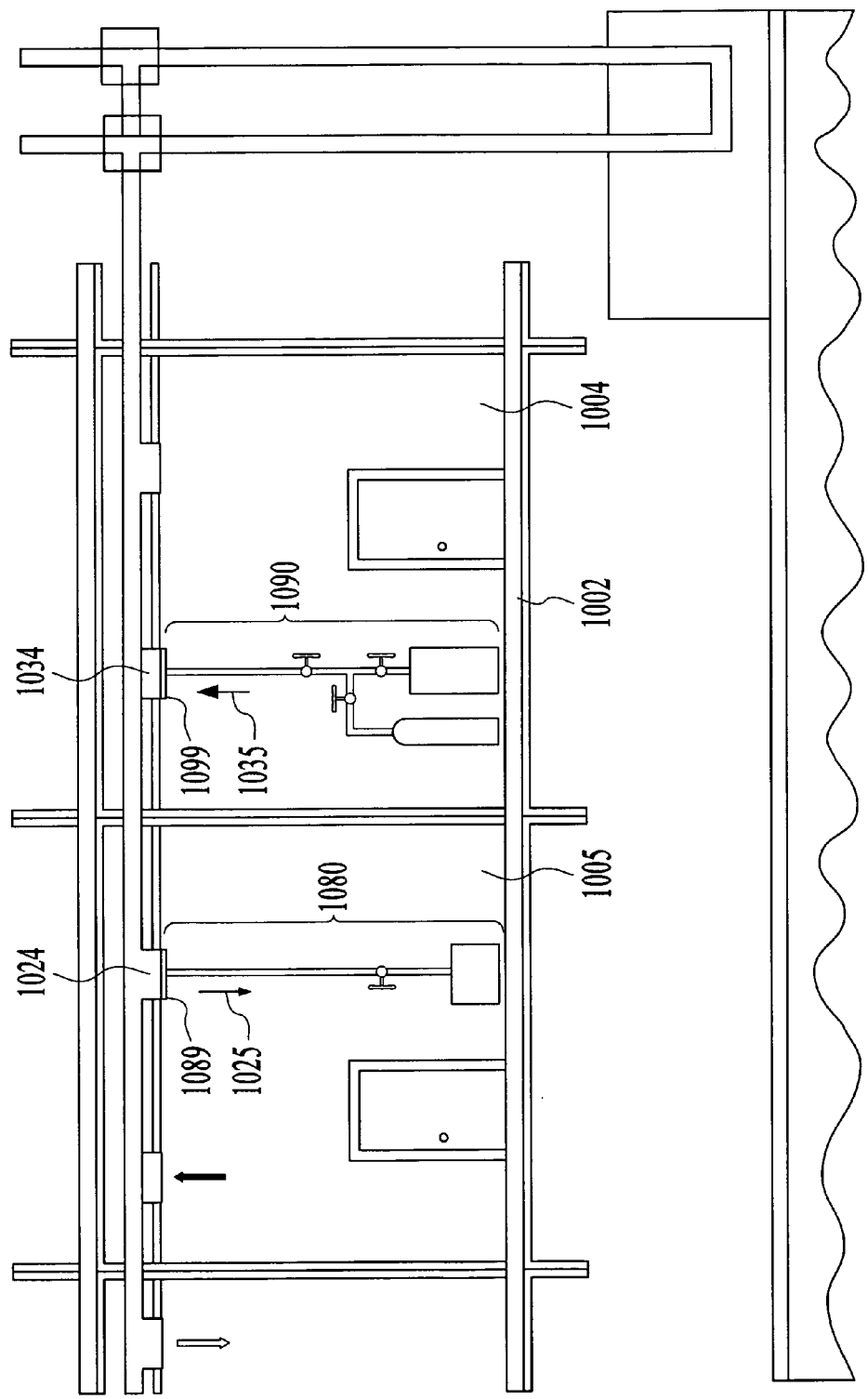
FIGS. 8i-8p are simplified illustrations of alternative embodiments of the present invention shown in FIGS. 8a-8h, except the tracer injection system used to inject tracer gases into the inlet duct in the room these figures has been moved to the return vent to inject racer gases into the return duct.
Figure 8J:
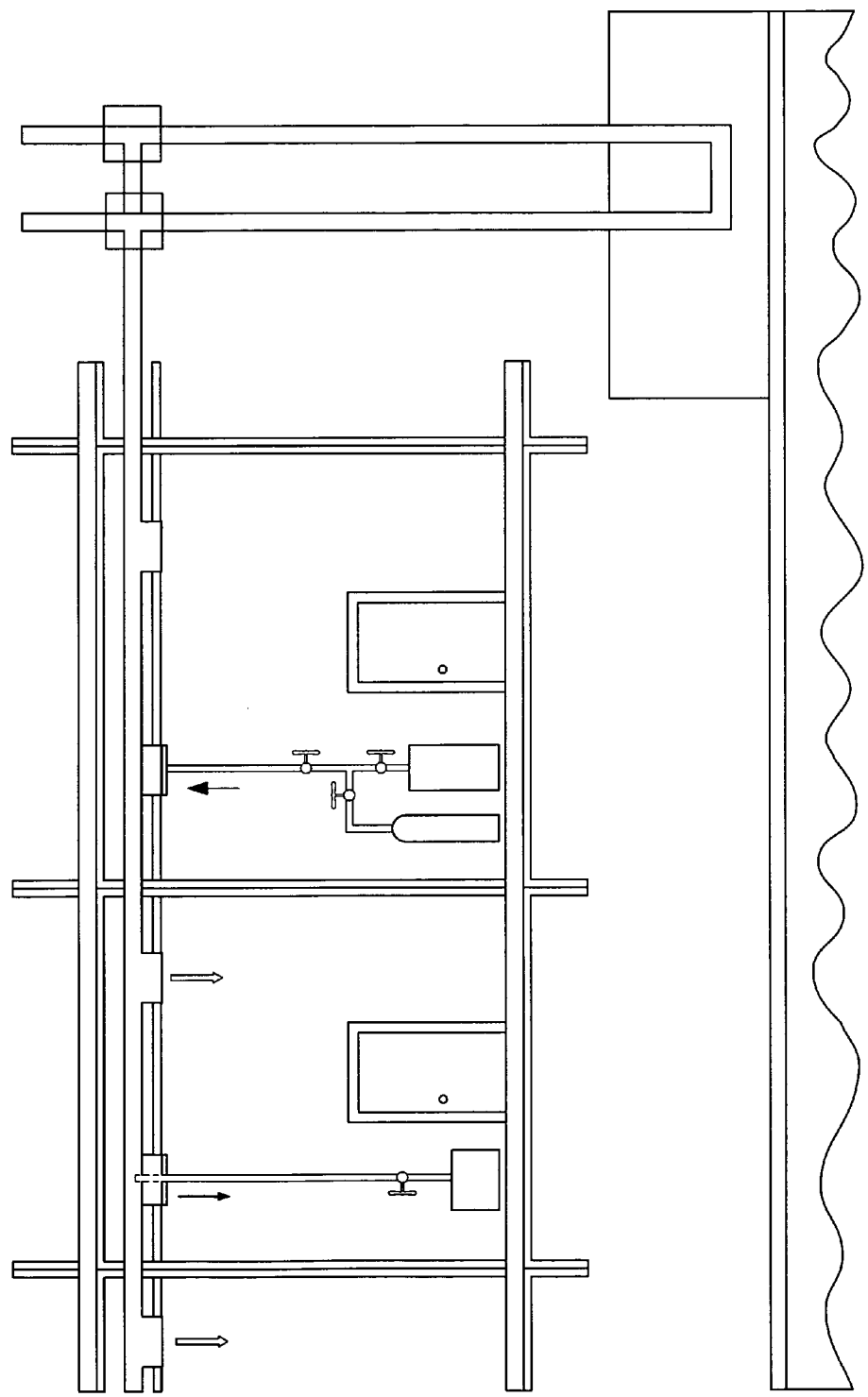
Figure 8K:
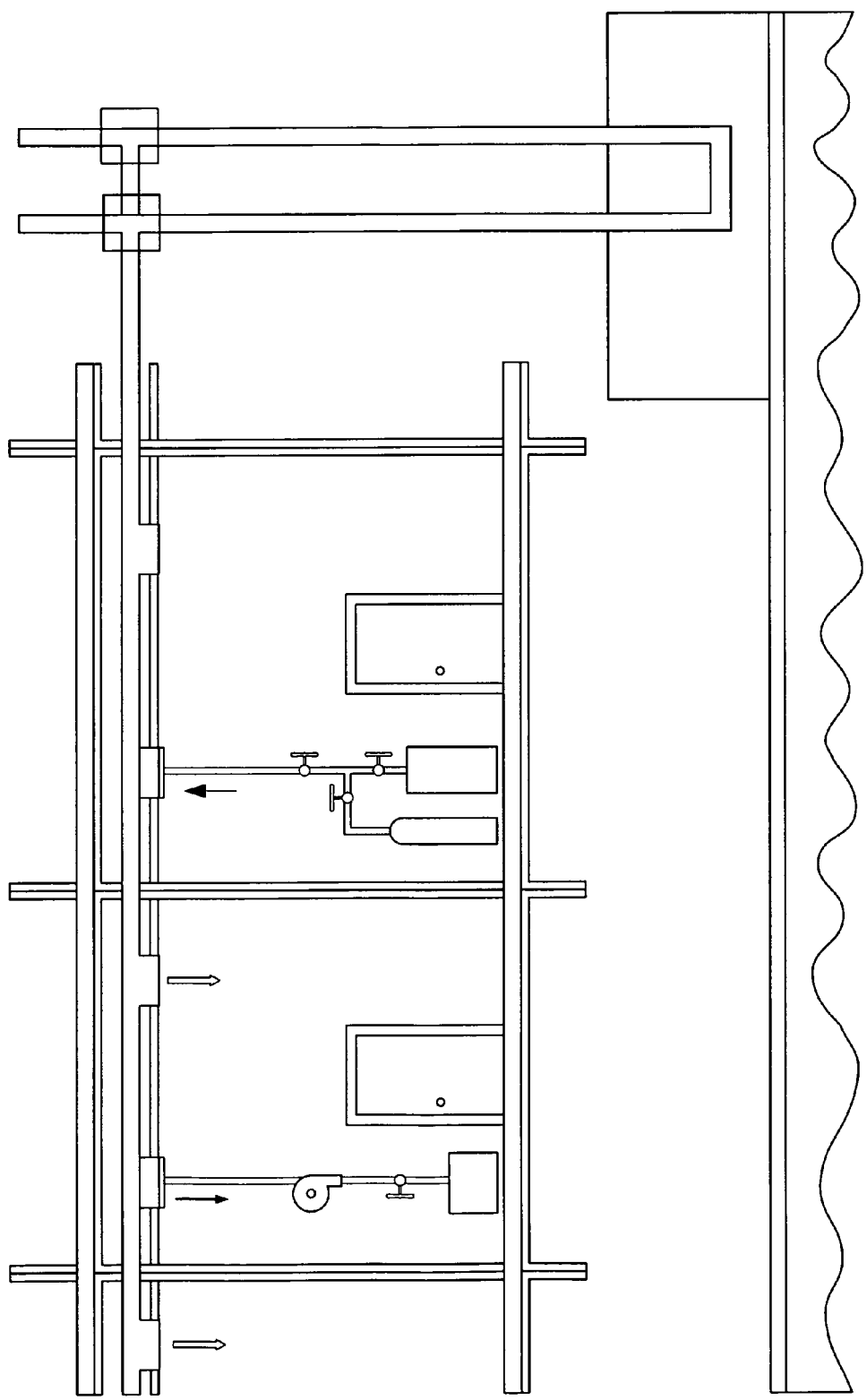
Figure 8X:
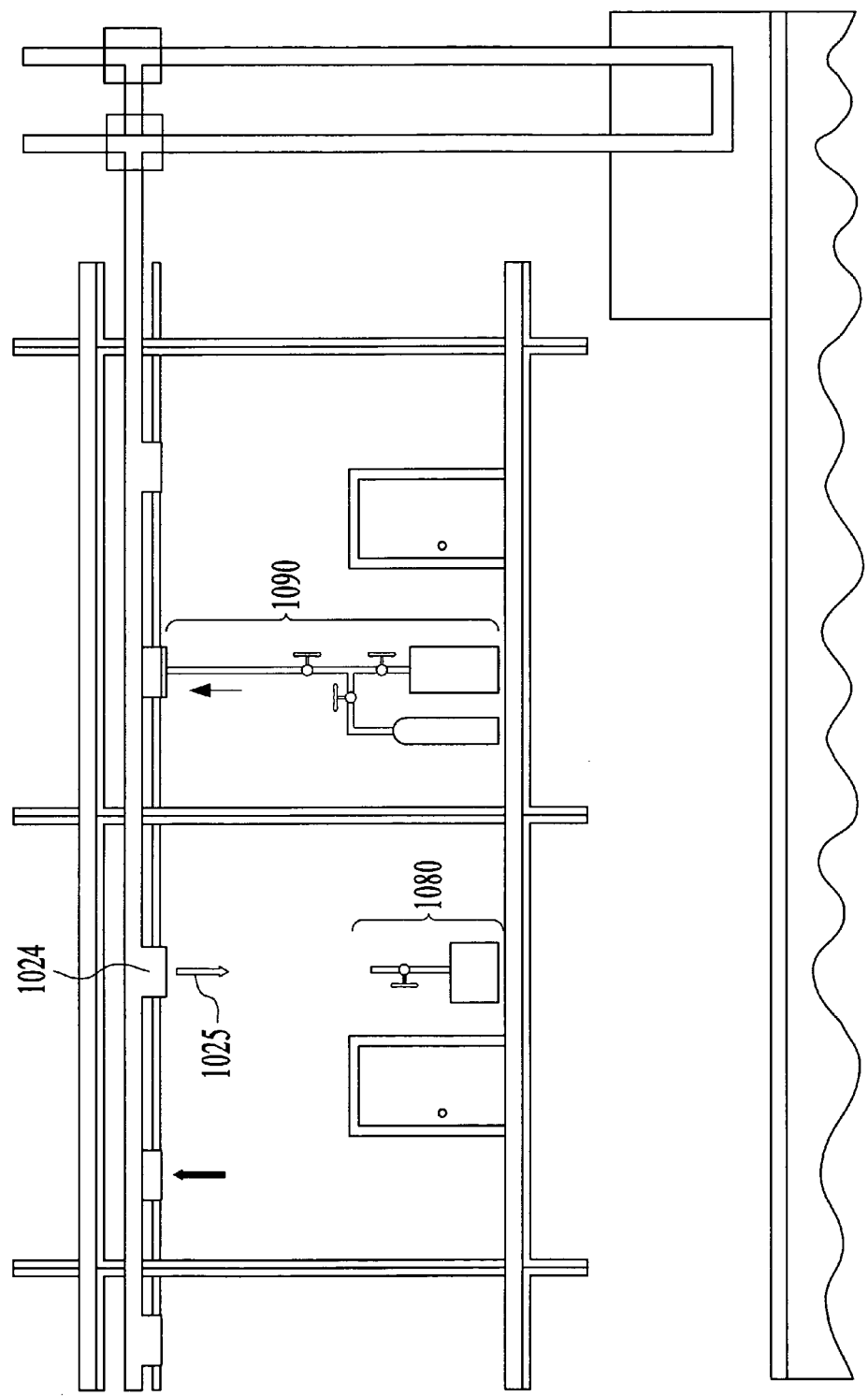
Figure 8M:
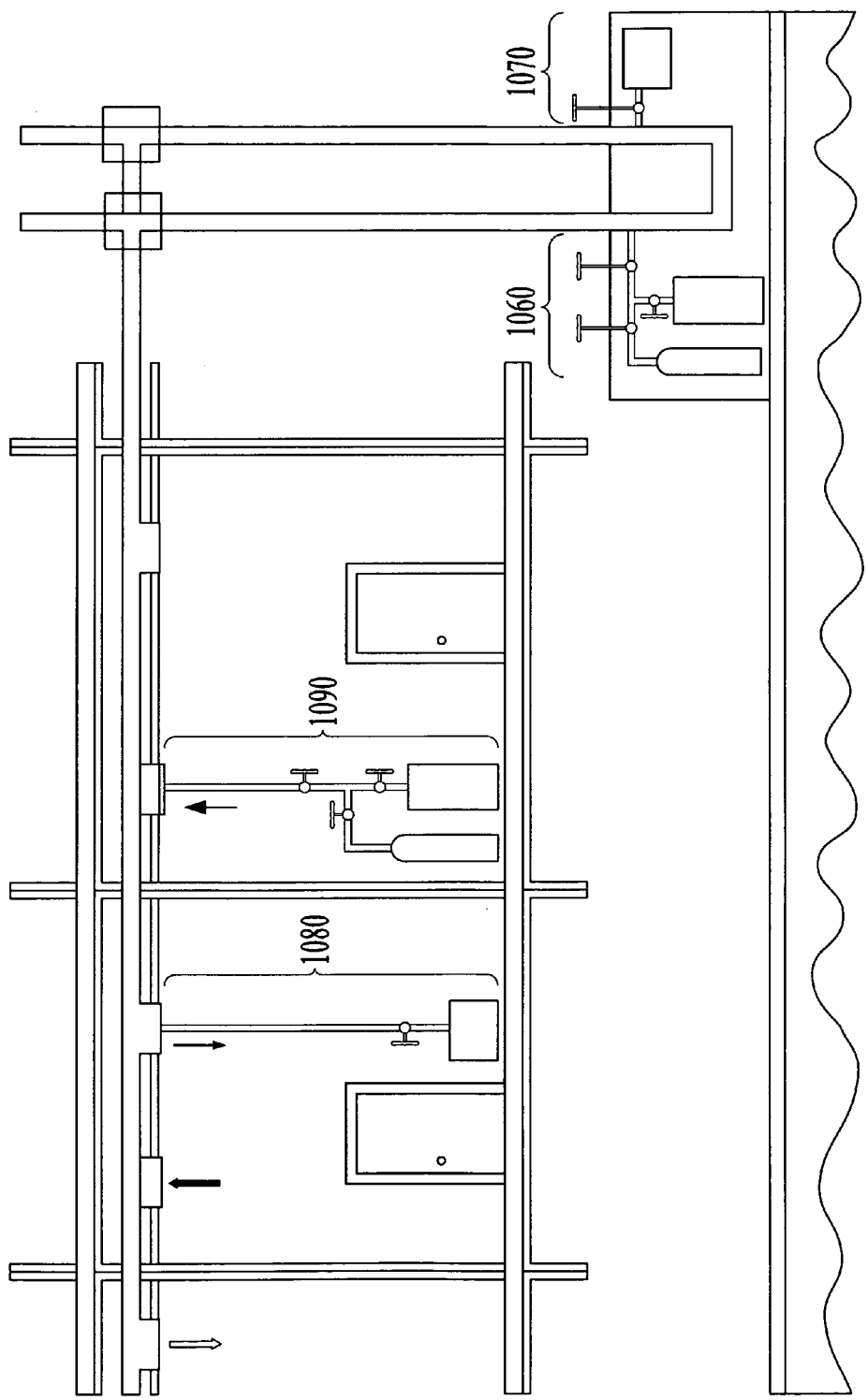
Figure 8N:
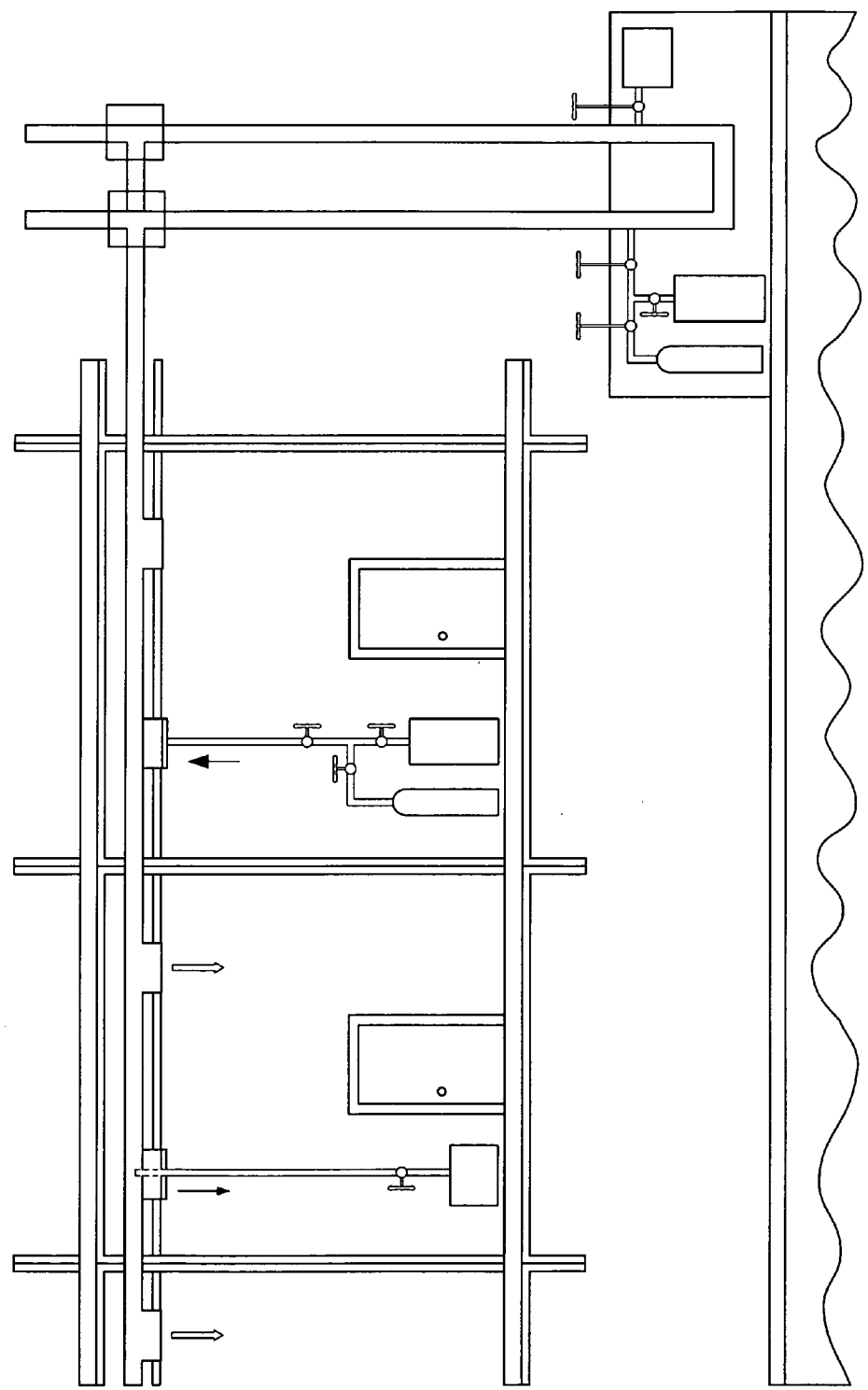
Figure 80:
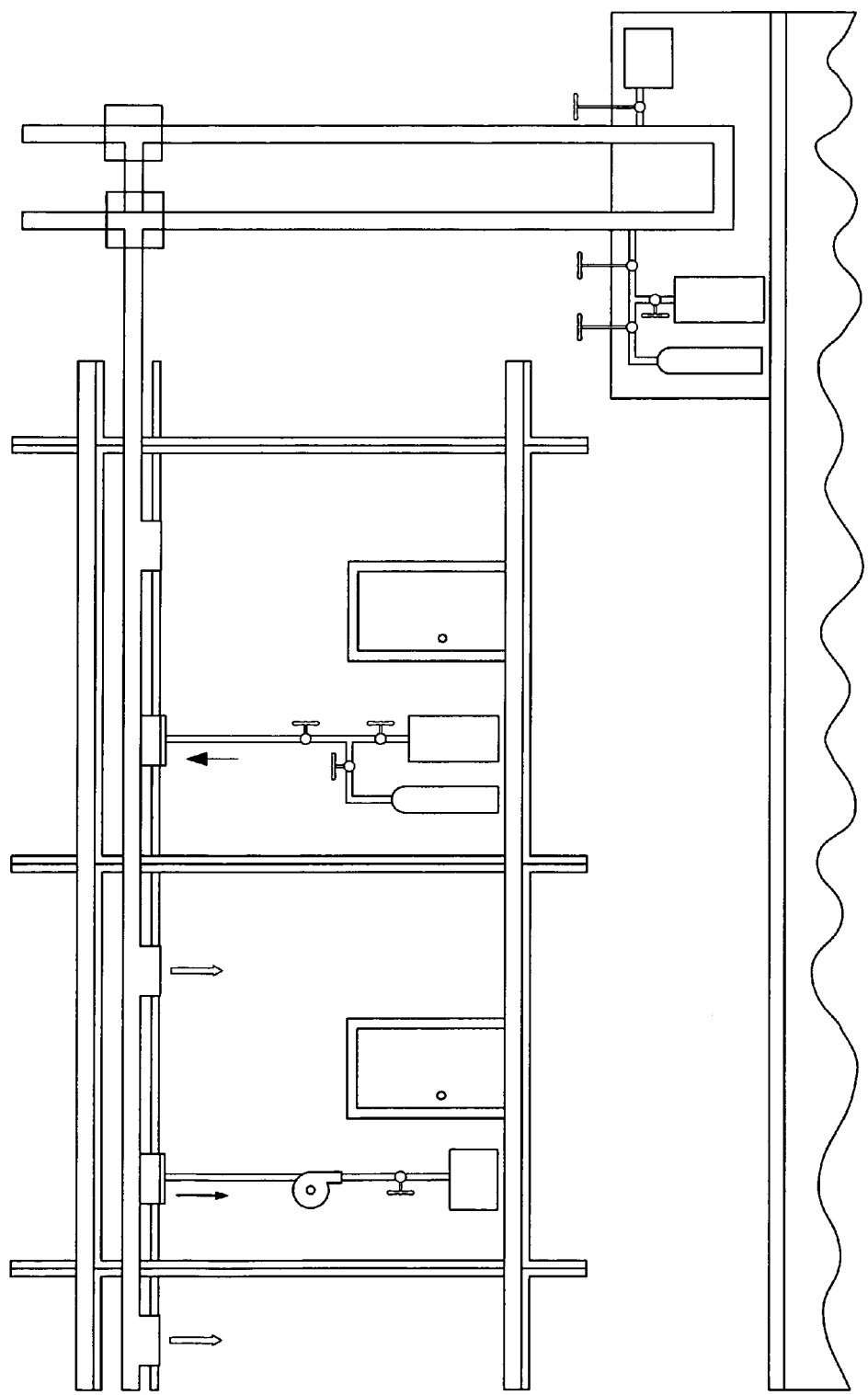
Figure 8P:
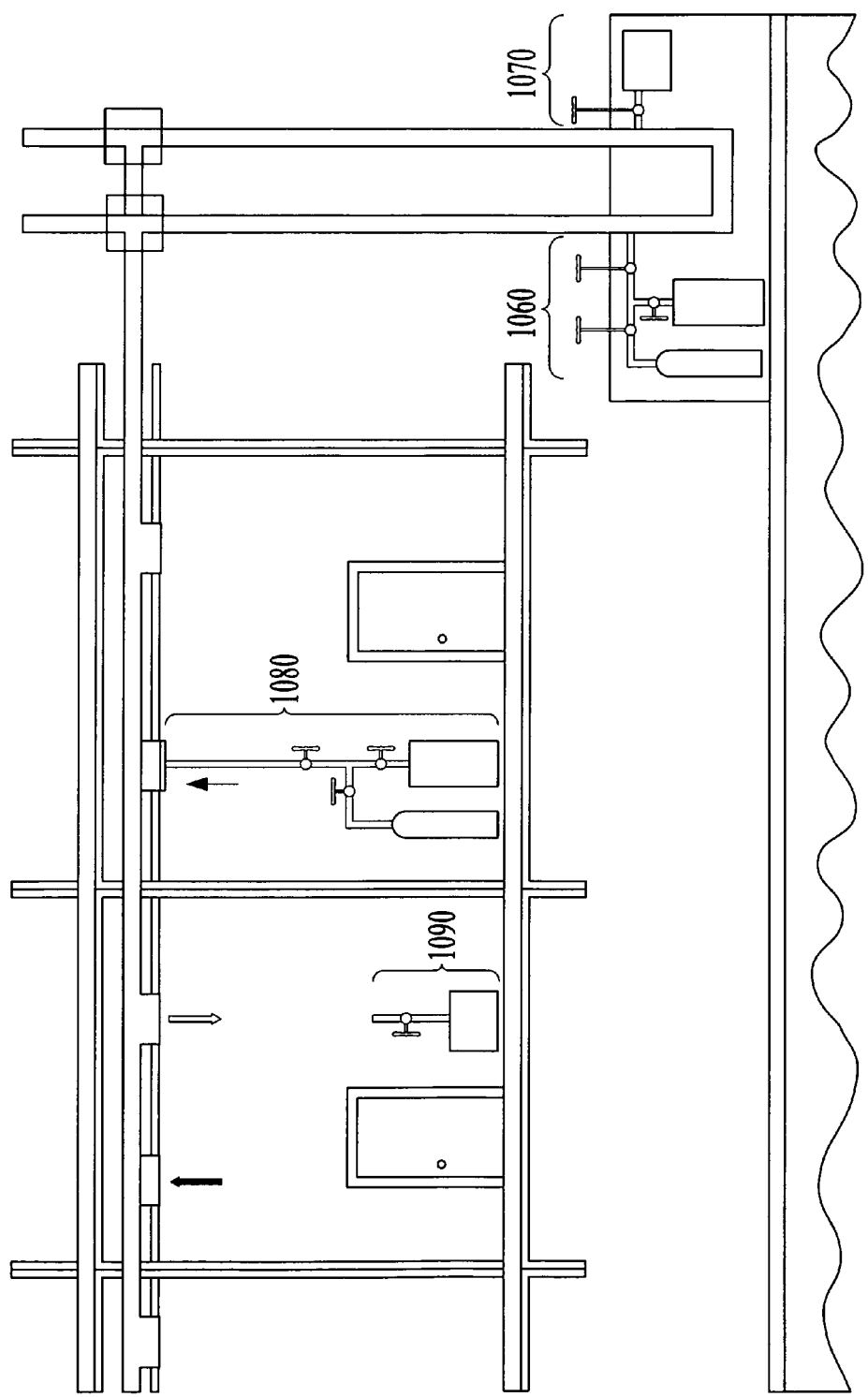

FIGS. 8*a*-8*p* illustrate various alternative embodiments of the method and apparatus of the present invention that are similar to the ones illustrated in FIG. 7. The main difference is that the room-based tracer injection unit 1090 and the room-based tracer measurement unit 1080 are located in different rooms 1004, 1005 in the building 1000. This configuration allows for a room-by-room measurement using a single location for the tracer injection unit 1090.

Figure 9A:
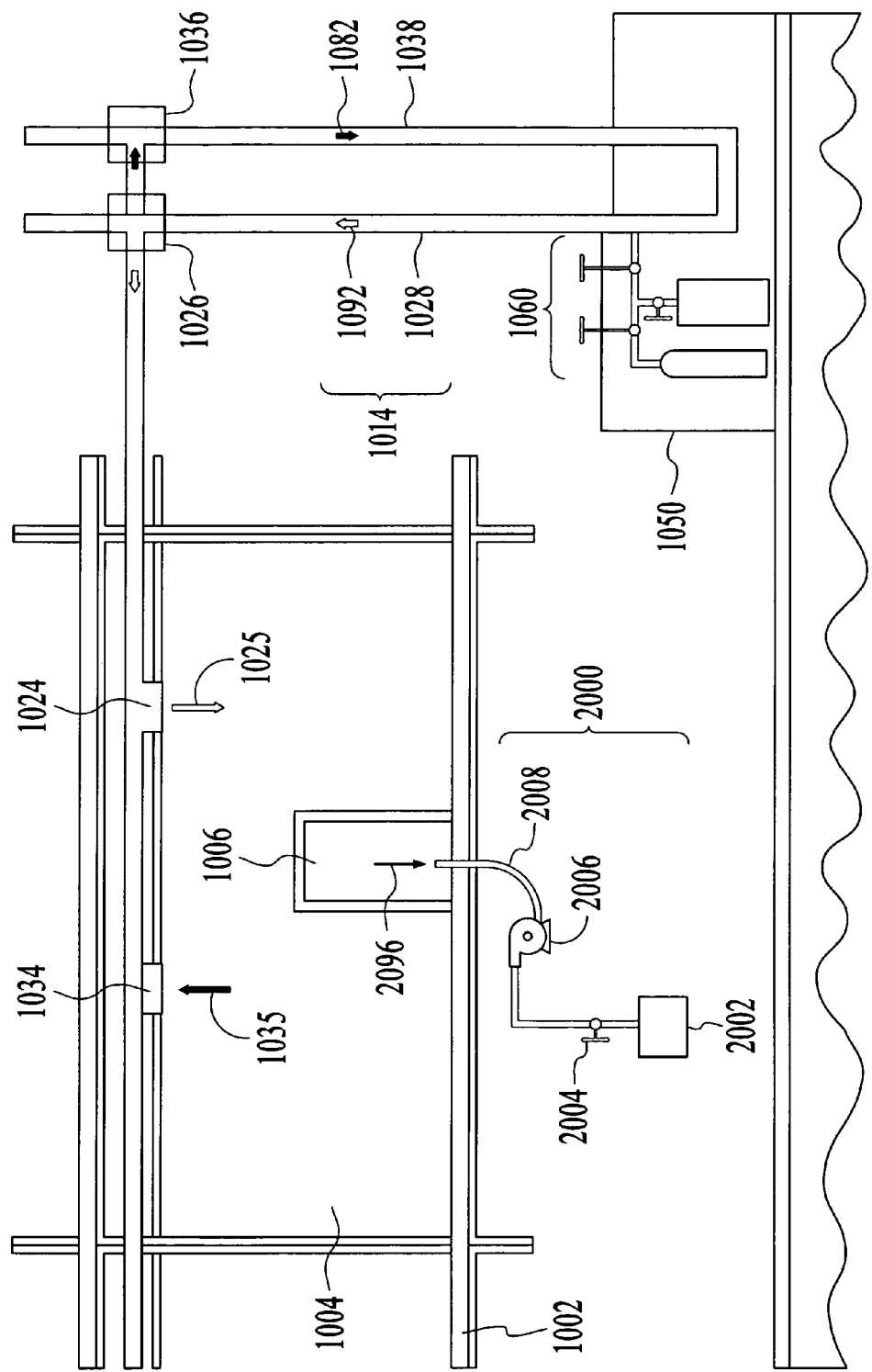
FIG. 9a is a simplified illustration of an alternative embodiment of the present invention with a tracer measurement system located immediately outside and with access to a room in a building to measure tracers in the room that may or may not have come from the ductwork and a tracer injection system located in a centrally located HVAC unit.
Figure 9B:
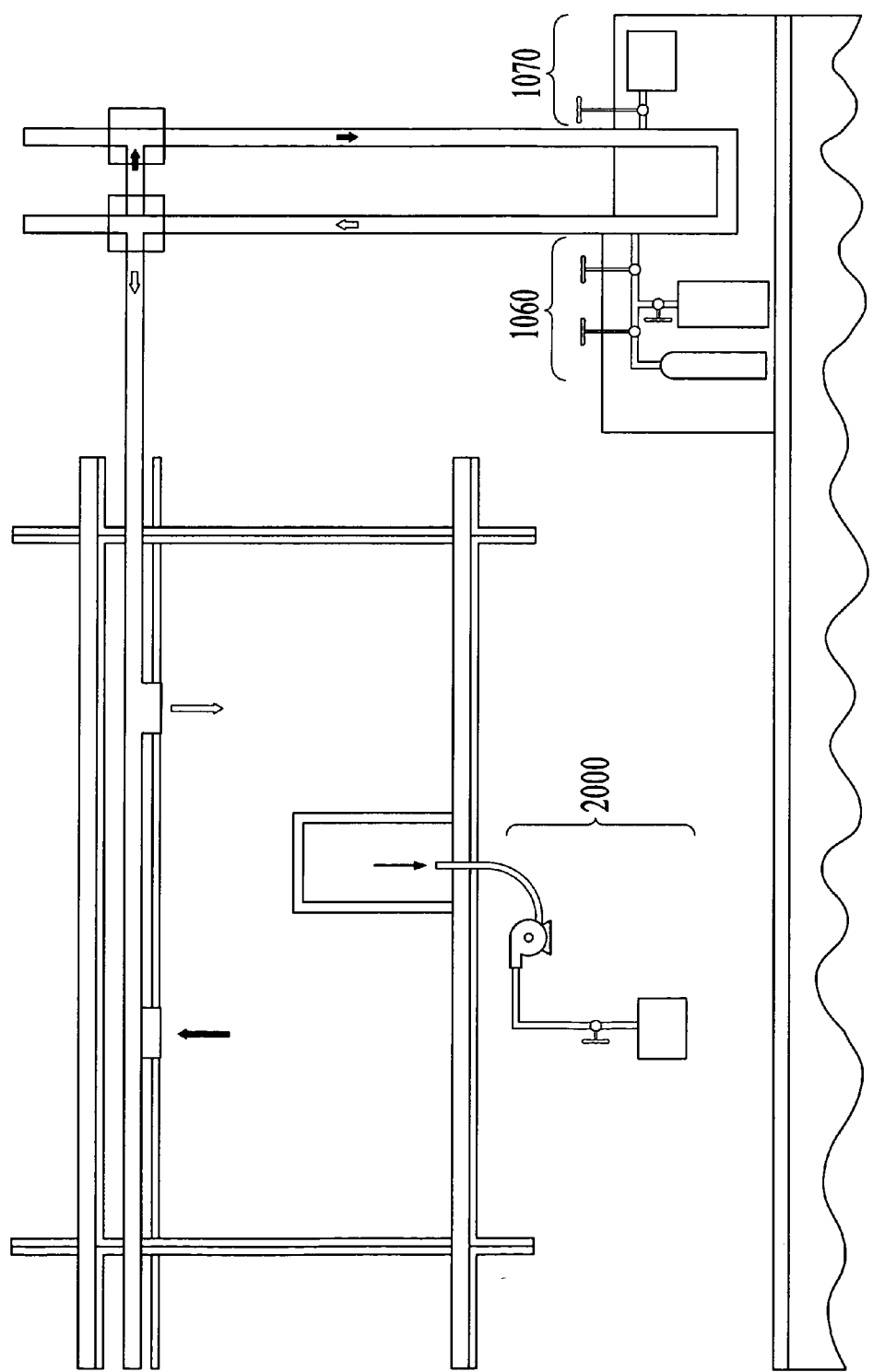
FIG. 9b is a simplified illustration of an alternative embodiment of the present invention shown in FIG. 9a with an additional tracer measurement system located in a centrally located HVAC unit.

FIGS. 9-11 illustrate several embodiments of the method and apparatus of the present invention for detecting the presence of a dangerous or hazardous substance in a room 1004 in a building 1000 (or in the ductwork 1010 in communication with the room) without entering the room 1004 because of safety concerns. FIG. 9a shows a tracer measurement unit 2000 located immediately outside and with access to a room 1004 in a building to measure tracers in the room that may or may not have entered the room from the inlet vent 1024 and a tracer injection unit 1060 located in a centrally located HVAC unit 1050. The tracer measurement unit 2000 is comprised of a vacuum pump unit 2006 that pulls the air 2096 from the room 1004 through a hose or conduit 2008 at an access point such as the door 1006. The valve 2004 and the tracer measurement unit 2002 are identical to the units previously described, for example, in FIG. 4a. FIG. 9b shows an embodiment of the system shown in FIG. 9a except an additional tracer measurement unit 1070 has been added at the central HVAC unit 1050.

Figure 10A:
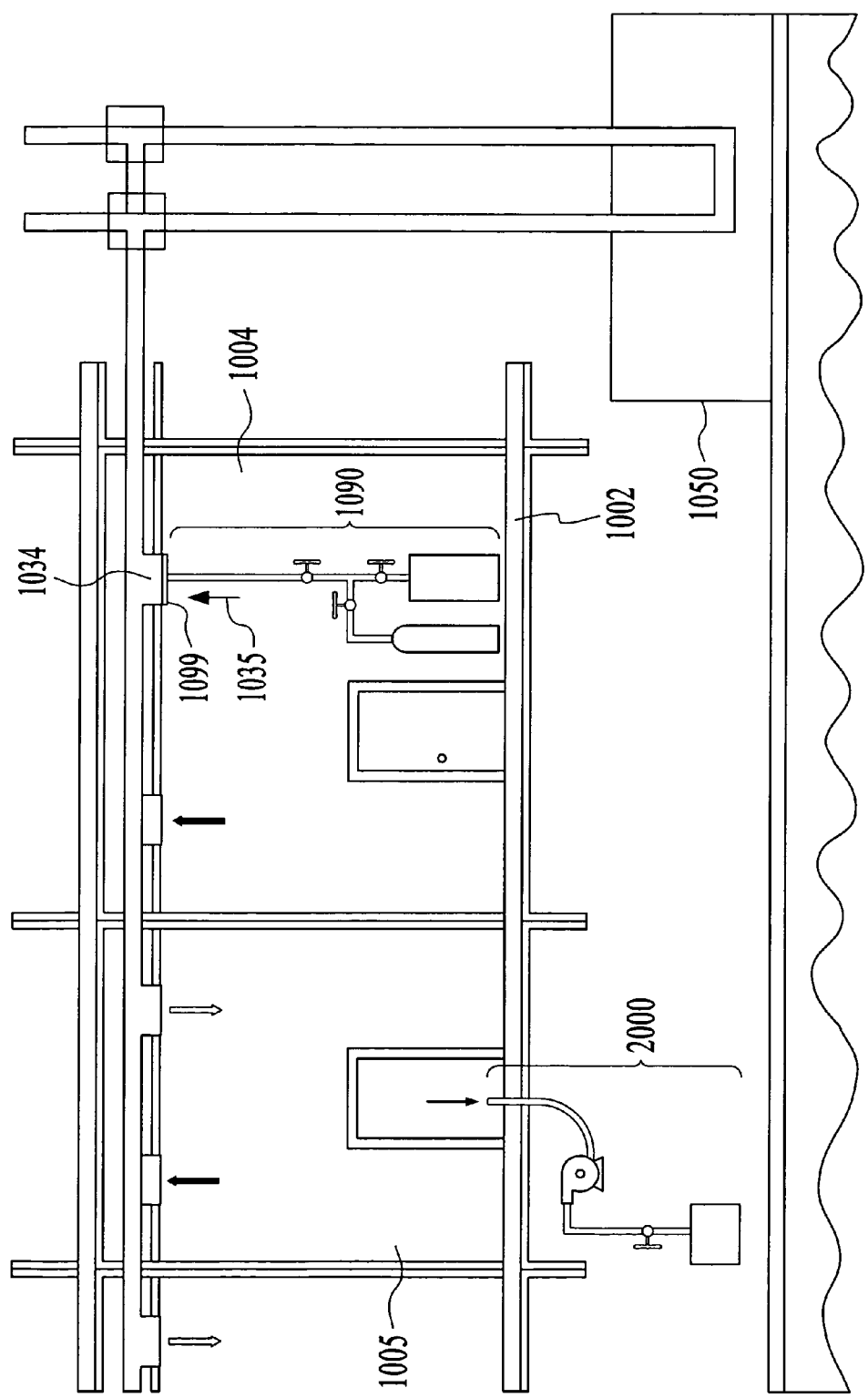
FIG. 10a is a simplified illustration of an alternative embodiment of the present invention with a tracer injection system located in one room in a building to inject tracers into the ductwork of the building and a tracer measurement system located immediately outside and with access to another room in the building to measure tracers in the room that may or may not have come from the ductwork.
Figure 10B:
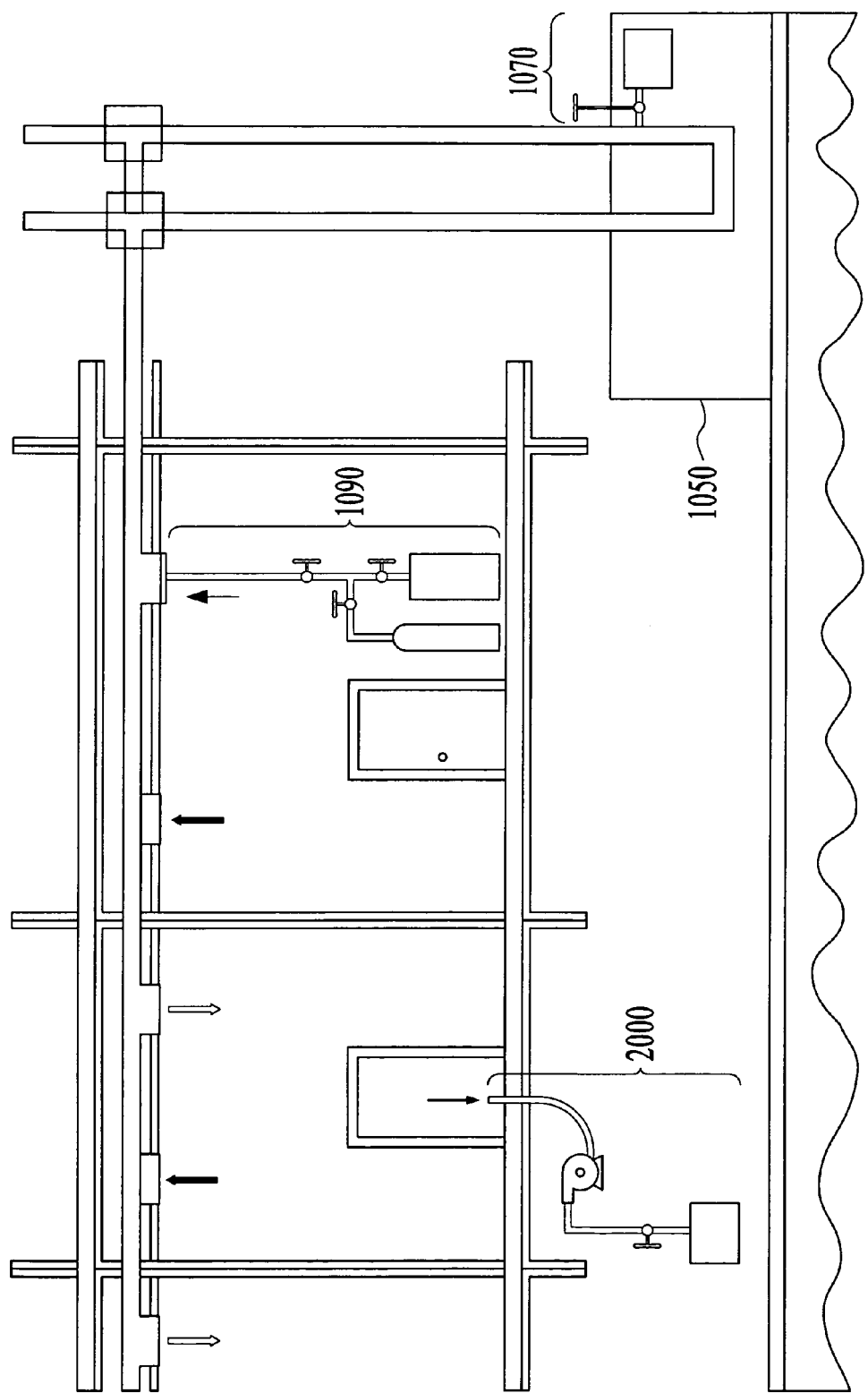
FIG. 10b is a simplified illustration of an alternative embodiment of the present invention illustrated in FIG. 10a with an additional tracer measurement system added to in a centrally located HVAC unit.
Figure 10C:
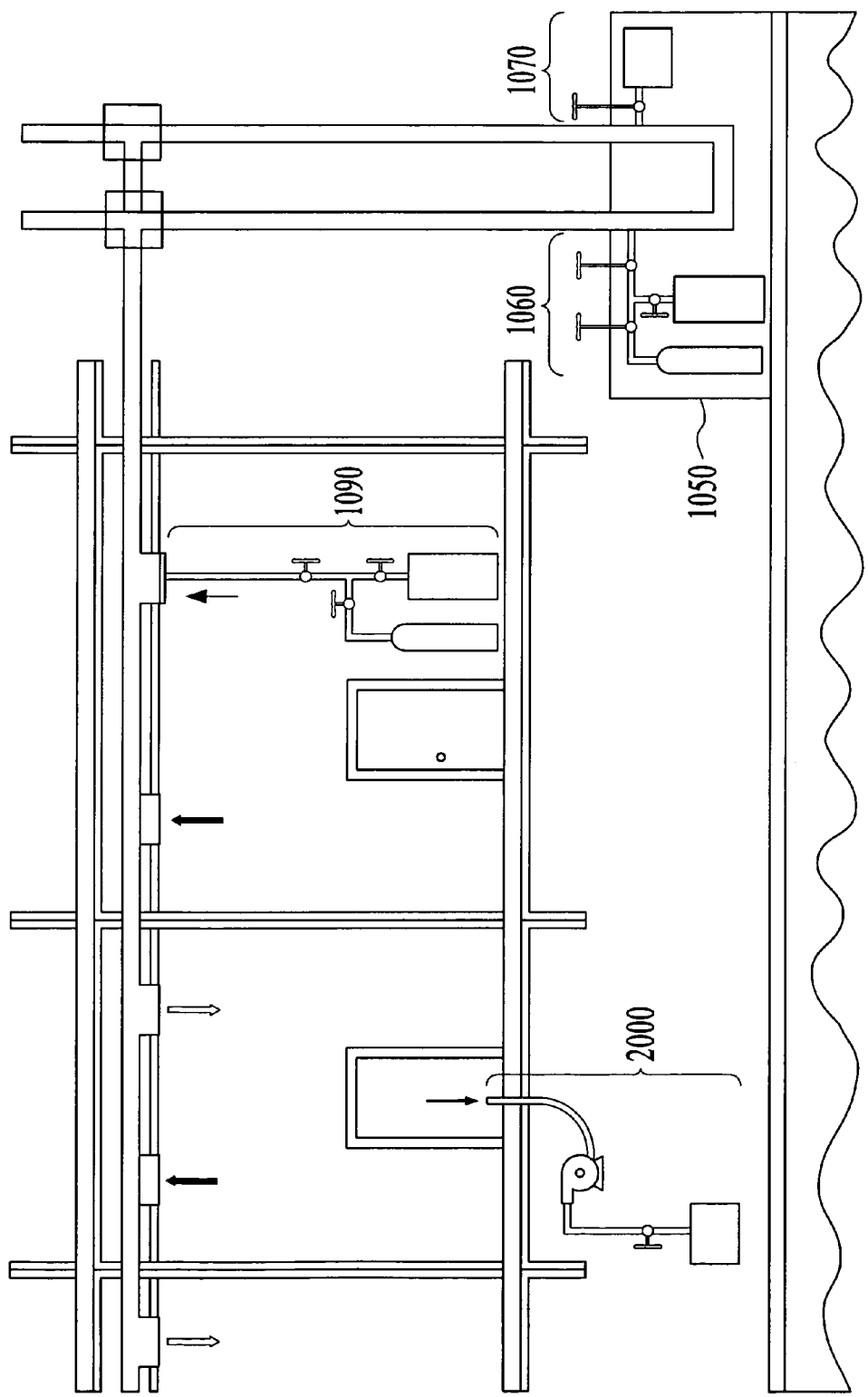
FIG. 10c is a simplified illustration of an alternative embodiment of the present invention illustrated in FIG. 10b with a tracer injection system added to a centrally located HVAC unit.
Figure 10D:
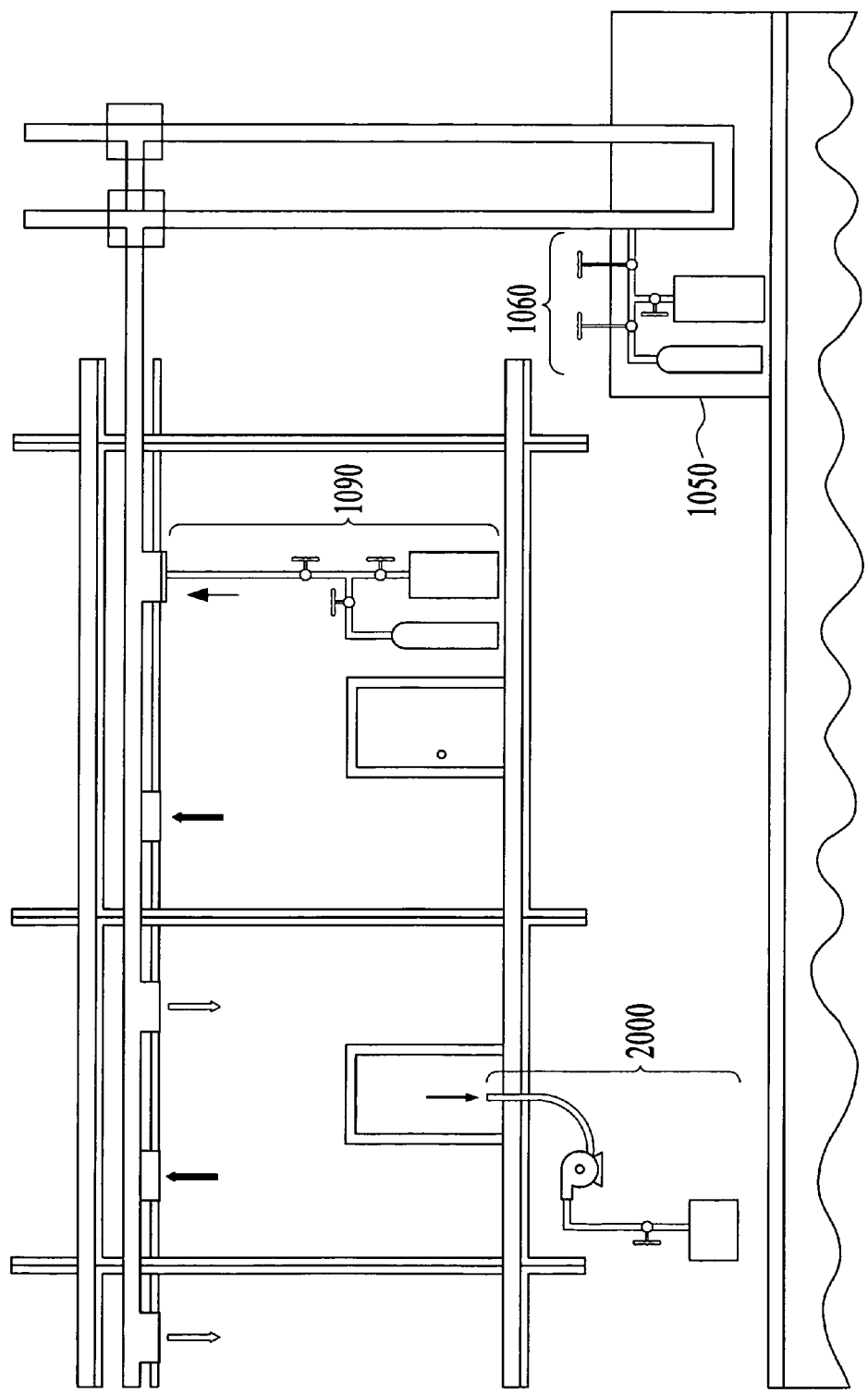
FIG. 10d is a simplified illustration of an alternative embodiment of the present invention illustrated in FIG. 10a with a tracer injection system added to a centrally located HVAC unit.

FIG. 10 illustrates another embodiment of the tracer injection and measurement system shown in FIG. 9, except a tracer injection unit 1090 has been added to an adjacent room (FIG. 10a) and also combined with a tracer injection unit at the HVAC unit 1050 (FIG. 10b-10d).

Figure 11A:
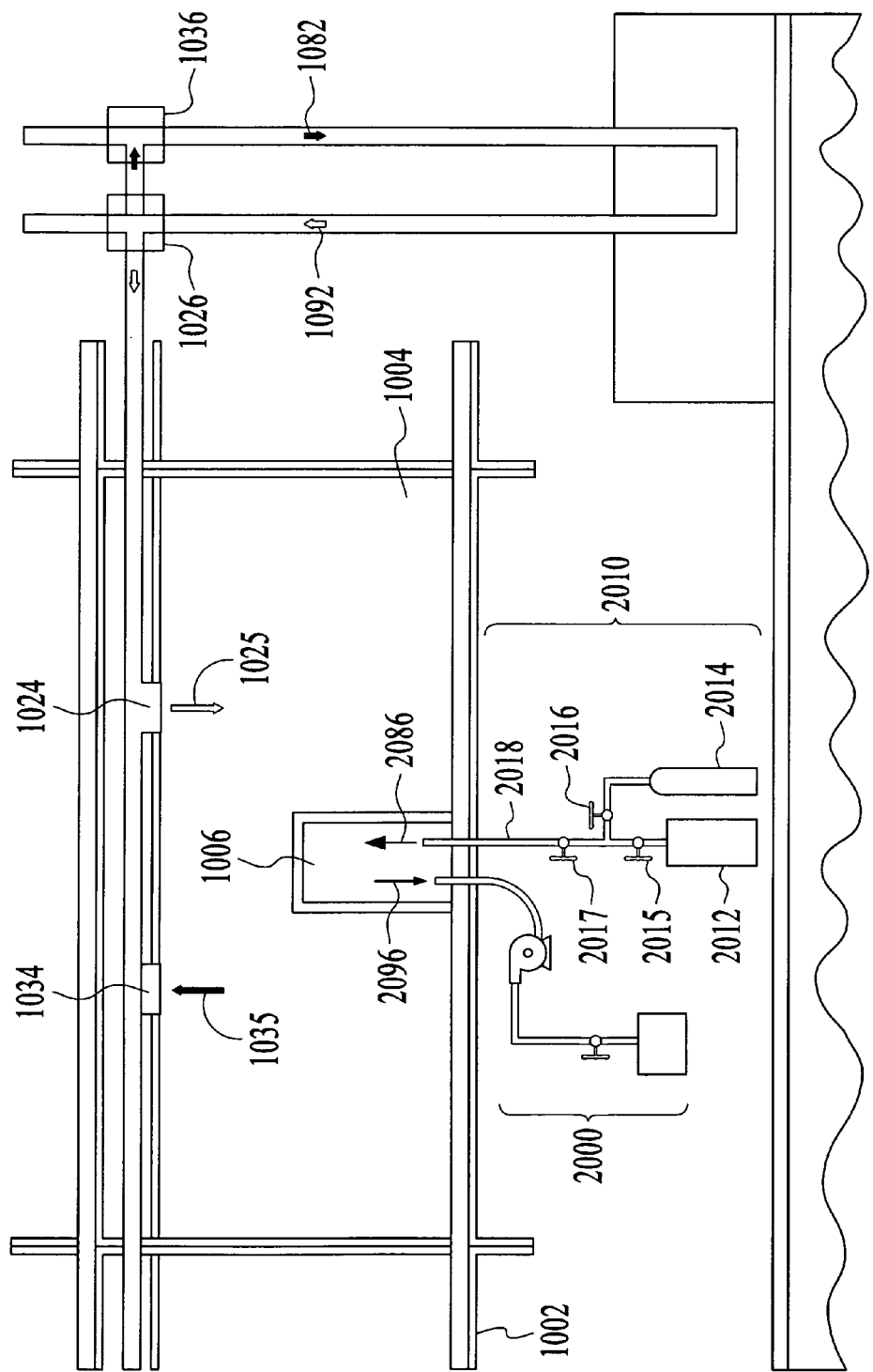
FIG. 11a is a simplified illustration of an alternative embodiment of the present invention with a tracer injection and measurement system located immediately outside and with access to a room in a building to inject and measure tracers in the room.
Figure 11B:
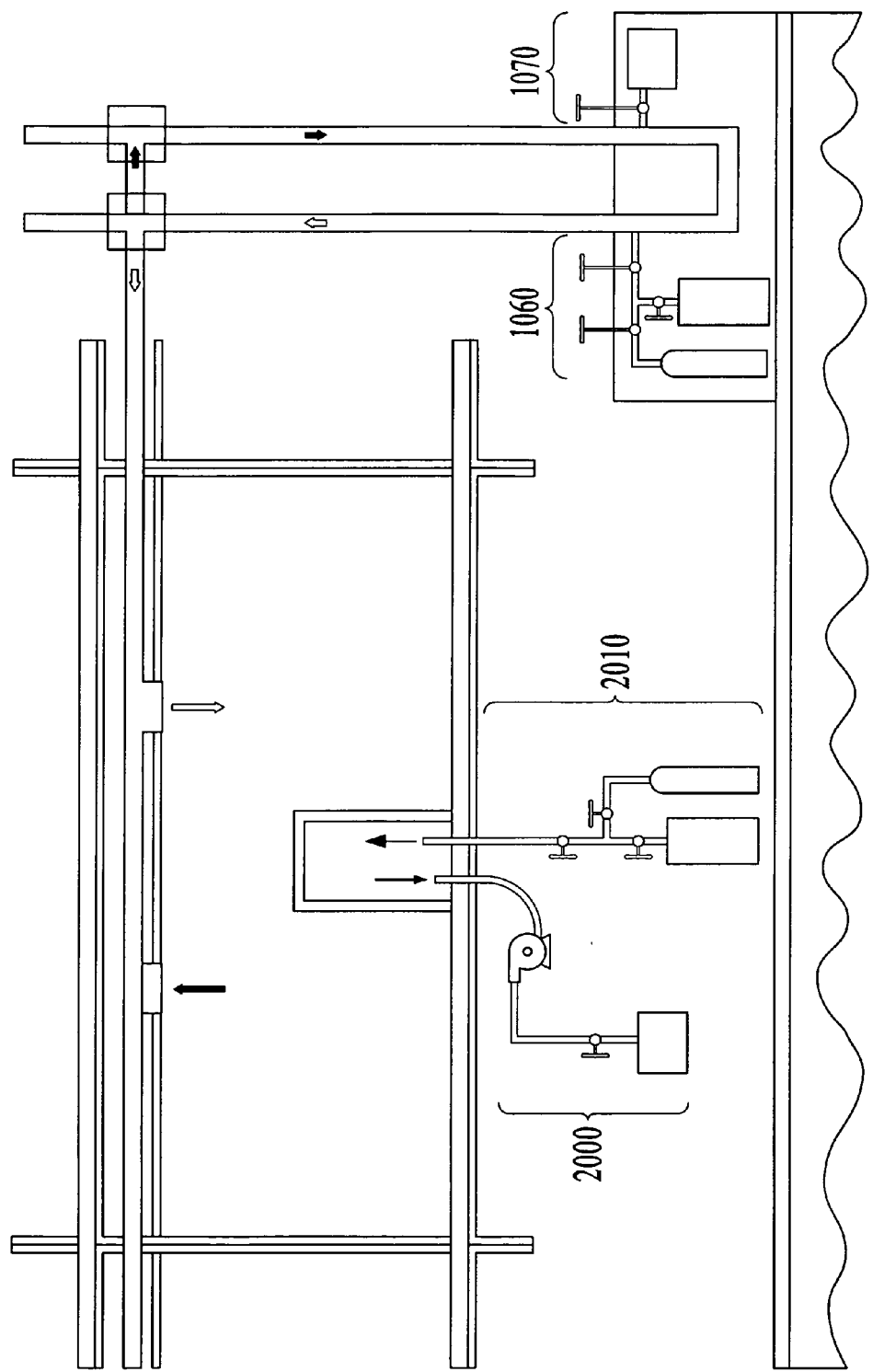
FIG. 11b is a simplified illustration of an alternative embodiment of the present invention shown in FIG. 11a with an additional tracer injection and/or measurement system located in a centrally located HVAC unit.

FIGS. 11a and 11b illustrate another embodiment of the tracer injection and measurement system shown in FIG. 9, except a tracer injection unit 2010 has been added outside the entry door 1008 of the room 1004. Also shown in FIGS. 11a and 11b are various configurations of tracer injection and tracer measurement units at the HVAC unit 1050 and those at door-entry.

There are a variety of partitioning and reactive tracer gases that can be used to implement this method. The method will work for any of these tracers.

4.2 Description of the Method and Apparatus for Detection, Location, and Quantification The preferred method of the present invention uses gaseous tracers to characterize dangerous and hazardous substance such as bio-hazardous, chemical and explosive substances and devices. The method used to detect, locate, and/or quantify (i.e., characterize) contamination in pipes, ducts, and other fluid flow systems, which was described in a previous patent application [1], is also used to detect, locate, and/or quantify the dangerous and hazardous substances for this application. The main difference is that the application is different and the focus tends to be more on detection and location of these dangerous or hazardous materials in ducts or rooms in the many targeted structures. However, bio-hazardous, chemical or explosive substance are just another form of chemical contamination that can be detected, located, or quantified through use of the chemical properties of these substances. One can replace the word "contamination" the description of the tracer method and tracer measurements in [1] with "dangerous and hazardous substances." The detection and location of dangerous or hazardous substance tends to be more complicated and needs to be done more reliably than detection and location of contamination in piping or ducts. It is more complicated, because the duct and room system to be monitored tends to be more complicated than the pipes and ducts monitored for decommissioning and deactivation (D&D).

Detection, Location, and Quantification. The following description of the technology is very similar to the application of the present invention for detecting, locating, and quantifying contamination in a pipe or duct and is present in terms of a liquid or dry contaminant in a pipe. The application of this method for detecting and locating dangerous and hazardous materials in ducts and rooms in buildings, transportation systems, and infrastructure was described above. This description presents the details of the tracer measurements.

An embodiment of the method of the present invention injects and transports at least one gaseous conservative tracer and one or more gaseous partitioning tracers of known concentrations at a constant or known flow rate and flow velocity along a pipe using a gas that does not interact with any of the tracers or the contaminant. A gas chromatograph (GC) is used to measure the elution curves of tracer concentration at the other end of the pipe. The partitioning tracer or tracers are selected so that they interact with the contamination of interest as it flows along the pipe. Any interaction will change the magnitude and shape of the elution curves of concentration measured at the end of the pipe and will introduce a delay in the average flow time. The conservative tracer, which does not interact with the contamination, is unaffected and acts as a reference. The difference in the mean arrival times or the magnitude and shape of the elution curves of concentration for the conservative and partitioning tracers are used to detect the presence of the contaminant in the pipe. Using a very simple model, the amount of contamination can be determined from the difference the mean arrival times of the conservative and interactive tracer determined from the elution curves of tracer concentration.

A perturbation in the partitioning tracer flow field must be induced to locate the position of the contaminant in the pipe. This flow field variation can be introduced any time after the partitioning tracer has reached and begun partitioning into the contamination. This can be determined from the time history of the normalized concentration curves. As will be illustrated in FIG. 19, for $C_7F_{14}$ and $C_8F_{16}$, this can occur any time after 20 to 24 h when the peak of the normalized concentration of the partitioning tracers have become a fraction of the conservative tracer, $SF_6$. The flow field perturbation can be introduced during the peak portion of the curve or the exponential region of the concentration curve. If location is to be effectively combined with detection and quantification, then the flow field variation is best done when the concentration is changing exponential and when sufficient data have been collected to accurately extrapolate the exponential portion of the curve to zero.

The flow-field perturbation is produced by suddenly increasing the flow rate (i.e., velocity) of the nitrogen gas used to advect the tracers along the pipe. The purpose of this increase is to flush the partitioning tracers in the flow field. Once this is accomplished, the flow field can be returned to its original flow rate. The tracers present in the contamination will continue to come out of the contamination and be advected along the pipe. However, the leading edge of the partitioning tracers re-entering the nitrogen flow field will be clearly identifiable and distinguishable from the original concentration data. The distance between the contamination and the GC can be estimated by a measurement of the time of arrival of the partitioning tracer and the flow rate. The advection velocity does not have to be the same before and after the flushing, but it does have to be known.

The time of arrival can be estimated from the leading edge, the peak, or the first temporal moment of the concentration curve depending on what estimate of location is desired. The leading edge estimate will yield an estimate of the location of the tracer closest to the GC. The peak, first temporal moment, or other estimate of average arrival time will yield an estimate of the extent (i.e., length or beginning and end) of the contamination. If location and detection estimates are initially desired (not volume estimates), then the flow-field perturbation should be introduced near the beginning of the concentration curve to allow a quick test to be conducted. If a contaminant is found, the test can be repeated over a longer period of time if an estimate of the volume of contamination is desired.

Another approach is to introduce enough conservative and partitioning tracer at the beginning of the test to cover all sections of the pipe, then stop the flow and close both ends of the pipe to trap the tracer inside the pipe by closing the valves on the injection and extraction side of the pipe. After a period of time, for a reactive tracer, an advection flow field is established to transport the and GC samples are collected and analyzed. For a partitioning tracer, the line is rapidly flushed to remove all of the tracers from the pipe before setting up the advection flow field to transport and measure the tracer re-entering the flow stream from the contaminant. This approach can be used to detect, quantify and locate the contaminant.

In any length of pipe, there may be more than one region of contamination. For such cases, the concentration curve measured at the GC will be the summation of the elution from each region of contamination. The measured concentration curve will show multiple peaks.

The method will be described in terms of partitioning tracers, but, as described below, reactive tracers can also be used. The description will be made in terms of a simple pipe configuration, i.e., a single segment of pipe with no connecting branches.

The key feature of the present invention is that a suite of tracers are transported down a length of pipe (or duct) and come in contact with any and all possible contamination within the pipe. The conservative tracer will not interact with the contamination inside the pipe, and therefore, it has a partition coefficient of zero relative to the contamination. The partitioning tracers on the other hand will interact with the contamination, and therefore, have a non-zero partitioning coefficient. The partitioning coefficient ($K_i$) is defined as $$K_i = C_{i,D}/C_{i,M} \quad (1)$$

where $C_{i,D}$ is the concentration of the "i"th tracer in the contamination and $C_{i,M}$ is the concentration of the "i"th tracer in the mobile phase, i.e. the air transporting the tracer. The retardation of the tracers by the contamination for flow through a porous media is given by $$R_f = \frac{\langle t_p \rangle}{\langle t_c \rangle} = 1 + \frac{K_i S_D}{(1 - S_D)} \quad (2)$$

where $\langle t_p \rangle$ is the mean time of travel of the partitioning tracer, $\langle t_c \rangle$ is the mean time of travel of the conservative or non-partitioning tracer, and $S_D$ is the average contamination saturation, i.e. the fraction of the volume occupied by contamination in the total swept volume of the porous media. This model can be adapted for estimating $S_{Dpipe}$. The average contamination saturation for flow in a pipe or other fluid flow system, $S_{DPipe}$, is related to $S_D$, by an empirical constant, $\alpha$, where $\alpha$ should be approximately equal to 2 for flow in a pipe. In a pipe, only the top of the contaminant layer can interact with the tracer. In porous media, the tracer can interact with all sides of the contaminant. The values of $\langle t_p \rangle$ and $\langle t_c \rangle$ can be determined from the centroid of the elution curves of tracer concentration during a pipe test, and $K_i$ can be determined in laboratory calibration tests referred to as bag tests.

An estimate of the volume of the contamination can be estimated by solving Eqs. (1) and (2) for $S_{Dpipe}$, assuming $S_{Dpipe} = \alpha S_D$ $$S_{DPipe} = \alpha \frac{R_f - 1}{K_i + (R_f - 1)} = \alpha \frac{\frac{\langle t_p \rangle}{\langle t_c \rangle} - 1}{K_i + \left(\frac{\langle t_p \rangle}{\langle t_c \rangle}\right) - 1}, \quad (3)$$

where $\alpha=2$ for a thin layer of contamination at the bottom of a pipe.

Figure 12:
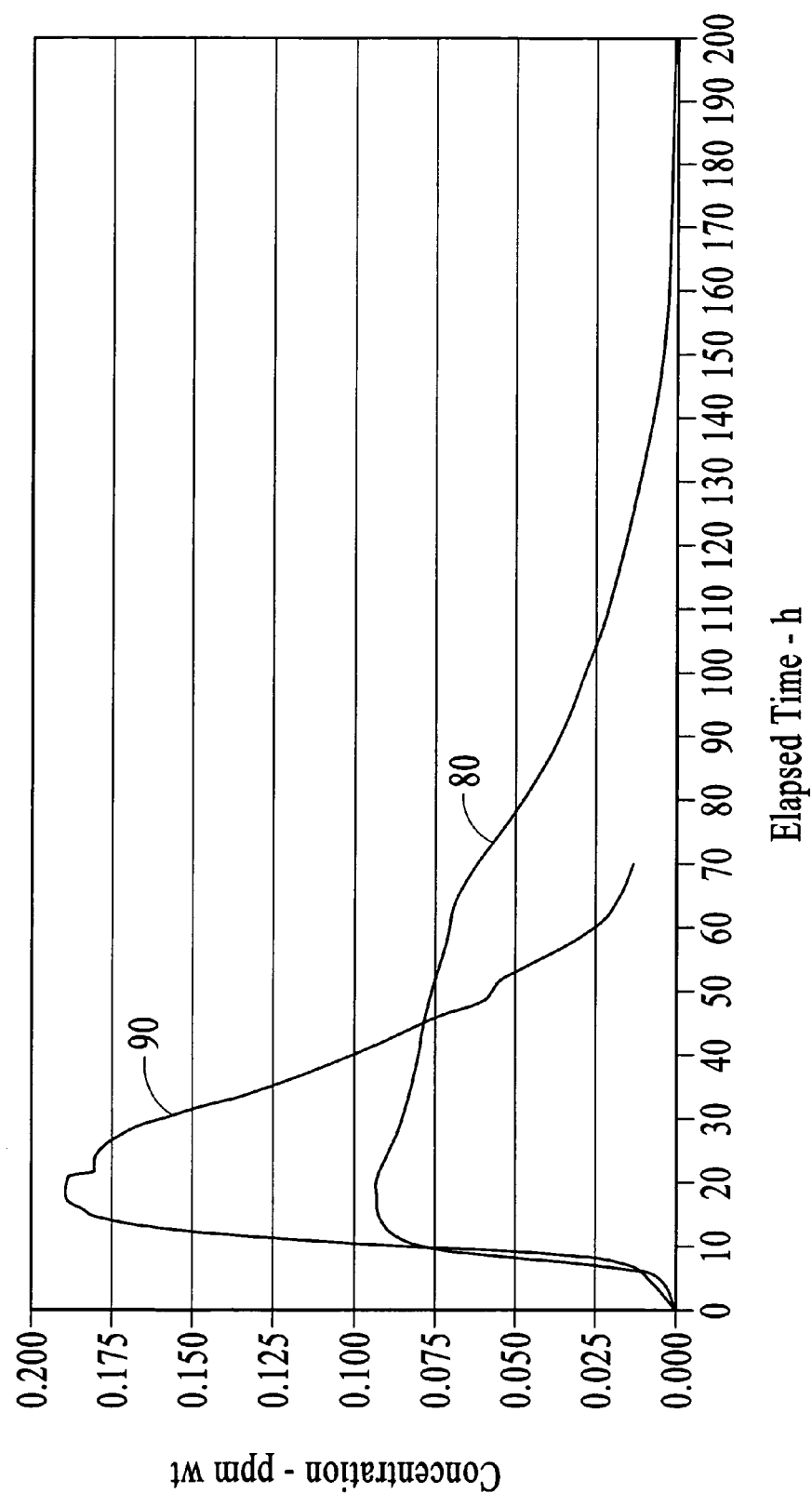
FIG. 12 illustrates the same partition tracer curve, $C_7F_{14}$, measured at the extraction point in a pipe test with and without any contamination present.

The partitioning tracers undergo retardation due to their partitioning into and out of the contamination, while the conservative tracers are unaffected by the presence of the contamination. FIG. 12 illustrates the difference in the measured concentration curves between a partitioning tracer that was injected into a pipe section free of contamination and the same pipe section when it contained a thin layer of diesel fuel contamination. The difference between tracer concentration curves with contamination 80 and without contamination 90 is clearly evident in FIG. 12. If a conservative tracer was also injected into the pipe section when the contamination was present, its concentration curve would be similar to the one measured without the contamination present 8. FIG. 12 clearly illustrates both a reduction in concentration and a time scale change due to the presence of contaminant in the pipe.

The partitioning process is caused by the mass transfer of the partitioning tracers into the contaminant until equilibrium partitioning has been reached. For this reason, the flow rate of the tracers must be designed so that sufficient time exists to allow the partitioning tracers to interact with the contaminant. Once the tracer slug has passed the contamination, the partitioning tracer elutes back into the flow field as dictated by the partitioning coefficient. Therefore, the net flux of the partitioning tracers will be from the contaminant back into the flow field to preserve the equilibrium partitioning dictated by the particular coefficient for the tracer. Thus, recovery of the partitioning tracers at the extraction point is delayed (i.e. retarded) relative to the recovery of the conservative tracer.

Figure 13:
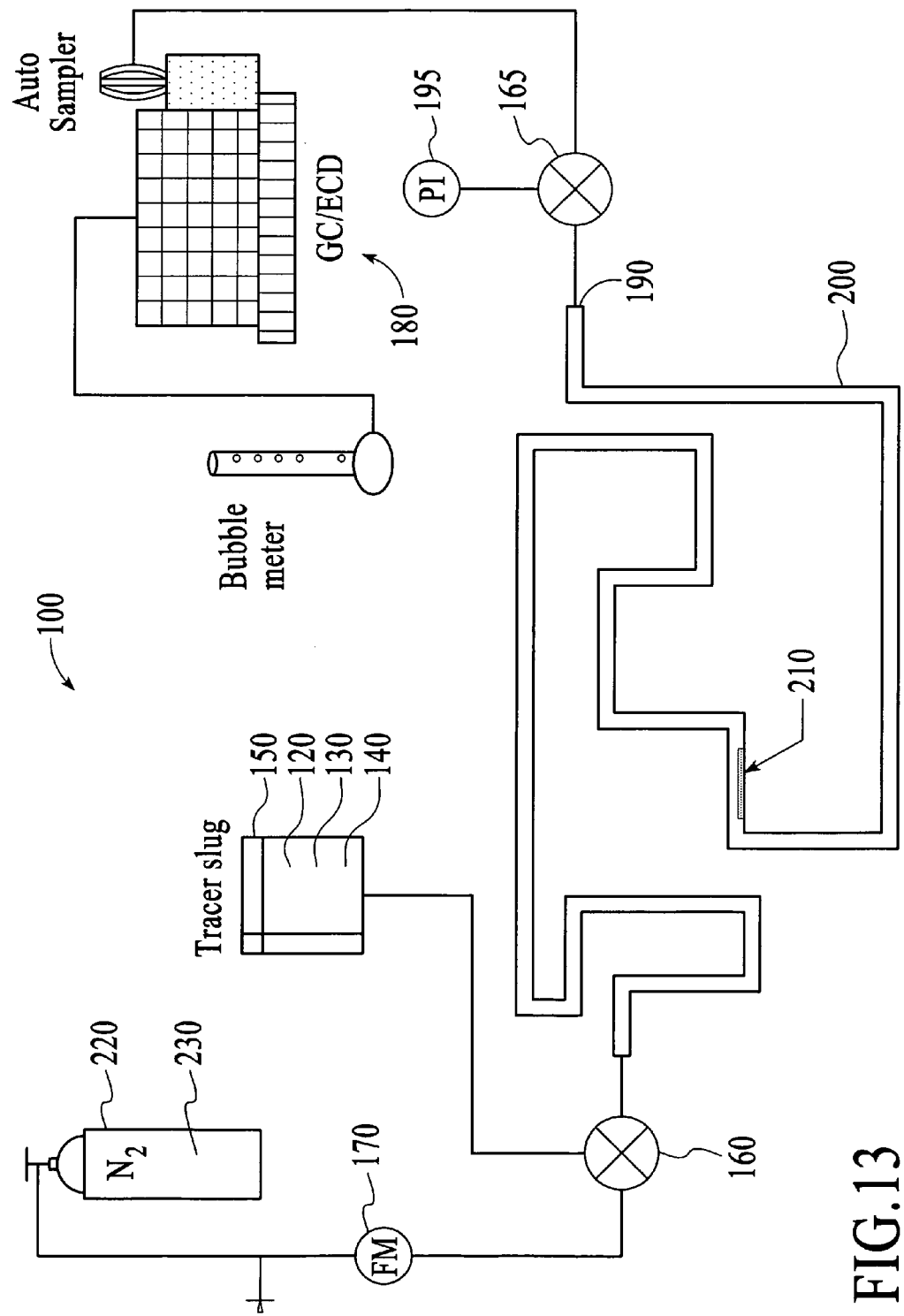
FIG. 13 illustrates an embodiment of an apparatus of the present invention to determine whether or not contamination is present in a pipe or any fluid flow system.

FIG. 13 is an illustration of an apparatus of the present invention 10 for application to a pipe, duct, or other enclosed flow system 200. Tracers 120, including at least one conservative tracer 130 of known concentration and at least one partitioning tracer 140 of known concentration are stored in a container 150 under sufficient pressure that they can be injected into the pipe 200 as a slug at a known but approximately constant concentration level. The pressurized container 150 containing the tracers is connected to the pipe 200 with a three-way valve 160 that can be used to isolate the gas tracers 120 from the pipe 200. Alternatively, two two-way valves can be used instead of the three-way valve 160 so that both the tracers and the advection fluid can be independently isolated. A flow meter or regulator can also be placed in the pipe between the valve 160 and the pressure container 150. An air flow field is established in the pipe using a compressed gas cylinder 220. A regulator or flow meter 170 is used to control the amount of tracer that is injected. The valve 160 can also be used to isolate the advection gas 230 from the pipe 200. The advection gas, which is nitrogen in the illustration, passes through a flow meter 170 so that a set flow rate can be maintained. A timer is used to determine the volume of tracer injected into the pipe. A gas chromatograph (GC) 180 is used at the extraction point to sample the tracers eluting from the pipe. A two-way valve 165 is used to isolate the gas chromatograph from the pipe. The pressure in the pipe is measured using a pressure sensor 195. A computer is used to analyze the elution concentration curves of the tracers.

The method and an apparatus of the present invention was successfully demonstrated in laboratory pipe section using gaseous partitioning tracers. The two sets of laboratory tests that were conducted will be used to illustrate and describe the method of the present invention.

Figure 14:
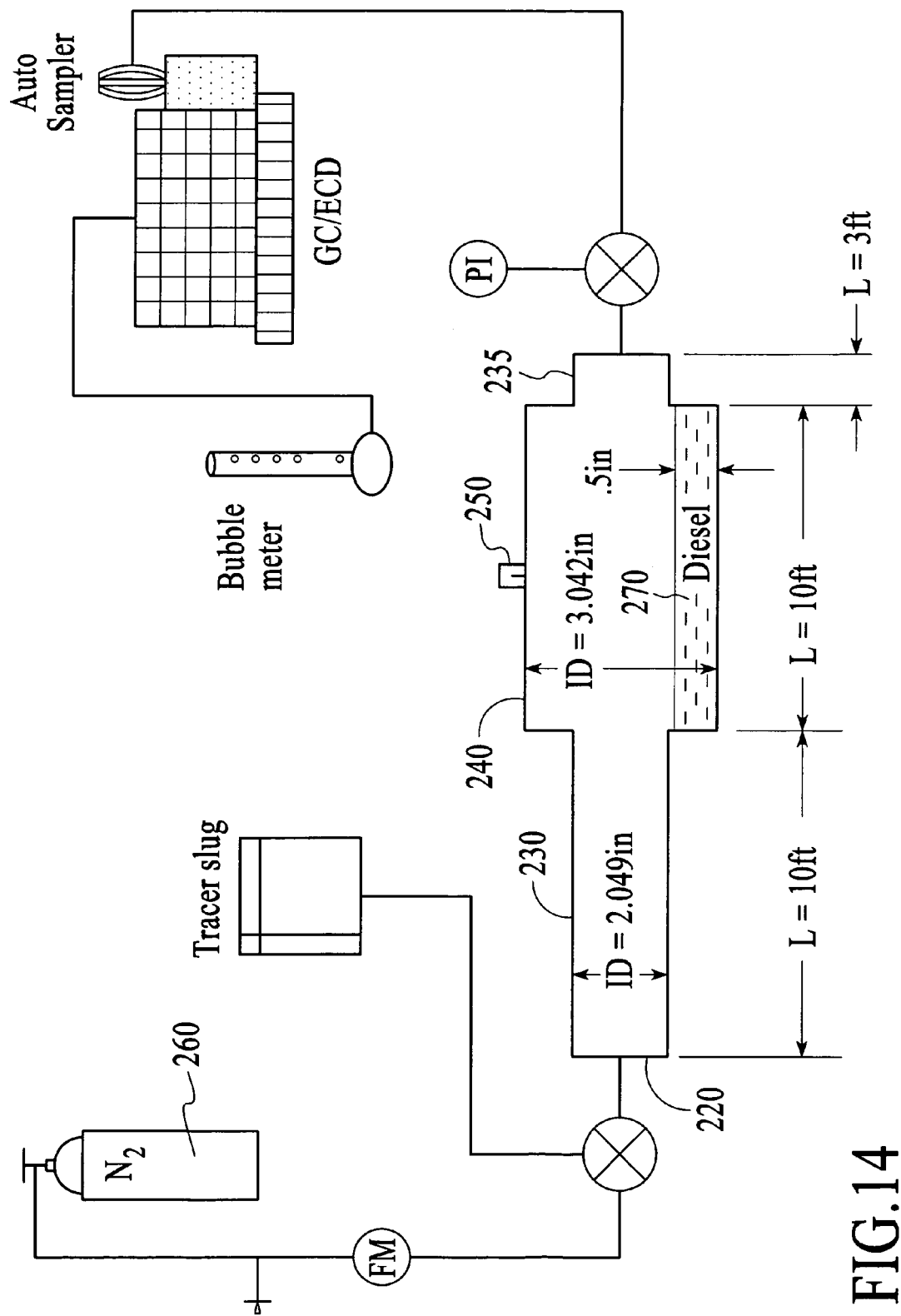
FIG. 14 illustrates the apparatus in FIG. 3 as applied to a laboratory pipe section.

Laboratory Testing in a Short Pipe Section. FIG. 14 illustrates the application of the apparatus in FIG. 13 as used in the laboratory tests. The method was implemented on a 23 ft. long, Schedule 40 PVC pipe 220. The 23-ft.-section of pipe 220 is comprised of 3 pipe sections 230, 235, 240. The first 10 ft of the pipe 230 and the last 3 ft of pipe 235 were assembled from 2-in.-diameter PVC pipe. The middle section of pipe 24, 10 ft in length, was assembled from 3-in.-diameter PVC pipe. The 3-in. diameter piping is equipped with a sample port 250 at the midpoint to allow for contaminate introduction to the pipe and to draw gas samples during testing. Nitrogen gas 260 was used to transport the tracers along the pipe.

The first set of tests was performed without any contamination in the 3-in.-diameter pipe section ("Uncontaminated Pipe Test") of the pipe. The second set of tests was performed with contamination in the pipe ("Contaminated Pipe Test"); the contamination consisted of a 0.5-in. thick, 1.5-L layer of diesel fuel 270 in the 3-in.-diameter section of the pipe. Four tracers were used in each set of tests, but for purposes of illustration, only the results using three tracers will be described. $SF_6$ was selected as the conservative tracer. It does not partition into the diesel fuel and has a partitioning coefficient, $K_i$, of approximately 0. The other two tracers, $C_7F_{14}$ and $C_8F_{16}$, were selected, because they will each partition into the diesel but with different partitioning characteristics.

Both sets of tests were conducted in a similar manner. The tracers were slowly injected into the inlet of the 10-ft, 2-in.-diameter section of the pipe at a constant rate over a short period of time. The tracers were injected over a 10.3 min period in the first set of tests without the contamination present and over a 30-min period in the second set of tests with the diesel-fuel contamination present. The tracers were slowly advected along the pipe at a constant flow rate using nitrogen gas. A slow flow rate was used to insure that the tracers had sufficient time to partition into and out of the diesel fuel contamination.

The partitioning coefficients of each of the tracers were determined in bag tests. The values of $K_i$ were determined from bag tests and are shown in Table 1. It is clear that each of the tracers used in the test had significantly different values of $K_i$ and would have very different partitioning characteristics. For example, because the partitioning coefficient of $C_8F_{16}$ was greater than the partitioning coefficient of $C_7F_{14}$, it was expected that more of the $C_8F_{16}$ would partition into the diesel fuel than the $C_7F_{14}$, and it would take longer for the $C_8F_{16}$ to come back out of the diesel after the slug of tracer passed over the contamination. The test results show this.

TABLE 1

Partitioning Coefficients of the Three Tracers used in Both Sets of Tests

| Tracer Gas | Partitioning Coefficient, $K_i$ |
| --- | --- |
| $C_7F_{14}$ | 28.28 |
| $C_8F_{16}$ | 61.09 |

Uncontaminated Pipe Tests. Table 2 summarizes the concentration and mass of each tracer used in the uncontaminated pipe test. All of the tracers 120 were injected into the pipe 220 at the beginning of the test. The tracers were introduced into the pipe over a 10.3-min period at a rate of 26.08 L/h (434.6 mL/min). The total volume of tracers introduced was 4.49 L, which represents approximately 7 ft of the 2-in.-diameter pipe 230.

TABLE 2

Mass and Concentration of the Tracers Added to the Pipe for the Contaminated Pipe Tests

| Tracer Injection | Molecular Weight | Concentration (μg/g = ppm wt) | Mass Added (μg) |
| --- | --- | --- | --- |
| $SF_6$ | 146.0 | 0.72 | 3.680 |
| $C_7F_{14}$ | 350.1 | 11.61 | 76.186 |
| $C_8F_{16}$ | 400.1 | 11.68 | 76.623 |
| $N_2$ | 28.0 | | |

The uncontaminated pipe test was conducted over a period of 69.5 h. A total of 159 gas samples were collected and analyzed at the GC located at the outlet side of the pipe at approximately 26 min intervals throughout the test. The output of the GC in area counts was converted to concentration in ppm wt (μg/g) using a calibration curve developed for each tracer before the beginning of the test. The tracers were transported down the pipe at a constant flow rate of 0.66 L/h (11.0 ml/min) using nitrogen gas. In the 2-in.-diameter pipe, this corresponds to an average flow velocity of 30.6 cm/h (1.003 ft/h), and in the 3-in.-diameter pipe, this corresponds to an average flow velocity of 13.9 cm/h (0.46 ft/h). Table 3 shows the travel time over each section.

TABLE 3

Travel Time of the Tracers in the Contaminated Pipe Tests

| Pipe Section | Length of Pipe Section (ft) | No Contamination Travel Time (h) | Contamination Travel Time (h) |
| --- | --- | --- | --- |
| 2-in. Pipe | 10 | 9.97 | 10.61 |
| 3-in. Pipe | 10 | 21.96 | 20.96 |
| 2-in. Pipe | 3 | 2.99 | 3.18 |
| Total | 23 | 34.92 | 34.75 |

Figure 15:
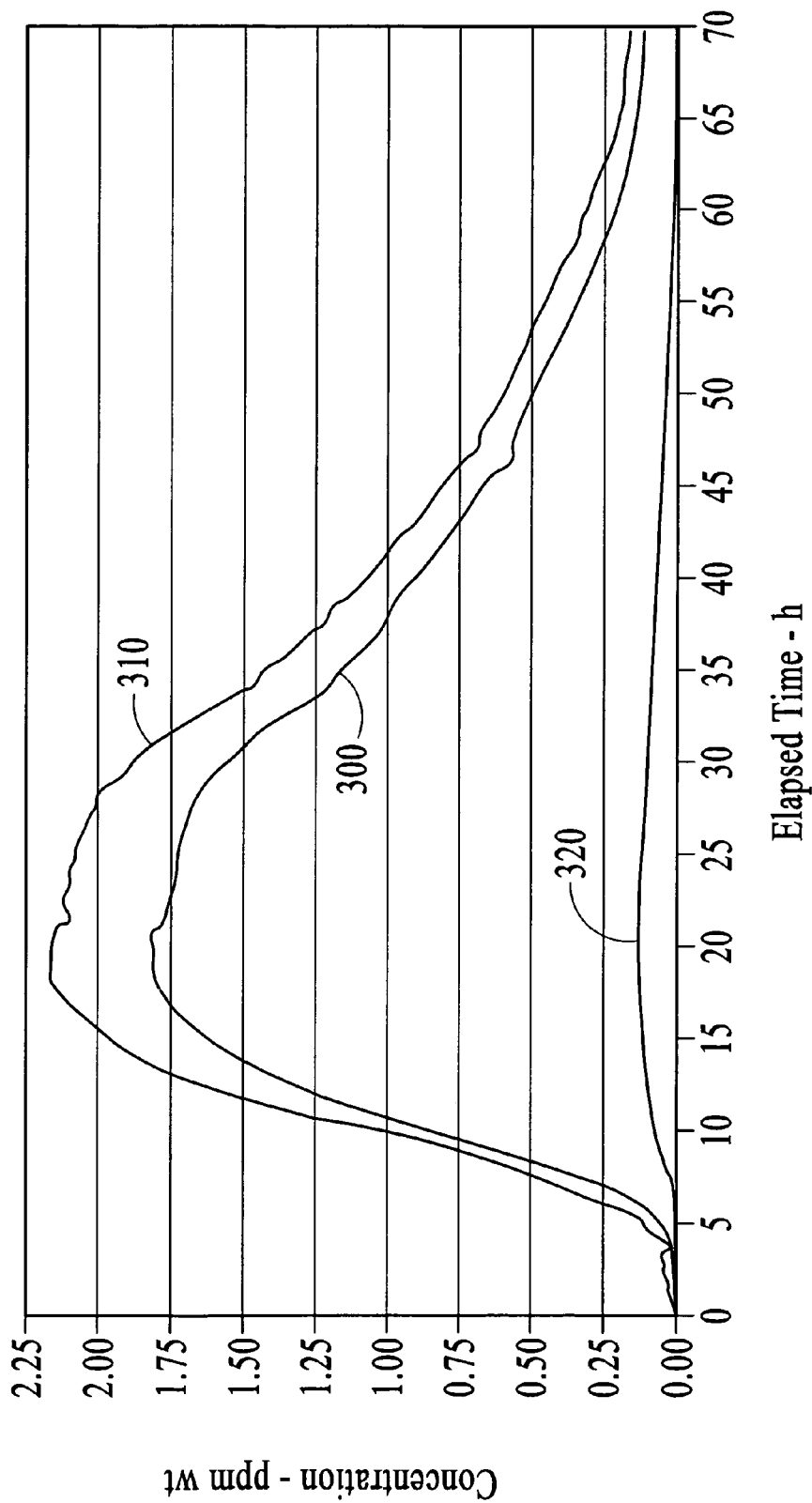
FIG. 15 illustrates the elution curve of tracer concentration for a conservative tracer, $SF_6$, and two partitioning tracers, $C_7F_{14}$ and $C_8F_{16}$, that were obtained in an uncontaminated laboratory pipe.

FIG. 15 shows the time history of the concentration curves for each tracer measured at the outlet of the pipe. The total mass of the tracer input to the system was given in Table 2. The concentrations of the partitioning tracers, $C_7F_{14}$ 300 and $C_8F_{16}$ 310, are about 15 times greater than the concentration of the conservative tracer $SF_6$ 320. The concentration curves show that the maximum concentration is reached at 15 to 20 h after the beginning of the test. The concentration curves show the effects of dispersion due to the slow travel of the original tracer slug initially injected into the pipe.

If 100% of the tracer injected into the pipe is recovered by the end of the test, the area under the concentration curve (i.e., the integral of the concentration between 0 and infinity) shown in FIG. 15 should be equal to the initial concentration, $C_i$. This presumes that the duration of the test is long enough for all of the tracers that partition into the diesel fuel 270 have time to elute into the flow field and arrive at the GC 180. Thus, $$C_i = \int_0^\infty C(t)\,dt \quad (4)$$

Figure 16:
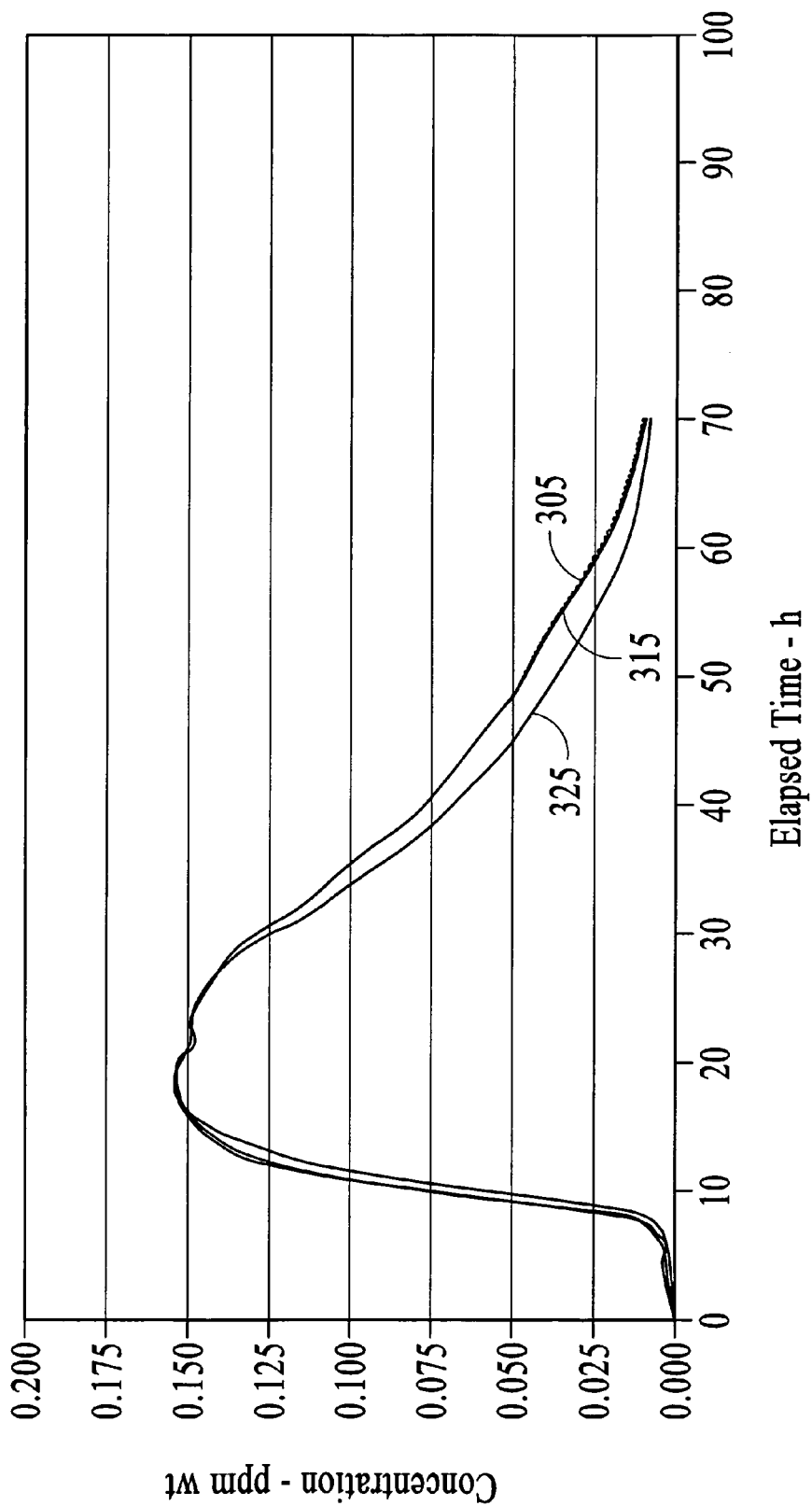
FIG. 16 illustrates the elution curve of the normalized tracer concentration of the partitioning tracers in FIG. 15.

FIG. 16 shows the concentration after normalizing the data by the initial concentration, $C_i$, of each of the respective tracers. The normalized elution curve of concentration is obtained by dividing the measured concentration by $C_i$. When each measured concentration is divided by the initial concentration, the integral of the concentration shown in FIG. 16 should equal 1 when all of the tracers are recovered. This is given by $$\frac{\int_0^\infty C(t)\,dt}{C_i} = 1 \quad (5)$$

The concentration curve for $C_7F_{14}$ is multiplied by 0.82 in FIG. 16 to account for a small calibration error.

Thus, if the dispersion characteristics of all of the tracer gases are the same and all of the tracer has had sufficient time to reach the GC at the outlet end of the pipe, the normalized concentration curves should be very similar. The normalized concentration curves of the conservative tracer, $SF_6$ 325, and the partitioning tracers, $C_7F_{14}$ 305 and $C_8F_{16}$ 315, in FIG. 16 illustrate this similarity. Since the tails of the concentration curves have not yet reached a concentration of 0 ppm wt, not all of the tracer have yet been recovered.

An estimate of the mean travel time, $<t_p>$ and $<t_c>$, of the tracers in FIG. 16 can be computed from the centroid of the elution curves of tracer concentration using the following equation.

$$\langle t_{p\_or\_c} \rangle = \frac{\int tC(t)\,dt / C_i}{\int C(t)\,dt / C_i} \quad (6)$$

Table 4 summarizes the result of this calculation. Two estimates of $<t_{p\,or\,c}>$ are presented. The first is the $<t_{p\,or\,c}>$ computed from the curves in FIG. 16. The second is obtained by extrapolating the tail of the curves in FIG. 16 with an exponential function to insure that 100% of the tracer initially injected into the pipe has been recovered. In this instance, we would expect both estimates of $<t_{p\,or\,c}>$ to be nearly identical, because the tails are close to zero.

TABLE 4

Mean Arrival Time of the Conservative and Partitioning Tracers in an Uncontaminated Pipe

| Tracer Gas | Measured $<t_{p\,or\,c}>$ (h) |
|---|---|
| $SF_6$ | 28.09 |
| $C_7F_{14}$ | 29.24 |
| $C_8F_{16}$ | 29.07 |

Figure 17:
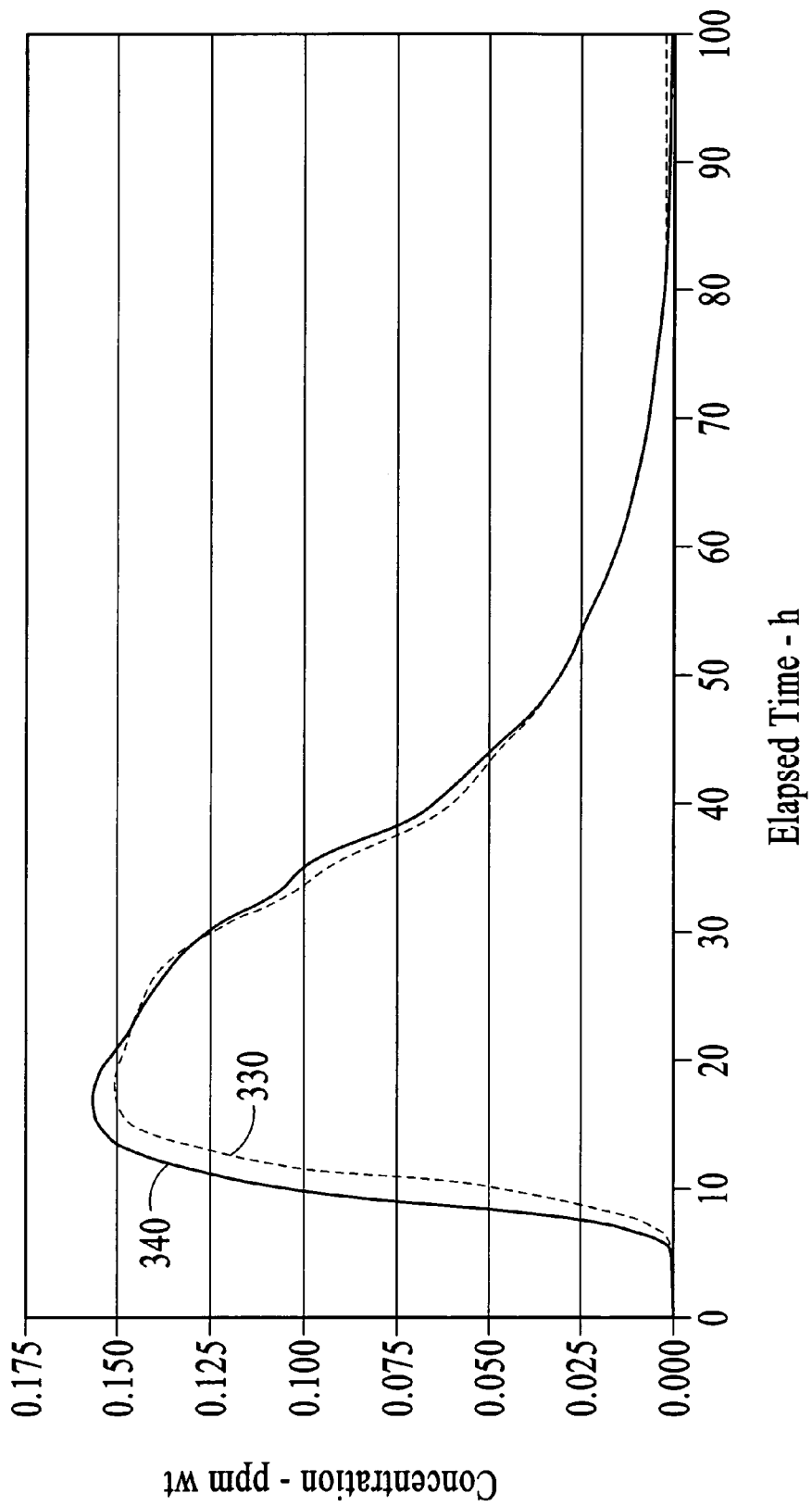
FIG. 17 illustrates the elution curves of the normalized tracer concentration for the conservative tracer, $SF_6$, obtained during the uncontaminated and contaminated pipe test.

FIG. 17 shows a comparison of the conservative tracer, $SF_6$, measured during the uncontaminated 330 and contaminated 340 pipe tests. Agreement between the two curves is very good. The small difference in the arrival of the leading edge is partially explained by the different advection velocity used in the two tests.

Contaminated Pipe Tests. The same procedure used to conduct the uncontaminated pipe tests was used to conduct the contaminated pipe tests. The main difference between the uncontaminated and the contaminated pipe tests was that 1.5 L of diesel fuel was added to the 3-in-diameter pipe; this resulted in a 0.5-in. thick layer of contamination. The other difference was that the 4.49 L of tracer, the same volume of tracers used in the contaminated pipe tests, was introduced more slowly (i.e. over a longer period of time). All four tracers were again injected into the pipe at the beginning of the test. The tracers were introduced into the pipe over a 30-min period (vice 10.3 min in the uncontaminated pipe tests) at a rate of 8.98 L/h (149.7 mL/min). Again, the tracer slug occupied 7 ft of the 2-in.-diameter pipe 230. Table 5 summarizes the concentration and the mass of each tracer used in the contaminated pipe test.

TABLE 5

Mass and Concentration of the Tracers Added to the Pipe for the Contaminated Pipe Test

| Tracer Injection | Molecular Weight | Concentration (ppm wt) | Mass Added (μg) |
|---|---|---|---|
| $SF_6$ | 146.0 | 0.61 | 3.135 |
| $C_7F_{14}$ | 350.1 | 9.89 | 64.90 |
| $C_8F_{16}$ | 400.1 | 9.95 | 65.27 |
| $N_2$ | 28.0 | | |

The contaminated pipe test was conducted over a period of 185.6 h. A total of 419 gas samples were collected and analyzed at the GC located at the outlet side of the pipe at approximately 26.6-min intervals throughout the test. The tracers were transported down the pipe at a constant flow rate of 0.622 L/h (10.36 ml/min) using nitrogen gas. In the 2-in.-diameter pipe, this corresponds to an average flow velocity of 28.73 cm/h (0.943 ft/h), and in the 3-in.-diameter pipe with contamination present, this corresponds to an average flow velocity of 14.54 cm/h (0.477 ft/h). The flow velocity is approximately 1.96 times slower in the 3-in.-diameter pipe than in the 2-in.-diameter pipe. This is within 5% of the flow field used during the uncontaminated pipe tests. Table 3 shows the travel time over each section.

Figure 18:
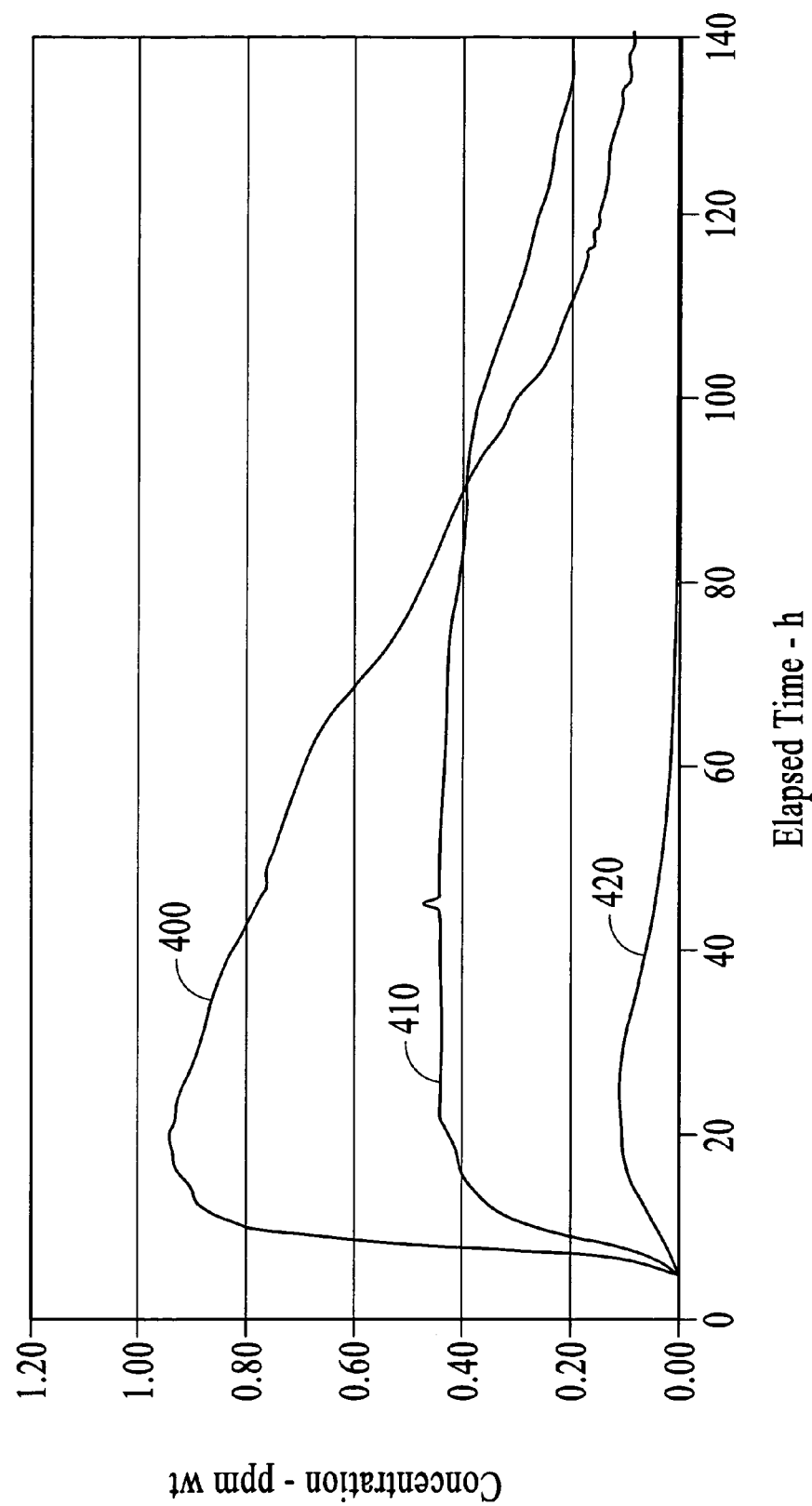
FIG. 18 illustrates the elution curve of tracer concentration for a conservative tracer, $SF_6$, and two partitioning tracers, $C_7F_{14}$ and $C_8F_{16}$, that partition in diesel fuel and were obtained in a laboratory pipe test using diesel fuel as the contaminant.

FIG. 18 shows the time history of the concentration of each tracer measured at the outlet of the pipe. The total mass of the tracer input to the system is given in Table 5. It is clear that the partitioning tracers ($C_7F_{14}$ 400 and $C_8F_{16}$ 410) behave differently than the conservative tracer ($SF_6$ 420). This alone is an indication of the presence of a contaminant in the line. In contrast to the uncontaminated pipe test, FIG. 15, the conservative tracer is fully recovered well before the partitioning tracers, and the conservative tracer has a different shape (i.e., amplitude response) than the partitioning tracers.

Figure 19:
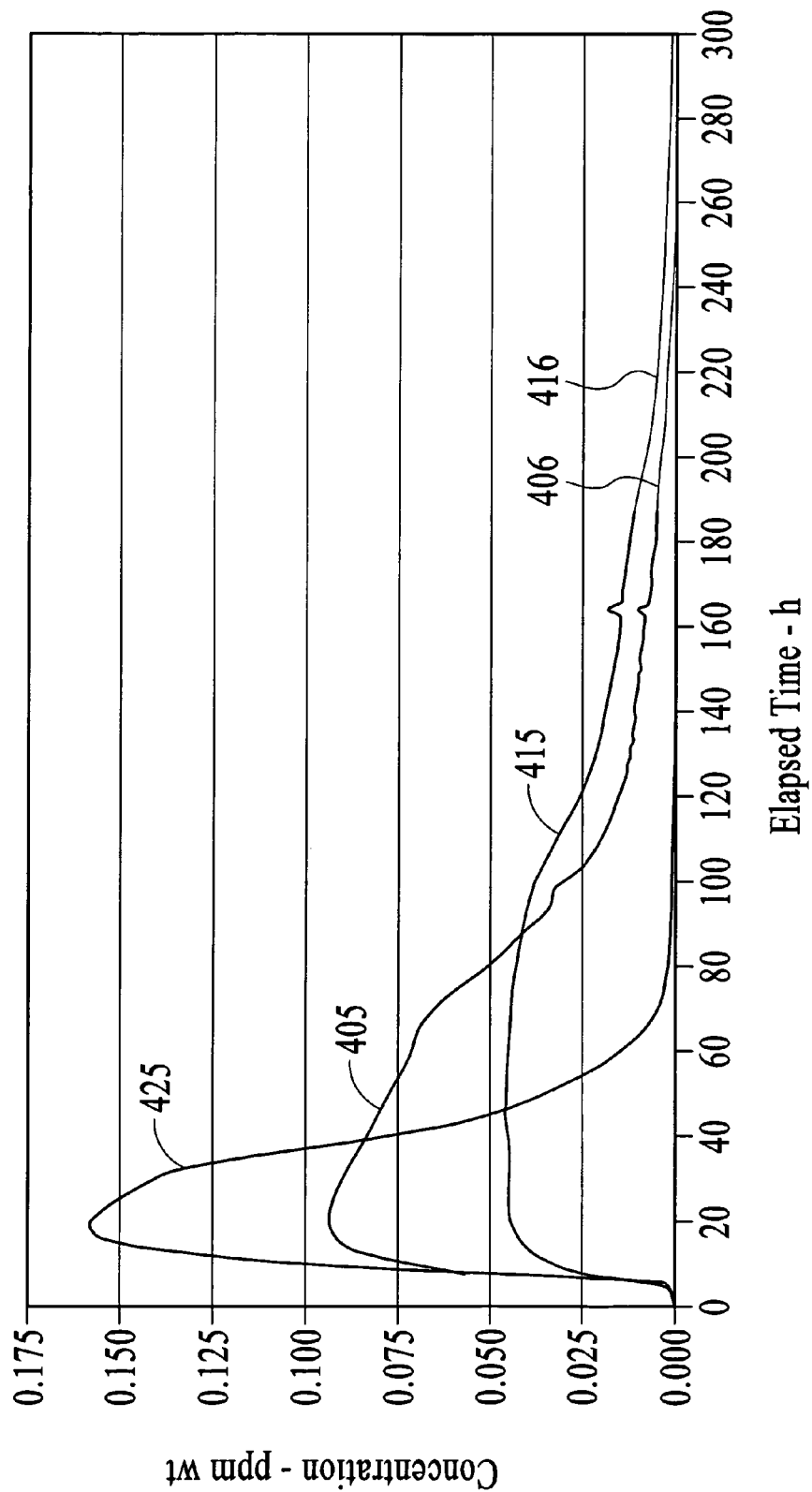
FIG. 19 illustrates the elution curve of the normalized tracer concentration of the partitioning tracers in FIG. 18.

This is better illustrated in the normalized curves shown in FIG. 19 obtained by dividing the measured concentration by the initial concentration. Based on these data, it is clear that the $SF_6$ 425 and almost all of the $C_7F_{14}$ 405 tracers have been recovered before the test was terminated. This observation is made because the exponential tails of both of these elution curves of concentration are very close to zero. Since the tail concentration curve for $C_8F_{16}$ 415 indicates it is approaching zero, we could also use $C_8F_{16}$ in the analysis if we extrapolate the tail mathematically 416.

Table 6 summarizes an estimate of the mass of the tracers recovered by the end of the test based on the data collected. Two estimates were made. The first (Measurement of the Mass Recovered) were made based on the measurements of the mass of each tracer recovered. The second is based on an integration of the area under the concentration curves (Mass Recovered Based on the Data). An exponential curve was fit to the data from 100 h to 186 h and is shown as the thin lines 406, 416 in FIG. 19. The first estimate has a larger uncertainty than the second one. For example, it is safe to assume that nearly 100% of the $SF_6$ tracer was recovered by the end of the test, but the measurement estimate showed only 81.8% recovery. This is because there is a large uncertainty in the estimate of the recovered volume of $SF_6$. The concentration curve in FIG. 19 shows that the tail reached zero before the completion of the test. This was nearly true for the $C_7F_{14}$ as well.

TABLE 6

Summary of the Total Mass of Each Tracer Recovered During the Contaminated Pipe Test

| Tracer Gas | Mass Added (μg) | Mass Recovered (μg) | Measurements of the Mass Recovered (%) | Mass Recovered Based on Data (%) |
| --- | --- | --- | --- | --- |
| $SF_6$ | 3.14 | 2.57 | 81.8 | ~100% |
| $C_7F_{14}$ | 64.90 | 57.64 | 88.8 | 99.3% |
| $C_8F_{16}$ | 65.27 | 44.98 | 68.9 | 93.9% |
| $C_{10}F_{18}$ | 65.10 | 20.97 | 32.2 | N/A |

The mean travel time of the tracers in the contaminated pipe test is compared to the mean travel time in the uncontaminated pipe test is presented in Table 3. The presence of the contamination reduces the mean travel time by approximately 1 h over the contaminated section of the pipe.

Figure 20:
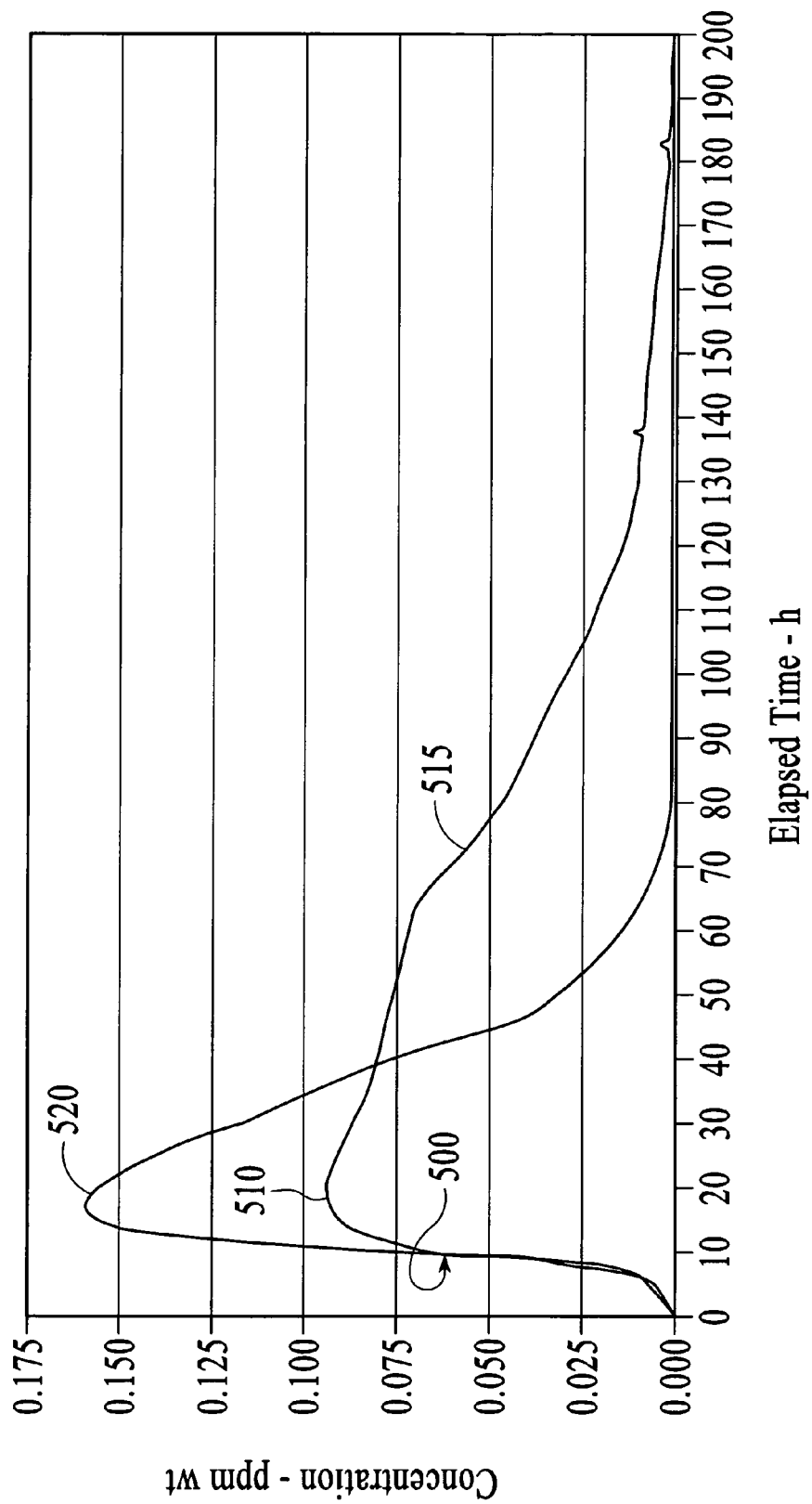
FIG. 20 illustrates the elution curve of tracer concentration for the conservative tracer, $SF_6$, and the partitioning tracer, $C_7F_{14}$, shown in FIG. 19.

FIG. 20 shows a comparison of the conservative tracer $SF_6$ and the partitioning tracer $C_7F_{14}$. A number of observations are noteworthy. The same observations are also true for $C_8F_{16}$ in FIG. 19.

First, the initial arrival time of both tracers 500, as illustrated by the leading edge of the concentration curve, is approximately the same.

Second, the peak of the partitioning tracer, $C_7F_{14}$ 510, is significantly lower than the conservative tracer $SF_6$ 520. It is clear that the $C_7F_{14}$ has an affinity for the diesel fuel and the partitioning into the diesel occurs very quickly. The difference in the peak amplitudes between the conservative and partitioning tracers can be exploited in the development of a detection algorithm.

Third, the conservative tracer indicates the travel time of the initial slug of tracers injected into the pipe. After 70 h, all of the initial tracer material (both conservative and partitioning tracers) should have total traveled the entire length of the pipe. Any tracer concentration being measured after this time is an indication that tracer is still being released from the diesel fuel.

Fourth, the peak of the partitioning tracer 510 is much broader than the peak of the conservative tracer 520. The conservative tracer is affected only by dispersion as it is transported along the pipe. The partitioning tracer is also includes this affect, but is dominated by the partitioning of the $C_7F_{14}$ tracer into and out of the diesel fuel. The partitioning tracer remains approximately constant for many hours and then falls off exponentially 515. These same observations are true of the other two partitioning tracers.

Fifth, as exhibited by the exponential tail of the concentration curve 515, the partitioning of the tracers like $C_7F_{14}$ from the diesel back into the flow field occurs slowly.

A estimate of the mean travel time, $<t_p>$ and $<t_c>$, of the tracers in FIG. 19 was computed from the centroid of the elution curves of tracer concentration using Eq. 6.

Table 7 summarizes the result of this calculation. Two estimates of $<t_{p\ or\ c}>$ are presented. The first is the $<t_{p\ or\ c}>$ computed from the data portion of the concentration curves in FIG. 19. The second is obtained by extrapolating the tail of the concentration curves in FIG. 19 with an exponential function to insure that 100% of the tracer initially injected into the pipe has been recovered. For $C_7F_{14}$, we would expect both estimates of $<t_p>$ to be nearly identical, because the tails are close to zero.

TABLE 7

Mean Arrival Time of the Conservative and Partitioning Tracers in an Uncontaminated Pipe

| Tracer Gas | Measured $<t_{p\ or\ c}>$ (h) | Extrapolated $<t_{p\ or\ c}>$ (h) |
| --- | --- | --- |
| $SF_6$ | 27.52 | 27.52 |
| $C_7F_{14}$ | 54.78 | 56.35 |
| $C_8F_{16}$ | 71.45 | 84.74 |

Table 8 presents the results of the volume of the diesel contamination estimated using Eq. (3) and the values of $K_i$ from Table 1 and the values of $<t_{SF6}>$, $<t_{C7F14}>$, and $<t_{C8F16}>$ from Table 7. The error is only 6.4% when the $C_7F_{14}$ tracer is used.

TABLE 8

Estimation of the Volume of the 1.5 L of Diesel Fuel Contamination

| Tracer Gas | $K_i$ | $<t_{SF6}>$ (h) | $<t_{C7F14}>$ or $<t_{C7F14}>$ (h) | $S_{DPipe}$ (L) | Error (%) |
| --- | --- | --- | --- | --- | --- |
| $C_7F_{14}$ | 28.28 | 27.52 | 56.34 | 1.40 | 6.4% |
| $C_8F_{16}$ | 61.09 | 27.52 | 84.74 | 1.29 | 13.7% |

In an operational scenario, it is best to determine if the pipe is contaminated in as short a period of time as possible, and if it is, then to collect sufficient data to verify the detection, quantify the volume of the contamination, and then locate the contamination. While volume measurements and detection verification using partitioning tracers will require that enough of the tail region of the elution curves of the partitioning tracer concentration be collected (to extrapolate the tail of the curve to zero), this is not be the case for the initial detection or the location of the contaminant. Since the location measurement requires a perturbation of the flow field, it is best accomplished after the volume measurement has been made or if the volume measurement is not to be made.

While there are a number of detection algorithms that might be developed, the most straightforward is to exploit the difference in amplitude between the conservative and one or more of the partitioning tracers at the peak region of the elution curves of the conservation tracer concentration. This approach can be used with both reactive and partitioning tracers. This can be accomplished by integrating under the conservative and non-conservative tracer concentration curves and differencing the results until the difference is statistically significant. It is important not to allow small time differences in the leading edge of the curves to bias the algorithm. Alternatively, enough data can be collected first to identify the maximum amplitude of the conservative tracer and analyze the data in this region. At this point in time, the second approach is the most practical to use. Once some operational experience is obtained, however, the former approach can be implemented. Both approaches will give the same result, but the former will be accomplished in a short measurement period.

Figure 21:
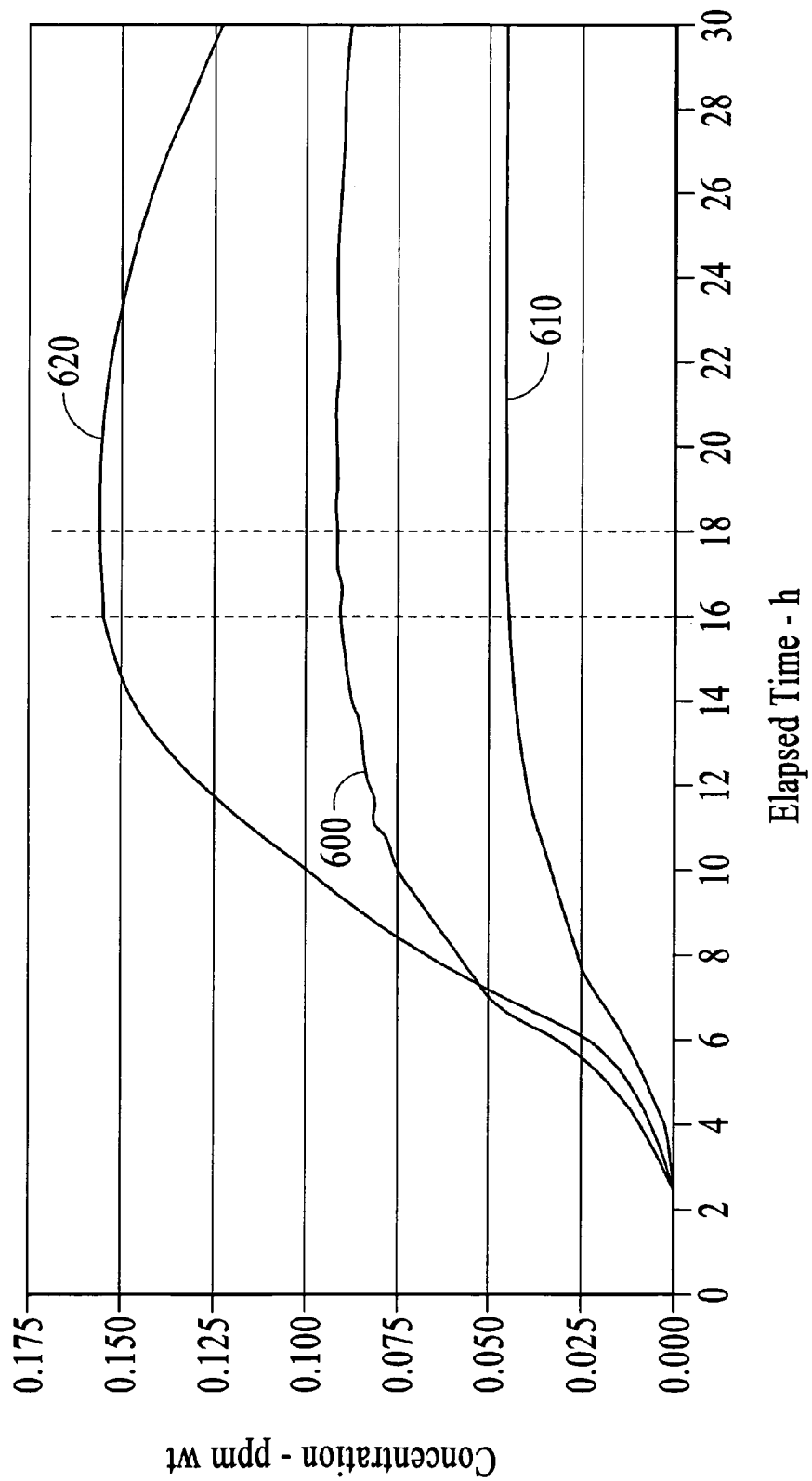
FIG. 21 illustrates the elution curves of the normalized concentration of the first 30 h of the conservative tracer, $SF_6$, and the partitioning tracers, $C_7F_{14}$ and $C_8F_{16}$ in FIG. 19.

FIG. 21 shows only the first 30 h of the normalized concentration curves for $SF_6$ 620, $C_7F_{14}$ 600, and $C_8F_{16}$ 610 shown in FIG. 19. The main difference between the conservative and partitioning tracer curves 600, 610 is amplitude. No information with regard to the shape of the curve is apparent. Detection is accomplished by first identifying a short region in time centered on the peak concentration of the conservative tracer to compute the mean amplitude of each concentration curve. The dashed lines, at 17.6 and 20.2 h, bracket a 2.4-h period centered on the peak of the conservative tracer ($SF_6$ 620). The mean amplitude can be computed for each curve over this 2.4-h period. The mean difference in concentration (in ppm wt) between each of the partitioning tracers and the conservative tracer represents the output of the system (designated Output of PCUT-1). Table 9 summarizes the results. It should be pointed out that the mean could have been computed over a shorter period than 2.4 h without changing the result. The ratio of the means between each partitioning tracer and the conservative tracer $SF_6$ in dB is also shown in Table 9 (Output of PCUT-2).

TABLE 9

Summary of the Output of the Detection Measurement

| Tracer Gas | Mean Amplitude (ppm wt) | Output of PCUT-1 Difference in Mean Amplitude (ppm wt) | Output of PCUT-2 Ratio of Mean Amplitudes (dB*) |
|---|---|---|---|
| $SF_6$ | 0.156 | 0 | 0 |
| $C_7F_{14}$ | 0.092 | 0.065 | −2.3 |
| $C_8F_{16}$ | 0.042 | 0.114 | −5.7 |

*10 $\log_{10}$ (Difference in Mean Amplitudes)

Laboratory Testing in a Long Pipe Section. Additional tests were performed in a longer pipe to verify the detection and quantification results obtained in the short pipe test and to demonstrate that these same measurements can be made in a longer pipe and to demonstrate the location capability of the present invention. These further tests were conducted with smaller volumes of contaminant, both wet and dry, for different cross-sectional areas and depths. The long pipe section was divided into three sections of different length for the tests. A total of 25 independent tests have been conducted to date in our laboratory to evaluate these three objectives. Table 10 presents a summary of the key characteristics of the tests.

TABLE 10

Summary of PCUT pipeline laboratory tests.

| Test # | Pipe | Tray | Contaminate | Injection Method | Notes |
|---|---|---|---|---|---|
| 1 | short | None | None | End | Found glue in box pipe |
| 2 | long | None | None | End | Check out of long pipe |
| 3 | long | 3 rd trays | 30 ml of Diesel | End | Volume too small - no partitioning |
| 4 | short | wide | 300 ml of Diesel | End | |
| 5 | short | wide | 300 ml of Diesel | End | Flow rate 18-20 ml/min |
| 6 | short | wide | 300 ml of Diesel | End | |
| 7 | long | wide | 300 ml of Diesel | End | |
| 8 | long | wide | 300 ml of Diesel | End | Location test |
| 9 | short | tall | 300 ml of Diesel | End | Bad test - equipment difficulties in the middle of the test |
| 10 | long | wide | 300 ml of Diesel | Flood | Location test - No SF6 to estimate volumes |
| 11 | long | cardboard | 21.5 gms of dried glue | Flood | Can't estimate volume due to flood procedure |
| 12 | long | cardboard | 33.5 gms of dried glue | Flood | Higher Tracer Concentration - No volumes due to flood |
| 13 | short | tall | 300 ml of Diesel | End | |
| 14 | short | tall | 300 ml of Diesel | End | Tracer conc. was 100 instead of 10 |
| 15 | short | wide | 150 ml of Diesel | End | |
| 16 | short | wide | 150 ml of Diesel | End | |
| 17 | short | wide | 145 ml of Diesel | End | |
| 18 | short | tall | 300 ml of Diesel | End | Good data |
| 19 | short | wide | 250 ml of Diesel | End | Flow data not collected due to PRB programming efforts |
| 20 | short | wide | 250 ml of Diesel | End | Test Performed Blind |
| 21 | short | wide | 225 ml of Diesel | End | Test Performed Blind |
| 22 | long | wide | 300 ml of Diesel | End | Test Performed Blind |
| 23 | long | wide | 300 ml of Diesel | Flood | Location Test - Flood so can't quantify |
| 24 | long | 2 trays | 300 & 300 ml of Diesel | Flood | Bad Test - Large pipe leak due to missing o-ring in compression joint |
| 25 | long | 2 trays | 300 & 300 ml of Diesel | End | |

Figure 22:
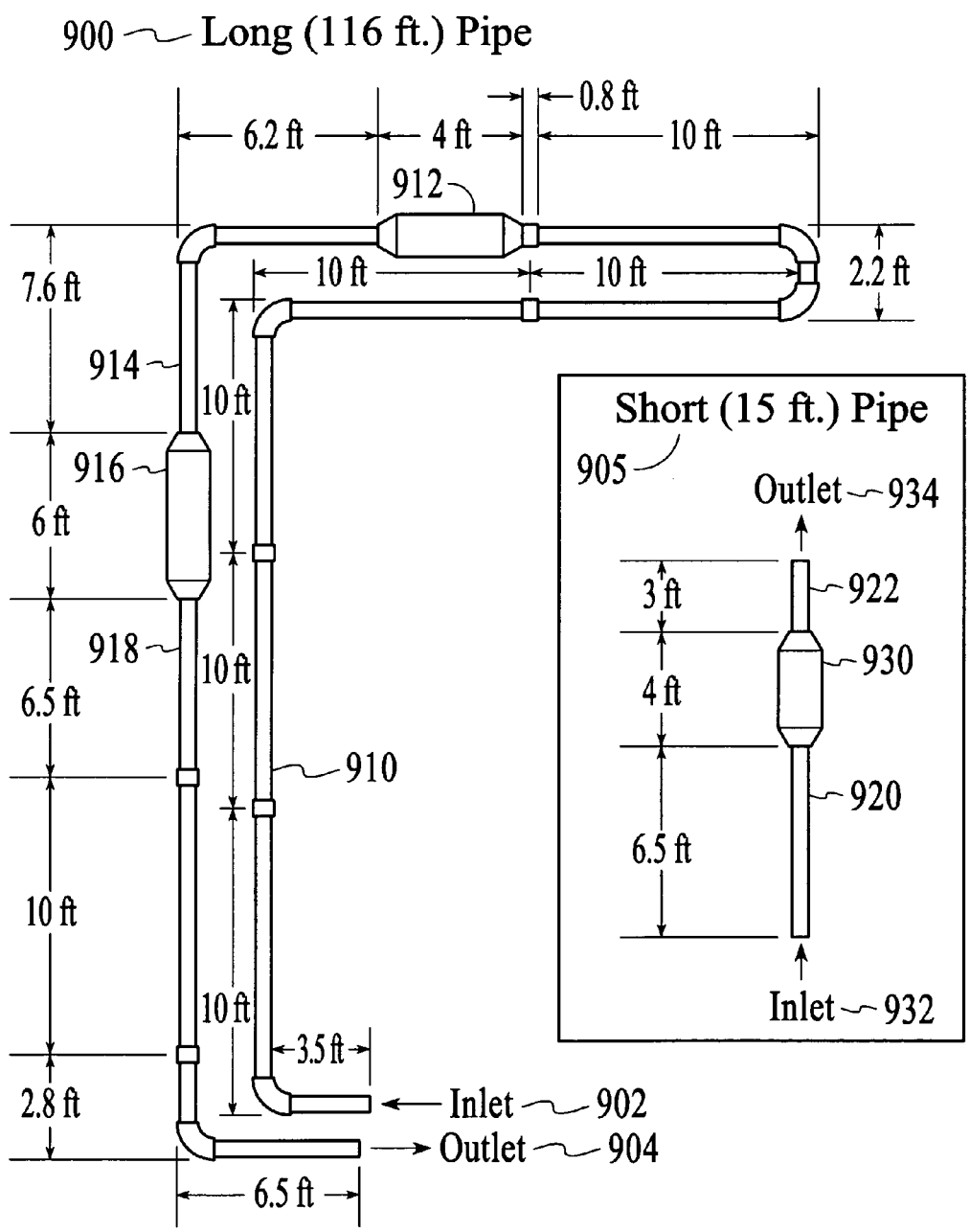
FIG. 22 Illustrates a schematic of a pipelines used in laboratory testing.

Testing was conducted in each of the three different pipe sections. The short pipeline 905 (15 ft) consisted of an 8 ft section 920 of 2-in. PVC pipe followed by a 4-ft section 930 of 3-in. PVC pipe followed by another 3-ft section 922 of 2-in. PVC pipe as depicted in FIG. 22. The 2-in. PVC pipe 920 has a screw connection such that it can be opened to accept trays of contamination. This makes the pipeline more versatile and allows the contamination to be easily removed or changed for different tests. Two types of contamination trays are used in the testing, each are 3-ft long. The shallow trays have a width of 1.625 in. The tall trays have a width of 0.8125 in. This allows the same volume of contaminant to have half the surface area, depending upon which tray is used. These trays were used to evaluate surface area effects as well as facilitate contaminant change outs.

The long pipeline 900 (116 ft) was constructed the same as the short pipeline 905 except the leading 2-in. of the pipe 910 between the inlet 902 and the first 4-ft 3-in.-diameter section of PVC pipe 912 was 66 ft long, and the trailing 2-in. PVC pipe sections 914, 916, 918 between the first 3-in.-diameter PVC pipe section 912 and the outlet 904 was 45 ft long. The middle section 912 for placing the contamination was the same as built for the short pipe middle section 930.

The third pipeline 900, which is the same length as the long pipe 900 added a second contaminated section 916 to the 116-ft long pipeline 900 to evaluate the effect of multiple zones of contamination as opposed to single point source. The pipe section for placing the contamination 916 is the same configuration as the first contamination section 912 shown in FIG. 22, except the new section 916 is located 24.3 from the end of the pipe 918 and is six ft long 916.

Laboratory Testing for Estimating Volume. To evaluate the effects, if any, that could impact the special conditions that exist in a pipeline, a series of four tests were conducted as described below. For each test, a weathered diesel product 950 (FIG. 23) was used for the contaminant of interest, because it was easy to work with and established tracers and tracer properties exist from the short pipe tests described above. These new test series were conducted in the short pipe section 905 shown in FIG. 22 using the trays inside the 3-in. PVC pipe section 930.

Figure 23:
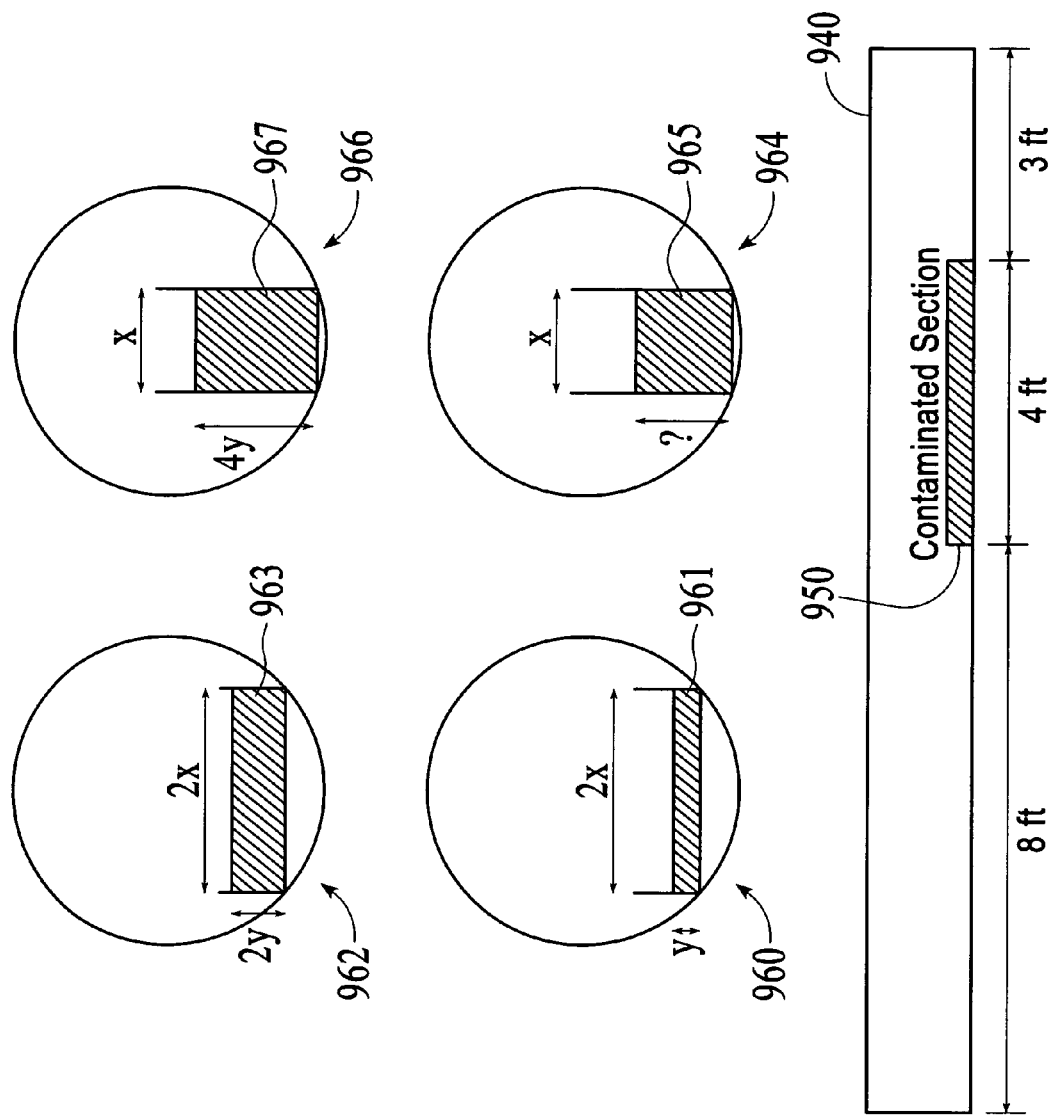
FIG. 23 illustrates the surface area and volume relationship test series.

FIG. 23 illustrates the possible tests. The short pipe section 940 contained contamination 950 in both the shallow tray 960, 962 and the tall tray 964, 966 configurations. The cross-sectional area of the two shallow tray configurations 960, 962 were the same but the volume of contamination 963, 961 was twice as large in the shallow tray configuration 962 as for the shallow tray configuration 960. Thus, the depth of the contamination 963 in the shallow tray configuration 962 was twice as large as the depth of the contamination 961 in the shallow configuration 960. The tall tray configuration 964 contained the same volume of contamination 965 as the volume of contamination 961 in the shallow tray configuration 960. Similarly, the tall tray configuration 966 contained the same volume of contamination 967 as the volume of contamination 963 in the shallow tray configuration 962; however, the cross-sectional area of the tall tray 964, 966 was only half the cross-sectional area of the shallow tray 960, 962. Like the shallow tray configurations 960, 962, the depth of the contamination 967 in the tall tray configuration 966 was twice as deep as the depth of the contamination 965 in the tall tray configuration 964. Thus, the tests were designed to examine the performance of the PCUT method for all combinations of volume, depth, and surface area.

Figure 24:
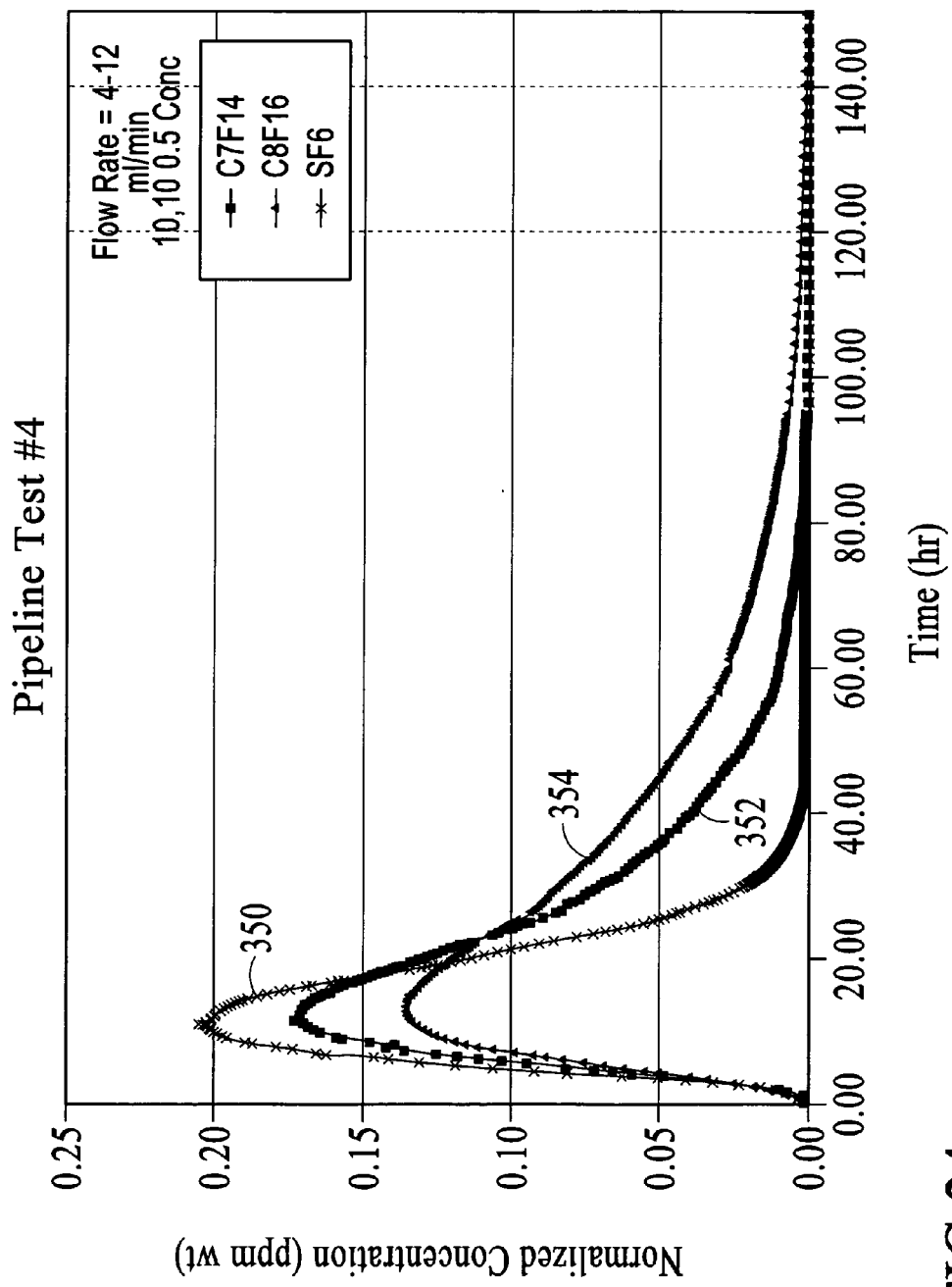
FIG. 24 illustrates PCUT test results from pipe test #4 with 300 ml of diesel.

300 ml Shallow Tray Test Series. The first series of tests were run with 300 ml in a shallow tray that has a width of 1.625 in. This consisted of Pipe Tests 4, 5 and 6 in Table 10. The results are presented in Table 11. The average errors in the volume estimates were 5.9% using the $C_7F_{14}$ tracer 352 and 7.4% using the $C_8F_{16}$ tracer 354. All estimates were less than the act volume. FIG. 24 presents the conservative 350 and partitioning tracer response curves 352, 354 for Pipe Test #4. The results from Pipe Test #5 are postulated to be below average because of the increase in the average flow rate from 8-12 ml/min up to around 20 ml/min. At this flow rate, it is probable that this did not allow sufficient time for the tracers to partition into the contaminant.

TABLE 11

Volumetric test results using shallow tray.

| | $C_7F_{14}$ | | $C_8F_{16}$ | |
|---|---|---|---|---|
| Test ID | Vol (ml) | Error (%) | Vol (ml) | Error (%) |
| Pipe Test #4 | 283.6 | −5.5% | 296.4 | −1.2% |
| Pipe Test #5* | 271.6 | −9.5% | 261.7 | −12.8% |
| Pipe Test #6 | 291.6 | −2.8% | 275.4 | −8.2% |
| Average | 282.3 | −5.9% | 277.8 | −7.4% |

*Flow rate for this test is nearly double the flow rate from Test #4 and Test #6

300 ml Tall Tray Test Series. For the second test series (Test #13, #14, and #18), the shallow tray 960, 962 illustrated in FIG. 23 was replaced with a tall tray 964, 966. The volume remained the same as for the first series of tests; however, the surface area exposed to the tracer was reduced by a factor of two. The results from Pipe Tests #13, #14, and #18 are presented in Table 12. The flow rates for these tests were similar to pipe tests using the shallow tray, yet the results show even smaller quantities and larger errors than the previous shallow tray test series results. Based upon the data, there does not appear to be a strong relationship between the estimated quantity and the surface area of the contaminant. If a relationship was present, then the volumes measured in this test series should have been a factor of two less than those measured in the previous test series. As shown in Table 12, the estimated volumes using an alpha ($\alpha$) factor of 1 in Eq. 3 are closer to the actual 300 ml, than 150 ml, which would be case if the alpha factor was directly related to surface area of the contaminant. The estimated quantities in Table 12 are generally less, which is probably related to the amount of residence time the tracers have over the contamination. With a larger surface area, the necessary residence time is less than if the surface area is smaller. For the tall tray, the tracers can only interact through half the surface area to detect the same volume as the first series of tests. It appears that as the residence time is reduced the amount of error in volume estimate increases. This was also observed in other tests using reduced volumes of contamination.

TABLE 12

Volumetric test results using tall tray.

| | $C_7F_{14}$ | | $C_8F_{16}$ | |
|---|---|---|---|---|
| Test ID | Vol (ml) | Error (%) | Vol (ml) | Error (%) |
| Pipe Test #13 | 263.4 | −12.2% | 317.5 | 5.8% |
| Pipe Test #14 | 250.9 | −16.4% | 220.4 | −26.5% |
| Pipe Test #18 | 301.3 | 0.4% | 260.6 | −13.2% |
| Average | 271.9 | −9.4% | 266.2 | −11.3% |

Figure 25:
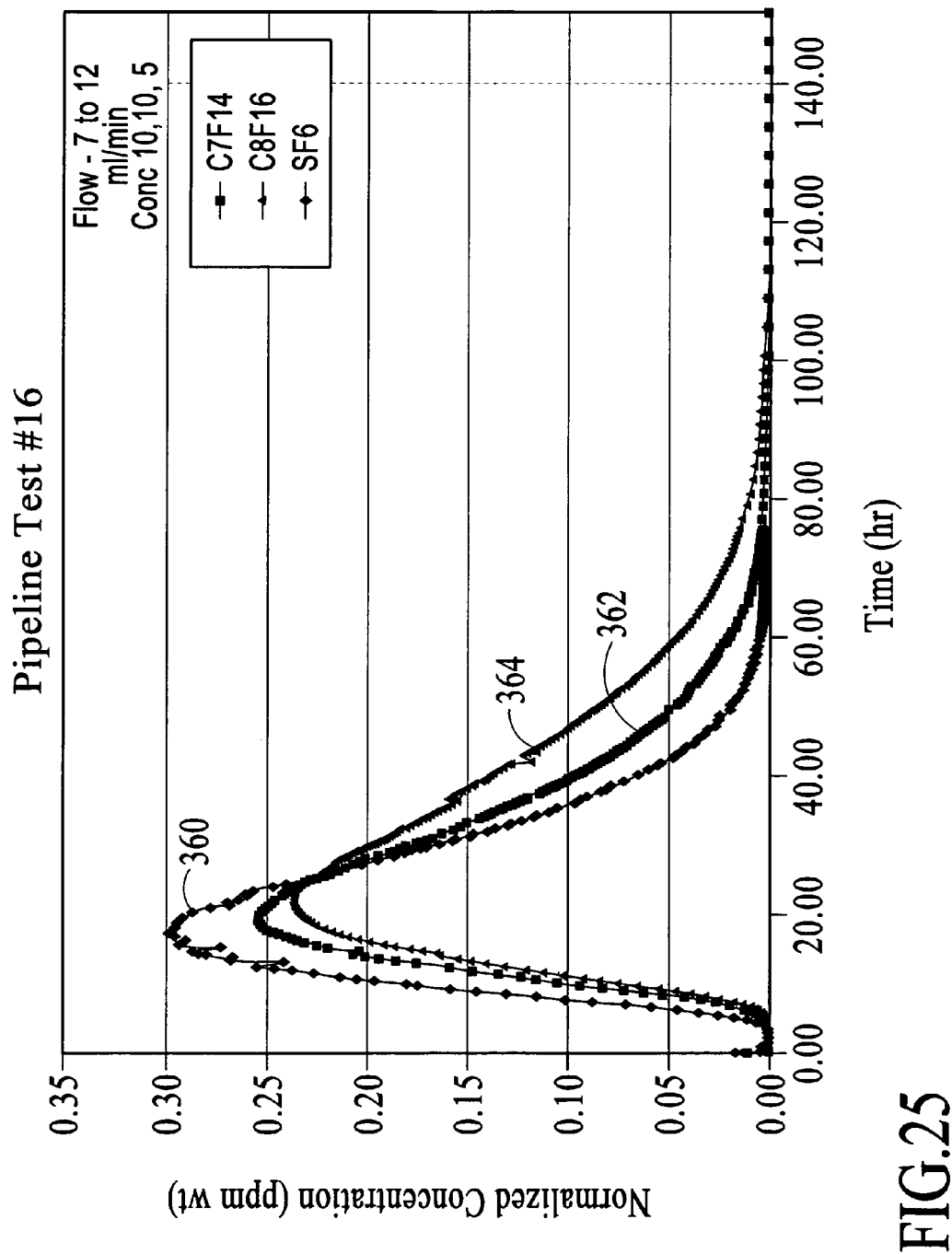
FIG. 25 illustrates a typical test results from testing with 150 ml showing separation of the conservative and partitioning tracers indicating detection of the contamination.

150 ml Shallow Tray Test Series. The third test series used the shallow trays, but the total volume placed in the trays was reduced to 150 ml, (half that used in the previous tests). Three replicates were again conducted using flow rates between 8 and 12 ml/min. The results are presented in Table 13. FIG. 25 illustrates the concentration of the conservative 360 and the partitioning 362, 364 tracers for Pipe Test #16. In all three pipe tests conducted with a contamination of 150 ml, the quantification errors were higher than the quantification errors obtained from any of the 300-ml test runs. Although quantification of a 150 ml volume of diesel was not as accurate as the 300-ml results, as illustrated by the quantification errors, the detection or presence of the contamination was easily accomplished as the partitioning tracer curves were well separated from the conservative tracer curve. It should be noted that detecting the presence of contamination in a pipeline is much easier than accurately quantifying the contamination. Although the PCUT method had an average error of over 25% for quantifying 150 ml of diesel, it can easily detect this volume and could likely detect volumes even smaller given sufficient partitioning time.

TABLE 13

Volumetric test results using shallow tray and 150 ml of contaminant.

| | $C_7F_{14}$ | | $C_8F_{16}$ | |
|---|---|---|---|---|
| Test ID | Vol (ml) | Error (%) | Vol (ml) | Error (%) |
| Pipe Test #15 | 124.2 | −17.2% | 113.6 | −24.3% |
| Pipe Test #16 | 102.2 | −31.8% | 96.6 | −35.6% |
| Pipe Test #17 | 108.8 | −24.9% | 99.4 | −31.5% |
| Average | 111.7 | −24.6% | 103.2 | −30.5% |

Blind Test Series. A fourth test series was also conducted to confirm the final analysis approach. These tests were conducted in a "blind" manner to determine how well the method works for unknown scenarios. For these tests, the test operator placed an unknown volume in the tray for each test. After the test was conducted a person other than the test operator analyzed the data and determined the volume estimate. Only then were the actual volume placed in each test revealed and compared to the measured volume. These results are presented in Table 14.

TABLE 14

Blind Volumetric test results.

| | $C_7F_{14}$ | | $C_8F_{16}$ | |
|---|---|---|---|---|
| Test ID | Vol (ml) | Error (%) | Vol (ml) | Error (%) |
| Pipe Test #20 (250 ml) | 268.2 | 7.3% | 217.9 | −12.8% |
| Pipe Test #21 (225 ml) | 218.0 | −3.1% | 244.7 | −8.7% |
| Pipe Test #22 (300 ml) | 277.8 | −7.4% | 298.9 | −0.4% |
| Average | | −1.1% | | −7.2% |

The results from the blind testing strongly support the ability of PCUT method to both accurately detect contamination as well as quantify the amount of contamination present. Using the three blind tests presented in Table 14, a total of six quantifications were made using two partitioning tracers in each test. The average quantification error for each tracer was less than 10%, with $C_7F_{14}$ producing an average of 1.1%. These average errors for the blind testing is within the desired range and typical of the average test error from all the testing which was not conducted blind.

Figure 26:
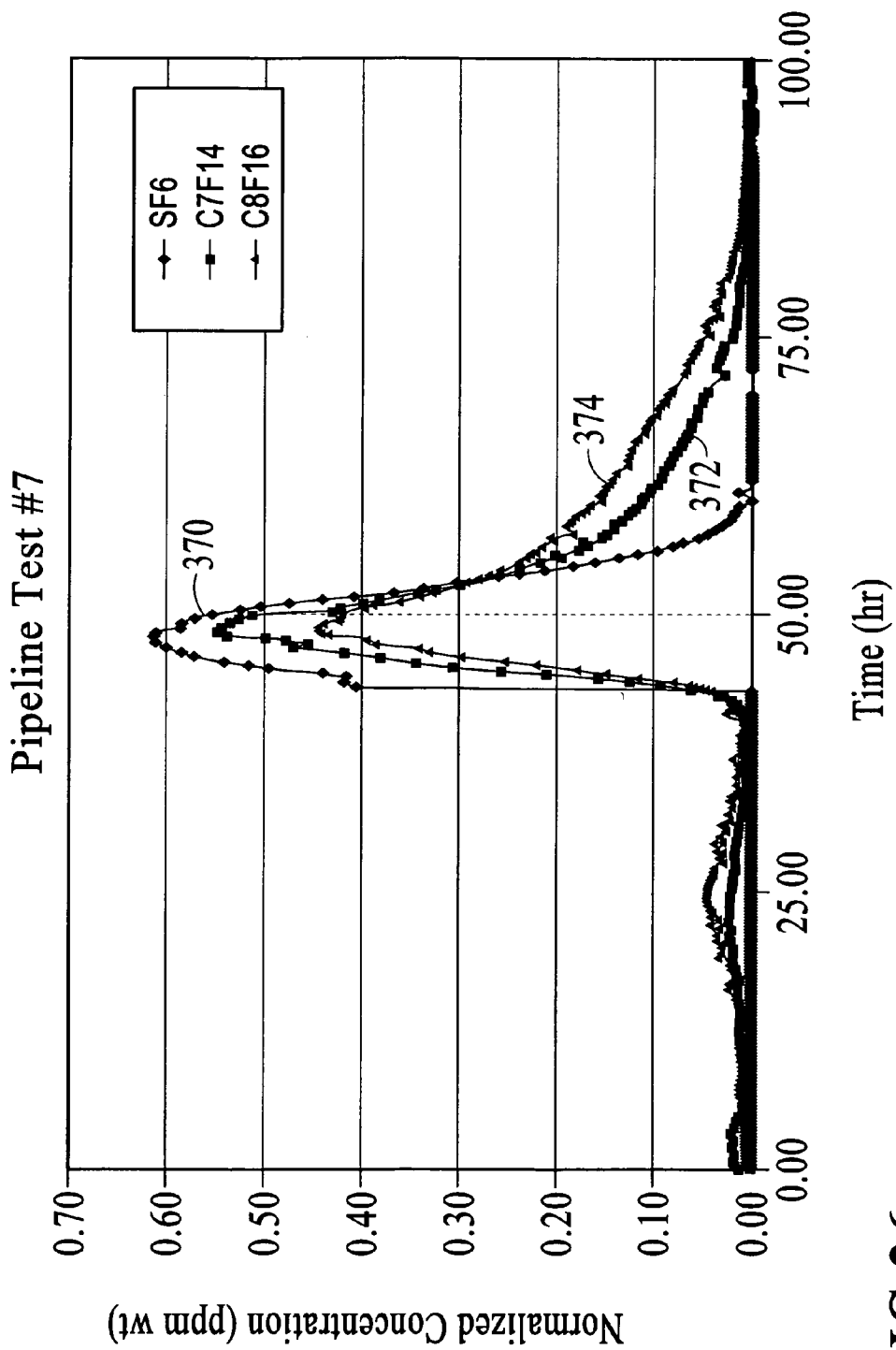
FIG. 26 illustrates tracer concentration time histories from the long pipe with 300 ml of diesel located two thirds of the length of the pipe.

Long Pipe Test. The accuracy of the PCUT method for quantifying the volume of a contaminant in a long pipe was also determined in a series of tests in the long pipe 900 illustrated in FIG. 22. The results for Pipe Test #7 are illustrated in FIG. 26 for the conservative 370 and the partitioning 372, 374 tracers obtained in a shallow tray test 966. A flow rate of 8 to 20 ml/min was used in the test. The volume of contamination was 300 ml. The contamination was detected and quantified at 285 ml, which is similar to the results from the short pipe 905.

Testing Summary. The various tests conducted using the short pipeline 905 and long pipe 900 illustrated in FIG. 22, have clearly demonstrated that that PCUT method is a viable method for detecting and quantifying contamination within pipelines. These tests have established specific testing procedures for conducting the PCUT tests that can be applied to other pipeline scenarios. The major first-order effects have been investigated and established as minor in relating to the quantification estimates. Based upon the test results obtained on the longer pipe section, the alpha factor (α) has been determined to be 1. A second-order relationship has been noted between the residence time of the portioning tracers and quantification error, implying that sufficient time for the tracer transport should be utilized to obtain accurate contaminant volume estimates. In summary, the PCUT test procedures are established and have been proven to be effective for detecting and estimating contamination within pipeline.

Test with a Dry Contaminant. In addition to the diesel detection and quantification tests, three demonstration tests were also performed using dried glue as a semi-solid test material. The glue is a standard epoxy called WELDER, which is manufactured by Homax Products, Inc., and can be purchased at any local building supply store. The glue is 46% by weight Toluene and has a vapor pressure of 22 mm Hg at 68° F. as a liquid when first applied. The manufacturer stated that the vapor pressure decreases significantly (<<1 mm Hg at room temperature) as the glue dries and the toluene evaporates, however the manufacturer does not have a value for the vapor pressure of a dried glue sample.

Figure 27:
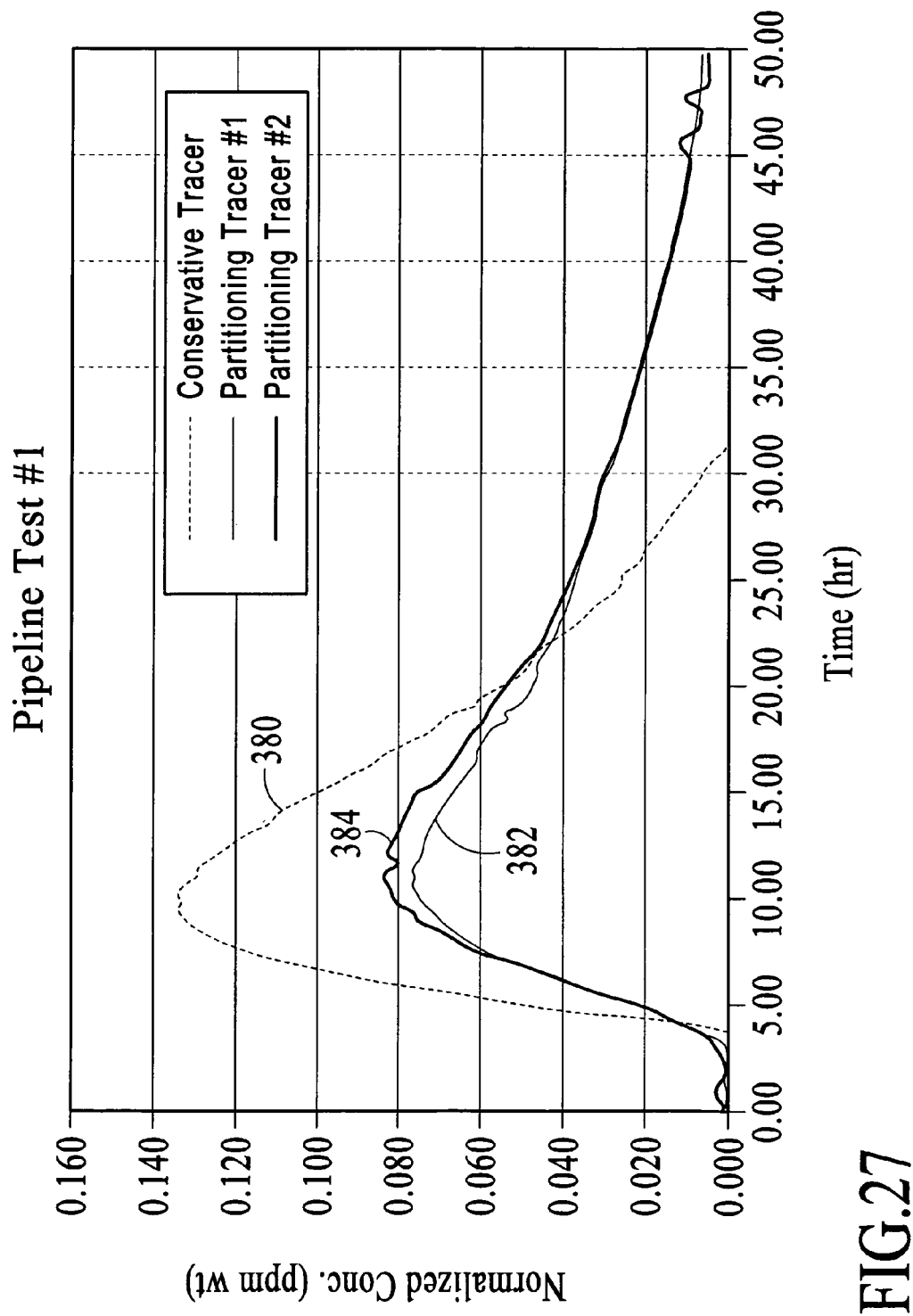
FIG. 27 illustrates tracer elution time history for dried glue in a short pipeline test.

For the first test, approximately 10 grams (5 ml) of dried glue were placed in the short pipe 905 illustrated in FIG. 22. The same tracer suite ($SF_6$, $C_7F_{14}$, and $C_8F_{16}$) was advected through the pipe and the tracer elution curves shown in FIG. 27 were observed. In FIG. 27, there is clear indication of a partitioning effect occurring as the peaks of the Partitioning Tracers #1 382 and #2 384 ($C_7F_{14}$ and $C_8F_{16}$ respectively) are not nearly as high has the conservative tracer 380 ($SF_6$). In addition, the partitioning tracers continue to emerge even after all the conservative tracer has been swept out of the pipe. The center of mass for both partitioning tracers 382, 384 is also much longer in time than the conservative tracer 380. In this test, both partitioning tracers 382, 384 are nearly identical, indicating that partitioning coefficient for both tracers, which are chemically very similar, are about the same in the dried glue material. This is different than for the aged diesel in the short-pipe tests described above, where the partitioning coefficient into diesel for Partitioning Tracer #2 ($C_8F_{16}$) is about three times the partitioning coefficient of that for Partitioning Tracer #1 ($C_7F_{14}$) into the aged diesel. The other two tests were conducted in the long pipe 900 illustrated in FIG. 22 and showed similar results, indicating that even small amounts of a semi-solid material can be detected in typical pipe lengths. The contaminant was placed in the middle of the 4-ft, 3-in.diameter PVC section 912.

Alternative Method for Characterizing a Contaminant. To reduce the overall time required to conduct a test, an alternative tracer injection method was evaluated in Pipe Test #10. For all the other tests, tracers of known volume were introduced at the inlet of the pipe and transported along the pipe and over the contamination using an advective flow. For Pipe Test #10, the pipe was flooded with tracer and then sealed up overnight allowing the tracer to reside over the contamination regions. The next morning the tracer was swept out using a high flow rate and then a lower advective flow was established. As the partitioning tracers are eluted into the advective flow stream they are carried to the GC for measurement. This approach reduced the total time of the test and permitted the location of the contamination to be estimated. The location calculations are discussed below.

Test Procedure for Contaminant Location. The location capability of the PCUT technology was demonstrated in the laboratory using the 116-ft, long-pipe illustrated in FIG. 22. The 3-ft by 1.625-in. rectangular tray (i.e., the shallow tray) was inserted into the 4-ft section of 3-in.diameter PVC pipe 912 whose center position was located 47.5 ft from the outlet end of the pipe 904 where the GC measurements were made. The shallow tray was used to hold 300 ml of aged diesel fuel. The same two partitioning tracers ($C_7F_{14}$ and $C_8F_{16}$) and the same advection gas (nitrogen) as used in the aged-diesel detection and quantification tests described above.

Figure 28A:
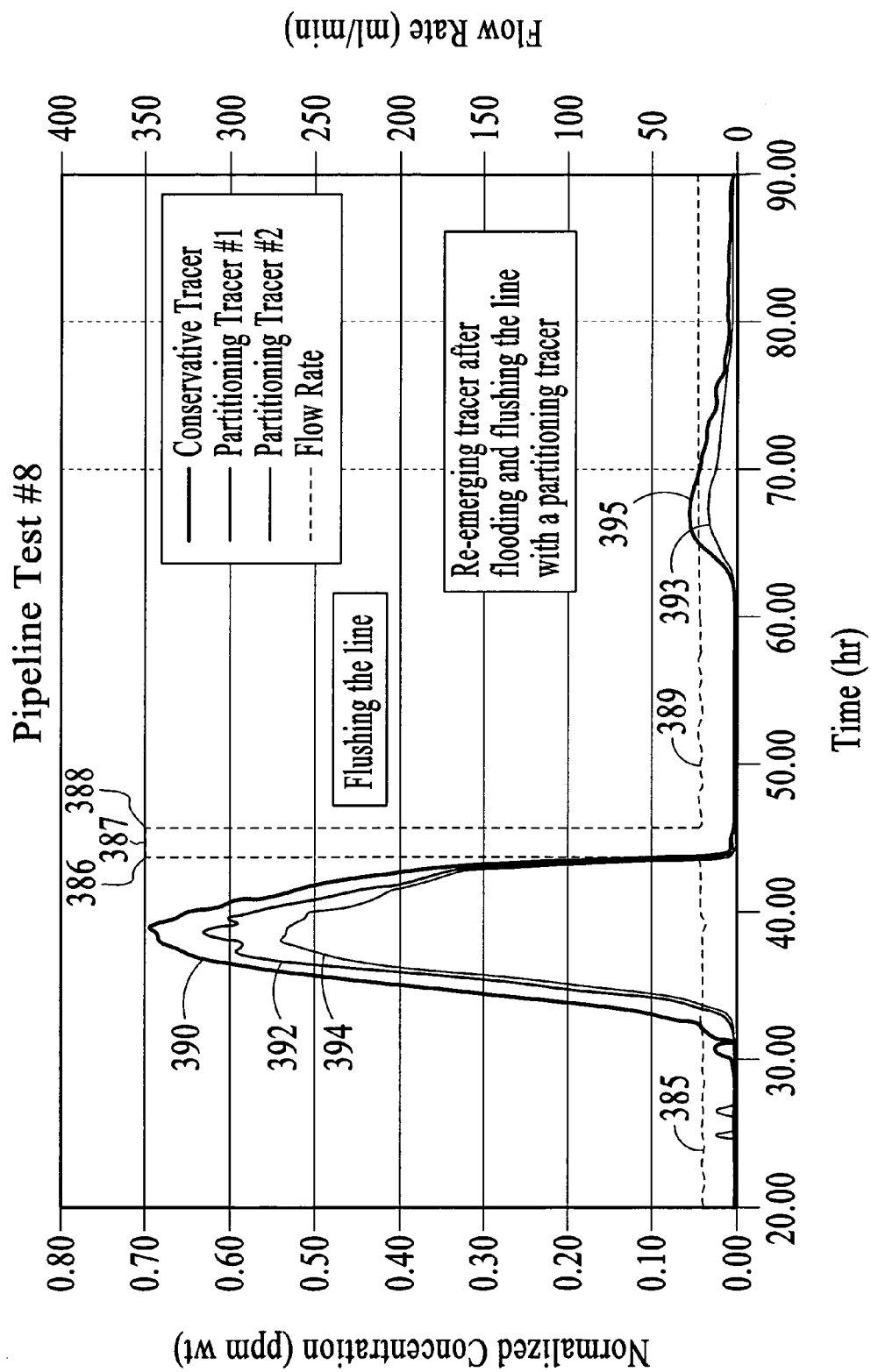
FIG. 28a illustrates test results from a test to determine the location of contamination within the long pipe using 300 ml of diesel as the contaminant located two thirds of the pipe length.
Figure 28B:
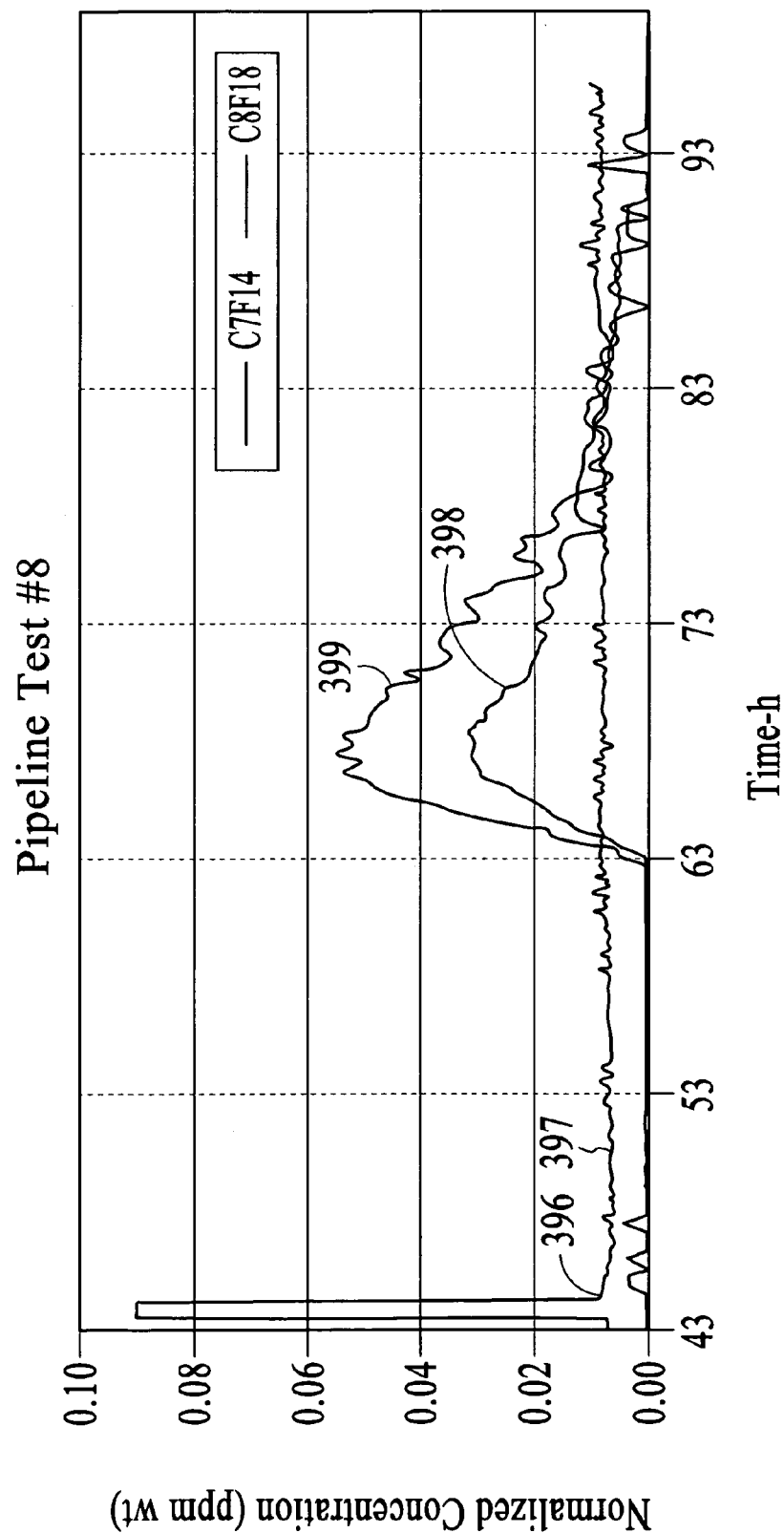
FIG. 28b illustrates tracer concentration curve that re-emerges from the contaminant after the line has been flooded and flushed.

FIG. 28a shows the time history of the concentration curves of the two partitioning tracers 392, 394 and the conservative tracer 390 from one of the location tests (Pipe Test #8). Superimposed on these curves is the flow rate of the advection gas 385, 387, 389. The location measurement is made after the detection measurement. The data required for detection is the same as for previous tests except only enough data needs to be collected to define the peak of the conservative tracer. This allows a comparison between the partitioning tracers and the conservative tracer for detection and also allows sufficient time for the tracers to partition into the contaminant. The next step is to rapidly flush 387 the conservative and partitioning tracers through the pipe and then to re-establish the advection flow stream 388 at a known velocity 389. As shown in FIG. 28a, the line was flushed at 350 ml/min 387, which is over 10 times the initial flow rate of the measurements 385. Once the flow rate is re-established 388 at a flow rate of approximately 20 ml·min 389, the partitioning tracers 393, 395 in the diesel fuel re-enter the flow stream and are advected to the end of the line at a known flow rate 389. The location of the contamination is then determined from the advection velocity 389 and the arrival time of the tracers. The arrival time is the time between the end of the flush 388 at the high flow rate 387 and the arrival of the partitioning tracers 393, 395 being emitted from the contaminant. FIG. 28b shows the two partitioning tracers 398, 399 arriving at about 63 hours; the advection flow field 397 was re-established at 44 hours 396.

Table 15 summarizes the location results for the tests conducted in the long pipe 900 illustrated in FIG. 22. Two methods were used to locate the contamination. Both methods used the time of arrival of the leading edge of the tracer concentration curves. (The average time of arrival can also be used.)

TABLE 15

PCUT estimation of the location of the 300 ml of diesel fuel contamination.

| Test | Method 1 | | Method 2 | |
| --- | --- | --- | --- | --- |
| | Location (ft) | Error (%) | Location (ft) | Error (%) |
| Pipe Test #8 | 51.3 | 3.3% | 53.2 | 4.9 |
| Pipe Test #10 | 38.1 | 6.4% | | |
| Pipe Test #12 | 45.4 | 0.1% | | |
| Pipe Test #23 | 44.7 | 0.6% | | |
| Average | | 2.6% | | |

*The actual location of the contamination is centered 47.5 ft from the outlet end of the 116-ft pipe.

The first method, which requires a priori information about the diameter or geometry of the pipe, uses the maximum velocity of the advection fluid within the pipe and the time of arrival of the tracer(s) after flushing. The average velocity is computed by dividing the measured volumetric flow rate by the diameter of the pipe; the maximum velocity (for laminar flow in a pipe) is twice this value. The second method, which does not require a priori information about the diameter or geometry of the pipe, only the total length of the pipe, utilizes the ratio of the time of arrival of the leading edge of the first tracer pulse 392 or 394, which traveled over the full length of the pipe (i.e., 116 ft) 900 and the time of arrival of the second tracer pulse 393 or 395, which traveled only the distance from the contamination 912 to the outlet end 904 of the pipe 900. After weighting the arrival times by the mean of the measured flow rates, the distance from the outlet end 904 of the pipe to the contamination 912 can be determined. Both methods were applied to Pipe Test #8 and only the first method was applied to Pipe Tests #10, #12, and #23.

The location test was also repeated (Pipe Test #12) using a dried glue sample of approximately 20 grams (10 ml). For this test the pipeline was flooded with tracer overnight and then flushed with 350 ml/min of the advection gas. After the flush, an advective flow stream was established and used to determine the location of the dried glue specimen. The distance from the end of the pipe to the glue sample was calculated to be 49.2 ft which is less that 10% error on the actual value of 47.5 ft.

Reactive Tracers. Reactive tracers can be used in a similar manner to partitioning tracers. A suite of tracers consisting of at least one tracer that is conservative i.e. does not react with the contaminant of interest and one or more tracers that reacts to the contaminant would be injected as a slug into the duct or pipe. The tracer slug would be transported or advected through the duct or pipe using a gas that does not interact with the tracers. When the reactive tracers come in contact with the contamination or hazardous substance in the duct or pipe, rather than partitioning into the contaminant and diffusing out of the contamination, the reactive tracers would react with the contaminant of interest and either change form or be partially consumed by the contamination or hazardous substance. FIG. 32 illustrates a computer model illustration estimate of the tracer concentration curves measured at the extraction point 190 (FIG. 13) with a GC 180 for a test in a contaminated 810, 820, 830 pipe and uncontaminated 800 pipe. The results for the conservative tracer and the reactive tracers are similar to those of the partitioning tracers for a test in an uncontaminated pipe. There are two important differences between the reactive concentration curves and the partitioning tracer concentration curves when the contamination is present. First, the total injected concentration of the reactive tracers is not recovered over time as it is for partitioning tracers. Second, all of the reactive tracers have the same mean time of arrival while the partitioning tracers have different mean arrival times. The reactive tracers have the same mean time of arrival in both the uncontaminated and contaminated pipe tests. FIG. 32 suggests that tests involving reactive tracers should be shorter than those using partitioning tracers, because the partitioning tracers do not have to diffuse out of the contamination.

For the scenario where the tracers are consumed by the contaminant or the hazardous substance, it is still possible to estimate the contaminant volume based upon the amount of tracer detected in the contaminant or hazardous material in a duct or pipe. The ratio between the injected concentration and the measured concentration should be related to the amount of contamination or hazardous material present, with consideration given to the effects of the reaction rate.

For the scenario where a tracer reacts with the contaminant or hazardous substance of interest and changes form, determination of the contamination or hazardous substance volume may be difficult. However, detection and location is straightforward.

Figure 29:
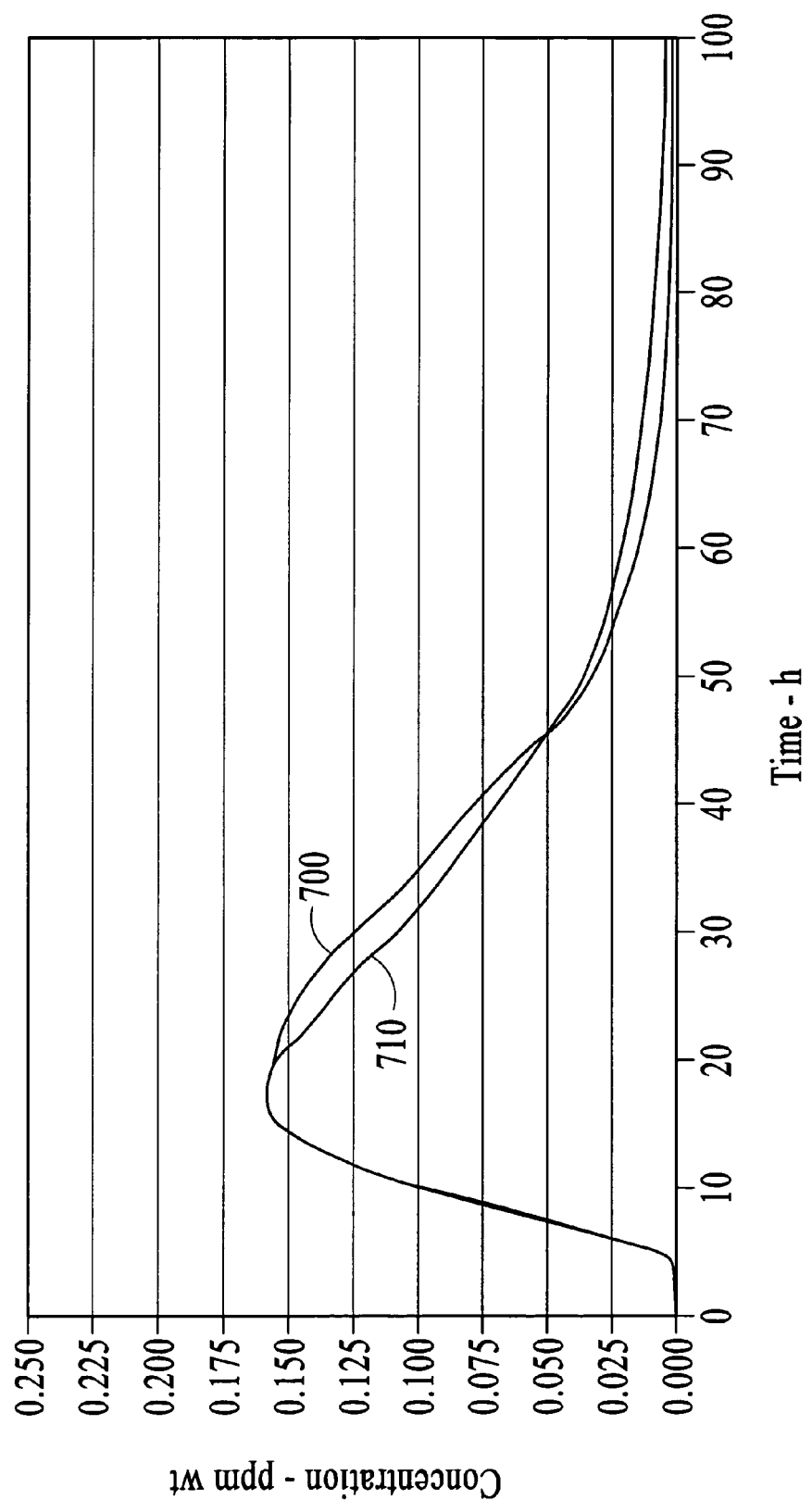
FIG. 29 shows a comparison between the output from advection-diffusion flow model and measured normalized concentration curve for the conservative tracer, $SF_6$.

Analytical Model Estimates of the Advection and Dispersion of the Tracers in a Pipe. A one-dimensional convective-diffusion (dispersion) model was used to describe the flow of a conservative substance in a pipe. The results from the 23-ft pipe tests were used to validate the model. Eq. (7) is a solution for a finite volume of substance injected into a pipe and transported at a steady and uniform flow rate with a constant longitudinal-dispersion coefficient.

$$\langle C_A(x, t) \rangle = \beta \left[ \frac{M}{\rho A (4\pi E_T t)^{0.5}} \right] e^{\frac{-(x-Ut)^2}{4\pi E_T t}} \qquad (7)$$

where M is the mass of the tracer material introduced, $\rho$ is density of the tracer mixture= the mass of the mixture divided by the volume of the tracer mixture, A is the cross-section area of the flow, $E_T$ is the one-dimensional longitudinal dispersion coefficient, x is the distance along the length of the pipe section, t is the time after introducing the tracer, U is the average velocity of flow along the pipe. This model was used to estimate $E_T$, and once $E_T$ was estimated, the model was used to predict the flow of the conservative tracers for different U. FIG. 29 shows a comparison of the model output, $\langle C_A(x=23 \text{ ft}, t) \rangle$ for $C_7F_{14}$ 710 and the measured concentration curve for $C_7F_{14}$ 700 at the GC, 23 ft from the tracer injection point as a function of time. Agreement is good.

Figure 30:
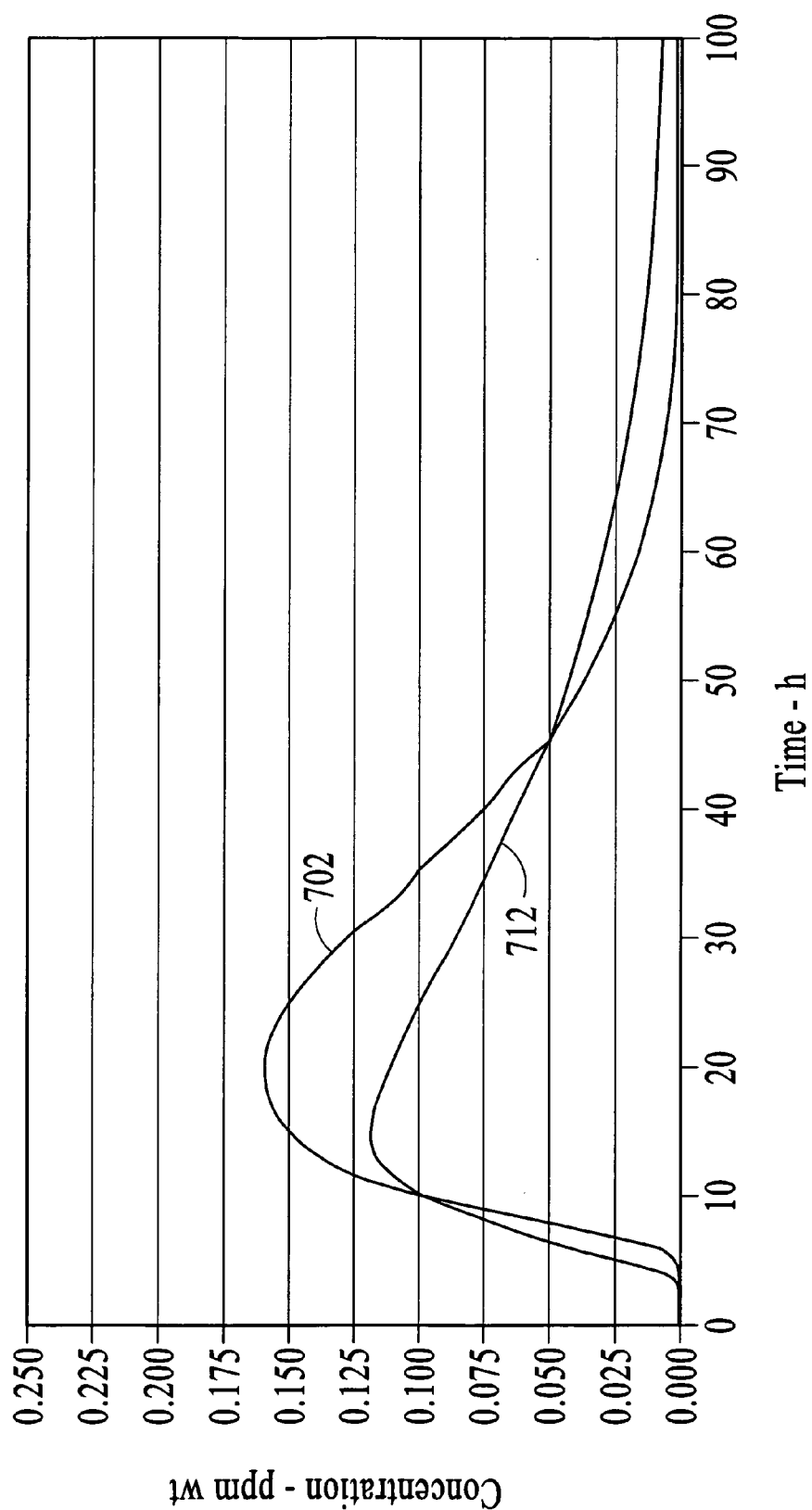
FIG. 30 shows a comparison between the output from advection-diffusion flow model and measured normalized concentration curve for the conservative tracer, $SF_6$, after the diffusion coefficient, $E_T$, was doubled.
Figure 31:
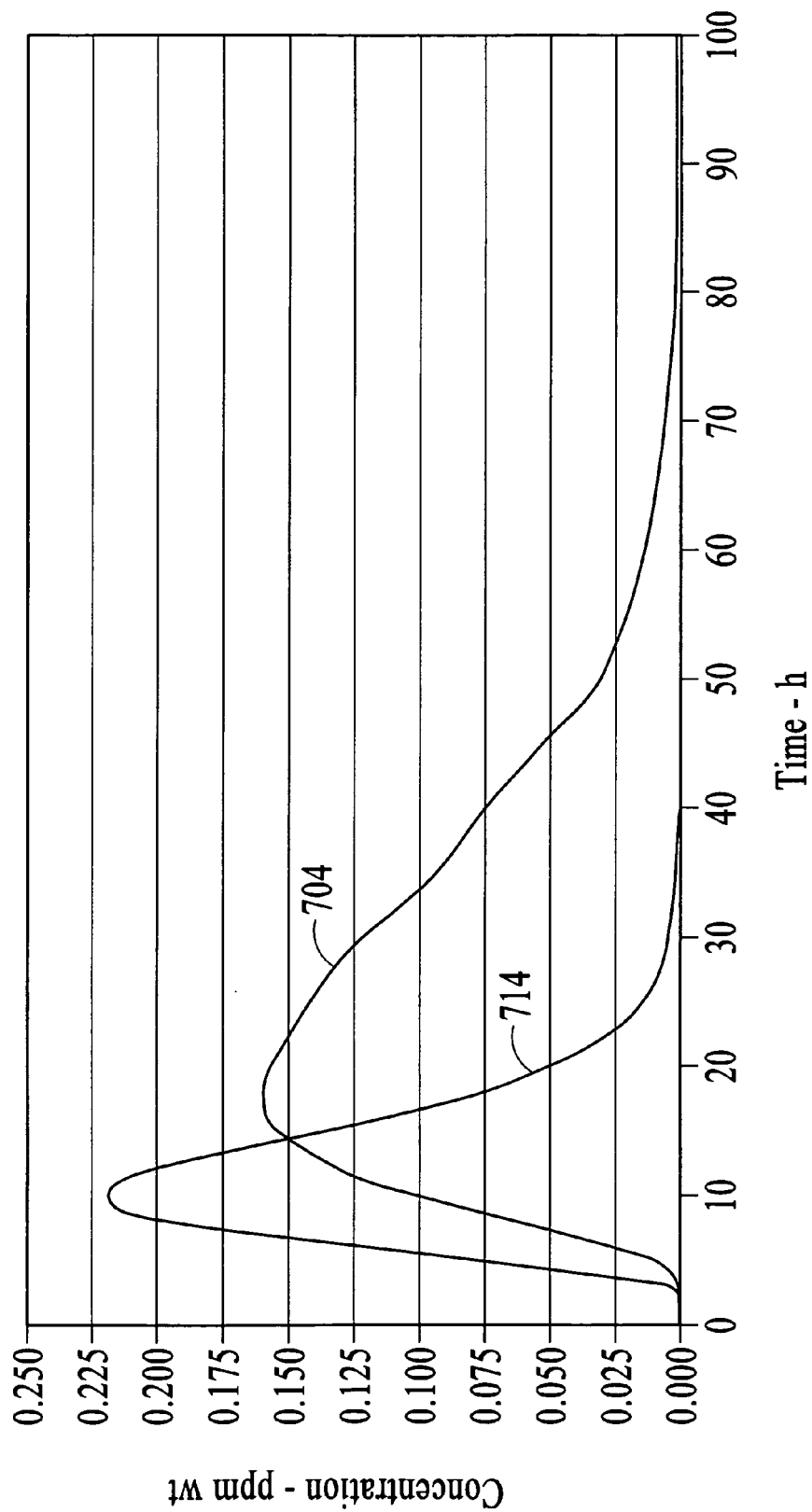
FIG. 31 shows a comparison between the output from advection-diffusion flow model and measured normalized concentration curve for the conservative tracer, $SF_6$, after the advection velocity, U, was doubled.

FIGS. 30 and 31 illustrate the effects of a flow field with a more rapid flow field and a larger dispersion coefficient, respectively. The values of U and $E_T$ were doubled. The model concentration curve 712 in FIG. 30 exhibits more dispersion (as compared to the measured concentration curve for $C_7F_{14}$ 702) with the larger diffusion coefficient, $E_T$. Doubling the advection velocity would allow the test to be completed is less time. The model concentration curve 714 in FIG. 31 exhibits a quicker time of arrival (as compared to the time of arrival of the measured concentration curve for $C_7F_{14}$ 704).

Figure 33:
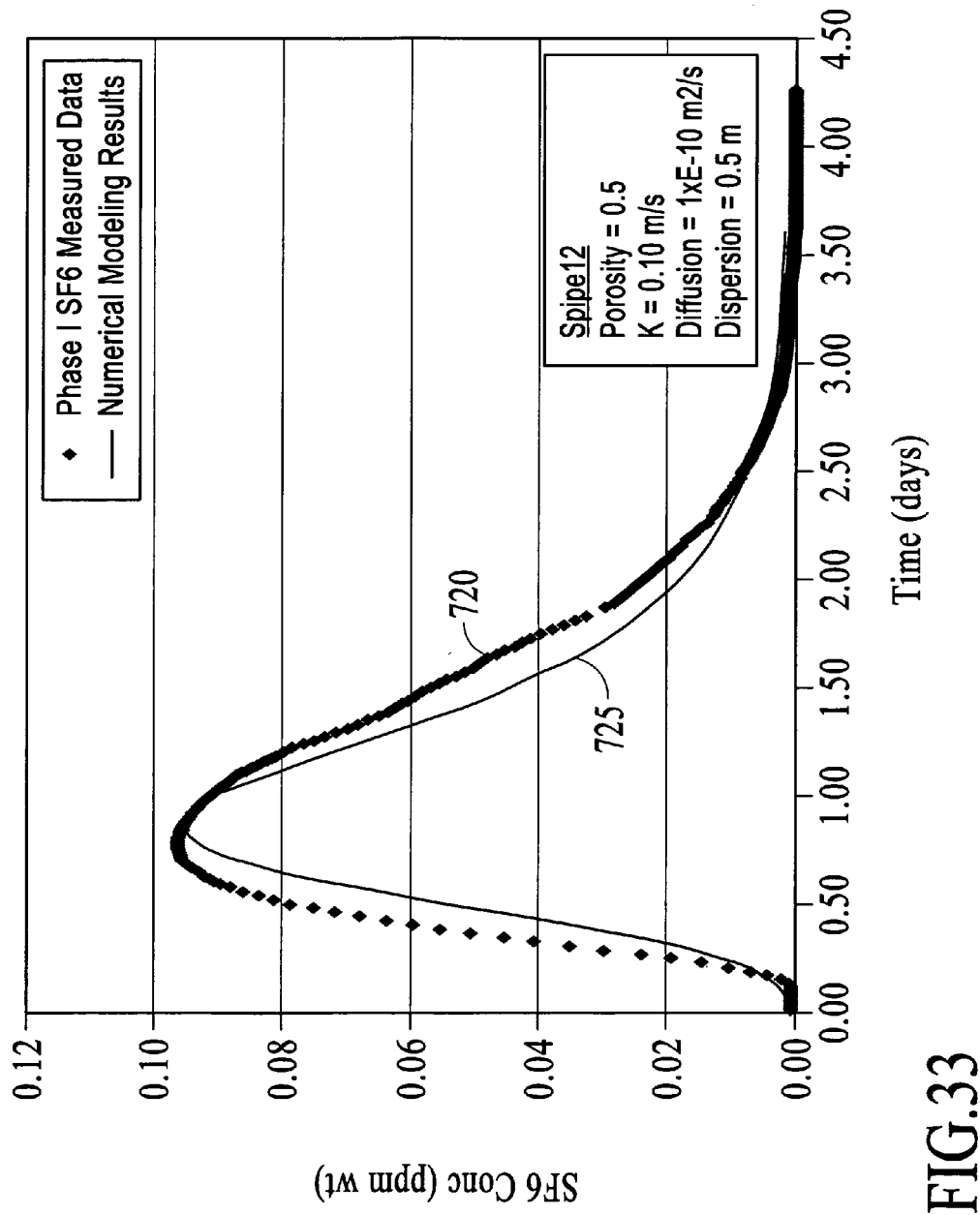
FIG. 33 illustrates a comparison of the numerical modeling results and the actual results for a short pipe for the conservative tracer.
Figure 34:
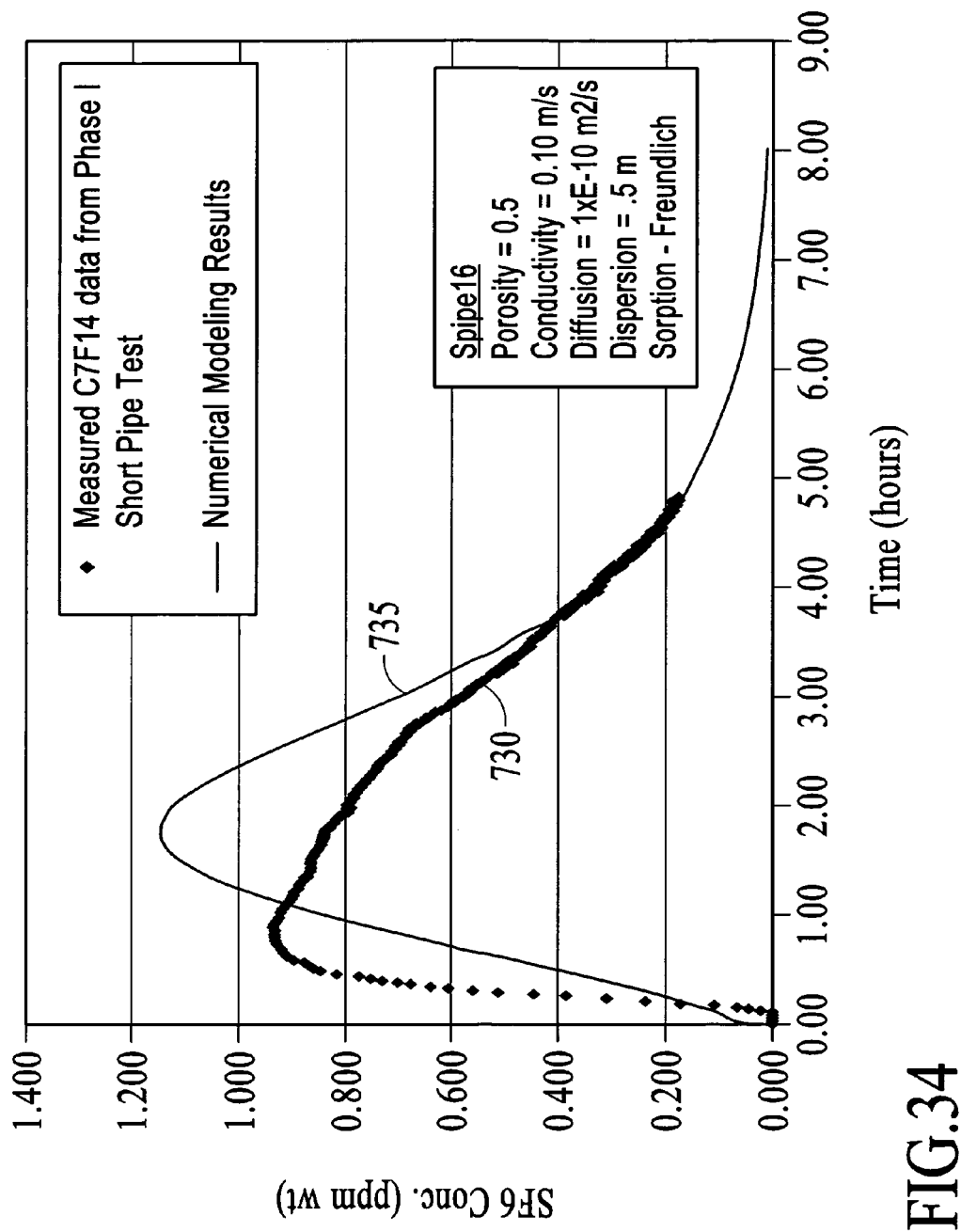
FIG. 34 illustrates a comparison of the numerical modeling results and the actual results for a short pipe for a partitioning tracer ($C_7F_{14}$).

Numerical Model Estimates of the Advection and Dispersion of the Tracers in a Pipe. Additional modeling was performed using a Finite Element Groundwater flow code, FEFLOW. A numerical model was used because it has the capability of not only accurate modeling the conservative tracers, but also of modeling the partitioning tracers. As a groundwater flow code, FEFLOW already has the advective transport equation, dispersion effects and chemical sorption on the soil particles, which is numerically the same as partitioning. The results of the numerical model of the conservative tracer time histories obtained in the 23-ft pipe tests are in good agreement with the measured results. FIG. 33 presents the comparison between the numerical model results 725 and the actual measured conservative tracer time history 720 from the short pipeline test section under the same flow field. Once the appropriate coefficient of conductivity was obtained using the conservative tracer, then a sorption term was added to represent the partitioning behavior. The coefficient of sorption was adjusted until the two curves matched. The resulting comparison of the model 735 and the partitioning tracer 730 $C_7F_{14}$ with the aged diesel contamination present is presented in FIG. 34. The fit is not as strong as that obtained for the conservative tracer due to some unique characteristics of the model. Due to the relative percentage of the pipe length that the initial tracer flood incorporates, a portion of the tracer slug arrives at the pipe exit (analytical instrument) very quickly without having experienced sufficient time to partition into the contaminant. In the numerical model, the sorption characteristics occur instantaneously, and therefore, capture some of the tracer and delay the peak as shown in FIG. 34. This is different from what occurs in the real pipe, since the leading edge of the tracer slug reaches the contamination and is then swept to the exit without sufficient partitioning time. This causes the tracer to arrive quicker for the actual test tests than the numerical. As will be shown for the long pipe, this same characteristic does not occur since the tracer slug is all moving a slow fixed speed before any contaminant is reached and therefore has uniform exposure time over the contaminated region.

Figure 35:
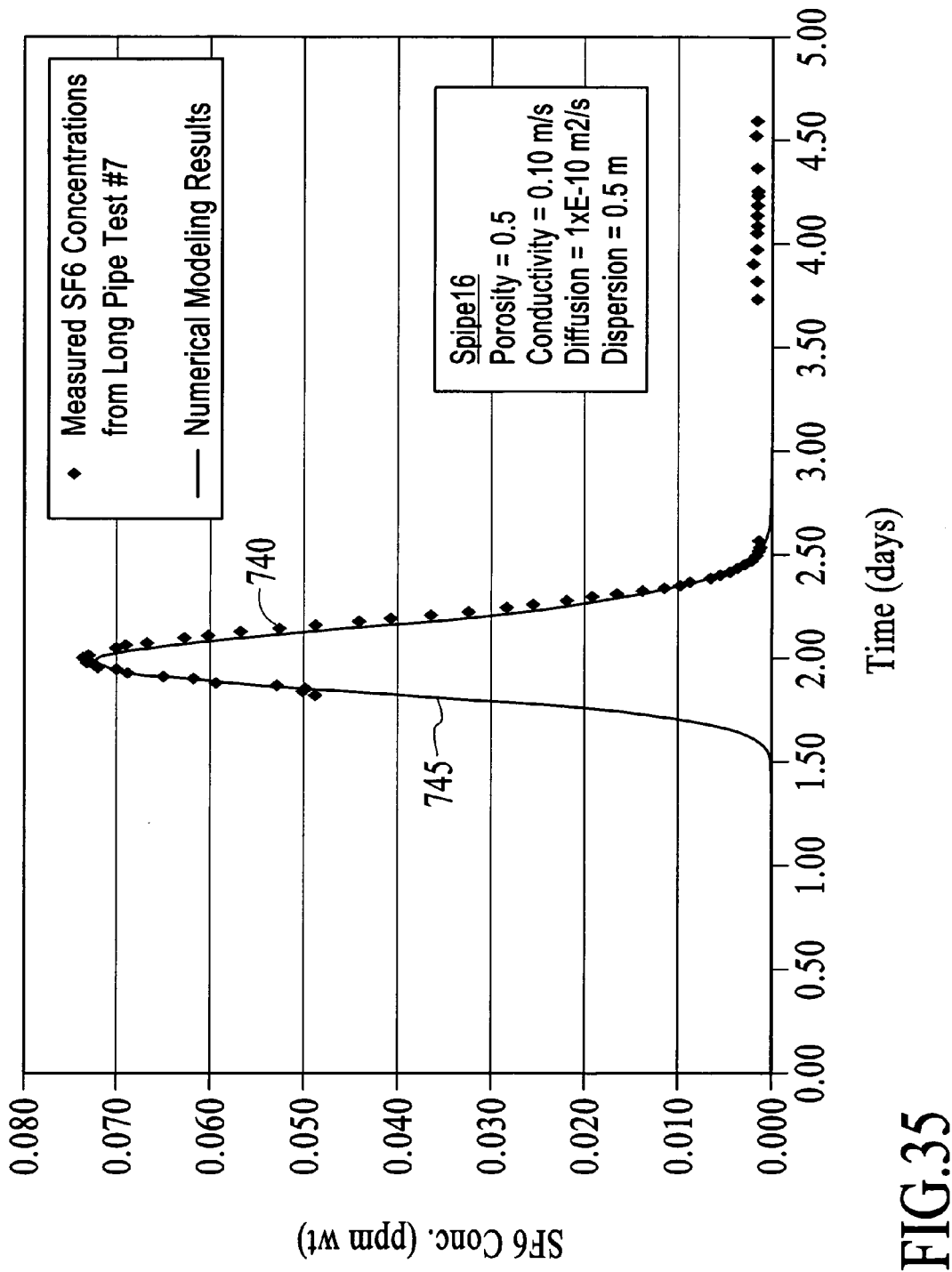
FIG. 35 illustrates a comparison of the numerical modeling results and the actual $SF_6$ results for a long pipe test (Pipe Text #7).
Figure 36:
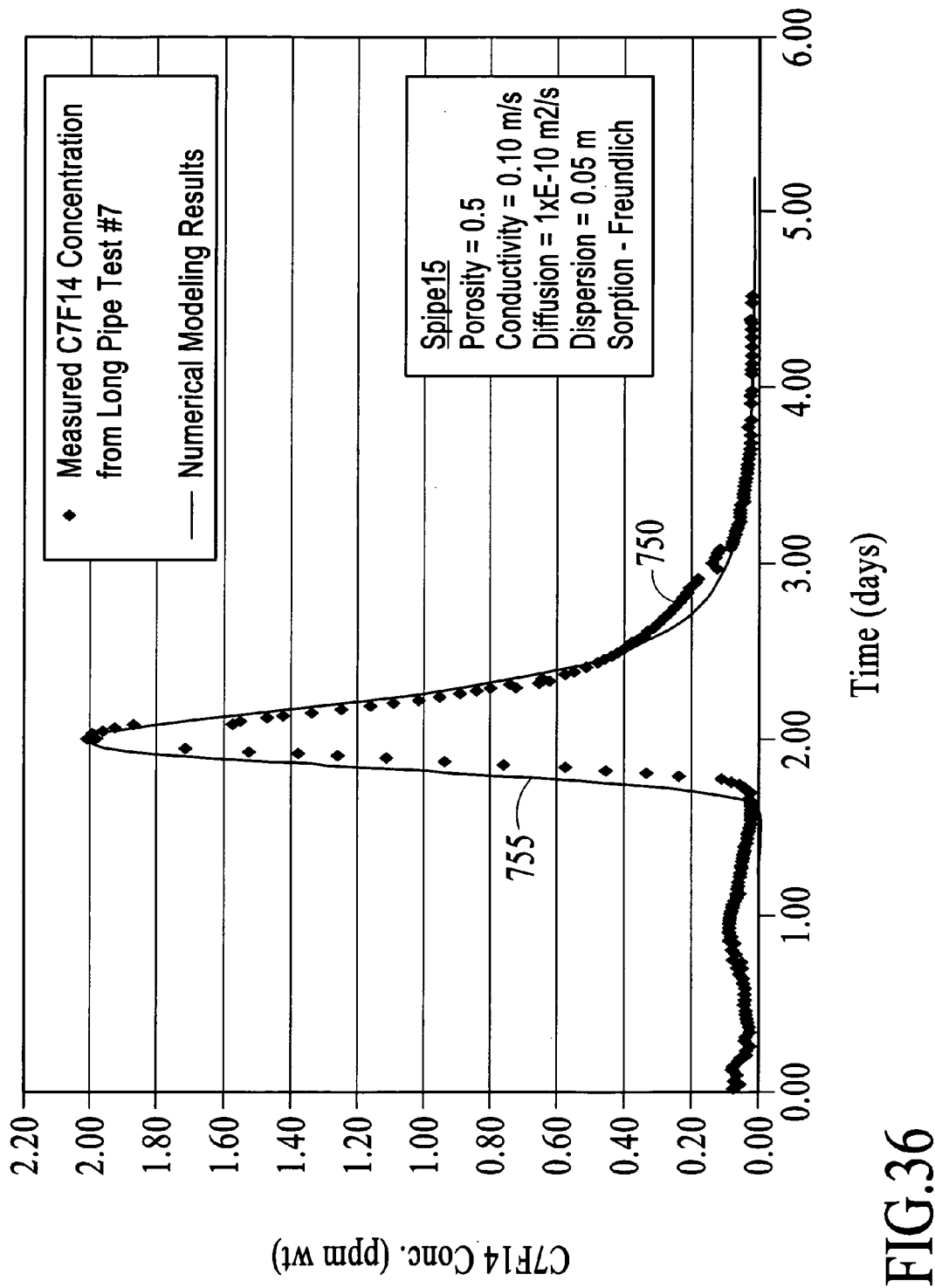
FIG. 36 illustrates a comparison of the numerical modeling results and the actual $C_7F_{14}$ results for a long pipe test (Pipe Test #7).

Using the baseline information developed from the short pipe modeling, the same model parameters were used to model the flow in a long pipe; Pipe Test #7 illustrates the results. The same coefficients worked nicely producing a good fit between the model results and the experimental results. The comparison between the model 745 and experimental 755 results for the conservative tracer in the long pipe configuration is presented in FIG. 35, and the comparison between the model 755 and experimental 750 results for a partitioning tracer, $C_7F_{14}$, also in the long pipe configuration, is presented in FIG. 36. Both model fits are good agreement with the data and demonstrate the ability to model the tracer movement in pipes. This allows the numerical models to be used as planning tools for future deployments of the technology. Other pipeline models can be easily created to evaluate how the tracers might react under various different flow conditions and pipe configurations. With the modeling capability an operational design capability exists.

Explosives. The PCUT method can be used for any contaminant characterization provided that an appropriate interactive tracer is available or can be developed. While the proof-of-concept tests have been accomplished in a pipe using aged diesel fuel and dried glue, the invention can be applied to any contaminant or chemical substance for which a tracer exists or can be developed.

Figure 37:
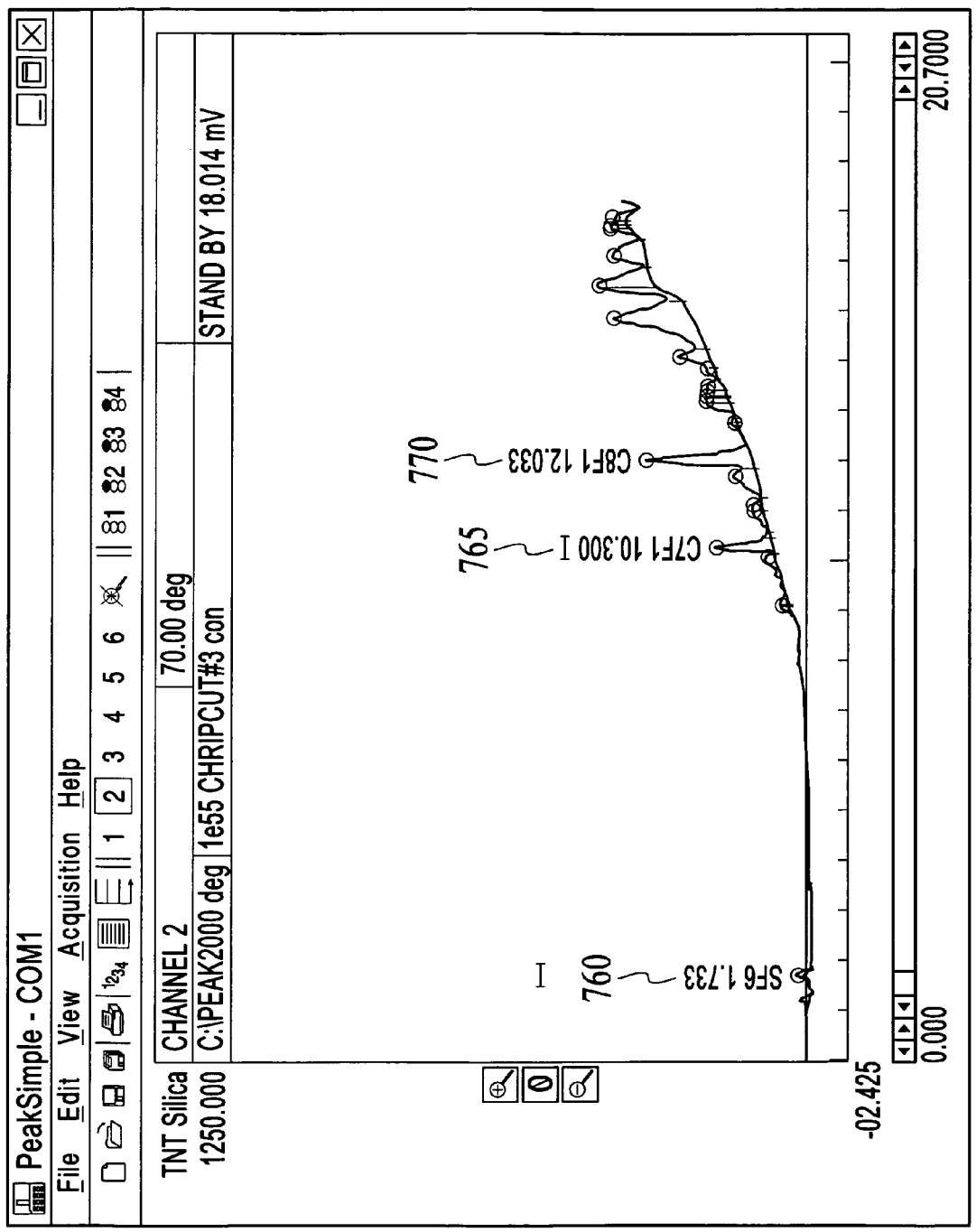
FIG. 37 illustrates a chamber test of 10 grams of K-9 TNT simulate consisting of 0.8 grams of TNT exposed to a tracer suite and then flushed an allowed to re-equilibrate. The $SF_6$ is nearly all gone but the sample continues to elude both partitioning tracers $C_7F_{14}$ and $C_8F_{16}$.

To determine whether or not PCUT has the ability to detect explosives, a sample of 10 gm of a K-9 TNT training simulant, which consists of 0.8 gm of 2,4,6 TNT and 9.2 gm of silica sand, was placed inside a 100-ml sample chamber. The chamber was filled with a mixture of three tracers. The conservative tracer was $SF_6$ at a concentration of 5 ppm. The other two tracers were $C_7F_{14}$ and $C_8F_{16}$, both at a concentration of 100 ppm. The tracers were exposed to the sample for a period of four hours. After that the sample chamber was purged of the tracer by flushing the chamber with 3 pore volumes of nitrogen, the chamber was then refilled with nitrogen and allowed to equilibrate for a period of 15 min. The resulting GC chromatogram, after 15 min, is presented in FIG. 37. It is clear from this data that the $SF_6$ 760 is completely gone from the sample chamber due to the purging process, but both $C_7F_{14}$ 765 and $C_8F_{16}$ 770 are present, as they partitioned into the sample and are eluting as partitioning tracers.

What is claimed is:

1. A method for determining the location of a contaminant in an enclosed gaseous flow system within a structure, comprising the steps of:
   (a) injecting a gaseous conservative tracer and a gaseous partitioning tracer into the gaseous flow system at a first location;
   (b) advecting the tracers along the gaseous flow system at a first speed to create an advection flow field;
   (c) extracting the tracers at a second location in the gaseous flow system;
   (d) introducing a perturbation to the advection flow field at a perturbation time by changing and then re-establishing the advection flow at a second advection speed, which may be different than the first advection speed, creating a unique change in the concentration of the partitioning tracer;
   (e) extracting the partitioning tracer as a function of time relative to the perturbation time;
   (f) measuring the concentration of the partitioning tracer as a function of the time; and
   (g) determining the location of contamination from the time of arrival of the partitioning tracer relative to the perturbation time and the advection flow speed.

2. The method of claim 1 wherein detection of the presence of a contaminant is determined from the presence of the interactive tracer that is being emitted from the contaminant after the tracers originally injected into the structure have been removed.

3. The method of claim 1 wherein the distance from the contaminant to the extraction point is determined from the time of arrival of the partitioning tracer after said advection flow field has been re-established.

4. The method of claim 3 wherein the mean time of arrival is determined from the first arrival of the tracer at the extraction point.

5. The method of claim 3 wherein the mean time of arrival is determined from the leading edge of the measured concentration curve at the extraction point.

* * * * *